United States Patent [19]
Thomas et al.

[11] Patent Number: 6,140,305
[45] Date of Patent: Oct. 31, 2000

[54] HEREDITARY HEMOCHROMATOSIS GENE PRODUCTS

[75] Inventors: Winston J. Thomas, San Mateo, Calif.;
Dennis T. Drayna, Bethesda, Md.;
John N. Feder, Mountain View, Calif.;
Andreas Gnirke, San Carlos, Calif.;
David Ruddy, San Francisco, Calif.;
Zenta Tsuchihashi, Menlo Park, Calif.;
Roger K. Wolff, Mill Valley, Calif.

[73] Assignee: Bio-Rad Laboratories, Inc., Hercules, Calif.

[21] Appl. No.: 08/834,497

[22] Filed: Apr. 4, 1997

Related U.S. Application Data

[63] Continuation-in-part of application No. 08/630,912, Apr. 4, 1996, abandoned, and a continuation-in-part of application No. 08/632,673, Apr. 16, 1996, Pat. No. 5,712,098, and a continuation-in-part of application No. 08/652,265, May 23, 1996, Pat. No. 6,025,130.

[51] Int. Cl.⁷ .......................... A61K 38/17; C07R 14/74; A61P 7/00
[52] U.S. Cl. ................................. 514/2; 530/350
[58] Field of Search ............. 424/185.1, 192.1, 424/195.11, 198.1; 530/350, 324, 325, 326, 327, 328, 329; 514/2

[56] References Cited

U.S. PATENT DOCUMENTS

| | | |
|---|---|---|
| 4,399,216 | 8/1983 | Axel et al. . |
| 4,434,156 | 2/1984 | Trowbridge . |
| 4,666,927 | 5/1987 | Hider et al. . |
| 4,683,202 | 7/1987 | Mullis . |
| 4,711,845 | 12/1987 | Gelfand et al. . |
| 4,912,118 | 3/1990 | Hider et al. . |
| 5,075,469 | 12/1991 | Chevion . |
| 5,104,865 | 4/1992 | Hider et al. . |
| 5,116,964 | 5/1992 | Capon ....................................... 536/27 |
| 5,185,368 | 2/1993 | Peter et al. . |
| 5,256,676 | 10/1993 | Hider et al. . |
| 5,328,992 | 7/1994 | Peter et al. . |
| 5,385,918 | 1/1995 | Connell et al. . |
| 5,399,346 | 3/1995 | Anderson et al. . |
| 5,420,008 | 5/1995 | Nishida et al. . |
| 5,424,057 | 6/1995 | Peter et al. . |

FOREIGN PATENT DOCUMENTS

| | | |
|---|---|---|
| 2115221 | 2/1994 | Canada . |
| 2115222 | 2/1994 | Canada . |
| 2115224 | 2/1994 | Canada . |
| 0 315 434 | 5/1989 | European Pat. Off. . |
| 0 346 281 | 12/1989 | European Pat. Off. . |
| 208 609 | 4/1984 | Germany . |
| 4 327 226 | 2/1995 | Germany . |

(List continued on next page.)

OTHER PUBLICATIONS

Sood, et al., Proc. Natl. Acad. Sci. USA 73(1):616–620, Jan. 1981.
Gorski, J J. Immunol. 143(1):329–333, Jul. 1, 1989.
Patterson, et al., Mol. Cell Biol. 6:1590–1598, 1986.
Harlow, E., Antibodies: A Laboratory Manual. Cold Spring Harbor Laboratory, Cold Spring Harbor, p. 76, 1988.
Sevier, Ed. Clin. Chem. 27(11):1797–1806, 1981.

(List continued on next page.)

*Primary Examiner*—David Saunders
*Assistant Examiner*—Mary B. Tung
*Attorney, Agent, or Firm*—Pennie & Edmonds LLP

[57] ABSTRACT

The invention relates generally to the gene, and mutations thereto, that are responsible for the disease hereditary hemochromatosis (HH). More particularly, the invention relates to the identification, isolation, and cloning of the DNA sequence corresponding to the normal and mutant HH genes, as well as the characterization of their transcripts and gene products. The invention also related to methods and the like for screening for HH homozygotes and further relates to HH diagnosis, prenatal screening and diagnosis, and therapies of HH disease, including gene therapeutics, protein and antibody based therapeutics, and small molecule therapeutics.

17 Claims, 22 Drawing Sheets

FOREIGN PATENT DOCUMENTS

| | | |
|---|---|---|
| 2 293 269 | 3/1996 | United Kingdom . |
| WO 94/01463 | 1/1994 | WIPO . |
| WO 94/04186 | 3/1994 | WIPO . |
| WO 94/11367 | 5/1994 | WIPO . |
| WO 94/21243 | 9/1994 | WIPO . |
| WO 95/16663 | 6/1995 | WIPO . |
| WO 96/17870 | 6/1996 | WIPO . |
| WO 96/35802 | 11/1996 | WIPO . |

OTHER PUBLICATIONS

Hashimoto, K. Biochem. Biophys. Res. Comm. 230:35–39, 1997.

Darnell, J. Molecular Cell Biology. Scientific American Books, New York, pp. 227–229, 1986.

Halliday, JW. Nutr. Rev. 56(2)S30–S37, 1998.

Camachella, C and Piperno, A. Haematologica 82:77–84, 1997.

Abravaya, K. et al., "Detection of point mutations with a modified ligase chain reaction (Gap–LCR)," *Nucl. Acids Res.* 23(4):675–682 (1995).

Bacon, B.R., "Causes of Iron Overload," *N. Engl. J. Med.* 326(2):126–127 (1992).

Barany, F., "Genetic disease detection and DNA amplification using cloned thermostable ligase," *Proc. Natl. Acad. Sci. U.S.A.* 88:189–193 (1991).

Barton, J.C. et al., "Blood lead concentrations in hereditary hemochromatosis," *J. Lab. Clin. Med.* 124(2):193–198 (1994).

Barton, J.C. et al., "Hemochromatosis: The genetic disorder of the twenty–first century," *Nature Medicine* 2(4):394–395 (1996).

Beutler, E. et al., "A Strategy for Cloning the Hereditary Hemochromatosis Gene," *Blood Cells. Molecules, and Diseases* 21(21):206–216 (1995).

Bjorkman, P.J. et al., "Structure, Function, and Diversity of Class I Major Histocompatibility Complex Molecules," *Annu. Rev. Biochem.* 59:253–288 (1980).

Calandro, L.M. et al., "Characterization of a recombinant that locates the hereditary hemochromatosis gene telomeric to HLA–F," *Hum. Genet.* 96:339–342 (1995).

Capecchi, M.R. et al., "Altering the Genome by Homologous Recombination," *Science* 244:1288–1292 (1989).

Cartwright, G.E. et al., "Inheritance of Hemochromatosis: Linkage to HLA," *Trans. Assoc. Am. Phys.* 91:273–281 (1978).

Chen, X. et al., "Template–directed dye–terminator incorporation (TDI) assay: a homogeneous DNA diagnostic method based on fluorescence resonance energy transfer," *Nucl. Acids Res.* 25(2):347–353 (1997).

Cotton, R.G.H. et al., "Reactivity of cytosine and thymine in single–base–pair mismatches with hydroxylamine and osmium tetroxide and its application to the study of mutations," *Proc. Natl. Acad. Sci. U.S.A.* 85:4397–4401 (1988).

Crawford, D.H.G. et al., "Evidence that the Ancestral Haplotype in Australian Hemochromatosis Patients May be Associated with a Common Mutation in the Gene," *Am. J. Hum. Genet.* 57:362–367 (1995).

Crystal, R.G. et al., "Gene Therapy Strategies for Pulmonary Disease," *Am. J. Med.* 92(6A):6A–44S–6A–51S (1992).

Dugast, I.J. et al., Identification of Two Human Ferritin H Genes on the Short Arm of Chromosome 6,*Genomics* 6:204–211 (1990).

Edwards, C.Q. et al., "The locus for hereditary homochromatosis maps between HLA–A and HLA–B," *Cytogenet. Cell Genet.* 40:620 (1985).

Edwards, C.Q. et al., "Screening for Hemochromatosis," *New Engl. J. Med.* 328(22):1616–1619 (1993).

El Kahloun, A. et al., "Localization of seven new genes around the HLA–A locus," *Hum Molec. Genet.* 2(1):55–60 (1992).

Fahy, E. et al., "Self–sustained Sequence Replication (3SR): An Isothermal Transcription–based amplification System Alternative to PCR," *PCR Methods and Applications* 1:25–33 (1991).

Feder J.N. et al., "A novel MHC class I–like gene is mutated in patients with hereditary haemochromatosis," *Nature Genet.* 13:399–408 (1996).

Finch, C.A., "Hemochromatosis—Treatment is Easy, Diagnosis Hard," *Western J. Med.* 153:323–325 (1990).

Fischer, S.G. et al., "DNA fragments differing by single base–pair substitutions are separated in denaturing gradient gels: Correspondence with melting theory," *Proc. Natl. Acad. Sci. U.S.A.* 80:1579–1583 (1983).

Friedmann, T., "Progress Toward Human Gene Therapy," *Science* 244:1275–1281 (1989).

Fullan, A. et al., "A polymorphic dinucleotide repeat at the human HLA–F locus," *Hum. Mol. Genet.* 3(12):2266.

Gasparini, P. et al., "Linkage analysis of 6p21 polymorphic markers and the hereditary hemochromatosis: locatization of the gene centromeric to HLA–F," *Hum Molec. Genet.* 2(5):571–576 (1993).

Gasparini, P. et al., "Where does the gene for hemochromatosis lie in relation to HLA–A," *Hepatology* 19:1050–1056 (1994).

Gnirke, A. et al., "Physical Calibration of Yeast Artificial Chromosome Contig Maps by RecA–Assisted Restriction Endonuclease (RARE) Cleavage," *Genomics* 24:199–210 (1994).

Goei, V.L. et al., "Isolation of Novel Non–HLA Gene Fragments from the Hemochromatosis Region (6p21.3) by cDNA Hybridization Selection," *Am. J. Hum. Genet.* 54:244–251 (1994).

Gruen, J.R. et al., "Physical and Genetic Mapping of the Telomeric Major Histocompatibility Complex Region in Man and Relevance to the Primary Hemochromatosis," *Genomics* 14:232–240 (1992).

Gyapay, G. et al., "The 1993–1994 Genethon human genetic linkage map," *Nature Genetics* 7:246–339 (1994).

Jakobovits, A. et al., "Production of Antigen–Specific Human Antibodies from Mice Engineered with Human Heavy and Light Chain YACs$^{a}$", *Ann. N.Y. Acad. Sci.* 764:525–535 (1995).

Jazwinska, E.C. et al., "Localization of the Hemochromatosis Gene Close to D6S105," *Am. J. Hum. Genet.* 53:347–352 (1993).

Jazwinska, E.C. et al., "Haplotype Analysis in Australian Hemochromatosis Patients: Evidence for a Predominant Ancestral Haplotype Exclusively Associated with Hemochromatosis," *Am. J. Hum. Genet.* 56:428–433 (1995).

Jazwinska, E.C. et al., "Hemochromatosis and 'HLA–H': Definite!", *Hepatology*, 25(2):495–496 (1997).

Jouet, M.M.H. et al., "Isolation of YAC clones containing class I HLA genes which map in the vicinity of the hereditary haemochromatosis gene," *J. Med. Genet.* 28(8):572 (1991).

Kan, Y.W. et al., "Antenatal Diagnosis of Sickle–Cell Anæmia by D.N.A. Analysis of Amniotic–Fluid Cells," *Lancet* ii:910–911 (1978).

Koller, B.H. et al., "Normal Development of Mice Deficient in $\beta_2$M, MHC Class I Proteins, and CD8$^+$ T Cells," *Science* 248:1227–1230 (1990).

Kramer, M.F and Coen, D.M. in *Current Protocols in Molecular Biology*, Ausubel, F.M. et al., eds., Wiley, Chapter 15 (1994).

Landegren, U. et al., "A Ligase–Mediated Gene Detection Technique," *Science* 241:1077–1080 (1988).

Lemarchand, P. et al., "Adenovirus–mediated transfer of a recombinant human $\alpha_1$–antitrypsin cDNA to human endothelial cells," *Proc. Natl. Acad. Sci. U.S.A.* 89:6482–6486 (1992).

Lin, A.Y. et al., "Expression of T Cell Antigen Receptor Heterodimers in a Lipid–Linked Form," *Science* 249:677–679 (1990).

Lipinski, M. et al., "Idiopathic Hemochromatosis: Linkage with HLA," *Tissue Antigens* 11:471–474 (1978).

Maskos, U. et al., "A novel method for the parallel analysis of multiple mutations in multiple samples," *Nucl. Acids Res.* 21(9):2269–2270 (1993).

Miyazaki, J. et al., "Intracellular transport blockage caused by disruption of the disulfide bridge in the third external domain of major histocompatibility complex class I antigen," *Proc. Natl. Acad. Sci. U.S.A.* 83:757–761 (1986).

Morgan, J.G. et al., "The selective isolation of novel cDNAs encoded by the regions surrounding the human interleukin 4 and 5 genes," *Nucl. Acids Res.* 20(19):5173–5179 (1992).

Mulford, C.A. et al., "Endocytosis of the Transferrin Receptor Is Altered During Differentiation of Murine Erythroleukemic Cells," *J. Biol. Chem.* 263(11):5455–5461 (1988).

Murray, J.C. et al., "A Comprehensive Human Linkage Map with Centimorgan Density," *Science* 265:2049–2054 (1994).

Myers, R.M. et al., "Detection of Single Base Substitutions by Ribonuclease Cleavage at Mismatches in RNA:DNA Duplexes," *Science* 230:1242–1246 (1985).

Newton, C.R. et al., "Analysis of any point mutation in DNA. The amplification refractory mutation system (ARMS)," *Nucl. Acids Res.* 17(7):2503–2516 (1989).

Nickerson, D.A. et al., "Automated DNA diagnostics using an ELISA–based oligonucleotide ligation assay," *Proc. Natl. Acad. Sci. U.S.A.* 87:8923–8927 (1990).

Nickerson et al., in *Current Protocols in Human Genetics*, Ausubel, F.M. et al., eds., Wiley, Chapter 2.6 (1994).

Nikiforov, T.T. et al., "Genetic Bit Analysis: a solid phase method for typing single nucleotide polymorphisms," *Nucl. Acids Res.* 22(20):4167–4175 (1994).

Olynyk, J.K. et al., "Hepatic Iron Concentration as a Predictor of Response to Interferon Alfa Therapy in Chronic Hepatitis C," *Gastroenterology* 108:1104–1109 (1995).

Orphanos, V. et al., "Thirteen dinucleotide repeat polymorphism on chromosome 6," *Hum. Mol. Genet.* 2(12):2196 (1993).

Phatak, P.D. et al., "Cost–effectiveness of Screening for Hereditary Hemochromatosis," *Arch. Intern. Med.* 154:769–776 (1994).

Raha–Chowdhury, R. et al., "New polymorphic microsatellite markers place the haemochromatosis gene telomeric to D6S105," *Hum. Mol. Genet.* 4(10):1869–1874 (1995).

Raha–Chowdhury, R. et al., "Allelic associations and homozygosity at loci from HLA–B to D6S299 in genetic haemochromatosis," *J. Med. Genet.* 32:446–452 (1995).

Roberts, A.G. et al., "Increased frequency of the haemochromatosis Cys282Tyr mutation in sporadic porphyria cutanea tarda," *Lancet* 349:321–323 (1997).

Roth, M.P. et al., "The Human Myelin Oligodendrocyte Glycoprotein (MOG) Gene: Complete Nucleotide Sequence and Structural Characterization," *Genomics* 28:241–250 (1995).

Rothenberg, B.E. et al., "The molecular mechanisms of iron overload: an animal model for hemochromatosis," *FASEB J.* 8. Abstract No. 5217, p. A900 (1994).

Saiki, R.K. et al., "Primer–Directed Enzymatic Amplification of DNA with a Thermostable DNA Polymerase," *Science* 239:487–491 (1988).

Saiki, R.K. et al., "Genetic analysis of amplified DNA with immobilized sequence–specific oligonucleotide probes," *Proc. Natl. Acad. Sci. U.S.A.* 86:6230–6234.

Salter, R.D., "Intracellular transport of class I HLA molecules is affected by polymorphic residues in the binding groove," *Immunogenetics* 39:266–271 (1994).

Schild, H. et al., "The Nature of Major Histocompatiblity Complex Recognition by $\gamma\delta$ T Cells," *Cell* 76:29–37 (1994).

Simon M. et al., "Association of HLA–A3 and HLA–B14 antigens with idiopathic Hæmochromotasis," *Gut* 17:332–334 (1976).

Simon, M. et al., "A Study of 609 HLA Haplotypes Marking for the Hemochromatosis Gene: (1) Mapping of the Gene near the HLA–A Locus and Characters Required to Define a Heterozygous Population and (2) Hypothesis Concerning the Underlying Cause of Hemochromatosis–HLA Association," *Am. J. Hum. Genet.* 41:89–105 (1987).

Stone, C. et al., "Isolation of CA dinucleotide repeats close to D6S105; linkage disequilibrium with haemochromatosis," *Hum. Molec.Genet.* 3(11):2043–2046 (1994).

Summers, K.M. et al., "Fine mapping of a human chromosome 6 ferritin heavy chain pseudogene: relevance to haemochromatosis," *Hum Genet.* 88:175–178 (1991).

Syvänen, A.C. et al., "A Primer–Guided Nucleotide Incorportion assay in the Genotyping of Apolipoprotein E," *Genomics* 8:684–692 (1990).

Thiede, C. et al., "Simple and sensitive detection of mutations in the ras proto–oncogenes using PNA–mediated PCR clamping," *Nucl. Acids Res.* 24(5):983–984 (1996).

Totaro, A. et al., "New polymorphisms and markers in the HLA class I region: relevance to hereditary hemochromatosis (HFE)," *Hum. Genet.* 95:429–434 (1995).

Totaro, A. et al., "Hereditary Hemochromatosis: Generation of a Transctiption Map within a Refined and Extended Map of the HLA Class I Region," *Genomics* 31:319–326 (1996).

Wagner, R. et al., "Mutation detection using immobilized mismatch binding protein (MutS)," *Nucl. Acids Res.* 23(19):3944–3948 (1995).

Wallace, R.B. et al., "Hybridization of synthetic oligodeoxyribonucleotides to $\Phi\chi 174$ DNA: the effect of single base pair mismatch," *Nucl. Acids Res.* 6:3543–3557 (1978).

Weber, J.L. et al., "Dinucleotide repeat polymorphism at the D6S105 locus," *Nucl. Acids Res.* 19(4):968 (1991).

Wettstein, D.A. et al., "Expression of a Class II Major Histocompatibility Complex (MHC) Heterodimer in a Lipid–linked Form with Enhanced Peptide/Soluble MHC Complex Formation at Low pH," *J. Exp. Med.* 174:219–228 (1991).

Worwood, M. et al., "Alleles at D6S265 and D6S105 define a haemochromatosis–specific genotype," *Brit. J. Hematol.* 86:863–866 (1994).

Wu, D.Y. et al., "The Ligation Amplification Reaction (LAR)–Amplification of Specific DNA Sequences Using Sequential Rounds of Template–Dependent Ligation," *Genomics* 4:560–569 (1989).

Youil, R. et al., "Screening for mutations by enzyme mismatch cleavage with T4 endonuclease VII," *Proc. Natl. Acad. Sci. U.S.A.* 92:87–91 (1995).

Zijlstra, M. et al., "β2–Microglobulin deficient mice lack CD4–8+ cytolytic T cells," *Nature* 344:742–746 (1990).

Zinkernagel, R.M. et al., "MHC–Restricted Cytotoxic T Cells: Studies on the Biological Role of Polymorphic Major Transplantation Antigens determining T–Cell Restriction–Specificity, Function, and Responsiveness," *Adv. Immunol.* 27:51–177 (1979).

*ATCC/NIH Repository Catalogue of Human and Mouse DNA Probes and Libraries*, Nierman, W.C. and Maglott, D.R., eds., (1994).

| PATIENTS | 241-4 | 65-2 | 65-1 | 241-6 | 241-29 | 24d1 | 241-5 | 63-3 | 63-1 | 63-2 | 373-8 |
|---|---|---|---|---|---|---|---|---|---|---|---|
| HC2 | 144 | 161 | 208 | 193 | 117 | A | 108 | 169 | 151 | 113 | 151 |
|  | 144 | 159 | 206 | 205 | 113 | A | 108 | 169 | 151 | 113 | 151 |
| HC22 | 144 | 159 | 206 | 205 | 113 | A | 108 | 169 | 151 | 113 | 151 |
|  | 144 | 161 | 208 | 193 | 117 | A | 108 | 169 | 151 | 113 | 151 |
| HC25 | 144 | 167 | 210 | 205 | 113 | A | 108 | 169 | 151 | 113 | 159 |
|  | 144 | 159 | 206 | 205 | 113 | A | 108 | 169 | 151 | 113 | 151 |
| HC29 | 144 | 159 | 206 | 205 | 113 | A | 108 | 169 | 135 | 133 | 155 |
|  | 144 | 159 | 208 | 205 | 113 | A | 108 | 169 | 151 | 113 | 151 |
| HC41 | 144 | 159 | 206 | 205 | 113 | A | 108 | 169 | 151 | 113 | 151 |
|  | 144 | 159 | 206 | 205 | 113 | A | 108 | 169 | 151 | 113 | 151 |
| HC50 | 144 | 161 | 210 | 193 | 119 | A | 108 | 169 | 151 | 113 | 151 |
|  | 144 | 159 | 206 | 205 | 113 | A | 108 | 169 | 151 | 113 | 151 |
| HC75 | 144 | 159 | 206 | 205 | 113 | A | 108 | 167 | 139 | 131 | 153 |
|  | 144 | 159 | 206 | 205 | 113 | A | 108 | 169 | 151 | 113 | 149 |
| HC87 | 144 | 161 | 208 | 193 | 117 | A | 108 | 169 | 151 | 113 | 147 |
|  | 144 | 159 | 206 | 205 | 113 | A | 108 | 169 | 151 | 113 | 151 |
| HC91 | 144 | 159 | 208 | 193 | 117 | A | 108 | 169 | 151 | 113 | 155 |
|  | 144 | 159 | 206 | 205 | 113 | A | 108 | 169 | 151 | 113 | 149 |
| HC125 | 146 | 161 | 210 | 205 | 115 | A | 108 | 169 | 151 | 113 | 153 |
|  | 144 | 159 | 206 | 205 | 113 | A | 108 | 169 | 151 | 113 | 151 |
| HC143 | 146 | 161 | 210 | 193 | 117 | A | 108 | 169 | 151 | 113 | 151 |
|  | 146 | 159 | 206 | 205 | 113 | A | 108 | 169 | 151 | 113 | 151 |

MARKERS

FIG.2

```
-360  tctaaggttg  agataaaatt  tttaaatgta  tgattgaatt  ttgaaaatca
-310  taaatattta  aatatctaaa  gttcagatca  gaacattgcg  aagctacttt
-260  cccaatcaa   caacacccct  tcaggattta  aaaaccaagg  gggacactgg
-210  atcacctagt  gtttcacaag  caggtacctt  ctgctgtagg  agagagagaa
-160  ctaaagttct  gaaagacctg  ttgcttttca  ccaggaagtt  ttactgggca -110  tctcctgagc  ctaggcaata  gctgtagggt  gacttctgga  gccatccccg
 -60  ttttcccgcc  cccaaaaga   agcggagatt  taacggggac  gtgcggccag
 -10  agctggggaa
   1  ATGGGCCCGC  GAGCCAGGCC  GGCGCTTCTC  CTCCTGATGC  TTTTGCAGAC
  51  CGCGGTCCTG  CAGGGGCGCT  TGCTGCgtga  gtccgagggc  tgcgggcgaa 101  ctagggcgc   ggcggggtg   gaaaaatcga  aactagcttt  ttctttgcgc
 151  ttgggctcc   gctaactttg  gaggacctgc  tcaaccctat  ccgcaagccc
 201  ctctccctac  tttctgcgtc  cagacccgt   gagggagtgc  ctaccactga
 251  actgcagata  ggggtccctc  gccccaggac  ctgccccctc  ccccggctgt
 301  cccggctctg  cggagtgact  tttggaaccg  cccactccct  tcccccaact 351  agaatgcttt  taaataaatc  tcgtagttcc  tcacttgagc  tgagctaagc
 401  ctgggctcc   ttgaacctgg  aactcgggtt  tatttccaat  gtcagctgtg
 451  cagttttttc  cccagtcatc  tccaaacagg  aagttcttcc  ctgagtgctt
 501  gccgagaagg  ctgagcaagg  ccacagcagg  atccgcacgg  ggtttccacc
 551  tcagaacgaa  tgcgttgggc  ggtggggcg   cgaaagagtg  gcgttgggga
```

FIG. 3A

```
 601 tctgaattct tcaccattcc acccactttt ggtgagacct ggggtggagg
 651 tctctagggt gggaggctcc tgagagaggc ctacctcggg cctttcccca
 701 ctcttggcaa ttgttctttt gcctggaaaa ttaagtatat gttagttttg
 751 aacgtttgaa ctgaacaatt ctcttttcgg ctaggcttta ttgatttgca
 801 atgtgctgtg taattaagag gcctctctac aaagtactga taatgaacat 851 gtaagcaatg cactcacttc taagttacat tcatatctga tcttatttga
 901 ttttcactag gcataggggag gtaggagcta ataatacgtt tattttacta
 951 gaagttaact ggaattcaga ttatataact cttttcaggt tacaaagaac
1001 ataaataatc tggttttctg atgttatttc aagtactaca gctgcttcta
1051 atcttagttg acagtgattt tgccctgtag tgtagcacag tgttctgtgg 1101 gtcacacgcc ggcctcagca cagcactttg agttttggta ctacgtgtat
1151 ccacatttta cacatgacaa gaatgaggca tggcacggcc tgcttcctgg
1201 caaatttatt caatggtaca ctgggctttg gtggcagagc tcatgtctcc
1251 acttcatagc tatgattctt aaacatcaca ctgcattaga ggttgaataa
1301 taaaattcca tgttgagcag aaatattcat tgtttacaag tgtaaatgag 1351 tcccagccat gtgttgcact gttcaagccc caaggagag agcagggaaa
1401 caagtcttta ccctttgata ttttgcattc tagtgggaga gatgacaata
1451 agcaaatgag cagaaagata tacaacatca ggaaatcatg ggtgttgtga
1501 gaagcagaga agtcaggca agtcactctg gggctgacac ttgagcagag
1551 acatgaagga aataagaatg atattgactg atattttacag ttcccaggca
```

FIG. 3B

```
1601  aactgagtgg  gctgtgcaag  ttggattaaa  aagcgggttt  tctcagcact
1651  actcatgtgt  gtgtgtgtgg  ggggggggg   cggcgtgggg  gtgggaaggg
1701  ggactaccat  ctgcatgtag  gatgtctagc  cgcgcctgta  cctccctact
1751  cactaggtgc  taggagcact  cccccagtct  agtatcctgt  aaatgtctct
1801  aaactttgcc  acatgtcacc  tagtagacaa  tgacaaccaa  aagaagctcg 1851  ggttgaaaaa  aataaacaag  tagtgctggg  gagtagaggc  caagaagtag
1901  gtaatgggct  cagaagagga  gccacaaaca  aggttgtgca  ggcgcctgta
1951  ggctgtggtg  tgaattctag  ccaaggagta  acagtgatct  gtcacaggct
2001  tttaaaagat  tgctctggct  gctatgtgga  aagcagaatg  aagggagcaa
2051  cagtaaaagc  agggagccca  gccaggaagc  tgttacacag  tccaggcaag 2101  aggtagtgga  gtgggctggg  tgggaacaga  aaagggagtg  acaaaccatt
2151  gtctcctgaa  tatattctga  aggaagttgc  tgaaggattc  tatgttgtgt
2201  gagagaaaga  gaagaattgg  ctgggtgtag  tagctcatgc  caaggaggag
2251  gccaaggaga  gcagattcct  gagctcagga  gttcaagacc  agcctgggca
2301  acacagcaaa  acccctctc   tacaaaaaat  acaaaaatta  gctgggtgtg 2351  gtggcatgca  cctgtgatcc  tagctactcg  ggaggctgag  gtggagggta
2401  ttgcttgagc  ccaggaagtt  gaggctgcag  tgagccatga  ctgtgccact
2451  gtacttcagc  ctaggtgaca  gagcaagacc  ctgtctcccc  tgacccctg
2501  aaaagagaa   gagttaaagt  tgactttgtt  ctttatttta  atttattgg
2551  cctgagcagt  ggggtaattg  gcaatgccat  ttctgagatg  gtgaaggcag
```

FIG.3C

```
2601  aggaaagagc  agtttggggt  aaatcaagga  tctgcatttg  ggacatgtta
2651  agtttgagat  tccagtcagg  cttccaagtg  gtgaggccac  ataggcagtt
2701  cagtgtaaga  attcaggacc  aaggctgggc  acggctggctc  acttctgtaa
2751  tcccagcact  ttggtggctg  agcaggtag   atcatttgag  gtcaggagtt
2801  tgagacaagc  ttggccaaca  tggtgaaacc  ccatgtctac  taaaaataca 2851  aaaattagcc  tggtgtggtg  gcgcacgcct  atagtcccag  gttttcagga
2901  ggcttaggta  ggagaatccc  ttgaacccag  gaggtgcagg  ttgcagtgag
2951  ctgagattgt  gccactgcac  tccagcctgg  gtgatagagt  gagactctgt
3001  ctcaaaaaaa  aaaaaaaaa   aaaaaaaaa   aactgaagga  attattcctc
3051  aggatttggg  tctaatttgc  cctgagcacc  aactcctgag  ttcaactacc 3101  atggctagac  acaccttaac  atttctaga   atccaccagc  tttagtggag
3151  tctgtctaat  catgagtatt  ggaataggat  ctgggggcag  tgaggggtg
3201  gcagccacgt  gtggcagaga  aaagcacaca  aggaaagagc  accaggact
3251  gtcatatgga  agaagacag   gactgcaact  cacccttcac  aaaatgagga
3301  ccagacacag  ctgatggtat  gagttgatgc  aggtgtgtgg  agcctcaaca 3351  tcctgctccc  ctcctactac  acatggttaa  ggcctgttgc  tctgtctcca
3401  gGTTCACACT  CTCTGCACTA  CCTCTTCATG  GGTGCCTCAG  AGCAGGACCT
3451  TGGTCTTTCC  TTGTTTGAAG  CTTTGGGCTA  CGTGGATGAC  CAGCTGTTCG
              G           T 3501  TGTTCTATGA  TCATGAGAGT  CGCCGTGTGG  AGCCCGAAC   TCCATGGGTT
3551  TCCAGTAGAA  TTTCAAGCCA  GATGTGGCTG  CAGCTGAGTC  AGAGTCTGAA
```

FIG. 3D

```
3601  AGGGTGGGAT CACATGTTCA CTGTTGACTT CTGGACTATT ATGGAAAATC
3651  ACAACCACAG CAAGGtatg  tggagagggg gcctcacctt cctgaggttg
3701             tcagagcttt tcatctttc  atgcatcttg aggaaacag  ctggaagtct
3751             gaggtcttgt gggagcagg  aagaggaag  gaatttgctt cctgagatca
3801             tttggtcctt ggggatggtg gaaataggga cctattcctt tggttgcagt 3851             taacaaggct ggggattttt ccagAGTCCC ACACCCTGCA GGTCATCCTG
3901  GCTGTGAAA  TGCAAGAAGA CAACAGTACC GAGGGCTACT GGAAGTACGG
3951  GTATGATGGG CAGGACCACC TTGAATTCTG CCCTGACACA CTGGATTGGA
4001  GAGCAGCAGA ACCCAGGCC  TGGCCCACCA AGCTGGAGTG GGAAAGGCAC
4051  AAGATTCGGG CCAGGCAGA  CAGGCCCTAC CTGGAGAGGG ACTGCCCTGC 4101  ACAGCTGCAG CAGTTGCTGG AGCTGGGGAG AGGTGTTTTG GACCAACAAG
4151             gtatggtgga aacacacttc  tgccctata  ctctagtggc agagtggagg
4201             aggttgcagg gcacgaatc  cctggttgga gtttcagagg tggctgaggc
4251             tgtgtgcctc tccaaattct gggaagggac tttctcaatc ctagagtctc
4301             taccttataa ttgagatgta tgagacagcc acaagtcatg ggtttaattt 4351             cttttctcca tgcatatggc tcaaaggaa  gtgtctatgg cccttgcttt
4401             ttatttaacc aataatcttt tgtatattta tacctgttaa aaattcagaa
4451             atgtcaaggc cgggcacggt ggctcacccc tgtaatccca gcactttggg
4501             aggccgaggc gggtggtcac aaggtcagga gtttgagacc agcctgacca
4551             acatggtgaa accccgtctct aaaaaaatac aaaaaattagc tggtcacagt
```

FIG. 3E

```
4601  catgcgcacc  tgtagtccca  gctaattgga  aggctgaggc  aggagcatcg
4651  cttgaacctg  ggaagcggaa  gttgcactga  gccaagatcg  cgccactgca
4701  ctccagccta  ggcagcagag  tgagactcca  tcttaaaaaa  aaaaaaaaaa
4751  aaaaaaagag  aattcagaga  tctcagctat  catatgaata  ccaggacaaa
4801  atatcaagtg  aggccactta  tcagagtaga  agaatccttt  aggttaaaag 4851  tttctttcat  agaacatagc  aataatcact  gaagctacct  atcttacaag
4901  tccgcttctt  ataacaatgc  ctcctaggtt  gacccaggtg  aaactgacca
4951  tctgtattca  atcattttca  atgcacataa  agggcaattt  tatctatcag
5001  aacaaagaac  atgggtaaca  gatatgtata  tttacatgtg  aggagaacaa
5051  gctgatctga  ctgctctcca  agtgacactg  tgttagagtc  caatcttagg 5101  acacaaaatg  gtgtctctcc  tgtagcttgt  ttttttctga  aaagggtatt
5151  tccttcctcc  aacctataga  aggaagtgaa  agtccagtc   ttcctgcaa
5201  gggtaaacag  atccccctc   ctcatccttc  ctctttcctg  tcaagTGCCT
5251  CCTTTGGTGA  AGGTGACACA  TCATGTGACC  TCTTTCAGTGA CCACTCTACG
5301  GTGTCGGGCC  TTGAACTACT  ACCCCAGAA   CATCACCATG  AAGTGGCTGA
                                     A
5351  AGGATAAGCA  GCCAATGGAT  GCCAAGGAGT  TCGAACCTAA  AGACGTATTG
5401  CCCAATGGGG  ATGGGACCTA  CCAGGGCTGG  ATAACCTTGG  CTGTACCCCC 5451  TGGGAAAGAG  CAGAGATATA  CGTGCCAGGT  GGAGCACCCA  GGCCTGGATC
5501  AGCCCCTCAT  TGTGATCTGG  Ggtatgtgac  tgatgagagc  caggagctga
5551  gaaaatctat  tggggttga   gaggagtgcc  tgaggaggta  attatggcag
```

FIG.3F

```
5601  tgagatgagg  atctgctctt  tgttaggggg  tgggctgagg  gtggcaatca
5651  aaggctttaa  cttgctttt   ctgttttttagA GCCCTCACCG  TCTGGCACCC
5701  TAGTCATTGG  AGTCATCAGT  GGAATTGCTG  TTTTGTCGT   CATCTTGTTC
5751  ATTGGAATTT  TGTTCATAAT  ATTAAGGAAG  AGGCAGGGTT  CAAgtgagta
5801  ggaacaaggg  ggaagtctct  tagtacctct  gccccagggc  acagtgggaa 5851  gaggggcaga  ggggatctgg  catccatgag  aagcatttt   ctcatttata
5901  ttctttgggg  acaccagcag  ctccctggga  gacagaaaat  aatggttctc
5951  cccagaatga  aagtctctaa  ttcaacaaac  atcttcagag  cacctactat
6001  tttgcaagag  ctgttttaagg tagtacaggg  gctttgaggt  tgagaagtca
6051  ctgtggctat  tctcagaacc  caaatctggt  agggaatgaa  attgatagca 6101  agtaaatgta  gttaaagaag  acccccatgag gtcctaaagc  aggcaggaag
6151  caaatgctta  gggtgtcaaa  ggaaagaatg  atcacattca  gctggggatc
6201  aagatagcct  tctggatctt  gaaggagaag  ctggattcca  ttaggtgagg
6251  ttgaagatga  tgggaggtct  acacacaggg  agcaaccatg  ccaagtagga
6301  gagtataagg  catactggga  gattagaaat  aattactgta  ccttaaccct 6351  gagtttgcgt  agctatcact  caccaattat  gcatttctac  cccctgaaca
6401  tctgtgtgt   agggaaaaga  gaatcagaaa  gaagccagct  catacagagt
6451  ccaagggtct  tttgggatat  tgggttatga  tcactgggt   gtcattgaag
6501  gatcctaaga  aaggaggacc  acgatctccc  ttatatggtg  aatgtgttgt
6551  taagaagtta  gatgagaggt  gaggagacca  gaggagagca  caataagcat
```

FIG. 3G

```
6601 ttccagatga gagataatgg ttcttgaaat ccaggtctaa
6651 attgagatgg gtgaatgagg aaaataagga ggcaagatgg
6701 tgcctaggtt tgtgatgcct cttcctggg  tctcttgtct ccacagGAGG
6751 AGCCATGGGG CACTACGTCT TAGCTGAACG TGAGTGAcac gcagcctgca
6801 gactcactgt gggaaggaga caaaactaga gactcaaaga gggagtgcat 6851 ttatgagctc ttcatgtttc aggagagagt tgaacctaaa catagaaatt
6901 gcctgacgaa ctccttgatt ttagccttct ctgttcattt cctcaaaaag
6951 atttcccat  ttaggtttct gagttcctgc atgccggtga tccctagctg
7001 tgacctctcc cctgaactg  tctctcatga acctcaagct gcatctagag
7051 gcttccttca tttcctccgt caccctcagag acatacacct atgtcatttc 7101 atttcctatt tttggaagag gactccttaa atttggggga cttacatgat
7151 tcattttaac atctgagaaa agctttgaac cctggacgt  ggctagtcat
7201 aaccttacca gattttaca  catgtatcta tgcattttct ggacccgttc
7251 aacttttcct ttgaatcctc tctctgtgtt accagtaac  tcatctgtca
7301 ccaagccttg gggattcttc catctgattg tgatgtgagt tgcacagcta 7351 tgaaggctgt acactgcacg aatgaagag  gcacctgtcc cagaaaaagc
7401 atcatggcta tctgtgggta gtatgatggg tgttttagc  aggtaggagg
7451 caaatatctt gaaggggtt  gtgaagaggt gttttttcta attggcatga
7501 aggtgtcata cagatttgca aagtttaatg gtgccttcat ttgggatgct
7551 acctctagtat tccagaccta ataatttct  acctggtctc
```

FIG. 3H

```
7601  tccttgttct  gataatgaaa  attatgataa  ggatgataaa  agcacttact
7651  tcgtgtccga  ctcttctgag  cacctactta  catgcattac  tgcatgcact
7701  tcttacaata  attctatgag  atagtacta   ttatcccat   ttctttttta
7751  aatgaagaaa  gtgaagtagg  ccgggcacgg  tggctcacgc  ctgtaatccc
7801  agcactttgg  gaggccaaag  cgggtggatc  acgaggtcag  gagatcgaga 7851  ccatcctggc  taacatggtg  aaacccatc   tctaataaaa  atacaaaaaa
7901  ttagctgggc  gtggtggcag  acgcctgtag  tcccagctac  tcggaaggct
7951  gaggcaggag  aatggcatga  acccaggagg  cagagcttgc  agtgagccga
8001  gtttgcgcca  ctgcactcca  gcctaggtga  cagagtgaga  ctccatctca
8051  aaaaaataaa  aataaaaata  aaaaaatgaa  aaaaaaaaga  aagtgaagta 8101  tagagtatct  catagtttgt  cagtgataga  aacaggtttc  aaactcagtc
8151  aatctgaccg  tttgatacat  ctcagacacc  actacattca  gtagtttaga
8201  tgcctagaat  aaatagagaa  ggaaggagat  ggctcttctc  ttgtctcatt
8251  gtgtttcttc  tgagtgagct  tgaatcacat  gaaggggaac  agcagaaaac
8301  aaccaactga  tcctcagctg  tcatgtttcc  tttaaaagtc  cctgaaggaa 8351  ggtcctggaa  tgtgactccc  ttgctccct   gttgctctct  ttggcattca
8401  tttcttttga  ccctacgcaa  ggactgtaat  tggtggggac  agctagtggc
8451  cctgctgggc  ttcacacacg  gtgtcctccc  taggccagtg  cctctggagt
8501  cagaactctg  gtggtattc   cctcaatgaa  gtggagtaag  ctctctcatt
8551  ttgagatggt  ataatgaag   ccaccaagtg  gcttagagga  tgcccaggtc
```

FIG.3I

```
8601  cttcctgga  gccactgggg  ttccgtgca  cattaaaaaa  aaaatctaac
8651  caggacattc  aggaattgct  agattctggg  aaatcagttc  accatgttca
8701  aaagagtctt  tttttttttt  ttgagactct  attgcccagg  ctggagtgca
8751  atggcatgat  ctcggctcac  tgtaacctct  gcctcccagg  ttcaagcgat
8801  tctcctgtct  cagcctccca  agtagctggg  attacaggcg  tgcaccacca 8851  tgcccggcta  atttttgtat  ttttagtaga  gacagggttt  caccatgttg
8901  gccaggctgg  tctcgaactc  tcctgacctc  gtgatccgcc  tgcctcggcc
8951  tcccaaagtg  ctgagattac  aggtgtgagc  cacCCtgccc  agccgtcaaa
9001  agagtcttaa  tatatatatc  cagatggcat  gtgtttactt  tatgttacta
9051  catgcacttg  gctgcataaa  tgtggtacaa  gcattctgtc  ttgaagggca 9101  ggtgcttcag  gataccatat  acagctcaga  agtttcttct  ttaggcatta
9151  aattttagca  aagatatctc  atctcttctt  ttaaaccatt  ttctttttt
9201  gtggttagaa  aagttatgta  gaaaaagta  aatgtgattt  acgctcattg
9251  tagaaaagct  ataaaatgaa  tacaattaaa  gctgttattt  aattagccag
9301  tgaaaaacta  ttaacaactt  gtctattacc  tgttagtatt  attgttgcat 9351  taaaaatgca  tatactttaa  taaatgtata  ttgtattgta  tactgcatga
9401  ttttattgaa  gttcctgttc  atcttgtgta  tatacttaat  cgctttgtca
9451  ttttggagac  attattttg  cttctaattt  ctttacattt  tgtcttacgg
9501  aatattttca  ttcaactgtg  gtagccgaat  taatcgtgtt  tcttcactct
9551  agggacattg  tcgtctaagt  tgtaagacat  tggttatttt  accagcaaac
```

FIG. 3J

```
9601  cattctgaaa  gcatatgaca  aattattct   ctcttaatat  cttactatac
9651  tgaaagcaga  ctgctataag  gcttcactta  ctcttctacc  tcataaggaa
9701  tatgttacaa  ttaatttatt  agtaagcat   ttgttttata  ttgtttttat
9751  ttcacctggg  ctgagatttc  aagaaacacc  ccagtcttca  cagtaacaca
9801  tttcactaac  acatttacta  aacatcagca  actgtggcct  gttaatttt 9851  ttaatagaaa  ttttaagtcc  tcatttctt   tcggtgtttt  ttaagcttaa
9901  tttttctggc  ttattcata   aattcttaag  gtcaactaca  tttgaaaaat
9951  caaagacctg  catttaaat   tcttattcac  ctctgcaaa   accattcaca
10001 aaccatggta  gtaaagagaa  gggtgacacc  tggtggccat  agtaaatgt
10051 accacggtgg  tccggtgacc  agagatgcag  cgctgagggt  tttcctgaag 10101 gtaaaggaat  aaagaatggg  tgagggggcg  tgcactggaa  atcacttgta
10151 gagaaaagcc  cctgaaaatt  tgagaaaaca  aacaagaaac  tacttaccag
10201 ctatttgaat  tgctggaatc  acaggccatt  gctgagctgc  ctgaactggg
10251 aacacacaag  aaggaaaaca  aaccactctg  ataatcattg  agtcaagtac
10301 agcaggtgat  tgaggactgc  tgagaggtac  aggccaaaat  tcttatgttg 10351 tattataata  atgtcatctt  ataatactgt  cagtatttta  taaacattc
10401 ttcacaaact  cacacacatt  taaaaacaa   acactgtctc  taaaatcccc
10451 aaatttttca  taaac
```

```
ggggacactg gatcacctag tgtttcacaa gcaggtacct tctgctgtag gagagagaga
actaagttc  tgaaagacct tgtgctttc  accaggaagt tttactgggc atctcctgag
cctaggcaat agctgtaggg tgacttctgg agccatcccg gtttcccgc  ccccaaaag
aagcggagat ttaacgggga cgtgcggcca gagctgggga a
```

```
                                           atgggcccg  cgagccaggc
                                            M  G  P    R  A  R cggcgcttct cctcctgatg cttttgcaga ccgcggtcct gcaggggcgc tgctgcgtt
 P  A  L  L  L  L  M  L  L  Q    T  A  V  L   Q  G  R    L  L  R cacactctct gcactactc  ttcatggtg  cctcagagca ggaccttgt  ctttccctgt
 S  H  S  L   H  Y  L   F  M  G   A  S  E  Q   D  L  G   L  S  L ttgaagcttt gggctacgtg gatgaccagc tgttcgtgtt ctatgatcat gagagtcgcc
 F  E  A  L   G  Y  V   D  D  Q   L  F  V  F   Y  D  H   E  S  R  C
                                              24d2 [G]         24d7 [T]
                                                              [D]   [C]

gtgtggagcc ccgaactcca tgggttttcca gtagaatttc aagccagatg tggctgcagc
 R  V  E  P   R  T  P   W  V  S    R  I  S     Q  M  W   L  Q tgagtcagag tctgaaaggg tggttttcca tgttcactgt tgacttctgt actattatgg
 L  S  Q  S   L  K  G   W  F  P   M  F  T  V   D  F  W   T  I  M
```

```
aaaatcacaa  ccacagcaag  gagtccaca   cctgcaggt   catcctgggc  tgtgaaatgc
 E  N  H  N  H  S  K    E  S  H     T  L  Q  V  I  L  G     C  E  M aagagacaa   cagtaccgag  ggctactgga  agtacgggta  tgatgggcag  gaccacctg
 Q  E  D  N  S  T  E    G  Y  W     K  Y  G  Y  D  G  Q     D  H  L aattctgccc  tgacacactg  gattggagag  cagcagaacc  cagggcctgg  cccaccaagc
 E  F  C  P  D  T  L    D  W  R     A  A  E  P  R  A  W     P  T  K tggagtggga  aaggcacaag  attcggccca  ggcagaacag  ggcctacctg  gagagggact
 L  E  W  E  R  H  K    I  R  A     R  Q  N  R  A  Y  L     E  R  D gccctgcaca  gctgcagcag  ttgctggagc  tggggagagg  tgtttggac   caacaagtgc
 C  P  A  Q  L  Q  Q    L  L  E     L  G  R  G  V  L  D     Q  Q  V ctcctttggt  gaaggtgaca  catcatgtga  cctctttcagt gaccactcta  cggtgtcggg
 P  P  L  V  K  V  T    H  H  V     T  S  S  V  T  T  L     R  C  R cctgaacta   ctaccccag   aacatcacca  tgaagtggct  gaaggataag  cagccaatgg
 A  L  N  Y  Y  P  Q    N  I  T     M  K  W  L  K  D  K     Q  P  M atgccaagga  gttcgaacct  aaagacgtat  tgcccaatgg  ggatgggacc  taccagggct
 D  A  K  E  F  E  P    K  D  V     L  P  N  G  D  G  T     Y  Q  G
```

FIG. 4B

```
ggataacctt ggctgtaccc cctggggaag agcagagata tacg cag gtggagcacc
 W  I  T  L  A  V  P  P  G  E  E  Q  R  Y  T 24d1
                                              C  Q  V  E  H
                                              Y caggcctgga tcagcccctc attgtgatct gggagccctc accgtcctgg acctagtca
 P  G  L  D  Q  P  L  I  V  I  W  E  P  S  P  S  G  T  L  V ttggagtcat cagtggaatt gctgttttg tcgtcatctt gttcattgga attttgttca
 I  G  V  I  S  G  I  A  V  F  V  V  I  L  F  I  G  I  L  F taatattaag gaagaggcag ggttcaagag gagccatggg gcactacgtc ttagctgaac
 I  I  L  R  K  R  Q  G  S  R  G  A  M  G  H  Y  V  L  A  E gtgagtga
 R  E  * ca cgcagcctgc agactcactg tgggaaggag acaaaactag agactcaaag
   agggagtgca tttatgagct cttcatgttt caggagagag ttgaacctaa acatagaaat
   tgcctgacga actcccttgat tttagccttc tctgttcatt tcctcaaaaa gatttcccca
```

FIG.4C

PCR Primers used for Amplification Of 24d1 Alleles

24d1.P1 (forward primer)
5'-TGGCAAGGGTAAACAGATCC-3'    (SEQ ID NO:13)

24d1.P2 (reverse primer)
5'-CTCAGGCACTCCTCTCAACC-3'    (SEQ ID NO:14)

OLA Oligonucleotides for 24d1

Upstream Oligonucleotides (5'-biotinylated)

24d1.A (common allele)
5'-bio-GGAAGAGCAGAGATATACGTG-3'
                                (SEQ ID NO:15)

24d1.B (hemochromatosis allele)
5'-bio-GGAAGAGCAGAGATATACGTA-3'
                                (SEQ ID NO:16)

Downstream Oligonucleotides (5'-phosphorylated)

24d1.X   5'-p-CCAGGTGGGAGCACCCAGG-dig-3'
                                (SEQ ID NO:17)

FIG. 5

5'-TATTCCTTCCTCCAACCTATAGAAGGAAGTGAAAGTTCCAGTCTTCCTGGCAAGGGTAAACAGATCCCC
TCTCCTCATCCTTCCTCTGTCAAGTGCCTCTCCTTGGTGAAGGTGACACATCATGTGACCTCTTCAG
TGACCACTCTACGGTGTCGGGCCTTGAACTACTACCCCAGAACATCACCATGAAGTGGCTGAAGGATA
AGCAGCCAATGGATGCCAAGGAGTTCGAACCTAAAGACGTATTGCCCAATGGGGATGGGACCTACCAGG
GCTGGATAACCTTGGCTGTACCCCCTGGGAAGAGCAGAGATATACGTGCCAGGTGGGAGCACCCAGGC
CTGGATCAGCCCCCTCATTGTGATCTGGGTATGTGACTGATGAGAGCCAGGAGCTGAGAAAATCTATTGG
GGGTTGAGAGGAGTGCCTGAGGAGGTAATTATGGCAGTGAGAGATGAGGATCTGCTCTTTGTTAGGGGGTG
GGCTGAGGGTGGCAATCAAAGGCTTTAACTT-3'        (SEQ ID NO:20)

FIG. 6A

5'-TATTTCCTTCCTCCAACCTATAGAAGGAAGTGAAAGTTCCAGTCTTCCTGGCAAGGGTAAACAGATCCCC
                                                         ‾‾‾‾‾‾‾‾‾‾‾‾‾‾‾‾‾‾‾‾‾‾‾‾‾‾‾‾‾
                                                                  24d1.P1
TCTCCTCATCCTCCTCTTCCTGTCAAGTGCCTCCTTGGTGAAGGTGACACATCATGTGACCTCTTCAG

TGACCACTCTACGGTGTCGGGCCCTTGAACTACTACCCCCAGAACATCACCATGAAGTGGCTGAAGGATA

AGCAGCCAATGGGATGCCAAGGAGTTCGAACCTAAAGACGTATTGCCCAATGGGATGGGACCTACCAGG

GCTGGATAACCTTGGCTGTACCCCCTGGGAAGAGCAGAGATATACGTACCAGGTGGAGCACCCAGGC

CTGGATCAGCCCCTCATTGTGATCTGGGTATGTGACTGATGAGAGCCAGGAGCTGAGAAAATCTATTGG

GGGTTGAGAGGAGTGCCTGAGGAGGTAATTATGGCAGTGAGATGAGGATCTGCTCTTGTAGGGGGTG
‾‾‾‾‾‾‾‾‾‾‾‾‾‾‾‾‾‾‾‾‾‾‾‾‾
         24d1.P2
GGCTGAGGGTGGCAATCAAAGGCTTTAACTT-3'

(SEQ ID NO:21)

PCR Primers used for Amplification Of 24d2 Alleles

24.P2.1 (forward primer)
5'-ACATGGTTAAGGCCTGTTGC-3' (SEQ ID NO:24)

24.P2.2 (reverse primer)
5'-GCCACATCTGGCTTGAAAATT-3' (SEQ ID NO:25)

OLA Oligonucleotides for 24d2

Upstream Oligonucleotides (5'-biotinylated)

24d2.A (common allele)
5'-bio-AGCTGTTCGTGTTCTATGATC-3'
(SEQ ID NO:26)

24d2.B (hemochromatosis allele)
5'-bio-AGCTGTTCGTGTTCTATGATG-3'
(SEQ ID NO:27)

Downstream Oligonucleotides (5'-phosphorylated)
24d2.X 5'-p-ATGAGAGTCGCCGTGTGGA-dig-3'
(SEQ ID NO:28)

FIG. 9

HEREDITARY HEMOCHROMATOSIS GENE PRODUCTS

This application is a continuation-in-part of Ser. No. 08/630,912, now abandoned, filed Apr. 4, 1996, Ser. No. 08/632,673, filed Apr. 16, 1996 U.S. Pat. No. 5,712,098 and Ser. No. 08/652,265, filed May 23, 1996, U.S. Pat. No. 6,025,130.

BACKGROUND OF THE INVENTION

Hereditary hemochromatosis (HH) is an inherited disorder of iron metabolism wherein the body accumulates excess iron. In symptomatic individuals, this excess iron leads to deleterious effects by being deposited in a variety of organs leading to their failure, and resulting in cirrhosis, diabetes, sterility, and other serious illnesses. Neither the precise physiological mechanism of iron overaccumulation nor the gene which is defective in this disease has been described.

HH is typically inherited as a recessive trait; in the current state of knowledge, homozygotes carrying two defective copies of the gene are most frequently affected by the disease. In addition, heterozygotes for the HH gene are more susceptible to sporadic porphyria cutanea tarda and potential other disorders (Roberts et al., Lancet 349:321–323 (1997). It is estimated that approximately 10–15% of individuals of Western European descent carry one copy of the HH gene mutation and that there are about one million homozygotes in the United States. HH, thus, represents one of the most common genetic disease mutations in individuals of Western European descent. Although ultimately HH produces debilitating symptoms, the majority of homozygotes and heterozygotes have not been diagnosed.

The symptoms of HH are often similar to those of other conditions, and the severe effects of the disease often do not appear immediately. Accordingly, it would be desirable to provide a method to identify persons who may be destined to become symptomatic in order to intervene in time to prevent excessive tissue damage associated with iron overload. One reason for the lack of early diagnosis is the inadequacy of presently available diagnostic methods to ascertain which individuals are at risk, especially while such individuals are presymptomatic.

Although blood iron parameters can be used as a screening tool, a confirmed diagnosis often employs liver biopsy which is undesirably invasive, costly, and carries a risk of mortality. Thus, there is a clear need for the development of an inexpensive and noninvasive diagnostic test for detection of homozygotes and heterozygotes in order to facilitate diagnosis in symptomatic individuals, provide presymptomatic detection to guide intervention in order to prevent organ damage, and for identification of heterozygote carriers.

The need for such diagnostics is documented, for example, in Barton, J. C. et al. Nature Medicine 2:394–395 (1996); Finch, C. A. West J Med 153:323–325 (1990); McCusick, V. Mendelian Inheritance in Man pp. 1882–1887, 11th ed., (Johns Hopkins University Press, Baltimore (1994)); Report of a Joint World Health Organization/Hemochromatosis Foundation/French Hemochromatosis Association Meeting on the Prevention and Control of Hemochromatosis (1993); Edwards, C. Q. et al. New Engl J Med 328:1616–1620 (1993); Bacon, B. R. New Engl J Med 326:126–127 (1992); Balan, V. et al. Gastroenterology 107:453–459 (1994); Phatak, P. D. et al. Arch Int Med 154:769–776 (1994).

Although the gene carrying the mutation or mutations that cause HH has previously been unknown, genetic linkage studies in HH families have shown that the gene that causes the disease in Caucasians appears to reside on chromosome 6 near the HLA region at 6p21.3 (Cartwright, Trans Assoc Am Phys 91:273–281 (1978); Lipinski, M. et al. Tissue Antigens 11:471–474 (1978)). It is believed that within this locus, a single mutation gave rise to the majority of disease-causing chromosomes present in the population today. See Simon, M. et al. Gut 17:332–334 (1976); McCusick, V. supra. This is referred to herein as the "common" or "ancestral" or "common ancestral" mutation. These terms are used interchangeably. It appears that about 80% to 90% of all HH patients carry at least one copy of the common ancestral mutation which is closely linked to specific alleles of certain genetic markers close to this ancestral HH gene defect. These markers are, as a first approximation, in the allelic form in which they were present at the time the ancestral HH mutation occurred. See, for example, Simon, M. et al. Am J Hum Genet 41:89–105 (1987); Jazwinska, E. C. et al. Am J Hum Genet 53:242–257 (1993); Jazwinska, E. C. et al. Am J Hum Genet 56:428–433 (1995); Worwood, M. et al. Brit J Hematol 86:863–866 (1994); Summers, K.M. et al. Am J Hum Genet 45:41–48 (1989).

Several polymorphic markers in the putative HH region have been described and shown to have alleles that are associated with HH disease. These markers include the published microsatellite markers D6S258, D6S306 (Gyapay, G. et al. Nature Genetics 7:246–339 (1994)), D6S265 (Worwood, M. et al. Brit J Hematol 86:833–846 (1994)), D6S105 (Jazwinska, E. C. et al. Am J Hum Genet 53:242–257 (1993); Jazwinska, E. C. et al. Am J Hum Genet 56:428–433 (1995)), D6S1001 (Stone, C. et al. Hum Molec Genet 3:2043–2046 (1994)), D6S1260 (Raha-Chowdhury et al. Hum Molec Genet 4:1869–1874 (1995)) as well as additional microsatellite and single-nucleotide-polymorphism markers disclosed in co-pending PCT application WO 96/35802 published Nov. 14, 1996, the disclosure of which is hereby incorporated by reference in its entirety.

Although each of such markers may be of use in identifying individuals carrying the defective HH gene, crossing-over events have, over time, separated some of the ancestral alleles from the mutation that is responsible for HH, thereby limiting the utility of such surrogate markers. The limited diagnostic power of surrogate markers is obvious considering the fact that the frequency of the ancestral allele in the population is generally higher than the estimated frequency of the disease-causing mutation. The desirability of identifying the gene responsible for HH has long been recognized due to the health benefits that would be available via gene-based diagnostics, which has an intrinsically higher predictive power than surrogate markers and may eventually lead to the identification and diagnosis of disease-causing mutations other than the ancestral mutation. In addition, identification of the HH gene would further our understanding of the molecular mechanisms involved in HH disease thereby opening new approaches for therapy. This goal has motivated numerous, but previously unsuccessful attempts to identify the HH gene.

These attempts have been made by a variety of methods. For example, genes known to be involved in iron transport or metabolism have been examined as candidates. An example of one unsuccessful attempt is the assignment of the ferritin heavy chain gene to Chromosome 6p, and subsequent exclusion of this gene on the basis of its precise localization outside of the HH region, and failure to find mutations in HH patients. See Dugast, I. J. et al. Genomics 6:204–211 (1990); Summers et al. Hum Genet 88:175–178 (1991).

Another strategy has been to employ the genomic DNA surrounding the postulated HH locus to select expressed genes from this region. These genes have been evaluated in HH patients for mutations in an attempt to identify them as the causative gene. Examples of searches that have not resulted in the identification of the HH gene are illustrated in El Kahloun et al. *Hum Molec Genet* 2:55–60 (1992), Goei et al. *Am J Hum Genet* 54:244–251 (1994), and Beutler et al. *Blood Cells, Molecules, and Diseases* 21:206–216 (1995).

Finally, although the strategy of using positional information obtained from genetic studies has long been a widely used approach, estimates of the position of the HH gene remained imprecise. Examples of this uncertainty are demonstrated in Gruen et al. *Genomics* 14:232–240 (1992) and in Gasparini et al. *Hematology* 19:1050–1056 (1994). Indeed, a number of contradictory conclusions have been reported, some placing the HH gene proximal of HLA-A (Edwards et al. *Cytogenet Cell Genet* 40:620 (1985); Gasparini, P. et al. *Hum Molec Genet* 2:571–576 (1993)) while others placed the gene distal of HLA-A (Calandro et al. *Hum Genet* 96:339–342 (1995)).

Until very recently, in spite of the linkage studies placing the HH disease gene in the HLA region of Chromosome 6, the biological relevance of alterations in HLA Class I components has not been particularly well explored. Work by de Sousa et al. *Immun Lett* 39:105–111 (1994), and more recent work by Rothenberg, B. E. and Voland, J. R. *Proc Natl Acad Sci USA* 93:1529–1534 (1996) indicated that β-2-microglobulin knock-out mice develop symptoms of iron overload. β-2-microglobulin is presented on cell surfaces as a complex with HLA Class I MHC's. de Sousa et al. supra. (1994) and Barton, J. C. and Bertoli, L. F. *Nature Medicine* 2:394–395 (1996) speculated that β-2-microglobulin associated proteins or a unique Class I gene could be involved in the control of intestinal iron absorption and possibly HH disease.

In spite of the extensive efforts in the art to find the gene responsible for HH, the gene has remained elusive. Nevertheless, as will be appreciated it would be highly desirable to identify, isolate, clone, and sequence the gene responsible for HH and to have improved diagnostic methods for detection of affected individuals, whether homozygotes or heterozygotes.

SUMMARY OF THE INVENTION

One aspect of the invention is an isolated nucleic acid comprising a nucleic acid sequence selected from the group consisting of:

nucleic acid sequences corresponding to the nucleic acid sequence of SEQ ID NO:1 (which corresponds to the genomic sequence of the HH gene including introns and exons as shown in FIG. 3);

nucleic acid sequences corresponding to the nucleic acid sequences selected from the group consisting of SEQ ID NO:3 (which corresponds to the genomic sequence of the HH gene containing the 24d1 mutation as shown in FIG. 3), SEQ ID NO:5 (which corresponds to the genomic sequence of the HH gene containing the 24d2 mutation as shown in FIG. 3), SEQ ID NO: 7 (which corresponds to the genomic sequence of the HH gene containing the 24d1 and the 24d2 mutations as shown in FIG. 3);

nucleic acid sequences corresponding to the nucleic acid sequence of SEQ ID NO:9 (which corresponds to the cDNA sequence including the coding sequence of the HH gene as shown in 4);

nucleic acid sequences corresponding to the nucleic acid sequences selected from the group consisting of SEQ ID NO:10 (which corresponds to the cDNA sequence including the coding sequence of the HH gene containing the 24d1 mutation as shown in FIG. 4), SEQ ID NO:11 (which corresponds to the cDNA sequence including the coding sequence of the HH gene containing the 24d2 mutation as shown in FIG. 4), and SEQ ID NO:12 (which corresponds to the cDNA sequence including the coding sequence of the HH gene containing the 24d1 and the 24d2 mutations as shown in FIG. 4);

In one embodiment, the nucleic acid is DNA. In another embodiment, the DNA is cDNA. In another embodiment, the nucleic acid is RNA. In another embodiment, the nucleic acid is a nucleic acid sequence corresponding to the nucleic acid sequence of SEQ ID NO:1. In another embodiment, the nucleic acid is a nucleic acid sequence corresponding to the nucleic acid sequence of SEQ ID NO:9. In another embodiment, the nucleic acid is a nucleic acid sequence corresponding to a nucleic acid sequence selected from the group consisting of SEQ ID NO:3, SEQ ID NO:5, and SEQ ID NO:7. In another embodiment, the nucleic acid is a nucleic acid sequence corresponding to a nucleic acid sequence selected from the group consisting of SEQ ID NO:10, SEQ ID NO:11, and SEQ ID NO:12.

A further aspect of the invention is a cloning vector comprising a coding sequence of a nucleic acid as set forth above and a replicon operative in a host cell for the vector.

A further aspect of the invention is an expression vector comprising a coding sequence of a nucleic acid set forth above operably linked with a promoter sequence capable of directing expression of the coding sequence in host cells for the vector.

A further aspect of the invention is host cells transformed with a vector as set forth above.

A further aspect of the invention is a method of producing a mutant HH polypeptide comprising: transforming host cells with a vector capable of expressing a polypeptide from a nucleic acid sequence as set forth above; culturing the cells under conditions suitable for production of the polypeptide; and recovering the polypeptide.

A further aspect of the invention is a peptide product selected from the group consisting of: a polypeptide having the amino acid sequence corresponding to the sequence of SEQ ID NO:2; a polypeptide having the amino acid sequence corresponding to the sequence of SEQ ID NO:4, SEQ ID NO:6, and SEQ ID NO:8; a peptide comprising at least 6 amino acid residues corresponding to the sequence of SEQ ID NO:2; a peptide comprising at least 6 amino acid residues corresponding to the sequence of SEQ ID NO:4, SEQ ID NO:6, and SEQ ID NO:8. In one embodiment, the peptide is labeled. In another embodiment, the peptide is a fusion protein.

A further aspect of the invention is a use of a peptide as set forth above as an immunogen for the production of antibodies. In one embodiment, there is provided an antibody produced in such application. In one embodiment, the antibody is labeled. In another embodiment, the antibody is bound to a solid support. In a further embodiment, the antibody is monoclonal.

A further aspect of the invention is a method to determine the presence or absence of the common hereditary hemochromatosis (HH) gene mutation in an individual, comprising: providing DNA or RNA from the individual; and assessing the DNA or RNA for the presence or absence of the HH-associated allele A of a base-pair mutation 24d1, wherein, as a result, the absence of the allele indicates the absence of the HH gene mutation in the genome of the individual and the presence of the allele the presence of the HH gene mutation in the genome of the individual. In a further embodiment, the method further comprises assessing the DNA or RNA for the presence of the base-pair mutation designated 24d2.

In a further embodiment the assessment can be made in combination with one or more microsatellite repeats or other polymorphisms. Thus, in a further aspect of the invention, the assessing step further comprises assessing the DNA or RNA for the presence or absence of any one of the following HH-associated alleles of base pair polymorphisms HHP-1, HHP-19, or HHP-29, wherein, as a result, the presence of the 24d1 and/or 24d2 allele in combination with the presence of at least one of the base pair polymorphisms HHP-1, HHP-19, or HHP-29 indicates the likely presence of the HH gene mutation in the genome of the individual and the absence of 24d1 and/or 24d2 allele in combination with the absence of at least one of the base pair polymorphisms HHP-1, HHP-19, or HHP-29 indicates a likely absence of the HH gene mutation in the genome of the individual. In another embodiment, the assessing step further comprises assessing the DNA or RNA for the presence of absence of any one of the following alleles defined by markers having microsatellite repeats: 19D9:205; 18B4:235; 1A2:239; 1E4:271; 24E2:245; 2B8:206; 3321-1:98; 4073-1:182; 4440-1:180; 4440-2:139; 731-1:177; 5091-1:148; 3216-1:221; 4072-2:170; 950-1:142; 950-2:164; 950-3:165; 950-4:128; 950-6:151; 950-8:137; 63-1:151; 63-2:113; 63-3:169; 65-1:206; 65-2:159; 68-1:167; 241-5:108; 241-29:113; 373-8:151; and 373-29:113, D6S258:199, D6S265:122, D6S105:124; D6S306:238; D6S464:206; and D6S1001: 180, wherein, as a result, the presence of the 24d1A and/or 24d2 allele in combination with the presence of at least one microsatellite repeat allele indicates the likely presence of the HH gene mutation in the genome of the individual and the absence of the 24d1 and/or 24d2 allele in combination with the absence of any one or all of the microsatellite repeat alleles indicates the likely absence of the HH gene mutation in the genome of the individual. In another embodiment, the assessing step is performed by a process which comprises subjecting the DNA or RNA to amplification using oligonucleotide primers flanking the base-pair polymorphism 24d1 and/or 24d2 and oligonucleotide primers flanking at least one of the base-pair polymorphisms HHP-1, HHP-19, and HHP-29. In another embodiment, the assessing step is performed by a process which comprises subjecting the DNA or RNA to amplification using oligonucleotide primers flanking the base-pair polymorphism 24d1 and/or 24d2 and oligonucleotide primers flanking at least one of the microsatellite repeat alleles. In another embodiment, the assessing step is performed by a process which comprises subjecting the DNA or RNA to amplification using oligonucleotide primers flanking the base-pair polymorphism 24d1 and/or 24d2, oligonucleotide primers flanking at least one of the base-pair polymorphisms HHP-1, HHP-19, and HHP-29, and oligonucleotide primers flanking at least one of the microsatellite repeat alleles.

A further aspect of the invention is a set of oligonucleotides for use in an oligonucleotide ligation assay determination of the presence or absence of an HH-associated allele of a base-pair polymorphism, wherein the base pair polymorphisms comprises 24d1 and the oligonucleotides comprise the sequences of SEQ ID NO:15, SEQ ID NO:16, and SEQ ID NO:17.

A further aspect of the invention is a kit for the detection of the presence or absence or an HH-associated allele of a base-pair polymorphism, the base-pair polymorphism comprising 24d1, as designated herein, the kit comprising the above oligonucleotide primer set. In another embodiment, the kit further comprises oligonucleotide primers for amplifying the DNA containing the base-pair polymorphism.

Another aspect of the invention is a kit for detection of a polymorphism in the HH gene in a patient, the sample kit comprising at least one oligonucleotide of at least 8 nucleotides in length selected from the group consisting of SEQ ID NOS: 1, 3, 5, 7, 9, 10, 11, or 12, wherein the oligonucleotide is used to amplify a region of HH DNA or RNA in a patient sample. In another aspect of the invention the kit further comprises at least a second oligonucleotide selected from the group consisting of SEQ ID NOS: 1, 3, 5, 7, 9, 10, 11, or 12, wherein the first and second oligonucleotides comprise a primer pair.

A further aspect of the invention is a method to evaluate potential responsiveness of an individual infected with hepatitis C to interferon treatment, comprising determining the presence or absence of the common hereditary hemochromatosis gene in the individual according to any of the above methods.

A further aspect of the invention is an oligonucleotide primer useful for amplification of DNA, the oligonucleotide primer designed on the basis of the DNA sequence of any one of SEQ ID NO: 18, SEQ ID NO:19, SEQ ID NO:29, and SEQ ID NO:30.

A further aspect of the invention is a method for diagnosing whether a patient is afflicted with hereditary hemochromatosis (HH) disease, comprising: contacting cells of the patient with antibodies directed against an epitope on an HH protein product corresponding substantially to SEQ ID NO:2; and observing whether the antibodies localize on the cells, wherein, in the observing step, if antibodies do not localize to the cell there is a probability that the patient is afflicted with HH. In one embodiment, the method is conducted in vitro. In another embodiment, the method is conducted in vivo.

A further aspect of the invention is a method for treating a patient diagnosed as having hereditary hemochromatosis (HH) disease, comprising delivering a polypeptide corresponding to the amino acid sequence of SEQ ID NO:2 to tissues of the patient. The patient can be homozygous or heterozygous for 24d1, and may be a compound 24d1/24d2 heterozygote. In an embodiment, the polypeptide is delivered directly to the tissues. In another embodiment, the polypeptide is delivered intravenously. In another embodiment, the polypeptide is delivered to the tissues through gene therapy.

A further aspect of the invention is an animal model for hereditary hemochromatosis (HH) disease, comprising a mammal possessing a mutant or knocked-out HH gene.

A further aspect of the invention is metal chelation agents derived from nucleic acid sequences described above or from a peptide product as described above in a physiologically acceptable carrier. In one embodiment, the metal is selected from the group consisting of iron, mercury, cadmium, lead, and zinc.

A further aspect of the invention is a method to screen mammals for susceptibility to metal toxicities, comprising, screening such mammals for a mutation in the HH gene and wherein those mammals identified as having a mutation are more susceptible to metal toxicities than mammals not identified as having a mutation. In one embodiment, the metal is selected from the group consisting of iron, mercury, cadmium, lead, and zinc.

A further aspect of the invention is a method for selecting patients infected with hepatitis virus for α-interferon treatment, comprising screening such patients for a mutation in the HH gene and wherein those patients not identified as having a mutation are selected to proceed with α-interferon treatment and those identified as having a mutation are selected to undergo phlebotomy prior to α-interferon treatment.

A further aspect of the invention is a T-cell differentiation factor comprising a moiety selected from the group consisting of molecules derived from nucleic acid sequences described above and from peptide products described above.

A further aspect of the invention is a method for screening potential therapeutic agents for activity in connection with HH disease, comprising: providing a screening tool selected from the group consisting of a cell line, a cell free, and a mammal containing or expressing a defective HH gene or gene product; contacting the screening tool with the potential therapeutic agent; and assaying the screening tool for an activity selected from the group consisting of HH protein folding, iron uptake, iron transport, iron metabolism, receptor-like activities, upstream processes, downstream processes, gene transcription, and signaling events.

A further aspect of the invention is a therapeutic agent for the mitigation of injury due to oxidative processes in vivo, comprising a moiety selected from the group consisting of molecules derived from nucleic acid sequences described above and from peptide products described above.

A further aspect of the invention is a method for diagnosing a patient as having an increased risk of developing HH disease, comprising: providing DNA or RNA from the individual; and assessing the DNA or RNA for the presence or absence of the HH-associated allele A of a base mutation designated herein 24d1 in combination with assessing the DNA or RNA for the HH-associated allele G of a base mutation designated herein 24d2, wherein, as a result, the absence of the alleles indicates the absence of the HH gene mutation in the genome of the individual and the presence of the alleles indicates the presence of the HH gene mutation in the genome of the individual and an increased risk of developing HH disease. In an embodiment, this assessment is done in combination with one or more microsatellite repeats or other polymorphisms. Thus, in a further aspect of the invention, the assessing step further comprises assessing the DNA or RNA for the presence or absence of any one of the following HH-associated alleles of base pair polymorphisms HHP-1, HHP-19, or HHP-29, wherein, as a result, the presence of the 24d1 and/or 24d2 allele in combination with the presence of at least one of the base pair polymorphisms HHP-1, HHP-19, or HHP-29 indicates the likely presence of the HH gene mutation in the genome of the individual and the absence of 24d1 and/or 24d2 allele in combination with the absence of at least one of the base pair polymorphisms HHP-1, HHP-19, or HHP-29 indicates a likely absence of the HH gene mutation in the genome of the individual. In another embodiment, the assessing step further comprises assessing the DNA or RNA for the presence of absence of any one of the following alleles defined by markers having microsatellite repeats: 19D9:205; 18B4:235; 1A2:239; 1E4:271; 24E2:245; 2B8:206; 3321-1:98; 4073-1:182; 4440-1:180; 4440-2:139; 731-1:177; 5091-1:148; 3216-1:221; 4072-2:170; 950-1:142; 950-2:164; 950-3:165; 950-4:128; 950-6:151; 950-8:137; 63-1:151; 63-2:113; 63-3:169; 65-1:206; 65-2:159; 68-1:167; 241-5:108; 241-29:113; 373-8:151; and 373-29:113, D6S258:199, D6S265:122, D6S105:124; D6S306:238; D6S464:206; and D6S1001:180, wherein, as a result, the presence of the 24d1A and/or 24d2 allele in combination with the presence of at least one microsatellite repeat allele indicates the likely presence of the HH gene mutation in the genome of the individual and the absence of the 24d1 and/or 24d2 allele in combination with the absence of any one or all of the microsatellite repeat alleles indicates the likely absence of the HH gene mutation in the genome of the individual.

A further aspect of the invention is a therapeutic agent for the mitigation of iron overload, comprising a moiety selected from the group consisting of molecules derived from nucleic acid sequences described above and from peptide products described above.

A further aspect of the invention is a method for treating hereditary hemochromatosis (HH) disease, comprising: providing an antibody directed against an HH protein sequence or peptide product; and delivering the antibody to affected tissues or cells in a patient having HH.

A further aspect of the invention is an antisense oligonucleotide directed against a transcriptional product of a nucleic acid sequence selected from the group consisting of therapeutic agent for the mitigation of iron overload, comprising a moiety selected from the group consisting of SEQ ID NO:1, SEQ ID NO:3, SEQ ID NO:5, SEQ ID NO:7, SEQ ID NO:9, SEQ ID NO:10, SEQ ID NO:11, and SEQ ID NO:12.

A further aspect of the invention is an oligonucleotide of at least 8 nucleotides in length selected from nucleotides 1-46, 48-123; 120-369; 365-394; 390-540; 538-646; 643-1004; 1001-1080; 1083-1109; 1106-1304; 1301-1366; 1363-1386; 1389- 1514; 1516-1778; 1773-1917; 1921-2010; 2051-2146; 2154-2209; 2234-2368; 2367-2422; 2420-2464; 2465-2491; 2488-2568; 2872-2901; 2902-2934; 2936-2954; 2449-3001; 3000-3042; 3420-3435; 3451-3708; 3703-3754; 3750-3770; 3774-3840; 3840-3962; 3964-3978; 3974-3992; 3990-4157; 4153-4251; 4257-4282; 4284-4321; 4316-4333; 4337-4391; 4386-4400; 4398-4436; 4444-4547; 4572-4714; 4709-4777; 5165-5397; 5394-6582; 5578-5696; 5691-5709; 5708-5773; 5773-5816; 5818-5849; 5889-6045; 6042-6075; 6073-6108; 6113-6133; 6150-6296; 6292-6354; 6356-6555; 6555-6575; 6575-6616; 6620-6792; 6788-6917; 6913-7027; 7023-7061; 7056-7124; 7319-7507; 7882-8000; 7998-8072; 8073-8098; 9000-9037; 9486-9502; 9743-9811; 9808-9831; 9829-9866; 9862-9986; 9983-10075; 10072-10091; 10091-10195; 10247-10263; 10262-10300; 10299-10448; 10448-10539; 10547-10564; 10580-10612; 10608-10708; 10703-10721; 10716-10750; 10749-10774; 10774-10800; and 10796-10825 of SEQ ID NO:1, 3, 5, or 7.

A further aspect of the invention is an oligonucleotide of at least 9 nucleotides in length selected from nucleotides 1-47; 47-124; 119-370; 364-395; 389-541; 537-647; 642-1005; 1000-1081; 1082-1110; 1105-1305; 1300-1367; 1362-1387; 1388-1515; 1515-1918; 1920-2011; 2050-2147; 2153-2210; 2233-2369; 2366-2423; 2419-2465; 2464-2492; 2487-2569; 2871-2935; 2935-3002; 2999-3043; 3419-3436; 3450-3755; 3749-3771; 3773-3841; 3839-3963; 3963-3979; 3973-3993; 3989-4158; 4152-4252; 4256-4283; 4283-4334; 4336-4401; 4397-4437; 4443-4548; 4571-4778; 5164-5398; 5393-5583; 5577-5710; 5707-5774; 5772-5817; 5817-5850; 5888-6046; 6041-6076; 6072-6109; 6112-6134; 6149-6355; 6355-6556; 6554-6576; 6574-6793; 6787-7125; 7318-7508; 7881-8001; 7997-8073; 8072-8099; 8999-9038; 9485-9503; 9742-9812; 9807-9832; 9828-9867; 9861-9987; 9982-10076; 10071-10092; 10090-10196; 10246-10264; 10261-10301; 10298-10449; 10447-10540; 10546-10565; 10579-10751; 10748-10775; 10773-10801; and 10795-10825 of SEQ ID NO:1, 3, 5, or 7.

A further aspect of the invention is an oligonucleotide of at least 10 nucleotides in length selected from nucleotides 1-48; 46-125; 118-1006; 999-1082; 1081-1111; 1104-1306;

1299-1368; 1361-1388; 1387-1516; 1514-1919; 1919-2012; 2049-2148; 2152-2211; 2232-2370 2365-2424; 2418-2466; 2463-2493; 2486-2570; 2870-2936; 2934-3003; 2998-3044; 3418-3437; 3449-3772; 3772-3842; 3838-3964; 3962-3994; 3988-4284; 4282-4335; 4335-4402; 4396-4438; 4442-4549; 4570-4779; 5163-5711; 5706-5775; 5771-5818; 5816-5851; 5867-6047; 6040-6077; 6071-6110; 6111-6135; 6148-6356; 6354-6577; 6573-7126; 7317-7509; 7880-8074; 8071-8100; 8998-9039; 9484-9504; 9741-9813; 9806-9833; 9827-9988; 9981-10093; 10089-10197; 10245-10265; 10260-10302; 10297-10450; 10446-10541; 10545-10566; 10578-10752; 10747-10776; and 10772-10825 of SEQ ID NO:1, 3, 5, or 7.

A further aspect of the invention is an oligonucleotide of at least 11 nucleotides in length selected from nucleotides 1-49; 45-1389; 1386-1517, 1513-1920; 1918-2013; 2048-2149; 2151-2212; 2231-2371; 2364-2425; 2417-2467; 2462-2571; 2869-2937; 2933-3004; 2997-3045; 3417-3438; 3448-3773; 3771-3843; 3837-3965; 3961-3995; 3987-4285; 4281-4336; 4334-4403; 4395-4439; 4441-4550; 4569-4780; 5162-5712; 5705-5776; 5770-5819; 5815-5852; 5886-6111; 6100-6136; 6147-6357; 6353-6578; 6572-7127; 7316-7510; 7879-8075; 8070-8101; 8997-9040; 9483-9505; 9740-10198; 10244-10266; 10257-10303; 10296-10451; 10445-10542; 10544-10567; 10577-10753; 10746-10777; and 10771-10825 of SEQ ID NO:1, 3, 5, or 7.

A further aspect of the invention is an oligonucleotide of at least 12 nucleotides in length selected from nucleotides 1-50, 44-1390; 1385-1518; 1512-1921; 1917-2014; 2047-2150; 2150-2213; 2230-2372; 2363-2468; 2461-2572; 2868-2938; 2932-3005; 2996-3046; 3416-3439; 3447-3774; 3770-3844; 3836-3966; 3960-4286; 4280-4337; 4333-4440; 4440-4551; 4568-4781; 5161-5713; 5704-5777; 5669-5820; 5814-5853; 5885-6112; 6109-6137; 6146-6358; 6352-6579; 6571-7128; 7315-7511; 7878-8076; 8069-8102; 8996-9041; 9482-9506; 9739-10199; 10243-10267; 10256-10304; 10295-10452; 10444-10543; 10543-10566; 10576-10754; 10745-10778; and 10770-10825 of SEQ ID NO:1, 3, 5, or 7.

A further aspect of the invention is an oligonucleotide of at least 13 nucleotides in length selected from nucleotides 1-51; 43-1391; 1384-1519; 1511-1922; 1916-2015; 2046-2151; 2149-2214; 2229-2469; 2460-2573; 2867-2939; 2931-3047; 3415-3440; 3446-3775; 3769-3845; 3835-3967; 3959-4287; 4279-4338; 4332-4441; 4439-4552; 4567-4782; 5160-5778; 5668-5821; 5813-5854; 5884-6113; 6108-6138; 6145-6359; 6351-6580; 6570-7129; 7314-7512; 7877-8077; 8068-8103; 8995-9042; 9481-9507; 9738-10200; 10242-10453; 10443-10544; 10542-10567; 10575-10779; and 10769-10825 of SEQ ID NO:1, 3, 5, or 7.

A further aspect of the invention is an oligonucleotide of at least 14 nucleotides in length selected from nucleotides 1-52; 42-1392; 1383-1520; 1510-1923; 1915-2016; 2045-2152; 2148-2215; 2228-2574; 2866-2940; 2930-3048; 3414-3441; 3445-3776; 3768-3968; 3959-4288; 4278-4339; 4331-4442; 4438-4553; 4566-4783; 5159-5822; 5812-5855; 5883-6114; 6107-6139; 6144-6360; 6350-6581; 6569-7130; 7313-7513; 7876-8078; 8067-8104; 8994-9043; 9480-9508; 9737-10201; 10241-10454; 10442-10545; 10541-10568; and 10574-10825 of SEQ ID NO:1, 3, 5, or 7.

A further aspect of the invention is an oligonucleotide of at least 15 nucleotides in length selected from nucleotides 1-53; 41-1393; 1382-1521; 1509-1924; 1914-2017; 2044-2153; 2147-2216; 2227-2575; 2865-2942; 2929-3049; 3413-3442; 3444-3777; 3767-3969; 3958-4289; 4277-4340; 4330-4443; 4437-4554; 4565-4784; 5158-5823; 5811-5856; 5882-6115; 6106-6140; 6143-6361; 6349-7131; 7312-7514; 7875-8105; 8993-9044; 9479-9509; 9736-10202; 10240-10546; 10540-10569; and 10573-10825 of SEQ ID NO:1, 3, 5, or 7.

A further aspect of the invention is an oligonucleotide of at least 16 nucleotides in length selected from nucleotides 1-1394; 1381-1925; 1913-2018; 2043-2154; 2146-2217; 2226-2576; 2864-3050; 3412-3443; 3443-3778; 3766-4341; 4329-4444; 4436-4555; 4564-4785; 5157-5857; 5881-6116; 6105-6141; 6142-7132; 7311-7515; 7874-8106; 8992-9045; 9478-9510; 9735-10203; 10239-10547; 10539-10570; and 10572-10825 of SEQ ID NO:1, 3, 5, or 7.

A further aspect of the invention is an oligonucleotide of at least 17 nucleotides in length selected from nucleotides 1-1926; 1912-2019; 2042-2155; 2145-2218; 2225-2577; 2863-3051; 3411-3779; 3765-4342; 4329-4445; 4435-4556; 4563-4786; 5156-5858; 5880-6117; 6104-6142; 6141-7133; 7310-7516; 7873-8107; 8991-9046; 9477-9511; 9734-10204; 10238-10548; 10538-10571; and 10571-10825 of SEQ ID NO:1, 3, 5, or 7.

A further aspect of the invention is an oligonucleotide of at least 18 nucleotides in length selected from nucleotides 1-2020; 2041-2156; 2144-2219; 2224-2578; 2862-3052; 3410-3780; 3764-4446; 4434-4557; 4562-4787; 5155-5859; 5879-6118; 6103-6143; 6140-7134; 7309-7517; 7872-8108; 8990-9047; 9476-9512; 9733-10205; 10237-10549; 10537-10572; and 10570-10825 of SEQ ID NO:1, 3, 5, or 7.

A further aspect of the invention is an oligonucleotide of at least 8 nucleotides in length selected from nucleotides 1-55; 55-251; 250-306; 310-376; 380-498; 500-528; 516-543; 541-578; 573-592; 590-609; 611-648; 642-660; 664-717; 712-727; 725-763; 772-828; 813-874; 872-928; 913-942; 940-998; 997-1046; 1054-1071; 1076-1116; 1115-1182; 1186-1207; 1440-1483; 1482-1620; 2003-2055; 2057-2107; 2116-2200; and 2453-2469 of SEQ ID NO:9, 10, 11 or 12.

A further aspect of the invention is an oligonucleotide of at least 9 nucleotides in length selected from nucleotides 1-56; 54-252; 249-307; 309-377; 379-499; 499-529; 515-544; 540-579; 572-593; 589-610; 610-649; 641-661; 663-718; 711-728; 724-764; 771-829; 812-875; 871-929; 912-943; 939-999; 996-1047; 1053-1072; 1075-1117; 1114-1183; 1185-1208; 1439-1484; 1481-1629; 2002-2056; 2056-2108; 2115-2201; and 2452-2470 of SEQ ID NO:9, 10, 11 or 12.

A further aspect of the invention is an oligonucleotide of at least 10 nucleotides in length selected from nucleotides 1-57; 53-253; 248-308; 308-378; 378-500; 498-530; 514-545; 539-580; 571-594; 588-611; 609-662; 662-729; 723-765; 770-876; 870-944; 938-1000; 995-1048; 1052-1073; 1074-1118; 1113-1184; 1184-1209; 1438-1485; 1480-1630; 2001-2057; 2055-2109; 2114-2202; and 2451-2471 of SEQ ID NO:9, 10, 11 or 12.

A further aspect of the invention is an oligonucleotide of at least 11 nucleotides in length selected from nucleotides 1-58; 52-254; 247-309; 307-379; 377-501; 497-531; 513-546; 538-595; 587-612; 608-663; 661-730; 722-766; 769-877; 869-1049; 1051-1074; 1073-1119; 1112-1185; 1183-1210; 1437-1486; 1479-1631; 2000-2058; 2054-2110; 2113-2203; and 2450-2472 of SEQ ID NO:9, 10, 11 or 12.

A further aspect of the invention is an oligonucleotide of at least 12 nucleotides in length selected from nucleotides 1-255; 246-310; 306-380; 376-502; 496-596; 586-613; 607-664; 660-767; 768-1050; 1050-1075; 072-1120; 1111-1186; 1182-1211; 1436-1487; 1478-1632; 1999-2059; 2053-2121; 2112-2204; and 2449-2473 of SEQ ID NO:9, 10, 11 or 12.

A further aspect of the invention is an oligonucleotide of at least 13 nucleotides in length selected from nucleotides 1-311; 305-381; 375-503; 495-614; 606-665; 659-768; 767-1051; 1049-1076; 1071-1121; 1110-1187; 1181-1212; 1435-1633; 1998-2060; 2052-2205 and 2448-2474 of SEQ ID NO:9, 10, 11 or 12.

A further aspect of the invention is an oligonucleotide of at least 14 nucleotides in length selected from nucleotides 1-312; 304-382; 374-504; 494-615; 605- 666; 658-769; 766-1052; 1048-1077; 1070-1188; 1180-1213; 1434-1634; 1997-2061; 2051-2206; and 2447-2475 of SEQ ID NO:9, 10, 11 or 12.

A further aspect of the invention is an oligonucleotide of at least 15 nucleotides in length selected from nucleotides 1-313; 303-383; 373-505; 493-616; 604-667; 657-770; 765-1053; 1047-1078; 1069-1189; 1179-1214; 1433-1635; 1996-2062; 2050-2207; and 2446-2476 of SEQ ID NO:9, 10, 11 or 12.

A further aspect of the invention is an oligonucleotide of at least 16 nucleotides in length selected from nucleotides 1-314; 302-384; 372-668; 656-771; 764-1054; 1046-1079; 1068-1190; 1178-1215; 1432-1636; 1995-2208; and 2445-2477 of SEQ ID NO:9, 10, 11 or 12.

A further aspect of the invention is an oligonucleotide of at least 17 nucleotides in length selected from nucleotides 1-315; 301-385; 371-669; 655-772; 763-1055; 1045-1080; 1067-1191; 1177-1216; 1431-1637; 1994-2209; and 2444-2478 of SEQ ID NO:9, 10, 11 or 12.

A further aspect of the invention is an oligonucleotide of at least 18 nucleotides in length selected from nucleotides 1-773; 762-1056; 1044-1081; 1066-1192; 1176-1217; 1430-1638; 1993-2210; and 2443-2479 of SEQ ID NO:9, 10, 11 or 12.

BRIEF DESCRIPTION OF THE DRAWING FIGURES

FIG. 1 is a physical map showing the positions of markers on Chromosome 6 telomeric of the HLA region and the set of genomic clones used in our gene discovery efforts. In the Figure, "y" designates a YAC (yeast artificial chromosome) clone, "p" designates a p1 clone, "b" designates a BAC (bacterial artificial chromosome) clone, and "pc" designates a PAC (p1 artificial chromosome).

FIG. 2 is a subset of chromosomes showing the overlap of ancestral DNA between HH affected chromosomes from patients at markers in a narrow region of Chromosome 6, approximately 4.8 Mbp telomeric of the HLA region. These overlapping regions were used to define the minimal HH region. Shaded regions are "ancestral regions" maintained "identical by descent." The region that is ancestral and in common between all of these chromosomes is between markers 241-29 and 63-3. This is where the HH gene should reside.

FIG. 3 is a nucleotide sequence of the genomic DNA containing the HH gene (SEQ ID NO:1). The sequence comprises approximately 11,000 nucleotides. The sequence corresponding to the HH gene coding regions have been capitalized and underlined. The positions of the 24d1 and the 24d2 mutations and the 24d7 sequence variants are shown where base 5474 corresponds to the position of the 24d1 mutation, base 3512 corresponds to the position of the 24d2 mutation, and base 3518 corresponds to the position of the 24d7 sequence variation. Sequences corresponding to the genomic DNA including the 24d1 mutation are referred to herein as SEQ ID NO:3, sequences corresponding to the genomic DNA including the 24d2 mutation are referred to herein as SEQ ID NO:5, and sequences corresponding to the genomic DNA including the 24d1 and the 24d2 mutations are referred to herein as SEQ ID NO:7.

FIG. 4 is the nucleotide sequence of the translated portion of the cDNA (SEQ ID NO:9) corresponding to coding regions in the HH gene. The nucleotide sequence of the cDNA is arbitrarily numbered beginning at 1 with the A in the start codon (ATG). The predicted amino acid sequence of the protein product is provided (SEQ ID NO:2); and sequence variants in the gene, as well as the associated changes in the amino acid sequence caused by such variants are indicated on the Figure at base 187 (residue 63), base 193 (residue 65), and base 845 (residue 282). Sequences corresponding to cDNA including the 24d1 mutation are referred to herein as SEQ ID NO:10, sequences corresponding to the cDNA including the 24d2 mutation are referred to herein as SEQ ID NO:11, and sequences corresponding to the cDNA including the 24d1 and the 24d2 mutations are referred to herein as SEQ ID NO:12. Sequences of the predicted protein product including the amino acid change caused by the 24d1 mutation is referred to herein as SEQ ID NO:4, sequences of the predicted protein product including the amino acid change caused by the 24d2 mutation is referred to herein as SEQ ID NO:6, and sequences of the predicted HH protein product including the amino acid change caused by the 24d1 and 24d2 mutations is referred to herein as SEQ ID NO:8.

FIG. 5 shows the oligonucleotide sequences used for amplification (SEQ ID NOS:13 and 14) and OLA determination (SEQ ID NOS: 15, 16 AND 17) of the 24d1 gene mutation of the present invention.

FIG. 6 shows a 517 base sequence representing the genomic DNA surrounding the 24d1 gene mutation of the present invention. FIG. 6a shows the position of 24d1 in the normal G allele and the portions of the sequence used for the design of the primers illustrated in FIG. 5 (SEQ ID NO:20), and FIG. 6b shows the position of 24d1 in the mutated A allele and the portions of the sequence used for the design of the primers illustrated in FIG. 5 (SEQ ID NO:21).

FIG. 7 shows the sequence alignment between the predicted amino acid sequence of the HH gene protein product (SEQ ID NO:2) in comparison to RLA (rabbit leukocyte antigen) (SEQ ID NO:22) and an MHC Class I protein (SEQ ID NO:23). The dots above certain amino acids correspond to conservative amino acid residue differences, i.e., glycine for alanine, valine for isoleucine for leucine, aspartic acid for glutamic acid, asparagine for glutamine, serine for threonine, lysine for arginine, and phenylalanine for tyrosine, or the reverse.

FIG. 9 shows the oligonucleotide sequences used for amplification (SEQ ID NOS:24 and 25) and OLA determination (SEQ ID NO:26, 27 and 28) of the 24d1 gene mutation of the present invention.

DETAILED DESCRIPTION OF THE INVENTION

I. Definitions

Figure 1:
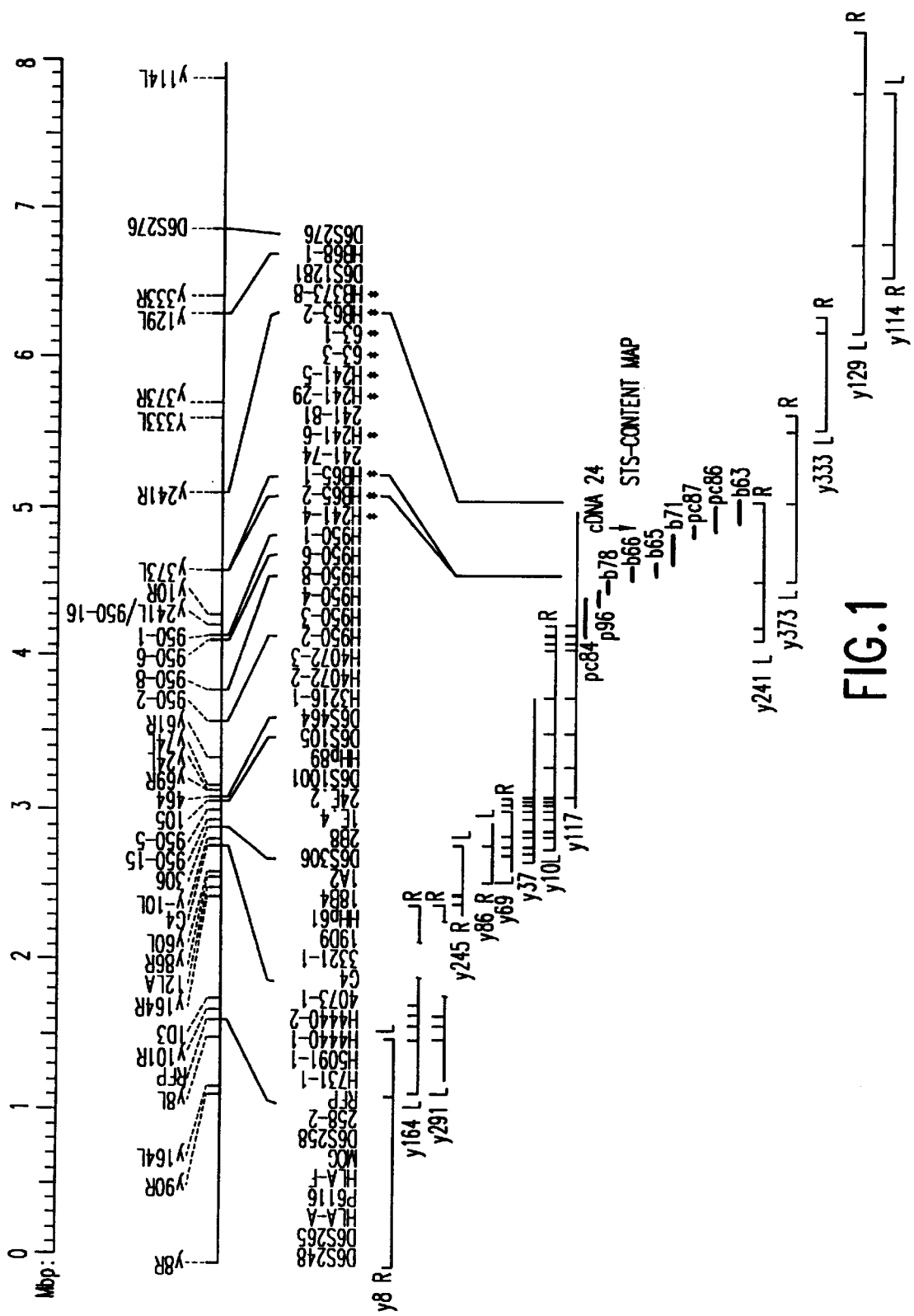
Figure 8:
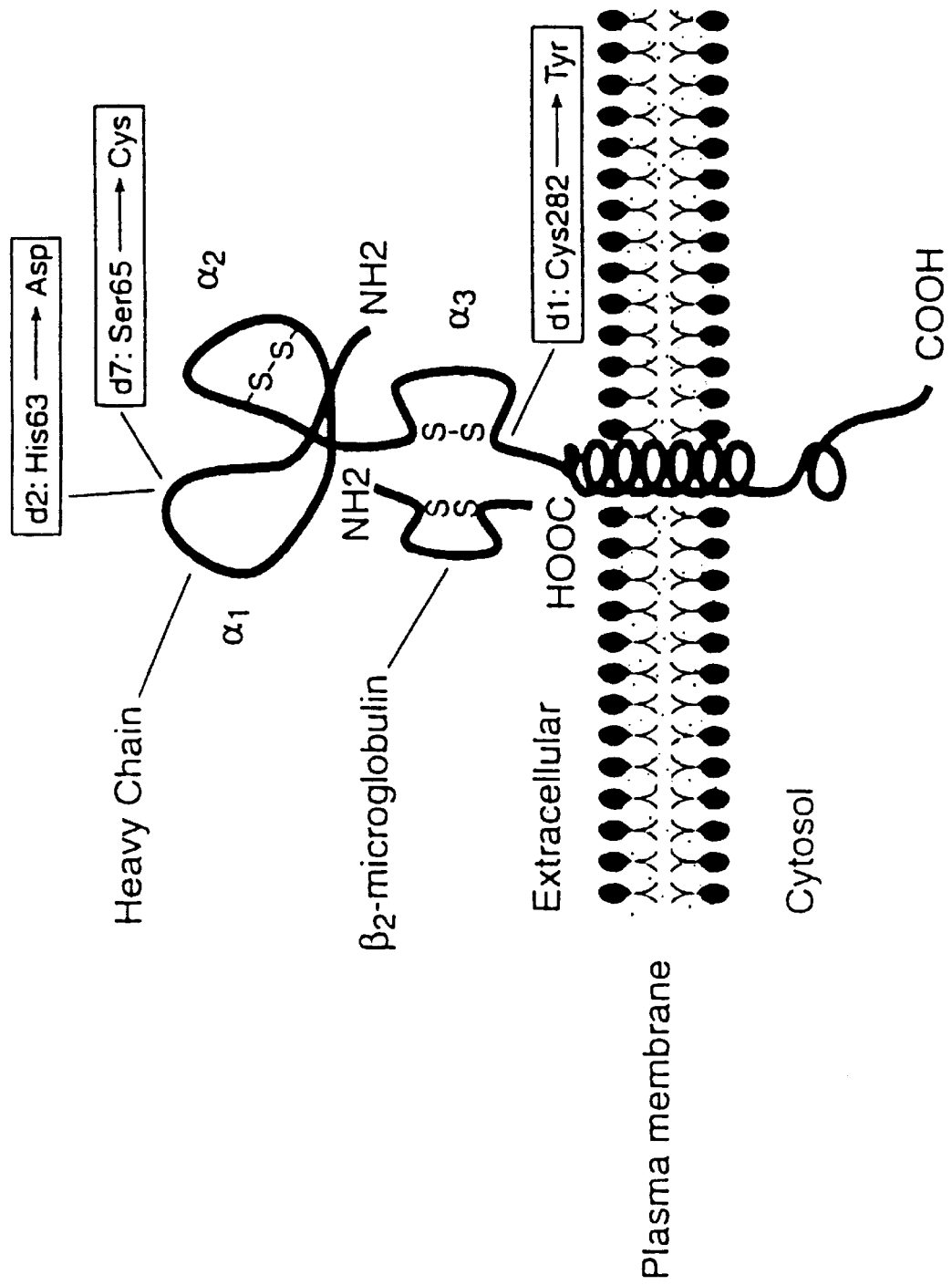
FIG. 8 is a schematic diagram showing the association between an HLA molecule and β-2-microglobulin highlighting the homologous positions of the three base-pair changes that have been found in the predicted HH gene protein product.

As used herein, the term "random chromosomes" refers to chromosomes from randomly chosen individuals who are not known to be affected with HH. Similarly, the term "unaffected individuals" refers to individuals who are not known to be affected with HH. The term "affected chromosomes" as used herein refers to chromosomes from individuals who have been diagnosed as having HH as determined by hepatic iron index and liver biopsy. Similarly, the term "affected individuals" refers to individuals who have been diagnosed as having HH.

As used herein, "marker" refers to a DNA sequence polymorphism flanked by unique regions. These regions flanking the "marker" can be utilized for the design and construction of oligonucleotides for amplifying the relevant DNA portions and detecting the polymorphisms therein.

The term "HH disease" refers to hereditary hemochromatosis disease. The criteria utilized herein to assess whether a patient is affected with the HH disease (i.e., whether the patient is an "affected individual" having "affected chromosomes") has been established by the diagnostic criteria set out in Crawford et al. *Am J Hum Genet* 57:362–367 (1995) where at least two of the following four criteria were met: (i) liver biopsy showing HIC greater than 4660 micrograms/gram of liver, (ii) HII greater than or equal to 2.0, (iii) Perl stain of 3 or greater, or (iv) greater than 4 grams of iron removed by phlebotomy (greater than 16 therapeutic phlebotomies).

"HH gene" as used herein refers to a gene whose mutated forms are associated with HH disease. This definition includes various sequence polymorphisms, mutations, and/ or sequence variants wherein nucleotide substitutions in the gene sequence do not affect the function of the gene product. Generally, the HH gene is found on Chromosome 6 and includes the DNA sequences shown in FIGS. 3 and 4 and all functional equivalents. The term "HH gene" includes not only coding sequences but also regulatory regions such as promoter, enhancer, and terminator regions. The term further includes all introns and other DNA sequences spliced from the final HH gene RNA transcript. Further, the term includes the coding sequences as well as the non-functional sequences found in non-human species. All DNA sequences provided herein are understood to include complementary strands unless otherwise noted. It is understood that an oligonucleotide may be selected from either strand of the HH genomic or cDNA sequences. Furthermore, RNA equivalents can be prepared by substituting uracil for thymine, and are included in the scope of this definition, along with RNA copies of the DNA sequences of the invention isolated from cells. The oligonucleotide of the invention can be modified by the addition of peptides, labels, and other chemical moieties and are understood to be included in the scope of this definition.

The terms "HH protein" and "HH gene product" refer to MHC Class I-like molecules encoded by the HH gene. The term includes protein as isolated from human and animal sources, produced by enzymatic or chemical means, or through recombinant expression in an organism. The term further includes "normal" and "wild-type" forms of the protein and mutant forms of the protein that are responsible or involved in HH disease. Encompassed within this definition are forms of the protein including polymorphic forms of the protein in which the amino acid changes do not affect the essential functioning of the protein in its role as either "normal" or "wild-type" or mutant forms of the protein.

"Ancestral DNA" as used herein refers to DNA that is inherited in unchanged form through multiple generations. Such DNA is sometimes referred to herein as DNA that is "identical by descent."

The term "ancestral mutation" as used herein refers to the disease causing mutation inherited through multiple generations.

II. Introduction to HH Gene Discovery

Through the analysis of affected chromosomes as compared to random chromosomes, in accordance with the present invention, we have identified, isolated, and sequenced the cDNA corresponding to the normal and mutant HH gene (Feder, J. N. et al., *Nature Genetics* 13:399–408(1996). In addition, we have sequenced the cDNA corresponding to the gene's mRNA and have predicted the gene's protein product. The HH disease gene is a novel gene on Chromosome 6 having significant sequence homology with HLA Class I genes. Interestingly, however, the gene is located at significant distance telomeric (approximately 4 Mbp) from the HLA Class I gene cluster on Chromosome 6. A single mutation in the gene appears responsible for the majority of HH disease. The mutation comprises a single nucleotide substitution of Guanine (G) to Adenine (A), where Guanine (G) is present in the unaffected DNA sequence and Adenine (A) is present in the affected DNA sequence. This mutation, referred to herein as 24d1, is illustrated in two partial sequences from the genomic DNA of the HH gene below and represented by SEQ ID NO:29 (unaffected) and SEQ ID NO:30 (affected):

24d1 Unaffected Sequence:

5'-GGAAGAGCAGAGATATACGTGCCAG GTGGAGCACCCAGG-3' (SEQ ID NO:29)

24d1 Affected Sequence:

5'-GGAAGAGCAGAGATATACGTACCAG GTGGAGCACCCAGG-3' (SEQ ID NO:30)

The G to A mutation at 24d1 is present in approximately 86% of all affected chromosomes and in only 4% of unaffected chromosomes, exemplifying its enrichment in the affected chromosomes.

As will be discussed in greater detail below, several factors provide a compelling conclusion that the above-mentioned gene of the present invention is in fact the HH gene, and that the 24d1 mutation is responsible for the majority of cases of HH disease. First, the location of the gene on Chromosome 6, in relative proximity to the HLA region, is the predicted location based on linkage disequilibrium mapping studies and haplotype analysis. Second, recent evidence demonstrated that β-2-microglobulin knock-out mice developed symptoms of iron overload disease. The predicted amino acid sequence of the gene product of the present invention possesses significant homology to HLA Class I molecules which are known to interact with β-2-microglobulin. Third, the principal mutation (24d1) causes a marked amino acid change (cys→tyr) at a critical disulfide bridge held in common with HLA Class I proteins that is important to the secondary structure of such protein products. Changes affecting the disulfide bridge in HLA Class I molecules have been shown to prevent or minimize presentation of the protein on cell surfaces. Further, such amino acid changes would appear to substantially modify the manner in which the protein could associate or interact with β-2-microglobulin. Fourth, the 24d1 mutation is present in over 87% of HH patients while only present in 4% of random individuals, consistent with estimates of the frequency of the ancestral HH mutation in patients and the carrier frequency in random individuals.

A. Discovery of the HH Gene

1. Strategy

In order to identify the HH gene, we set out to determine allelic association patterns between known markers and the HH locus in the HLA region of Chromosome 6. Based upon this data, we generated physical clone coverage extending from D6S265, which is a marker that is centromeric of HLA-A, in a telomeric direction through D6S276, a marker at which the allelic association was no longer observed.

2. Allelic Association

As mentioned above, it is believed that there was a common ancestor who possessed a distinct DNA sequence within whose genome the common or ancestral HH mutation occurred. It appears that approximately 87% of the patients today are descendants of this disease founding individual and thus share the common mutation. As will be appreciated, through the generations, chromosomes undergo genetic recombination during meiosis. Both genetic linkage mapping and disequilibrium mapping take advantage of this natural process to narrow and define the location of the disease causing gene. The smaller the distance between a disease locus and a genetic marker, the less likely that a recombination event will occur between them. Thus, as genetic markers are tested in a population of HH patients the markers closest to the disease locus will tend more often to have the allele that was present on the ancestral chromosome, while others farther away, will tend to have different alleles brought in by genetic recombination. Our strategy for identifying the HH gene, and the mutation(s) responsible for the HH disease, exploited this phenomenon by first reconstructing the haplotype of the founding or ancestral chromosome spanning an 8 Mb region. Secondly, we determined the minimal HH region that is "identical by descent" or shared in the chromosomes in our sample of HH patients.

The approach is shown in FIG. 2 where areas of ancestral sequence that is "identical by descent" are indicated in shade and areas of non-identity are unmarked. Particular markers are shown at the top of the Figure.

Towards the goal of identifying the HH gene, we undertook this type of strategy. Owing to the published allelic association of the HH gene with the HLA region, we directed our initial efforts to this region of Chromosome 6. Existing genetic markers were tested for association with the HH gene. Because of the founder or ancestral effect, described above, we expected that markers closer to the HH gene would display a greater degree of allelic association. Based upon this initial data we designed a strategy to develop markers over a 8 Mb region extending telomeric from HLA-A.

The markers were generally developed by cloning random pieces of genomic DNA, known to represent this region of the chromosome as described in the next section and as shown in FIG. 1. The clones containing CA repeat elements were identified by hybridization and their sequences determined. The sequence information was used to design primers within the unique DNA flanking the CA repeat, for use in PCR. If the CA repeat proved to be polymorphic in a random sample of chromosomes, then the markers were assayed in HH patients. In this effort 46 CA microsatellite markers covering approximately 8 Mb, were identified and scored in our patients. We detected the pattern of overlapping ancestral DNA present on patient chromosomes as depicted in FIG. 2. As will be appreciated, the minimal area of DNA that is "identical by descent" on all the ancestral HH chromosomes is between, but not including, markers 241–29 and 63-3, surrounding marker 241-5. This is the region within which the HH gene must lie and where we conducted our search for the gene as described below.

3. Physical Mapping

Primary clone coverage of the genomic region telomeric of the MHC locus on Chromosome 6p was obtained by assembling an overlapping set of YAC clones that span the region between D6S265 and D6S276. Initial YAC contigs were seeded by screening the CEPH MegaYAC library for the sequence tag sites (STSs) D6S258, D6S306, D6S105, D6S464 and D6S276. Additional YACs containing these STSs were identified in the CEPH and the MIT/Whitehead databases. The three initial YAC contigs were expanded and eventually merged into a single contig by bidirectional walking using STSs developed from the ends of YAC inserts. An STS-content map comprising 64 STSs and 44 YACs across the HH region was constructed. In order to determine precise physical distances, a set of 14 YACs were selected for RARE-cleavage mapping (Gnirke et al. *Genomics* 24:199–210 (1994)) and the construction of the distance-calibrated YAC-contig and STS content maps which are shown in FIG. 1.

Bacterial clones were identified by PCR-based and hybridization-based screening of comprehensive human cosmid, p1, BAC, and PAC libraries. FIG. 1 also shows the bacterial clone contig across approximately 1 Mbp of genomic DNA that includes the region represented by YAC 241. The STS-content map indicating the STS and clone order is depicted in FIG. 1. YACs, BACs, PACs and P1 clones are denoted by the suffices y, b, pc and p, respectively.

In FIG. 1, the markers are characterized as follows: D6S248 (Orphanos, V. et al. *Hum Mol Genet* 2:2196 (1993)); D6S258, D6S265, D6S276, D6S306, D6S464 (Gyapay, G. et al. *Nature Genetics* 7:246–339 (1994)); 258-2, G4, HHp61, HHp89, HLA-A, H241-4, H241-6, H4073-3, RFP (Unpublished STS's to genomic DNA developed by the Assignee of the present application.); D6S1281, P6116 (Murray, J. C. et al. *Science* 265:2049–2054 (1994)); HLA-F (Fullan, A. and Thomas, W. *Hum Molec Genet.* 3:2266 (1994)); MOG (Roth, M-P. et al. *Genomics* 28:241–250 (1995)); 1A2, 1E.4, 2B8, 18B4, 19D9, 24E.2, 63-1, 63-3, 3321-1, 4073-1, HB63-2, HB65-2, HB68-1, HB373-8, H241-5, H241-29, H731-1, H950-1, H950-2, H950-4, H950-6, H950-8, H3216-1, H4072-2, H4440-1, H4440-2, H5091-1 (CA repeats described in co-pending U.S. patent application Ser. No. 08/599,252, filed Feb. 9, 1996, which is a continuation-in-part of U.S. patent application Ser. No. 08/559,302, filed Nov. 15, 1995, which is a continuation-in-part of U.S. patent application Ser. No. 08/436,074, filed May 8, 1995, the disclosures of which are hereby incorporated by reference in their entirety.); D6S1001 (Stone, C. et al. *Hum Molec Genet* 3:2043-2046 (1994)); D6S105 (Weber, J. L. et al. *Nucl. Acids Res.* 19:968 (1991)).

The markers indicated at the top of FIG. 2 are those that are labeled with asterisks in FIG. 1. Other than marker 24d1, all of the markers indicated (i.e., 241-4, 96-1, 65-2, 65-1, 241-6, 241-29, 241-5, 63-3, 63-1, 63-2, 373-8, and 373-29) are CA repeat markers. The numbers indicated in the chart with respect to the CA repeat markers refers to the size of the allele upon PCR amplification and sizing of the resulting product on acrylamide gels. The 24d1 marker, as discussed above, is a single base-pair mutation as represented by the G to A base substitution that is present in affected chromosomes as illustrated in SEQ ID NO:29 and SEQ ID NO:30. The results of genotyping for each of the two chromosomes from the patients are indicated. DNA that is identical by descent is indicated by shading.

As will be appreciated, eight patient haplotypes displayed evidence of recombination events delineating the minimal HH region. The tract of DNA that is "identical by descent" on all of the ancestral HH chromosomes is between, but not including, markers 241-29 and 63-3. Genomic sequencing has determined this region to be approximately 250 Kb in size. This region includes markers 241-5 and 24d1. For definition of telomeric and centromeric boundaries, see FIG. 2, Patient HC75 and Patients HC2, HC22, HC50, HC87, HC91, HC125, and HC143.

4. Identification of cDNA 24

Based upon allelic association data, we delineated a region encompassed by YAC 241 as the region most likely to contain the HH gene. As one of our approaches to identify genes within the HH region, direct selection experiments were performed on YAC 241. Morgan, J. G. et al. *Nucl Acids Res* 20:5173-5179 (1992).

Briefly, YAC DNA was isolated by pulse-field gel electrophoresis, digested with Mbo I and linkers ligated to the resulting fragments. The DNA was then amplified by PCR using primers containing biotin on their 5' end. Similarly, cDNA was prepared from poly A+ RNA from fetal brain, small intestine and liver, digested with Mbo I, linkers ligated and amplified by PCR. The cDNA was 'blocked' with DNA clones representing human ribosomal RNA, histone genes as well as with repetitive DNA (Cot-1, Gibco).

Two rounds of solution hybridization were carried out to the prescribed value of Cot 100. The DNA fragments were cloned into pSP72 and sequenced. Four hundred and sixty-five clones were sequenced and arranged into 162 overlapping contigs, referred to herein as DS clones.

Representative DS clone sequences from each contig were searched against the public databases (NCBI) and interesting homologies were noted. One in particular, known as DS34 showed convincing homology to MHC Class I protein encoding genes. Small STSs were designed from each of the 162 contigs and the contigs were mapped in relation to the existing STS content map of the region.

Clones that mapped to the delineated minimal HH region of YAC 241 were given priority for further analysis. In conjunction with its homology to MHC Class I genes, DS34 mapped within our minimal region, and thus was considered a candidate for the HH gene. The STSs were subsequently used to determine which cDNA library was appropriate for obtaining full length cDNA clones.

Three directionally cloned plasmid-based cDNA libraries were employed (Gibco); brain, liver and testis. It was discovered that DS34 was present in all three libraries. Subsequently, DS34 was random primer labeled and used to screen colony lifts of cDNA libraries using standard procedures. Three clones were obtained from the testis library. The largest of these, 2.7 Kb, was designated cDNA24 and was sequenced completely on both strands.

5. Mutation Analysis of cDNA24

The candidate gene encompassed in cDNA24 was analyzed to detect mutations in the HH affected chromosomes as compared to unaffected chromosomes.

In connection with this work, patient DNA and RNA was obtained as follows. Lymphoblastoid cell lines from random and HH affected individuals were established by transformation of peripheral blood mononuclear cells with Epstein-Barr Virus. Chromosomal DNA was purified from these cells by standard methods (Maniatis et al. *Molecular Cloning—A Laboratory Manual* (2nd Ed., Cold Spring Harbor Laboratory Press, New York (1989))). PolyA+ RNA was purified using Fast Track (Invitrogen).

Mutation analysis was accomplished as follows. Initial searching for the HH mutation in cDNA24 was accomplished through RT-PCR (reverse transcription-polymerase chain reaction, Dracopoli, N. et al. eds. *Current Protocols in Human Genetics* (J. Wiley & Sons, New York (1994)) method. First, from the genotype analysis, homozygous HH patients with the ancestral haplotype were identified (see previous sections). First strand cDNAs were synthesized through use of Superscript reverse transcriptase (Life Technologies) using polyA+ RNA from transformed lymphoblastoid cell lines from two homozygous ancestral patients (HC9 and HC14) and those from two unaffected individuals (NY8 and CEPH 11840) as templates.

From these first strand cDNAs, coding regions corresponding to the cDNA24 sequence were amplified into three overlapping PCR products (designated herein as A, B, and C) to facilitate efficient amplification and sequencing. A nested set of primers were used to increase specificity in generating the three products. The primers utilized are shown in Table 1:

TABLE 1

| PCR Product | Name | Primer Set for 1st Nested PCR | Name | Primer Set for 2nd Nested PCR |
|---|---|---|---|---|
| "A" | P17 | 5'-CAA AAG AAG CGG AGA TTT AAC G-3' | P19 | 5'-AGA TTT AAC GGG GAC GTG C-3' |
|  | P18 | 5'-AGA GGT CAC ATG ATG TGT CAC C-3' | P20 | 5'-AGG AGG CAC TTG TTG GTC C-3' |
| "B" | P5 | 5'-CTG AAA GGG TGG GAT CAC AT-3' | P7 | 5'-AAA ATC ACA ACC ACA GCA AAG-3' |
|  | P6 | 5'-CAA GGA GTT CGT CAG GCA AT-3' | P8 | 5'-TTC CCA CAG TGA GTC TGC AG-3' |
| "C" | P9 | 5'-CAA TGG GGA TGG GAC CTA C-3' | P11 | 5'-ATA TAC GTG CCA GGT GGA GC-3' |
|  | P10 | 5'-CCT CTT CAC AAC CCC TTT CA-3' | P12 | 5'-CAT AGC TGT GCA ACT CAC ATC A-3' |

P17 (SEQ ID NO:31); P19 (SEQ ID NO:32); P18 (SEQ ID NO:33); P20 (SEQ ID NO:34), P5 (SEQ ID NO:18); P7 (SEQ ID NO:35); P6 (SEQ ID NO:19); P8 (SEQ ID NO:36); P9 (SEQ ID NO:37); P11 (SEQ ID NO:38); P10 (SEQ ID NO:39); and P12 (SEQ ID NO:40).

Amplified DNA products (PCR-products) were purified using gelase (Epicentre), and DNA sequences of these PCR-fragments were determined by the dideoxy chain termination method using fluorescently labeled dideoxy nucleotides on an ABI 377 DNA sequencer.

Comparison of DNA sequences derived from these PCR-fragments identified a single nucleotide change in the cDNA24 coding region as represented by SEQ ID NO:29 and SEQ ID NO:30 at nucleotide 845. (Note, the first nucleotide of the open reading frame was counted as nucleotide 1. See FIG. 4). The nucleotide at this position in two unaffected individuals was a G, while two HH affected individuals had an A at this position.

This mutation was designated as 24d1. The allele containing a G at this position was named as 24d1(G) and the allele containing an A in this position was named 24d1(A). The mutation causes an amino acid change from a cysteine (Cys282) to a tyrosine. This cysteine residue is conserved in all the known Class I MHC molecules and contributes a sulfur to the formation of a disulfide bridge that is present in the immunoglobulin constant region like domain (Ig domain, Gussow et al. *Immunogenetics* 25:313–322 (1987);

Bjorkman and Parham *Ann Rev Biochem* 59:253 (1990)). In the case of Class I MHC molecules, it has been shown that a similar change in the reciprocal cysteine involved in the disulfide bridge abolishes the function of the protein by causing a defect in cell surface expression (Miyazaki et al. *Proc. Natl. Acad. Sci. U.S.A.* 83:757–761 (1986)). Thus, due to the high degree of conservation seen in the structure, it is likely that the 24d1 mutation would interfere with the function of cDNA 24 protein products.

The genomic sequence surrounding the 24d1 mutation is provided in SEQ ID NO:29 (unaffected 24d1(G) allele) and SEQ ID NO:30 (affected 24d1(A) allele).

The frequency of the mutant 24d1(A) allele and the normal 24d1(G) allele was determined in random chromosomes and affected chromosomes through use of an oligonucleotide ligation assay (OLA assay). See Nickerson et al. *Proc. Natl. Acad. Sci. U.S.A.* 87:8923-8927 (1990). Chromosomal DNA from these individuals was prepared from either a lymphoblastoid cell line or peripheral blood cells. First, DNA corresponding to exon 4 was amplified by PCR using primers designed against intron DNA sequences flanking exon 4. See FIG. 6 which provides the precise location of the sequences used for primer design. The presence of the 24d1(A) allele or the 24d1(G) allele was determined by OLA using the oligonucleotides outlined in FIG. 5. FIG. 5 shows the sequences of preferred primers used for amplification and analysis of the above base mutation. The amplification primers for 24d1 are labeled 24d1.P1 (SEQ ID NO:13) and 24d1.P2 (SEQ ID NO:14). The oligonucleotides used in the sequence determination by OLA for 24d1 are designated 24d1.A (SEQ ID NO:15), 24d1.B (SEQ ID NO:16), and 24d1.X (SEQ ID NO:17). As indicated in the sequences shown, "bio" indicates biotin coupling, "p" indicates 5'-phosphate, and "dig" indicates coupled digoxigenin.

The result from this OLA assay with 164 HH affected individuals and 134 unaffected random individuals is shown in Table 2.

TABLE 2

Frequencies of Alleles as % of Chromosomes Tested

| | Affected Chromosomes (N = 328) | Random Chromosomes (N = 268) |
|---|---|---|
| 24d1 "A" | 86% | 4% |
| 24d1 "G" | 14% | 96% |

The 24d1(A) mutation occurs in 86% of the chromosomes from HH affected individuals (affected chromosomes) as compared to 4% in the chromosomes from random individuals (random chromosomes). This approximates the estimated frequency of the ancestral HH mutation in the general population. Among these 164 affected individuals, 137 were homozygous for the 24d1(A) allele and 9 were heterozygous for the 24d1(A) and the 24d1(G) alleles, while the remaining 18 were homozygous for the 24d1(G) allele. The distribution of homozygotes and heterozygotes for the 24d1 alleles significantly deviates from that expected by Hardy-Weinberg equilibrium, suggesting the possibility of either mutant alleles that complement one another or genetic heterogeneity. Regardless of this fact, 24d1 homozygosity provides identification of 84% of HH patients in our sample.

In addition to the 24d1 mutation, other sequence variants were also detected within certain subpopulations of patients. In this regard, sequence analysis of the cDNA24 gene was extended to the remaining individuals who are either 24d1 (G) homozygotes or 24d1(A)/24d1(G) heterozygotes. Eighteen 24d1(G) homozygous HH patient and nine 24d1 heterozygotes patients were analyzed. All the exons that contain the cDNA24 open reading frame were amplified from these individuals through the use of PCR primers directed against introns and exons. DNA sequences of these PCR products were determined by dideoxy chain termination methods. This analysis identified two additional sequence variants (24d2 and 24d7) in the coding region of cDNA24.

The first additional variant, 24d2, occurs at nucleotide 187. (Note, the first nucleotide of the open reading frame was counted as nucleotide 1. See FIG. 4). The two alleles of this variant are 24d2(C) (C at this position) and 24d2(G) (G at this position). CDNA24 as well as NY8 and CEPH 11840 were homozygous for the 24d2(C) allele, while DNAs from some patients (HC74, HC82 and others) were 24d2(C)/24d2 (G) heterozygous. The 24d2(C) allele encodes a histidine (His63) while 24d2(G) encodes an aspartic acid, thus creating an amino acid change in the presumed peptide binding domain of the protein product. As with 24d1, changes to certain amino acids in the peptide binding domains of MHC Class I proteins can also disrupt intracellular transport and assembly (Salter, *Immunogenetics* 39:266-271 (1994)).

The genomic sequence surrounding the variant for 24d2 (C) and 24d2(G) is provided below:
24d2(C):
AGCTGTTCGTGTTCTATGATCATGAGAGTCGC-CGTGTGGA (SEQ ID NO:41)
24d2(G):
AGCTGTTCGTGTTCTATGATGATGAGAGTCGC-CGTGTGGA (SEQ ID NO:42)

The frequency of the 24d2 mutant allele versus the normal allele was determined through OLA as described above. The results from the OLA assays are shown in Table 3.

TABLE 3

Frequencies of Alleles as % of Chromosomes Tested

| | Affected Chromosomes (N = 328) | Random Chromosomes (N = 158) |
|---|---|---|
| 24d2 "C" | 95% | 82% |
| 24d2 "G" | 5% | 18% |

As shown in Table 3, the 24d2(G) allele occurs in 5% of the chromosomes from HH affected individuals (affected chromosomes) and in 18% of the chromosomes from random individuals (random chromosomes). The frequency of the 24d2(G) allele in the patients was lower than that of random chromosomes because this allele was associated with some of the nonancestral chromosomes and the majority of the HH patient chromosomes were ancestral. The remainder of the chromosomes had the 24d2(C) allele. When one looks at the distribution of the 24d2(G) allele containing chromosomes within the patient population, one notices an enrichment of the 24d2(G) allele in 24d1 heterozygotes. Eighty-nine percent or 8 out of 9 heterozygotes for 24d1 have the 24d2(G) allele as compared to the expected 18%. Thus, the 24d2(G) allele is enriched in 24d1 heterozygous patients indicating that the 24d2 mutation has a role in HH disease.

A third nucleotide change was identified at nucleotide 193 in one patient (HC43) and was named 24d7. (Note, the first nucleotide of the open reading frame was counted as nucleotide 1. See FIG. 4). All other patients analyzed, as well as random controls, including NY8 and CEPH 11840 had an allele 24d7(A) (A at this position), while HC43 was a 24d7(A)/24d7(T) heterozygote. The 24d7(A) allele encodes a serine (Ser65) while the 24d7(T) allele changes this to a cysteine codon, also within the presumed peptide binding domain of the cDNA 24 protein product.

The genomic sequence surrounding the polymorphism for 24d7(A) and 24d7(T) is provided below:

24d7(A):

TGTTCTATGATCATGAGAGTCGCCGTGTGGAG (SEQ ID NO:43)

24d7(T):

TGTTCTATGATCATGAGTGTCGCCGTGTGGAG (SEQ ID NO:44)

The frequency of the 24d7 mutant allele versus normal allele was determined through OLA as described above. The results from the OLA assays are shown in Table 4.

TABLE 4

Frequencies of Alleles as % of Chromosomes Tested

|         | Affected Chromosomes (N = 266) | Random Chromosomes (N = 156) |
|---------|---------|---------|
| 24d7 "A" | 99.6% | 97% |
| 24d7 "T" | 0.4% | 3% |

In Table 4, The 24d7(T) allele was observed in only one chromosome present in the patient sample (HC43) (0.4%) and present in four chromosomes from the unaffected individuals (3%). The presence of the 24d7(T) allele shows no increase in risk of acquiring HH and thus may only be a polymorphic variant within the population.

B. Characterization of the HH Gene

1. Sequence

The complete sequence of cDNA24 (of which the coding region is shown in FIG. 4) was used to search public databases (NCBI) for homology to known gene sequences using the BlastX search algorithm. Substantial homology to MHC Class I molecules from a variety of species was obtained.

Next, the sequence was analyzed for the existence of open-reading frames (ORF's). The largest ORF, as shown in FIG. 4, encodes a polypeptide of 348 amino acids with a predicted molecular mass of approximately 38 KD. As will be appreciated, the molecular weight/mass can vary due to possible substitutions or deletions of certain amino acid residues. In addition, the molecular weight/mass of the polypeptide can vary due to the addition of carbohydrate moieties and in connection with certain phosphorylation events and other post-translational modifications. The remainder of the cDNA, 1.4 Kb appears to be non-coding; one poly A addition site (AATAAA) is present 20 bp upstream of the poly A tail (not shown in FIG. 4).

Figure 7:
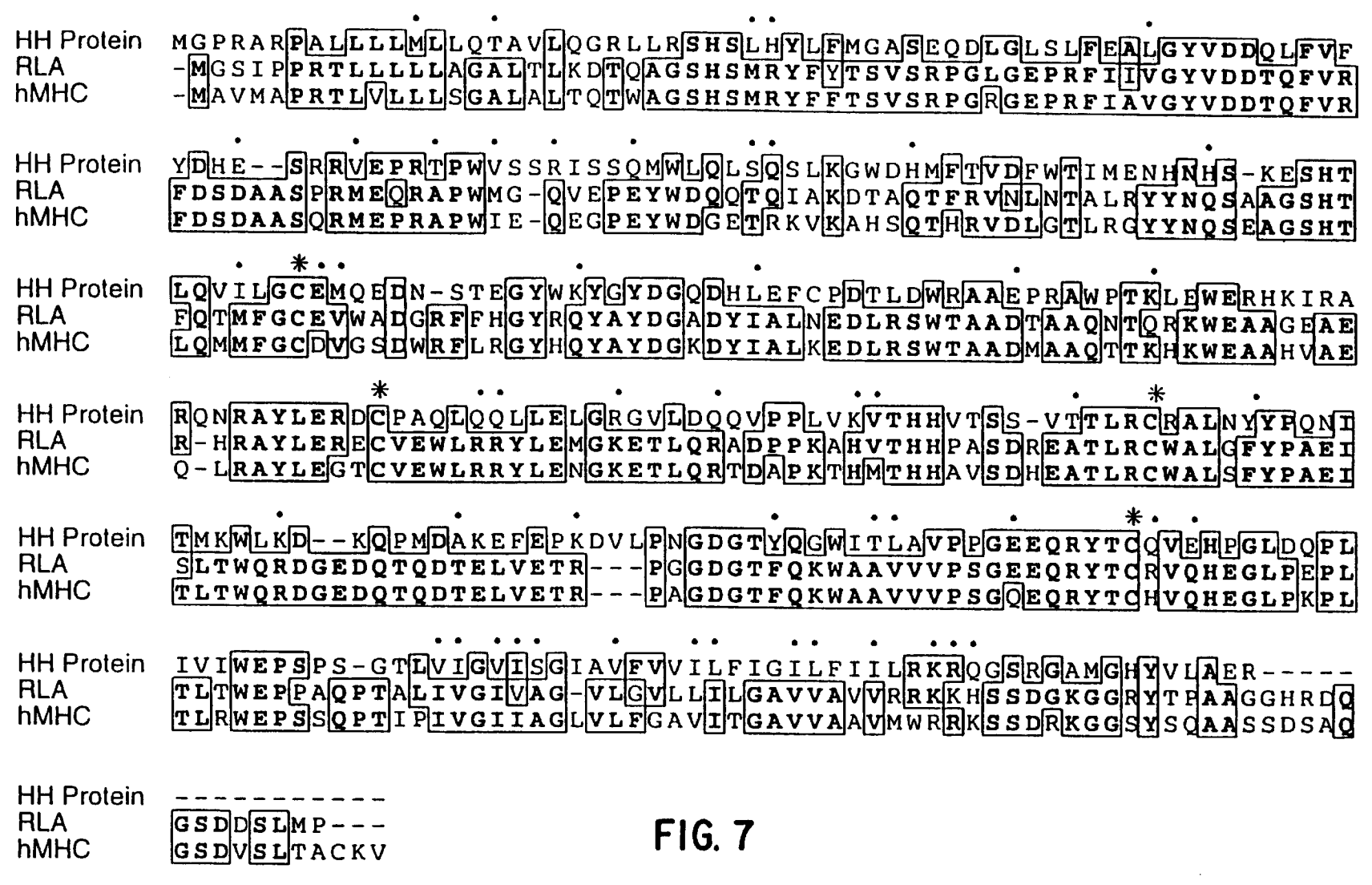

A search of translated public database (NCBI) using a six way translation of cDNA24 showed significant homology between cDNA 24 and previously cloned MHC proteins. The search revealed 39% identity and 58% similarity of the amino acid residues. Besides MHC Class I proteins, the HH gene product shows similarity to other proteins known to contain motifs related to the immunoglobulin constant region, such as β-2-microglobulin and zinc-α-2-glycoprotein. See Bjorkman, P. and Parham, P. *Ann Rev Biochem* 59:253 (1990). A multiple sequence alignment was carried out between several MHC Class I proteins (FIG. 7). The results indicate that the homology between cDNA 24 and MHC extends throughout the cDNA 24 protein, including the peptide-binding region, immunoglobulin-like region, transmembrane region and cytoplasmic region. Of particular interest is the conservation of the position of several cysteine residues which function in protein folding via disulfide bonds.

cDNA 24 tissue expression was determined by probing polyA+ RNA Northern blots (Clontech). One major transcript of approximately 4.4 Kb was observed in all of the 16 tissues tested including small intestine and liver.

The genomic region corresponding to cDNA 24 was cloned and sequenced. cDNA 24 is comprised of apparently seven exons, covering approximately 11 Kb of sequence. The putative seventh exon is completely non-coding and contains one poly (A)+ addition signal. In the region of the predicted start site of transcription, there are no consensus CAAT or TATA boxes, nor are there any start like βGAP-like sequences recently suggested by Rothenberg and Voland, supra (1996). One CpG island was found to overlap the first exon and extend into the first intron. Within this island are the consensus cis-acting binding sites for the transcription factors Sp1 (2 sites) and AP1 (1 site) (McVector software, Oxford Molecular). The lack of any recognizable TATA boxes and the presence of Sp1 and AP2 binding sites is consistent with the low level of transcription associated with the gene.

2. Structure/Function of the HH Gene Product

The predicted translation product of cDNA 24, herein referred to as the HH gene and HH gene product or HH protein, was aligned to other MHC proteins for which there was a high degree of homology at the amino acid level (FIG. 7). MHC Class I proteins are comprised of several distinct domains: peptide binding domains (α1 and α2), immunoglobulin like domain (α3), a transmembrane region, and a small cytoplasmic portion. The HH gene product shows homology throughout all four of these domains. Further confirmation of the structural relationship between the HH gene product and MHC Class I molecules was obtained through analysis of the primary sequence using software capable of structural comparison of polypeptides, like MCVECTOR software (Oxford Molecular).

The HH gene product is similar to MHC Class 1 molecules when comparing hydrophilicity, surface probability, and secondary structure. A conserved structural feature of Class 1 molecules is the presence of several intradomain disulfide bonds between positions Cys-101 and Cys-164 in the α2 helix and between Cys-203 and Cys-259 in the α3 helix. This domain structure is conserved between all Class 1 molecules. The disulfide bond in the α3 helix forms the interface through which the molecule interacts with the β-2-microglobulin protein, a protein which associates with MHC Class 1 molecules in the endoplasmic reticulum and functions as a molecular chaperone.

The HH protein possesses all four cysteine residues in conserved positions common to MHC Class I molecules. This data indicates a structural relationship with MHC Class I Molecules and a potential interaction with β-2-microglobulin (or a related protein) as well.

It has been demonstrated that when the cysteine at position 203 is mutated, thus disrupting the disulfide bridge that is formed between Cys-203 and Cys-259, intracellular transport of the mutated protein is blocked. See Miyazaki et al. supra (1986). As will be appreciated, the mutation (24d1) of the present invention corresponds to the reciprocal cysteine (Cys-259; Cys-282 in the HH protein) in the disulfide bridge that was demonstrated by Miyazaki et al. to abolish intracellular transport. Thus, it is predicted that the 24d1 mutation ablates expression of the HH protein on cell surfaces.

Sequence studies of MHC Class I molecules have shown that these molecules are among the most polymorphic proteins known to date. The majority of this variation is located in the α1 and α2 domains of the molecule. In contrast, the HH gene product displays little polymorphism in this region. In this respect, the HH protein is more similar to the non-classical MHC class of proteins which show little or no allelic variation. The functions of the non-classical MHC Class I proteins, such as HLA-E, F, and G proteins, are unknown, although HLA-G may play a role in maternal/fetal immune interactions. Campbell, R. D. and Trousdale, J. *Immunology Today* 14:349 (1993).

Therefore, the HH protein appears to differ from MHC Class I molecules in one important respect. Although it has maintained all of the structural hallmarks of MHC Class I molecules, it does not appear to be polymorphic and has presumably evolved a different function. This function appears to be participation in the control of body iron levels, for example, through the direct binding of free iron, binding of other iron-bound proteins, or signaling involved in regulation of iron levels. Iron-bound proteins or other proteins involved in signaling could associate with the HH protein in a manner similar to β-2-microglobulin or could be bound in the peptide-binding region of the protein.

In addition, the protein could exert its effects by indirectly regulating iron adsorption through intercellular signaling, i.e., T-cell activation and subsequent specific cell proliferation via cytokine release. Alternatively, the expression of the HH protein could be regulated by iron or cytokines. As such, its interaction with other signaling molecules or receptors, such as Tfr, would be modulated. Directly related to our discovery of the gene responsible for HH is the data of de Sousa et al. (*Immun Lett* 39:105-111 (1994)). Analysis of previously constructed, β-2-microglobulin knockout mice indicated that mice homozygous for the defect progressively accumulated iron in a manner indistinguishable from human hemochromatosis. These mice also mimic an additional phenotype observed in HH patients, an abnormally low number of CD8+ T cells. Therefore, β-2-microglobulin knock-out mice possess two characteristics of human HH, iron loading of the internal organs and a defective T cell repertoire. Clearly, human β-2-microglobulin which maps to Chromosome 15 is not responsible for HH. However, β-2-microglobulin knock-out mice could phenocopy HH by preventing the associated murine HH homolog of cDNA 24 from assuming its functional structure and presentation on the surface of cells.

An important link between the HH protein and iron metabolism has been demonstrated. One of the major mechanisms by which cells and tissues uptake iron is via receptor-mediated endocytosis of iron-loaded transferrin. Transferrin itself binds to cell surface receptors (transferrin receptors, Tfr) which are responsible for iron uptake. Transferrin receptors are regulated by a variety of physiologic stimuli including cytokines and iron. It has now been demonstrated that the HH protein interacts directly with the Tfr in the plasma membrane. Labeling of cell-surface proteins by biotinylation followed by immunoprecipitation with HH protein specific antibodies demonstrates that Tfr physically interacts with the HH protein. Co-immunoprecipitation experiments by first immunoprecipitating with HH protein antibodies followed by Western blotting with Tfr antibodies corroborates these results. In contrast, the HH protein containing the 24d1 mutation fails to interact with the Tfr. The normal HH protein/Tfr interaction could regulate the activity of the Tfr to transport iron-bound transferrin either by change in receptor affinity, receptor number (including expression), or by a change in the rate of receptor internalization and recycling. The HH protein containing the 24d1 mutation would then lead to unregulated iron metabolism and HH disease by failing to interact with the Tfr and modulating its activity.

Thus, the HH gene encodes a protein with striking similarity to MHC Class I proteins. The gene product has maintained a structural feature essential for proper and functional recognition of a chaperone protein (β-2-microglobulin) whose disruption in mice causes a phenocopy of HH disease. The HH protein interacts with β2-microglobulin and the Tfr and is expressed on the cell-surface. When mutated as in 24d1, the interactions with β2-microglobulin and Tfr are lost and the protein no longer is located on the cell-surface.

3. Protein Purification

The HH protein can be purified by one of several methods which have been selected based upon the molecular properties revealed by its sequence and its homology to MHC Class I molecules. Since the molecule possesses properties of an integral membrane protein, i.e. contains a transmembrane domain, the protein must first be isolated from the membrane fraction of cells using detergent solubilization. A variety of detergents useful for this purpose are well known in the art.

Once solubilized, the HH protein can be further purified by conventional affinity chromatography techniques. The conventional approaches of ion exchange, hydrophobic interaction, and/or organomercurial chromatographies can be utilized. These methodologies take advantage of natural features of the primary structure, such as: charged amino acid residues, hydrophobic transmembrane domains, and sulfhydryl-containing cysteine residues, respectively. In the affinity chromatography approach use is made of immunoaffinity ligands or of the proposed interaction of the HH protein with β-2-microglobulin, calnexin or similar molecules. In the former, the affinity matrix consists of antibodies (polyclonal or monoclonal) specific to the HH protein coupled to an inert matrix. The production of antibodies specific to the HH protein are described in Section (III)(A)(3), entitled "Antibodies". In the latter method, various ligands which are proposed to specifically interact with the HH protein based on its homology with MHC Class I molecules could be immobilized on an inert matrix. For example, β-2-microglobulin, β-2-microglobulin-like molecules, or other specific proteins such as calnexin or calnexin-like molecules, and the like, or portions and/or fragments thereof, can be utilized. General methods for preparation and use of affinity matrices are well known in the art.

Criteria for the determination of the purity of the HH protein include those standard to the field of protein chemistry. These include N-terminal amino acid determination, one and two-dimensional polyacrylamide gel electrophoresis, and silver staining. The purified protein is useful for use in studies related to the determination of secondary and tertiary structure, as aid in drug design, and for in vitro study of the biological function of the molecule.

III. Applications

A. HH Screening

With knowledge of the primary mutation of the HH gene as disclosed herein, screening for presymptomatic homozygotes, including prenatal diagnosis, and screening for heterozygotes can be readily carried out.

1. General

There are at least four levels at which the diagnostic information from the HH gene can be used. The first is to assist in the medical diagnosis of a symptomatic patient. In this application, a patient with a high index of suspicion for being affected with HH could be tested with the gene-based diagnostic. A positive result would show that the individual was homozygous for the common HH mutation. This would provide a rapid and non-invasive confirmation that the individual corresponded to the fraction of the population homozygous for this mutation. Such a result would help rule out other causes of iron overload in that individual. In the case of a heterozygote or compound heterozygote for 24d1 and 24d2, this individual may also be affected with HH.

The second level of application would be in first degree relatives of newly diagnosed probands. Currently recommended medical practice is to screen all such first degree relatives, as they are at a higher risk for disease and, if identified, could benefit from therapeutic intervention.

The third level of screening would be in individuals afflicted with diseases that are known to be sequelae of HH disease. Such diseases include cirrhosis of the liver, diabetes, arthritis, reproductive dysfunction, and heart disease. It has been estimated, for example, that as many as 1% of individuals with diabetes may be so afflicted because of HH disease. In addition, other conditions such as sporadic porphyria cutanea tarda can be screened for using an HH gene mutation diagnosis. When secondary to HH disease, some of the pathology of these diseases can be reversed upon phlebotomy therapy. Furthermore, it has been disclosed that the potential for hemochromatosis interferes with the effectiveness of interferon treatment of hepatitis C (Bacon, B. *Abstracts of the Fifth Conference of the International Association for the Study of Disorders of Iron Metabolism* 15–16 1995)). Therefore, it will be beneficial to perform screening with gene-based diagnostics in these disease populations.

The fourth level of screening is to screen the general population for homozygotes and, potentially, heterozygotes. Several cost-benefit analyses have suggested that there is value in such screenings for the identification of presymptomatic individuals. Once identified, such individuals could be targeted for preventative phlebotomy or treatment with the therapeutic compositions of the invention.

2. Nucleic Acid Based Screening

Individuals carrying mutations in the HH gene may be detected at either the DNA, the RNA, or the protein level using a variety of techniques that are well known in the art. The genomic DNA used for the diagnosis may be obtained from body cells, such as those present in peripheral blood, urine, saliva, bucca, surgical specimen, and autopsy specimens. The DNA may be used directly or may be amplified enzymatically in vitro through use of PCR (Saiki et al. *Science* 239:487-491 (1988)) or other in vitro amplification methods such as the ligase chain reaction (LCR) (Wu and Wallace *Genomics* 4:560–569 (1989)), strand displacement amplification (SDA) (Walker et al. *Proc. Natl. Acad. Sci. U.S.A.* 89:392-396 (1992)), self-sustained sequence replication (3SR) (Fahy et al. *PCR Methods Appl.* 1:25–33 (1992)), prior to mutation analysis. The methodology for preparing nucleic acids in a form that is suitable for mutation detection is well known in the art.

The detection of mutations in specific DNA sequences, such as the HH gene, can be accomplished by a variety of methods including, but not limited to, restriction-fragment-length-polymorphism detection based on allele-specific restriction-endonuclease cleavage (Kan and Dozy *Lancet* ii:910–912 (1978)), hybridization with allele-specific oligonucleotide probes (Wallace et al. *Nucl Acids Res* 6:3543–3557 (1978)), including immobilized oligonucleotides (Saiki et al. *Proc. Natl. Acad. Sci. U.S.A.* 86:6230–6234 (1989)) or oligonucleotide arrays (Maskos and Southern *Nucl Acids Res* 21:2269–2270 (1993)), allele-specific PCR (Newton et al. *Nucl Acids Res* 17:2503–2516 (1989)), mismatch-repair detection (MRD) (Faham and Cox *Genome Res* 5:474–482 (1995)), binding of MutS protein (Wagner et al. *Nucl Acids Res* 23:3944–3948 (1995), denaturing-gradient gel electrophoresis (DGGE) (Fisher and Lerman et al. *Proc. Natl. Acad. Sci. U.S.A.* 80:1579–1583 (1983)), single-strand-conformation-polymorphism detection (Orita et al. *Genomics* 5:874–879 (1983)), RNAase cleavage at mismatched base-pairs (Myers et al. *Science* 230:1242 (1985)), chemical (Cotton et al. *Proc. Natl. Acad. Sci. U.S.A.* 85:4397–4401 (1988)) or enzymatic (Youil et al. *Proc. Natl. Acad. Sci. U.S.A.* 92:87–91 (1995)) cleavage of heteroduplex DNA, methods based on allele specific primer extension (Syvanen et al. *Genomics* 8:684–692 (1990)), genetic bit analysis (GBA) (Nikiforov et al. *Nucl Acids Res* 22:4167–4175 (1994)), the oligonucleotide-ligation assay (OLA) (Landegren et al. *Science* 241:1077 (1988)), the allele-specific ligation chain reaction (LCR) (Barrany Proc. Natl. Acad. Sci. U.S.A. 88:189–193 (1991)), gap-LCR (Abravaya et al. *Nucl Acids Res* 23:675–682 (1995)), and radioactive and/or fluorescent DNA sequencing using standard procedures well known in the art.

In addition to the genotype described above, as described in co-pending PCT application WO 96/35802 published Nov. 14, 1996, genotypes characterized by the presence of the alleles 19D9:205; 18B4:235; 1A2:239; 1E4:271; 24E2:245; 2B8:206; 3321-1:98 (denoted 3321-1:197 therein); 4073-1:182; 4440-1:180; 4440-2:139; 731-1:177; 5091-1:148; 3216-1:221; 4072-2:170 (denoted 4072-2:148 therein); 950-1:142; 950-2:164; 950-3:165; 950-4:128; 950-6:151; 950-8:137; 63-1:151; 63-2:113; 63-3:169; 65-1:206; 65-2:159; 68-1:167; 241-5:108; 241-29:113; 373-8:151; and 373-29:113, alleles D6S258:199, D6S265:122, D6S105:124, D6S306:238, D6S464:206; and D6S 1001:180, and/or alleles associates with the HHP-1, the HHP-19 or HHP-29 single base-pair polymorphisms can also be used to assist in the identification of an individual whose genome contains the common HH mutation. For example, the assessing step can be performed by a process which comprises subjecting the DNA or RNA to amplification using oligonucleotide primers flanking the base-pair polymorphism 24d1 and/or 24d2 and oligonucleotide primers flanking at least one of the base-pair polymorphisms HHP-1, HHP-19, and HHP-29, oligonucleotide primers flanking at least one of the microsatellite repeat alleles, or oligonucleotide primers for any combination of polymorphisms or microsatellite repeat alleles thereof.

Oligonucleotides useful in diagnostic assays are typically at least 8 consecutive nucleotides in length, and may range upwards of 18 nucleotides in length. Such oligonucleotides can be derived from either the HH genomic or cDNA sequences. Preferred oligonucleotides of at least 8 nucleotides in length include 1-46, 48-123; 120-369; 365-394; 390-540; 538-646; 643-1004; 1001-1080; 1083-1109; 1106-1304; 1301-1366; 1363-1386; 1389-1514; 1516-1778; 1773-1917; 1921-2010; 2051-2146; 2154-2209; 2234-2368; 2367-2422; 2420-2464; 2465-2491; 2488-2568; 2872-2901; 2902-2934; 2936-2954; 2449-3001; 3000-3042; 3420-3435; 3451-3708; 3703-3754; 3750-3770; 3774-3840; 3840-3962; 3964-3978; 3974-3992; 3990-4157; 4153-4251; 4257-4282; 4284-4321; 4316-4333; 4337-4391; 4386-4400; 4398-4436; 4444-4547; 4572-4714; 4709-4777; 5165-5397; 5394-6582; 5578-5696; 5691-5709; 5708-5773; 5773-5816; 5818-5849; 5889-6045; 6042-6075; 6073-6108; 6113-6133; 6150-6296;

6292-6354; 6356-6555; 6555-6575; 6575-6616; 6620-6792; 6788-6917; 6913-7027; 7023-7061; 7056-7124; 7319-7507; 7882-8000; 7998-8072; 8073-8098; 9000-9037; 9486-9502; 9743-9811; 9808-9831; 9829-9866; 9862-9986; 9983-10075; 10072-10091; 10091-10195; 10247-10263; 10262-10300; 10299-10448; 10448-10539; 10547-10564; 10580-10612; 10608-10708; 10703-10721; 10716-10750; 10749-10774; 10774-10800; and 10796-10825 of SEQ ID NO:1, 3, 5, or 7.

Preferred oligonucleotides of at least 9 nucleotides in length include 1-47; 47-124; 119-370; 364-395; 389-541; 537-647; 642-1005; 1000-1081; 1082-1110; 1105-1305; 1300-1367; 1362-1387; 1388-1515; 1515-1918; 1920-2011; 2050-2147; 2153-2210; 2233-2369; 2366-2423; 2419-2465; 2464-2492; 2487-2569; 2871-2935; 2935-3002; 2999-3043; 3419-3436; 3450-3755; 3749-3771; 3773-3841; 3839-3963; 3963-3979; 3973-3993; 3989-4158; 4152-4252; 4256-4283; 4283-4334; 4336-4401; 4397-4437; 4443-4548; 4571-4778; 5164-5398; 5393-5583; 5577-5710; 5707-5774; 5772-5817; 5817-5850; 5888-6046; 6041-6076; 6072-6109; 6112-6134; 6149-6355; 6355-6556; 6554-6576; 6574-6793; 6787-7125; 7318-7508; 7881-8001; 7997-8073; 8072-8099; 8999-9038; 9485-9503; 9742-9812; 9807-9832; 9828-9867; 9861-9987; 9982-10076; 10071-10092; 10090-10196; 10246- 10264; 10261-10301; 10298-10449; 10447-10540; 10546-10565; 10579-10751; 10748-10775; 10773-10801; and 10795-10825 of SEQ ID NO:1, 3, 5, or 7.

Preferred oligonucleotides of at least 10 nucleotides in length include 1-48; 46-125; 118-1006; 999-1082; 1081-1111; 1104-1306; 1299-1368; 1361-1388; 1387-1516; 1514-1919; 1919-2012; 2049-2148; 2152-2211; 2232-2370 2365-2424; 2418-2466; 2463-2493; 2486-2570; 2870-2936; 2934-3003; 2998-3044; 3418-3437; 3449-3772; 3772-3842; 3838-3964; 3962-3994; 3988-4284; 4282-4335; 4335-4402; 4396-4438; 4442-4549; 4570-4779; 5163-5711; 5706-5775; 5771-5818; 5816-5851; 5867-6047; 6040-6077; 6071-6110; 6111-6135; 6148-6356; 6354-6577; 6573-7126; 7317-7509; 7880-8074; 8071-8100; 8998-9039; 9484-9504; 9741-9813; 9806-9833; 9827-9988; 9981-10093; 10089-10197; 10245-10265; 10260-10302; 10297-10450; 10446-10541; 10545-10566; 10578-10752; 10747-10776; and 10772-10825 of SEQ ID NO:1, 3, 5, or 7.

Preferred oligonucleotides of at least 11 nucleotides in length include 1-49; 45-1389; 1386-1517, 1513-1920; 1918-2013; 2048-2149; 2151-2212; 2231-2371; 2364-2425; 2417-2467; 2462-2571; 2869-2937; 2933-3004; 2997-3045; 3417-3438; 3448-3773; 3771-3843; 3837-3965; 3961-3995; 3987-4285; 4281-4336; 4334-4403; 4395-4439; 4441-4550; 4569-4780; 5162-5712; 5705-5776; 5770-5819; 5815-5852; 5886-6111; 6100-6136; 6147-6357; 6353-6578; 6572-7127; 7316-7510; 7879-8075; 8070-8101; 8997-9040; 9483-9505; 9740-10198; 10244-10266; 10257-10303; 10296-10451; 10445-10542; 10544-10567; 10577-10753; 10746-10777; and 10771-10825 of SEQ ID NO:1, 3, 5, or 7.

Preferred oligonucleotides of at least 12 nucleotides in length include 1-50, 44-1390; 1385-1518; 1512-1921; 1917-2014; 2047-2150; 2150-2213; 2230-2372; 2363-2468; 2461-2572; 2868-2938; 2932-3005; 2996-3046; 3416-3439; 3447-3774; 3770-3844; 3836-3966; 3960-4286; 4280-4337; 4333-4440; 4440-4551; 4568-4781; 5161-5713; 5704-5777; 5669-5820; 5814-5853; 5885-6112; 6109-6137; 6146-6358; 6352-6579; 6571-7128; 7315-7511; 7878-8076; 8069-8102; 8996-9041; 9482-9506; 9739-10199; 10243-10267; 10256-10304; 10295-10452; 10444-10543; 10543-10566; 10576-10754; 10745-10778; and 10770-10825 of SEQ ID NO:1, 3, 5, or 7.

Preferred oligonucleotides of at least 13 nucleotides in length include 1-51; 43-1391; 1384-1519; 1511-1922; 1916-2015; 2046-2151; 2149-2214; 2229-2469; 2460-2573; 2867-2939; 2931-3047; 3415-3440; 3446-3775; 3769-3845; 3835-3967; 3959-4287; 4279-4338; 4332-4441; 4439-4552; 4567-4782; 5160-5778; 5668-5821; 5813-5854; 5884-6113; 6108-6138; 6145-6359; 6351-6580; 6570-7129; 7314-7512; 7877-8077; 8068-8103; 8995-9042; 9481-9507; 9738-10200; 10242-10453; 10443-10544; 10542-10567; 10575-10779; and 10769-10825 of SEQ ID NO:1, 3, 5, or 7.

Preferred oligonucleotides of at least 14 nucleotides in length include 1-52; 42-1392; 1383-1520; 1510-1923; 1915-2016; 2045-2152; 2148-2215; 2228-2574; 2866-2940; 2930-3048; 3414-3441; 3445-3776; 3768-3968; 3959-4288; 4278-4339; 4331-4442; 4438-4553; 4566-4783; 5159-5822; 5812-5855; 5883-6114; 6107-6139; 6144-6360; 6350-6581; 6569-7130; 7313-7513; 7876-8078; 8067-8104; 8994-9043; 9480-9508; 9737-10201; 10241-10454; 10442-10545; 10541-10568; and 10574-10825 of SEQ ID NO:1, 3, 5, or 7.

Preferred oligonucleotides of at least 15 nucleotides in length include 1-53; 41-1393; 1382-1521; 1509-1924; 1914-2017; 2044-2153; 2147-2216; 2227-2575; 2865-2942; 2929-3049; 3413-3442; 3444-3777; 3767-3969; 3958-4289; 4277-4340; 4330-4443; 4437-4554; 4565-4784; 5158-5823; 5811-5856; 5882-6115; 6106-6140; 6143-6361; 6349-7131; 7312-7514; 7875-8105; 8993-9044; 9479-9509; 9736-10202; 10240-10546; 10540-10569; and 10573-10825 of SEQ ID NO:1, 3, 5, or 7.

Preferred oligonucleotides of at least 16 nucleotides in length include 1-1394; 1381-1925; 1913-2018; 2043-2154; 2146-2217; 2226-2576; 2864-3050; 3412-3443; 3443-3778; 3766-4341; 4329-4444; 4436-4555; 4564-4785; 5157-5857; 5881-6116; 6105-6141; 6142-7132; 7311-7515; 7874-8106; 8992-9045; 9478-9510; 9735-10203; 10239-10547; 10539-10570; and 10572-10825 of SEQ ID NO:1, 3, 5, or 7.

Preferred oligonucleotides of at least 17 nucleotides in length include 1-1926; 1912-2019; 2042-2155; 2145-2218; 2225-2577; 2863-3051; 3411-3779; 3765-4342; 4329-4445; 4435-4556; 4563-4786; 5156-5858; 5880-6117; 6104-6142; 6141-7133; 7310-7516; 7873-8107; 8991-9046; 9477-9511; 9734-10204; 10238-10548; 10538-10571; and 10571-10825 of SEQ ID NO:1, 3, 5, or 7.

Preferred oligonucleotides of at least 18 nucleotides in length include 1-2020; 2041-2156; 2144-2219; 2224-2578; 2862-3052; 3410-3780; 3764-4446; 4434-4557; 4562-4787; 5155-5859; 5879-6118; 6103-6143; 6140-7134; 7309-7517; 7872-8108; 8990-9047; 9476-9512; 9733-10205; 10237-10549; 10537-10572; and 10570-10825 of SEQ ID NO:1, 3, 5, or 7.

Preferred oligonucleotides of at least 8 nucleotides in length include 1-55; 55-251; 250-306; 310-376; 380-498; 500-528; 516-543; 541-578; 573-592; 590-609; 611- 648; 642-660; 664-717; 712-727; 725-763; 772-828; 813-874; 872-928; 913-942; 940-998; 997-1046; 1054-1071; 1076-1116; 1115-1182; 1186-1207; 1440-1483; 1482-1620; 2003-2055; 2057-2107; 2116-2200; and 2453-2469 of SEQ ID NO:9, 10, 11 or 12.

Preferred oligonucleotides of at least 9 nucleotides in length include 1-56; 54-252; 249-307; 309-377; 379-499; 499-529; 515-544; 540-579; 572-593; 589-610; 610-649; 641-661; 663-718; 711-728; 724-764; 771-829; 812-875; 871-929; 912-943; 939-999; 996-1047; 1053-1072; 1075-1117; 1114-1183; 1185-1208; 1439-1484; 1481-1629; 2002-2056; 2056-2108; 2115-2201; and 2452-2470 of SEQ ID NO:9, 10, 11 or 12.

Preferred oligonucleotides of at least 10 nucleotides in length include 1-57; 53-253; 248-308; 308-378; 378-500; 498-530; 514-545; 539-580; 571-594; 588-611; 609-662; 662-729; 723-765; 770-876; 870-944; 938-1000; 995-1048;

1052-1073; 1074-1118; 1113-1184; 1184-1209; 1438-1485; 1480-1630; 2001-2057; 2055-2109; 2114-2202; and 2451-2471 of SEQ ID NO:9, 10, 11 or 12.

Preferred oligonucleotides of at least 11 nucleotides in length include 1-58; 52-254; 247-309; 307-379; 377-501; 497-531; 513-546; 538-595; 587-612; 608-663; 661-730; 722-766; 769-877; 869-1049; 1051-1074; 1073-1119; 1112-1185; 1183-1210; 1437-1486; 1479-1631; 2000-2058; 2054-2110; 2113-2203; and 2450-2472 of SEQ ID NO:9, 10, 11 or 12.

Preferred oligonucleotides of at least 12 nucleotides in length include 1-255; 246-310; 306-380; 376-502; 496-596; 586-613; 607-664; 660-767; 768-1050; 1050-1075; 072-1120; 1111-1186; 1182-1211; 1436-1487; 1478-1632; 1999-2059; 2053-2121; 2112-2204; and 2449-2473 of SEQ ID NO:9, 10, 11 or 12.

Preferred oligonucleotides of at least 13 nucleotides in length include 1-311; 305-381; 375-503; 495-614; 606-665; 659-768; 767-1051; 1049-1076; 1071-1121; 1110-1187; 1181-1212; 1435-1633; 1998-2060; 2052-2205 and 2448-2474 of SEQ ID NO:9, 10, 11 or 12.

Preferred oligonucleotides of at least 14 nucleotides in length include 1-312; 304-382; 374-504; 494-615; 605-666; 658-769; 766-1052; 1048-1077; 1070-1188; 1180-1213; 1434-1634; 1997-2061; 2051-2206; and 2447-2475 of SEQ ID NO:9, 10, 11 or 12.

Preferred oligonucleotides of at least 15 nucleotides in length include 1-313; 303-383; 373-505; 493-616; 604-667; 657-770; 765-1053; 1047-1078; 1069-1189; 1179-1214; 1433-1635; 1996-2062; 2050-2207; and 2446-2476 of SEQ ID NO:9, 10, 11 or 12.

Preferred oligonucleotides of at least 16 nucleotides in length include 1-314; 302-384; 372-668; 656-771; 764-1054; 1046-1079; 1068-1190; 1178-1215; 1432-1636; 1995-2208; and 2445-2477 of SEQ ID NO:9, 10, 11 or 12.

Preferred oligonucleotides of at least 17 nucleotides in length include 1-315; 301-385; 371-669; 655-772; 763-1055; 1045-1080; 1067-1191; 1177-1216; 1431-1637; 1994-2209; and 2444-2478 of SEQ ID NO:9, 10, 11 or 12.

Preferred oligonucleotides of at least 18 nucleotides in length include 1-773; 762-1056; 1044-1081; 1066-1192; 1176-1217; 1430-1638; 1993-2210; and 2443-2479 of SEQ ID NO:9, 10, 11 or 12.

Such preferred oligonucleotides can also be used as part of an oligonucleotide pair, wherein the second member of the pair is any oligonucleotide of at least 8 consecutive nucleotides selected from SEQ ID NOS:1, 3, 5, 7, 9, 10, 11, or 12.

It will be appreciated that such preferred oligonucleotides can be a part of a kit for detecting polymorphisms in the HH gene, especially for the detection of polymorphisms in HH DNA or RNA in a patient sample.

As will be appreciated, the mutation analysis may also be performed on samples of RNA by reverse transcription into cDNA therefrom. Furthermore, mutations may also be detected at the protein level using antibodies specific for the mutant and normal HH protein, respectively. It may also be possible to base an HH mutation assay on altered cellular or subcellular localization of the mutant form of the HH protein.

3. Antibodies

As mentioned above, antibodies can also be used for the screening of the presence of the HH gene, the mutant HH gene, and the protein products therefrom. In addition, antibodies are useful in a variety of other contexts in accordance with the present invention. As will be appreciated, antibodies can be raised against various epitopes of the HH protein. Such antibodies can be utilized for the diagnosis of HH and, in certain applications, targeting of affected tissues.

Thus, in accordance with another aspect of the present invention a kit is provided that is suitable for use in screening and assaying for the presence of the HH gene by an immunoassay through use of an antibody which specifically binds to a gene product of the HH gene in combination with a reagent for detecting the binding of the antibody to the gene product.

Antibodies raised in accordance with the invention can also be utilized to provide extensive information on the characteristics of the protein and of the disease process and other valuable information which includes but is not limited to:

1. Antibodies can be used for the immunostaining of cells and tissues to determine the precise localization of the protein. Immunofluorescence and immuno-electron microscopy techniques which are well known in the art can be used for this purpose. Defects in the HH gene or in other genes which cause an altered localization of the HH protein are expected to be localizable by this method.

2. Antibodies to distinct isoforms of the HH protein (i.e., wild-type or mutant-specific antibodies) can be raised and used to detect the presence or absence of the wild-type or mutant gene products by immunoblotting (Western blotting) or other immunostaining methods. Such antibodies can also be utilized for therapeutic applications where, for example, binding to a mutant form of the HH protein reduces the consequences of the mutation.

3. Antibodies can also be used as tools for affinity purification of HH protein. Methods such as immunoprecipitation or column chromatography using immobilized antibodies are well known in the art and are further described in Section (II)(B)(3), entitled "Protein Purification" herein.

4. Immunoprecipitation with specific antibodies is useful in characterizing the biochemical properties of the HH protein. Modifications of the HH protein (i.e., phosphorylation, glycosylation, ubiquitization, and the like) can be detected through use of this method. Immunoprecipitation and Western blotting are also useful for the identification of associating molecules that are involved in signal transduction processes which regulate iron transport or other metabolic functions important in the HH disease process.

5. Antibodies can also be utilized in connection with the isolation and characterization of tissues and cells which express HH protein. For example, HH protein expressing cells can be isolated from peripheral blood, bone marrow, liver, and other tissues, or from cultured cells by fluorescence activated cell sorting (FACS) ("Antibodies" Cold Spring Harbor Press). Cells can be mixed with antibodies (primary antibodies) with or without conjugated dyes. If non-conjugated antibodies are used, a second dye-conjugated antibody (secondary antibody) which binds to the primary antibody can be added. This process allows the specific staining of cells or tissues which express the HH protein.

Antibodies against the HH protein are prepared by several methods which include, but are not limited to:

1. The potentially immunogenic domains of the protein are predicted from hydropathy and surface probability profiles. Then oligopeptides which span the predicted immunogenic sites are chemically synthesized. These oligopeptides can also be designed to contain the specific mutant amino acids to allow the detection of and discrimination between the mutant versus wild-type gene products. Rabbits or other animals are immunized with the synthesized oligopeptides coupled to a carrier such as KLH to produce anti-HH protein polyclonal antibodies. Alternatively, monoclonal antibodies can be produced against the synthesized oligopeptides using conventional techniques that are well known in the art ("Antibodies" Cold Spring Harbor Press). Both in vivo and in vitro immunization techniques can be used. For therapeutic applications, "humanized" monoclonal antibodies having human constant and variable regions are often preferred so as to minimize the immune response of a patient against the antibody. Such antibodies can be generated by immunizing transgenic animals which contain human immunoglobulin genes. See Jakobovits et al. *Ann NY Acad Sci* 764:525–535 (1995).

2. Antibodies can also be raised against expressed HH protein products from cells. Such expression products can include the full length expression product or parts or fragments thereof. Expression can be accomplished using conventional expression systems, such as bacterial, baculovirus, yeast, mammalian, and other overexpression systems using conventional recombinant DNA techniques. The proteins can be expressed as fusion proteins with a histidine tag, glutathione-S-transferase, or other moieties, or as nonfused proteins. Expressed proteins can be purified using conventional protein purification methods or affinity purification methods that are well known in the art. Purified proteins are used as immunogens to generate polyclonal or monoclonal antibodies using methods similar to those described above for the generation of antipeptide antibodies.

In each of the techniques described above, once hybridoma cell lines are prepared, monoclonal antibodies can be made through conventional techniques of priming mice with pristane and interperitoneally injecting such mice with the hybrid cells to enable harvesting of the monoclonal antibodies from ascites fluid.

In connection with synthetic and semi-synthetic antibodies, such terms are intended to cover antibody fragments, isotype switched antibodies, humanized antibodies (mouse-human, human-mouse, and the like), hybrids, antibodies having plural specificities, fully synthetic antibody-like molecules, and the like.

B. Molecular Biology

1. Expression Systems

"Expression systems" refer to DNA sequences containing a desired coding sequence and control sequences in operable linkage, so that hosts transformed with these sequences are capable of producing the encoded proteins. In order to effect transformation, the expression system may be included on a vector; however, the relevant DNA may then also be integrated into the host chromosome.

As used herein "cell", "cell line", and "cell culture" are used interchangeably and all such designations include progeny. Thus, "transformants" or "transformed cells" includes the primary subject cell and cultures derived therefrom without regard for the number of transfers. It is also understood that all progeny may not be precisely identical in DNA content, due to deliberate or inadvertent mutations. Mutant progeny which have the same functionality as screened for in the originally transformed cell, are included. Where distinct designations are intended, it will be clear from the context.

In general terms, the production of a recombinant form of HH gene product typically involves the following:

First a DNA encoding the mature (used here to include all normal and mutant forms of the proteins) protein, the preprotein, or a fusion of the IIH protein to an additional sequence cleavable under controlled conditions such as treatment with peptidase to give an active protein, is obtained. If the sequence is uninterrupted by introns it is suitable for expression in any host. If there are introns, expression is obtainable in mammalian or other eukaryotic systems capable of processing them. This sequence should be in excisable and recoverable form. The excised or recovered coding sequence is then placed in operable linkage with suitable control sequences in an expression vector. The construct is used to transform a suitable host, and the transformed host is cultured under selective conditions to effect the production of the recombinant HH protein. Optionally the HH protein is isolated from the medium or from the cells and purified as described in Section (II)(B)(3), entitled "Protein Purification".

Each of the foregoing steps can be done in a variety of ways. For example, the desired coding sequences can be obtained by preparing suitable cDNA from cellular mRNA and manipulating the cDNA to obtain the complete sequence. Alternatively, genomic fragments may be obtained and used directly in appropriate hosts. The construction of expression vectors operable in a variety of hosts are made using appropriate replicons and control sequences, as set forth below. Suitable restriction sites can, if not normally available, be added to the ends of the coding sequence so as to provide an excisable gene to insert into these vectors.

The control sequences, expression vectors, and transformation methods are dependent on the type of host cell used to express the gene. Generally, prokaryotic, yeast, insect, or mammalian cells are presently useful as hosts. Prokaryotic hosts are in general the most efficient and convenient for the production of recombinant proteins. However, eukaryotic cells, and, in particular, mammalian cells, are often preferable because of their processing capacity and post-translational processing of human proteins.

Prokaryotes most frequently are represented by various strains of *E. coli*. However, other microbial strains may also be used, such as *Bacillus subtilis* and various species of Pseudomonas or other bacterial strains. In such prokaryotic systems, plasmid or bacteriophage vectors which contain origins of replication and control sequences compatible with the host are used. A wide variety of vectors for many prokaryotes are known (Maniatis et al. *Molecular Cloning: A Laboratory Manual* (Cold Spring Harbor Laboratory, Cold Spring Harbor, N.Y. (1982)); Sambrook et al. *Molecular Cloning: A Laboratory Manual* (Cold Spring Harbor Laboratory, Cold Spring Harbor, N.Y. (1989)); *Meth. Enzymology* 68 (Academic Press, Orlando, Fla. (1979, 1983, 1987)); Pouwells et al. *Cloning Vectors: A Laboratory Manual* (Elsevier, Amsterdam (1987))). Commonly used prokaryotic control sequences which are defined herein to include promoters for transcription initiation, optionally with an operator, along with ribosome binding site sequences, include such commonly used promoters as the beta-lactamase (penicillinase) and lactose (lac) promoter systems, the tryptophan (trp) promoter system and the lambda derived PL promoter and N-gene ribosome binding, site, which has become useful as a portable control cassette (U.S. Pat. No. 4,711,845). However, any available promoter system compatible with prokaryotes can be used (Maniatis et al. supra. (1982); Sambrook et al. supra. (1989); *Meth. Enzymology* supra. (1979, 1983, 1987); Pouwells et al. supra. (1987)).

In addition to bacteria, eukaryotic microbes, such as yeast, may also be used as hosts. Laboratory strain *Saccharomyces cerevisiae* or Baker's yeast, is most often used although other strains are commonly available.

Vectors employing the 2 micron origin of replication and other plasmid vectors suitable for yeast expression are known (Maniatis et al. supra. (1982); Sambrook et al. supra. (1989); *Meth. Enzymology* supra. (1979, 1983, 1987); Pouwells et al. supra. (1987)). Control sequences for yeast vectors include promoters for the synthesis of glycolytic enzymes. Additional promoters known in the art include the promoters for 3-phosphoglycerate kinase, and those for other glycolytic enzymes, such as glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other promoters, which have the additional advantage of transcription controlled by growth conditions, are the promoter regions for alcohol dehydrogenase 2, isocytochrome C, acid phosphatase, degradative enzymes associated with nitrogen metabolism, and enzymes responsible for maltose and galactose utilization. See Maniatis et al. supra. (1982); Sambrook et al. supra. (1989); *Meth. Enzymology* supra. (1979, 1983, 1987); Pouwells et al. supra. (1987). It is also believed that terminator sequences at the 3' end of the coding sequences are desirable. Such terminators are found in the 3' untranslated region following the coding sequences in yeast-derived genes. Many of the useful vectors contain control sequences derived from the enolase gene containing plasmid peno46 or the LEU2 gene obtained from Yepl3, however, any vector containing a yeast compatible promoter, origin of replication, and other control sequences is suitable (Maniatis et al. supra. (1982); Sambrook et al. supra. (1989); *Meth. Enzymology* supra. (1979, 1983, 1987); Pouwells et al. supra. (1987)).

It is also, of course, possible to express genes encoding polypeptides in eukaryotic host cell cultures derived from multicellular organisms (Cruz and Patterson *Tissue Culture* (Academic Press, Orlando (1973)); *Meth. Enzymology* supra. (1979); Freshney *Culture of Animal Cells: A Manual of Basic Techniques* (2d ed., Alan R. Liss, N.Y. (1987))). Useful host cell lines include murine myelomas N51, VERO and HeT cells, SF9 or other insect cell lines, and Chinese hamster ovary (CHO) cells. Expression vectors for such cells ordinarily include promoters and control sequences compatible with mammalian cells such as, for example, the commonly used early and later promoters from Simian Virus 40 (SV 40), or other viral promoters such as those from polyoma, adenovirus 2, bovine papilloma virus, or avian sarcoma viruses, herpes virus family (such as cytomegalovirus, herpes simplex virus, or Epstein-Barr virus), or immunoglobulin promoters and heat shock promoters (Maniatis et al. supra. (1982); Sambrook et al. supra. (1989); *Meth. Enzymology* supra. (1979, 1983, 1987); Pouwells et al. supra. (1987)). In addition, regulated promoters, such as metallothionine (i.e., MT-1 and MT-2), glucocorticoid, or antibiotic gene "switches" can be used.

General aspects of mammalian cell host system transformations have been described by Axel (U.S. Pat. No. 4,399, 216). It now appears also that "enhancer" regions are important in optimizing transformation. Generally, "enhancer" regions are sequences found upstream of the promoter region. Origins of replication may be obtained, if needed, from viral sources. However, integration into the chromosome is a common mechanism for DNA replication in eukaryotes. Plant cells are also now available as hosts, and control sequences compatible with plant cells such as the nopaline synthase promoter and polyadenylation signal sequences are available (Pouwells et al. supra. (1987); *Meth Enzymology* 118 (Academic Press, Orlando (1987)); Gelvin et al. *Plant Molecular Biology Manual* (Kluwer Academic Publishers, Dudrecht (1990))).

Depending on the host cell used, transformation is done using standard techniques appropriate to such cells (Maniatis et al. supra. (1982); Sambrook et al. supra. (1989); *Meth. Enzymology* supra. (1979, 1983, 1987); U.S. Pat. No. 4,399,216; *Meth Enzymology* supra (1986); Gelvin et al. supra. (1990)). Such techniques include, without limitation, calcium treatment employing calcium chloride for prokaryotes or other cells which contain substantial cell wall barriers; infection with *Agrobacterium tumefaciens* for certain plant cells; calcium phosphate precipitation, DEAE, lipid transfection systems (such as Lipofectin™ and Lipofectamine™), and electroporation methods for mammalian cells without cell walls, and, microprojectile bombardment for many cells including, plant cells. In addition, DNA may be delivered by viral delivery systems such as retroviruses or the herpes family, adenoviruses, baculoviruses, or semliki forest virus, as appropriate for the species of cell line chosen.

C. Function Experiments

Expression systems for the HH gene product, for example as described in the previous Section, allow for the study of the function of the HH gene product, in either normal or wild-type form and/or mutated form. Such analyses are useful in providing insight into the disease causing process that is derived from mutations in the gene. Judging from the sequence similarity of the HH gene to MHC Class I molecules, the HH gene product is expected to be expressed on cell surfaces. As discussed earlier, the HH protein is known to be expressed on the surfaces of cells of tissues from normal individuals and on cells transfected with the non-mutated gene.

1. Analysis of Iron Metabolism

The HH gene (mutated, normal, or wild-type) can be utilized in an assay of iron metabolism. The gene is expressed, with or without any accompanying molecules, in cells lines or primary cells derived from HH patients, healthy individuals, or cells from other organisms (such as rodents, insects, bacteria, amphibians, etc.). Uptake of iron by these cells is measured, for example through the use of radioactive isotopes. Methodology for assessing affinity, binding, and transport of $I^{125}$-transferrin binding to the Tfr have been described in detail (Mulford and Lodish, *J. Biol. Chem.* 263(11):5455–5461 (1988)). It can be predicted that the unmutated HH protein would modulate the activity of the Tfr whereas, the HH protein containing the 24d1 mutation would be unable to modulate the Tfr by virtue of its failure to interact with and modulate other molecules important to iron metabolism such as iron transport "channels". In such cases the 24d1 mutation could be expected to result in unregulated iron transport. Further, binding of iron to the HH gene product can also be measured. Such experiments assist in assessing the role of the HH gene and HH gene product in iron uptake, binding, and transport by and in cells.

2. Analysis of Lead and other Metal Metabolism

Increased accumulation of lead and certain other metals has been reported in HH homozygotes. See Barton et al. *J Lab Clin Med* 124:193–198 (1994). As discussed above in connection with iron, the metabolism of lead and other metals can be assessed.

3. Analysis of MHC Function

As discussed above, the HH gene products share significant structural similarity with Class I MHC molecules. Class I MHC molecules have several well known and measurable activities. Expression of the HH gene products through the use of appropriate expression systems allows for the analysis of whether the HH gene products possess similar activities.

a. Peptide Presentation Assay

Peptide presentation can be measured through use of a number of well known techniques. One method is to express the HH gene product on the surface of mammalian cells. Thereafter, the HH gene product can be purified from the cell surface analyzed for peptide binding, through, for example, high performance liquid chromatography (HPLC) after elution. Amino acid sequences of any bound peptides can be determined through conventional sequencing techniques (i.e., Edman degradation).

Another technique to analyze peptide presentation is to express the HH gene product on a cell that does not conventionally possess peptide presentation activity (i.e., *Drosophila melanogaster* derived Schneider cells. See Rammensee et al. *Ann Rev Immunol* 11:213–244 (1993). In such a system, MHC Class I molecules are expressed on the cell surface "empty" (i.e., without any bound peptide). Thereafter, through the addition of a particular peptide to the system, the binding of the particular peptide to the empty Class I molecule can be measured. See Rammensee et al. supra. (1993). A similar assay can be utilized in connection with the HH gene products.

b. T-cell Activation and Activation of Other Cells

It has been observed that, in at least some HH patients, there is a decrease in the numbers of CD8+ T-cells. (Reimao et al. *C.R. Acad Sci Paris* 313:481 (1991)). This is a striking phenotype as a similar phenotype is associated with the $\beta$-2-microglobulin knock-out mice (Koller et al. *Science* 248:1127 (1990); Zijlstra et al. *Nature* 344:742 (1990)). The role of MHC Class I proteins in the development of the T-cell repertoire is well documented. See Doherty *Adv Immun* 27:51 (1979). Animals lacking CD8+ T-cells would be expected to be more susceptible to a variety of infections and cancers. The $\beta$-2-microglobulin knock-out mice have been kept under pathogen-free conditions so that the long-term consequences of lacking CD8+ T-cells has not been ascertained. *Humans, however, when deficient in CD8+ T-cells*, have shown several conditions that are consistent with a compromised immune system, most notably a 200 fold increase in the incidence of hepatocellular carcinomas. See Niederau et al. *N Engl J Med* 313:1256 (1985).

Further, it is known that Class I MHC molecules are involved in the activation and differentiation of T-cells through the interaction between MHC molecules and $\alpha/\beta$ or $\gamma/\delta$ T-cell receptors. Methods to measure T-cell activation are well known in the art. See Schild et al. *Cell* 76:29–37 (1994) and others). Signaling events in other cell types can also be measured. See Leibson *Immunity* 3:5–8 (1995). Thus, expression of the HH gene product on cells that are co-cultured with various T-cells can be used as an assay to measure T-cell differentiation and activation induced by the HH gene product. In particular, as mentioned above, differentiation and activation of CD8+ T-cells can be determined and measured and the role of the normal and mutant HH gene and gene products therein assessed.

c. Identification of Downstream Cells

The assays described above can be utilized to monitor and determine other cellular interactions between "downstream cells" and the HH gene protein product. Cells that interact with the HH gene protein product can be analyzed for uptake of iron and iron binding as described above.

d. Determination of Cellular Markers

As discussed above, the HH protein is expressed on the surface of cells. As such, the HH gene product can be utilized as a cell-surface marker and detected through the use of FACS or other means utilizing antibodies to the HH protein. The failure of the HH protein with the 24d1 mutation to be presented on cell surfaces provides the opportunity for use as a non-DNA based diagnostic for HH disease.

D. Therapeutics

Identification of the HH gene and its gene product also has therapeutic implications. Indeed, one of the major aims of the present invention is the development of therapies to circumvent or overcome the defect leading to HH disease. Envisioned are pharmacological, protein replacement, antibody therapy, and gene therapy approaches. In addition, the development of animal models useful for developing therapies and for understanding the molecular mechanisms of HH disease are envisioned.

Peptide binding domains of MHC molecules have ligands, or are known to bind ligands, and we expect that the HH protein may directly bind iron or other metals or bind to a ligand (such as a peptide) that binds iron or other metals. Therefore, we expect that the HH protein represents a new approach to iron and other metal chelation, which may be useful, in addition to its role in iron overload in HH disease, in a variety of other diseases and conditions that are secondary to other disease interventions, including, without limitation, transfusions, thalassaemias, and hemolytic anemias. Delivery of the HH protein or parts thereof, or its ligand by either gene therapy or through protein replacement represents a new approach to metal chelation or iron modulatory agents.

Further, because molecules that bind to iron or other metals, we envision that the approach can be utilized for chelation or sequestration of metals, such as copper, lead, zinc, cadmium, or other toxic moieties. Further, since iron is a catalyst for oxidative processes that are known to be deleterious in multiple biological systems, including, without limitation, vascular disease, inflammation, atherosclerosis, lung injury, ischemia, and the like, we envision that the HH protein and/or fragments thereof, including ligands and fragments thereof, can be utilized in anti-oxidative therapies.

An additional aspect of HH disease and iron overload disease is that hepatic iron concentration has been shown to correlate with non-response to $\alpha$-interferon treatment for chronic hepatitis. See Van Tiel et al. *J Hepatology* 20:410–415 (1994) and Olynyk et al. *Gastroenterology* 108:1104–1109 (1995). Thus, the HH protein and/or fragments or ligands thereto can be utilized in the lowering of hepatic iron levels so as to facilitate increased response to $\alpha$-interferon in the treatment of these diseases.

1. Pharmacological

In the pharmacological approach, drugs which circumvent or overcome the defective HH gene function are sought. In this approach modulation of HH gene function can be accomplished by agents or drugs which are designed to interact with different aspects of the HH protein structure or function or which mimic the HH protein interaction with other molecules such as the Tfr. For example, a drug, antibody or other modulating protein (i.e. $\beta$-2-microglobulin or calnexin or similarly acting molecules or parts thereof) could be designed to bind to the HH protein and correct a defective structure.

Alternatively, a drug might bind to a specific functional residue(s) thereby, increasing or decreasing the affinity for ligand, substrate or cofactor such as Tfr. The assay for such a compound would be to promote or inhibit an interaction between the HH protein and the Tfr or similar molecule or could be a measure of Tfr turnover or endocytosis.

Efficacy of a drug or agent can be identified in a screening program in which modulation is monitored in in vitro cell systems. Indeed, the present invention provides for host cell systems which express various mutant HH proteins (especially the 24d1 and 24d2 mutations noted in this application) and are suited for use as primary screening systems. Candidate drugs can be evaluated by incubation with these cells and measuring cellular functions dependent on the HH gene or by measuring proper HH protein folding or processing. Such assays might also entail measuring receptor-like activity, iron transport and metabolism, gene transcription or other upstream or downstream biological function as dictated by studies of HH gene function.

Alternatively, cell-free systems can also be utilized. Purified HH protein can be reconstituted into artificial membranes or vesicles and drugs screened in a cell-free system. Such systems are often more convenient and are inherently more amenable to high throughput types of screening and automation.

A variety of drugs and other therapeutic agents have been proposed as useful in the treatment of HH disease and other iron or other metal overload type diseases. See, for example, Great Britain Patent Application No. 2,293,269 A, assigned to Merck Sharp & Dohme Ltd., World Patent Application No. WO 95/16663, assigned to Ciba Geigy AG, German Patent Application No. 4,327,226 Al, assigned to Hoechst AG, World Patent Application No. WO 94/21243, assigned to the University of Nebraska, Canadian Patent Application No. 2,115,224 A, assigned to Bayer Corp., Miles Inc., and others, Canadian Patent Application No. 2,115,222 A, assigned to Bayer Corp., Miles Inc., and others, U.S. Pat. No. 5,385,918 and Canadian Patent Application No. 2,115,221 A, assigned to Bayer Corp., Miles Inc., and others, World Patent Application No. WO 94/11367, assigned to Ciba Geigy AG and the University of Florida, World Patent Application No. WO 94/01463, assigned to the University of British Columbia, U.S. Pat. No. 5,256,676, assigned to British Technology Group Ltd., U.S. Pat. No. 5,420,008, assigned to Oriental Yeast Co. Ltd., World Patent Application No. WO 94/04186, U.S. Pat. No. 5,075,469, assigned to Yissum Research and Development Co., European Patent Application No. 346,281, assigned to Ciba Geigy AG, European Patent Application No. 315,434, assigned to Yissum Research and Development Co., U.S. Pat. Nos. 5,424,057, 5,328,992, and 5,185,368, assigned to Ciba Geigy AG, U.S. Pat. Nos. 5,104,865, 4,912,118, 4,863,913, and 4,666,927, assigned to National Research and Development Corp., DD Patent Application No. 208,609, assigned to Akad Wissenschaft, and U.S. Pat. No. 4,434,156, assigned to the Salk Institute for Biological Studies. The invention is useful for the screening of such proposed drugs or other therapeutic agents for specific activity in HH disease models, assays, and design of molecules based thereon.

In vivo testing of HH disease-modifying compounds is also required as a confirmation of activity observed in the in vitro assays. Animal models of HH disease are envisioned and discussed in the section entitled "Animal Models", below, in the present application.

Drugs can be designed to modulate HH gene and HH protein activity from knowledge of the structure and function correlations of HH protein and from knowledge of the specific defect in various HH mutant proteins. For this, rational drug design by use of X-ray crystallography, computer-aided molecular modeling (CAMM), quantitative or qualitative structure-activity relationship (QSAR), and similar technologies can further focus drug discovery efforts. Rational design allows prediction of protein or synthetic structures which can interact with and modify the HH protein activity. Such structures may be synthesized chemically or expressed in biological systems. This approach has been reviewed in Capsey et al., Genetically Engineered Human Therapeutic Drugs, Stockton Press, New York (1988). Further, combinatorial libraries can be designed, synthesized and used in screening programs.

The present invention application also envisions that the treatment of HH disease can take the form of modulation of another protein or step in the pathway in which the HH gene or its protein product participates in order to correct the physiological abnormality. Without being limited to any one theory, Tfr may be the appropriate target for therapeutic treatments for HH. Furthermore, as an MHC-like molecule one could envision that the HH protein acts as a receptor or modulator for iron-binding or iron-regulating molecules. As such intracellular signalling or transport functions could be affected by alterations in HH protein function. Such functions and their effector molecules would also be targets for HH disease-modifying therapies.

In order to administer therapeutic agents based on, or derived from, the present invention, it will be appreciated that suitable carriers, excipients, and other agents may be incorporated into the formulations to provide improved transfer, delivery, tolerance, and the like.

A multitude of appropriate formulations can be found in the formulary known to all pharmaceutical chemists: Remington's Pharmaceutical Sciences, (15th Edition, Mack Publishing Company, Easton, Pa. (1975)), particularly Chapter 87, by Blaug, Seymour, therein. These formulations include for example, powders, pastes, ointments, jelly, waxes, oils, lipids, anhydrous absorption bases, oil-in-water or water-in-oil emulsions, emulsions carbowax (polyethylene glycols of a variety of molecular weights), semi-solid gels, and semi-solid mixtures containing carbowax.

Any of the foregoing formulations may be appropriate in treatments and therapies in accordance with the present invention, provided that the active agent in the formulation is not inactivated by the formulation and the formulation is physiologically compatible.

2. Protein Replacement Therapy

The present invention also relates to the use of polypeptide or protein replacement therapy for those individuals determined to have a defective HH gene. Treatment of HH disease could be performed by replacing the defective HH protein with normal protein or its functional equivalent in therapeutic amounts.

HH polypeptide can be prepared for therapy by any of several conventional procedures. First, HH protein can be produced by cloning the HH cDNA into an appropriate expression vector, expressing the HH gene product from this vector in an in vitro expression system (cell-free or cell-based) and isolating the HH protein from the medium or cells of the expression system. General expression vectors and systems are well known in the art. In addition, the invention envisions the potential need to express a stable form of the HH protein in order to obtain high yields and obtain a form readily amenable to intravenous administration. Stable high yield expression of proteins have been achieved through systems utilizing lipid-linked forms of proteins as described in Wettstein et al. *J Exp Med* 174:219–228 (1991) and Lin et al. *Science* 249:677–679 (1990).

HH protein or portions thereof can be prepared synthetically. Alternatively, the HH protein can be prepared from total protein samples by affinity chromatography. Sources would include tissues expressing normal HH protein, in vitro systems (outlined above), or synthetic materials. The affinity matrix would consist of antibodies (polyclonal or monoclonal) coupled to an inert matrix. In addition, various ligands which specifically interact with the HH protein could be immobilized on an inert matrix. For example, β-2-microglobulin or portions thereof, β-2-microglobulin-like molecules, or other specific proteins such as calnexin and calnexin-like molecules or portions thereof. General methods for preparation and use of affinity matrices are well known in the art.

Protein replacement therapy requires that HH protein be administered in an appropriate formulation. The HH protein can be formulated in conventional ways standard to the art for the administration of protein substances. Delivery may require packaging in lipid-containing vesicles (such as Lipofectin™ or other cationic or anionic lipid or certain surfactant proteins) that facilitate incorporation into the cell membrane. The HH protein formulations can be delivered to affected tissues by different methods depending on the affected tissue. For example, iron absorption is initiated in the GI tract. Therefore, delivery by catheter or other means to bypass the stomach would be desirable. In other tissues, IV delivery will be the most direct approach.

3. Gene Therapy

Gene therapy utilizing recombinant DNA technology to deliver the normal form of the HH gene into patient cells or vectors which will supply the patient with gene product in vivo is also contemplated within the scope of the present invention. In gene therapy of HH disease, a normal version of the HH gene is delivered to affected tissue(s) in a form and amount such that the correct gene is expressed and will prepare sufficient quantities of HH protein to reverse the effects of the mutated HH gene. Current approaches to gene therapy include viral vectors, cell-based delivery systems and delivery agents. Further, ex vivo gene therapy could also be useful. In ex vivo gene therapy, cells (either autologous or otherwise) are transfected with the normal HH gene or a portion thereof and implanted or otherwise delivered into the patient. Such cells thereafter express the normal HH gene product in vivo and would be expected to assist a patient with HH disease in avoiding iron overload normally associated with HH disease. Ex vivo gene therapy is described in U.S. Pat. No. 5,399,346 to Anderson et al., the disclosure of which is hereby incorporated by reference in its entirety. Approaches to gene therapy are discussed below:

a. Viral Vectors

Retroviruses are often considered the preferred vector for somatic gene therapy. They provide high efficiency infection, stable integration and stable expression (Friedman, T. Progress Toward Human Gene Therapy. Science 244:1275 (1989)). The full length HH gene cDNA or portions thereof can be cloned into a retroviral vector driven by its endogenous promoter or from the retroviral LTR. Delivery of the virus could be accomplished by direct implantation of virus directly into the affected tissue.

Other delivery systems which can be utilized include adenovirus, adeno-associated virus (AAV), vaccinia virus, bovine papilloma virus or members of the herpes virus group such as Epstein-Barr virus. Viruses with tropism to the gut and viruses engineered with tissue specific promoters are also envisioned. Viruses can be, and preferably are, replication deficient.

b. Cell-based Delivery

Much work has been performed in recent years regarding producing transgenic cells possessing therapeutic genes. Such cells could be directly implanted or implanted within a membrane-based matrix. For these purposes, many cells types would suffice but cells particularly derived from the target organs such as gut or liver are particularly useful. Examples include fetal liver or fetal gut epithelial cells.

c. Non-viral gene transfer

Other methods of inserting the HH gene into the appropriate tissues may also be productive. Many of these agents, however, are of lower efficiency than viral vectors and would potentially require infection in vitro, selection of transfectants, and reimplantation. This would include calcium phosphate, DEAE dextran, electroporation, and protoplast fusion. A particularly attractive idea is the use of liposomes (i.e., LIPOFECTIN™), which might be possible to carry out in vivo. Synthetic cationic lipids and DNA conjugates also appear to show some promise and may increase the efficiency and ease of carrying out this approach.

4. Animal Models

The generation of a mouse or other animal model of HH disease is important for both an understanding the biology of the disease but also for testing of potential therapies. Currently only a single animal model of HH disease exists. As was demonstrated by de Sousa et al. (*Immunol. Letts* 39:105–111 (1994)) and Rothenberg and Voland (*Proc. Natl. Acad. Sci. U.S.A.* 93:1529–1534 (1996)) it is possible to develop a model of HH disease by interfering with the normal expression of β-microglobulin. β-2-microglubin is necessary for the proper folding and surface presentation of MHC class I molecules. Mice with a disrupted β2-microglobulin gene were created that do not express β2-microglobulin protein on the surface of most cells. Mice with this mutation possess almost no CD8+ cytotoxic T lymphocytes and develop progressive hepatic iron overload similar to HH disease. This model is somewhat limited in its representation of HH disease in humans as β2-microglobulin serves as a chaperone-like molecule for most, if not all, MHC I molecules thereby, affecting more biological systems than just those anticipated to be affected by disruption of the HH gene.

This invention envisions the creation of a more specific animal model of HH disease by inactivation of the homologous HH gene in a number of species including mice, rats, pigs, and primates. These models will be novel in that targeting the homologous HH gene alone will more specifically represent the diseases as described in humans.

Techniques for specifically inactivating genes by homologous recombination in embryonic stem cells (ES cells) have been described (Capecci *Science* 244:1288 (1989)). More specifically, as isogenic SvJ-129 mouse genomic BAC library can be screened with a human HH gene cDNA probe. The resultant clones are then sequenced to ensure sequence identity to the house HH gene homologue cDNA. A targeting vector is then constructed from the mouse genomic DNA consisting of two approximately 3 Kb mouse HH gene genomic fragments as 5' and 3' arms. These arms would be chosen to flank a region critical to the function of the HH gene product, such as exon 4 (the immunoglobulin-like region which contains the proposed critical β2-microglobulin interactive domain and essential disulfide linkage). However, other regions such as the initiation codon in exon 1 or membrane-proximal regions could also be targeted. In place of the exon 4 region would be placed a neomycin resistance gene under the control of the phosphoglycerate kinase (pgk 1) promoter. The 5' arm of the vector is flanked externally by the pgk 1-herpes thymidine kinase gene for negative selection.

The targeting vector is then transfected into R1 ES cells and the transfectants subjected to positive and negative selection (G418 and ganciclovir, respectively). PCR is then used to screen surviving colonies for the desired homologous recombinations. These are confirmed by Southern blot analysis.

Subsequently, several mutant clones are picked and injected into C57BL/6 blastocysts to produce high-percentage chimeric animals. These are then mated to C57BL/6 females. Heterozygous offspring are then mated to produce homozygous mutants. These offspring can then be tested for the HH gene mutation by Southern blot analysis. In addition, these animals are tested by RT-PCR to assess whether the targeted homologous recombination results in ablation of HH gene mRNA. These results can be confirmed by Northern blot analysis and RNase protection assays.

Once established, the HH gene −/− mice can be studied for development of HH-like disease and also be utilized to examine which tissues and cell types are involved in the disease process. These animals can also be used to introduce the mutant or normal human HH gene or for introduction of the homologous gene to that species and containing the 24d1 or other HH disease-causing mutations. Methods for these transgenic procedures are well known to those versed in the art and have been described by Murphy and Carter, Transgenesis Techniques, Humana Press, 1993. Alternatively, homologous recombination procedures similar to those described above can be utilized to introduce the 24d1 or 24d2 mutations directly into the endogenous mouse gene.

5. Down Regulation of the HH Gene or HH Gene Product

In certain therapeutic applications, it is desirable to down regulate the expression and/or function of the HH gene, the mutant HH gene, the HH protein, or the mutant HH protein. For example, down regulation of the normal HH gene or the normal HH protein is desirable in situations where iron is underaccumulated in the body, for example in certain anemias (i.e., thalassaemias, hemolytic anemias, trans-fusions). On the other hand, down regulation of the mutant HH gene or the HH protein is desirable in situations where iron is overaccumulated in the body.

As discussed above in the Section entitled "Antibodies," antibodies specific to the normal or the mutant HH protein can be prepared. Such antibodies can be used therapeutically in HH disease. For example, to block the action of the mutant or normal HH gene if the function associated with the mutant protein is an upregulation of the normal HH protein function and leads to an overaccumulation of iron in the body, as mentioned above. Similarly, antibodies can be used therapeutically to block action of an HH protein that is causing an underaccumulation of iron in the body.

In a similar manner, the HH gene, either in normal or in a mutant form, can be downregulated through the use of antisense oligonucleotides directed against the gene or its transcripts. A similar strategy can be utilized as discussed above in connection with antibodies. For a particularly valuable review of the design considerations and use of antisense oligonucleotides, see Uhlmann et al. *Chemical Reviews* 90:543–584 (1990) the disclosure of which is hereby incorporated by reference. The antisense oligonucleotides of the present invention may be synthesized by any of the known chemical oligonucleotide synthesis methods. Such methods are generally described, for example, in Winnacker *From Genes to Clones: Introduction to Gene Technology*, VCH Verlagsgesellschaft mhH (H. Ibelgaufts trans. 1987). Antisense oligonucleotides are most advantageously prepared by utilizing any of the commercially available, automated nucleic acid synthesizers. One such device, the Applied Biosystems 380B DNA Synthesizer, utilizes β-cyanoethyl phosphoramidite chemistry.

Since the complete nucleotide synthesis of DNA complementary to the HH gene and the mutant HH genes' mRNA transcript is known, antisense oligonucleotides hybridizable with any portion of such transcripts may be prepared by oligonucleotide synthesis methods known to those skilled in the art. While any length oligonucleotide may be utilized in the practice of the invention, sequences shorter than 12 bases may be less specific in hybridizing to the target mRNA, may be more easily destroyed by enzymatic digestion, and may be destabilized by enzymatic digestion. Hence, oligonucleotides having 12 or more nucleotides are preferred. Long sequences, particularly sequences longer than about 40 nucleotides, may be somewhat less effective in inhibiting translation because of decreased uptake by the target cell. Thus, oligomers of 12–40 nucleotides are preferred, more preferably 15–30 nucleotides, most preferably 18–26 nucleotides. Sequences of 18–24 nucleotides are most particularly preferred.

ILLUSTRATIVE EXAMPLES

The following examples are provided to illustrate certain aspects of the present invention and not intended as limiting the subject matter thereof:

EXAMPLE 1

HH Diagnostic: OLA Assay

As discussed above, the oligonucleotide ligation assay (OLA) (Nickerson, D. A. et al. *Proc Natl Acad Sci USA* 87:8923–8927 (1990)) is highly effective for detecting single nucleotide changes in DNA and RNA, such as the 24d1, 24d2, and 24d7 mutations or sequence variations. Thus, in accordance with the present invention, there is provided an assay kit to detect mutations in the HH gene through use of an OLA assay.

In the OLA assay, a sample of DNA or cDNA reverse transcribed from RNA is amplified, generally through use of polymerase chain reaction (PCR) amplification, followed by ligation with upstream and downstream oligonucleotides specific to either side of the mutation sought to be assayed. Either the upstream or the downstream oligonucleotide includes a base complementary to the mutated or normal allele and the upstream or downstream oligonucleotide is labeled to enable detection of hybridization to the variant base.

Oligonucleotides complementary to the upstream or downstream sequence of the DNA or RNA in the sample, plus the mutated or normal allele, are ordinarily utilized in parallel so that detection of heterozygosity and homozygosity is possible.

Generally, the kit includes reaction chambers in which to conduct amplification of DNA or reverse transcribed RNA from patient samples, ligation reactions, and detection of ligation products. One exemplary reaction chamber that can be utilized to conduct such steps is a microtiter plate. The kit can be provided with or without reagents and oligonucleotides for use in the assay. In general, however, in a preferred embodiment, the kit is provided with oligonucleotides for amplifying at least a portion of a patient's DNA or RNA across the mutation that is to be detected. As will be appreciated, oligonucleotide primers can be designed to virtually any portion of the DNA or transcription products flanking the nucleotide sought to be assayed, up to and including, and in some cases even exceeding 500 bases away from the mutation to be assayed. Further, ligation oligonucleotides can be designed in a variety of lengths.

Samples (either DNA or reverse transcribed RNA) are placed into the reaction vessel(s) with appropriate primers, nucleotides, buffers, and salts and subjected to PCR amplification. The PCR products are then assayed for single base mutations using OLA.

Suitable genomic DNA-containing samples from patients can be readily obtained and the DNA extracted therefrom using conventional techniques. For example, DNA can be isolated and prepared in accordance with the method described in Dracopoli, N. et al. eds. *Current Protocols in Human Genetics* (J. Wiley & Sons, New York (1994)), the disclosure of which is hereby incorporated by reference in its entirety. Most typically, a blood sample, a buccal swab, a hair follicle preparation, or a nasal aspirate is used as a source of cells to provide the DNA.

Alternatively, RNA from an individual (i.e., freshly transcribed or messenger RNA) can be easily utilized in accordance with the present invention for the detection of the selected base mutation. Total RNA from an individual can be isolated according to the procedure outlined in Sambrook, J. et al. *Molecular Cloning—A Laboratory Manual* (2nd Ed., Cold Spring Harbor Laboratory Press, New York (1989)) the disclosure of which is hereby incorporated by reference.

When using either DNA or RNA samples for the detection of base mutations in an OLA assay, the patient DNA or reverse transcribed RNA is first amplified, followed by assaying for ligation. In a preferred embodiment, the amplification primers for detecting the 24d1 mutation in DNA are shown in FIG. 5 and labeled 24d1.P1 (SEQ ID NO:13) and 24d1.P2 (SEQ ID NO:14), designed as shown in FIG. 6. Also on FIG. 5, the oligonucleotides used in the sequence determination by OLA for 24d1 are designated 24d1.A (SEQ ID NO: 15), 24d1.B (SEQ ID NO:16), and 24d1.X (SEQ ID NO:17). As indicated in the sequences shown, "bio" indicates biotin coupling, "p" indicates 5'-phosphate, and "dig" indicates coupled digoxigenin. It will be appreciated that the binding of biotin and digoxigenin can be reversed. In other words, digoxigenin can be bound to the 5' end of oligonucleotides 24d1.A and 24d1.B and biotin can be bound to the 3' end of the 24d1.X oligonucleotide.

The use of RNA, as opposed to DNA, follows essentially an identical approach: the RNA is isolated and after reverse transcription the characteristic base mutation can be detected as described above. In order to perform PCR amplification of the RNA prior to OLA assay, the following oligonucleotide primers are preferably utilized:

```
Forward Primer
24d1.P3  CTG AAA GGG TGG GAT CAC AT (SEQ ID NO:18)

Reverse Primer
24d1.P4  CAA GGA GTT CGT CAG GCA AT (SEQ ID NO:19)
```

In amplification, a solution containing the DNA sample (obtained either directly or through reverse transcription of RNA) is mixed with an aliquot of each of dATP, dCTP, dGTP and dTTP (i.e., Pharmacia LKB Biotechnology, N.J.), an aliquot of each of the DNA specific PCR primers, an aliquot of Taq polymerase (i.e., Promega, Wis.), and an aliquot of PCR buffer, including $MgCl_2$ (i.e., Promega) to a final volume. Followed by pre-denaturation (i.e., at 95° C. for 7 minutes), PCR is carried out in a DNA thermal cycler (i.e., Perkin-Elmer Cetus, Conn.) with repetitive cycles of annealing, extension, and denaturation. As will be appreciated, such steps can be modified to optimize the PCR amplification for any particular reaction, however, exemplary conditions utilized include denaturation at 95° C. for 1 minute, annealing at 55° C. for 1 minute, and extension at 72° C. for 4 minutes, respectively, for 30 cycles. Further details of the PCR technique can be found in Erlich, "PCR Technology," Stockton Press (1989) and U.S. Pat. No. 4,683,202, the disclosure of which is incorporated herein by reference.

Following PCR amplification, the PCR products are subjected to a ligation assay. Generally, ligation of the oligonucleotides requires a 5'-phosphate and a 3'—OH held in proximity by annealing to a complementary DNA strand (i.e., the PCR product), ligation buffer, and DNA ligase. A phosphodiester bond is formed through the reaction. If, however, there is a sequence dissimilarity at the point of ligation, ligation will not be accomplished and no phosphodiester bond will be formed.

In a preferred assay, two ligation oligonucleotides are utilized (i.e., such as the ligation oligonucleotides mentioned above for the detection of the 24d1 mutation (SEQ ID NO:15 and SEQ ID NO:17 for detection of the G allele or SEQ ID NO:16 and SEQ ID NO:17 for detection of the A allele)). The PCR products and the ligation oligonucleotides are suspended in ligation buffer, including NAD, with a DNA ligase, preferably amp-ligase (Epicentre) which is a thermal ligase. Ten cycles of ligation are performed at 94° C. for 20 seconds and 58° C. for 2 minutes in a thermal cycler. The reaction is stopped with EDTA and the product is transferred to streptavidin-coated plates and incubated for 45 minutes. Thereafter the wells are alkaline washed to denature the oligonucleotides from the initial PCR products and then washed with TRIS buffer to remove any unbound materials (i.e., all products other than the biotinylated products which bind to the streptavidin on the plates).

Detection is accomplished, preferably, through use of an anti-digoxigenin antibody conjugated with alkaline phosphatase (Boehringer-Mannheim) which is added and incubated at 37° C. for 30 minutes. The plates are washed with TRIS buffer to remove any unbound antibody. An ELISA detection kit (Life Technologies) is utilized where NADPH is used as a substrate where the alkaline phosphatase conjugated to the antibody cleaves NADPH to NADH. The NADH produced by this reaction is used as a cofactor for diaphorase to turn INF-violet to Formazan which generates a red color. Presence of the red color provides a positive signal that ligation occurred and lack of the red color indicates that ligation did not occur, which indicates the presence or absence of the specific base being assayed.

As will be appreciated, the OLA assay allows the differentiation between individuals who are homozygous versus heterozygous for particular mutations (such as the 24d1 mutation, for which the ligation oligonucleotides mentioned above are designed, or the 24d2 mutation). This feature allows one to rapidly and easily determine whether an individual is at a significant risk of developing HH. Oligonucleotides useful for amplifying and detecting the 24d2 mutant and normal alleles are provided in FIG. 9.

In the OLA assay, when carried out in microtiter plates, for example, one well is used for the determination of the presence of the normal allele (i.e., the 24d1:G allele) and a second well is used for the determination of the presence of the mutated allele (i.e., the 24d1:A allele). Thus, the results for an individual who is heterozygous for the 24d1 mutation will show a signal in each of the A and G wells and an individual who is homozygous for the 24d1:A allele will show a signal in only the A well. Those individuals who are homozygous for the A allele at 24d1 are, as discussed above, homozygous for the common ancestral HH-mutation and are at a significant risk of developing HH disease.

In particular, therefore, a kit for detecting the 24d1 mutation by OLA assay is provided. In the kit, amplification primers for DNA or RNA (or generally primers for amplifying a sequence of genomic DNA, reverse transcription products, complementary products) including the 24d1 mutated and normal alleles are provided. Ligation assay oligonucleotides are also preferably provided. The kit further includes separate reaction wells and reagents for detecting the presence of homozygosity or heterozygosity for the 24d1 mutation.

Within the same kit, or in separate kits, oligonucleotides for amplification and detection of other differences (such as the 24d2 mutation and/or the 24d7 sequence variant) can also be provided. If in the same kit as that used for detection of the 24d1 mutation, separate wells and reagents are provided, and homozygosity and heterozygosity can similarly be determined.

Because of the enrichment of the 24d2 mutation in individuals who are heterozygous for the 24d1 mutation, kits are specifically envisioned in accordance with the invention which screen for the presence of the 24d2 mutation when 24d1 heterozygosity is detected.

EXAMPLE 2

HH Diagnostic: Other Nucleotide Based Assays

As will be appreciated, a variety of other nucleotide based detection techniques are available for the detection of mutations in samples of RNA or DNA from patients. See, for example, Section (III)(A)(2), above, entitled "Nucleic Acid Based Screening." Any one or any combination of such techniques can be used in accordance with the invention for the design of a diagnostic device and method for the screening of samples of DNA or RNA for HH gene mutations in accordance with the invention, such as the mutations and sequence variants identified herein (24d1, 24d2, and 24d7). Further, other techniques, currently available, or developed in the future, which allow for the specific detection of mutations and sequence variants in the HH gene are contemplated in accordance with the invention.

Through use of any such techniques, it will be appreciated that devices and methods can be readily developed by those of ordinary skill in the art to rapidly and accurately screen for mutations and sequence variants in the HH gene in accordance with the invention.

Thus, in accordance with the invention, there is provided a nucleic acid based test for HH gene mutations and sequence variants which comprises providing a sample of a patient's DNA or RNA and assessing the DNA or RNA for the presence of one or more HH gene mutations or sequence variants. Samples of patient DNA or RNA (or genomic, transcribed, reverse transcribed, and/or complementary sequences to the HH gene) can be readily obtained as described in Example 1. Through the identification and characterization of the HH gene as taught and disclosed in the present invention, one of ordinary skill in the art can readily identify the genomic, transcribed, reverse transcribed, and/or complementary sequences to the HH gene sequence in a sample and readily detect differences therein. Such differences in accordance with the present invention can be the 24d1, 24d2, and/or 24d7 mutations or sequence variations identified and characterized in accordance herewith. Alternatively, other differences might similarly be detectable.

Kits for conducting and/or substantially automating the process of identification and detection of selected changes, as well as reagents utilized in connection therewith, are therefore envisioned in accordance with the invention of the present invention.

EXAMPLE 3

HH Diagnostic: Antibody Based Assay

As discussed in Section (III)(A)(3), herein, entitled "Antibodies," antibodies specific to both the normal/wild-type or mutated gene products of the HH gene can be readily prepared. Thus, in accordance with the invention a kit for the detection of an HH gene product, and particularly, the mutated HH gene product is provided for use in a diagnostic test for the presence of HH disease.

Antibody based tests are well known in the art. In general, a sample of tissue, cells, or bodily fluid is obtained, or provided, from a patient. If the sample contains cells or tissues, typically the sample is disrupted to free the HH gene product. Alternatively, if surface expression exists, whole cells can be utilized. Thereafter, the sample is contacted with an antibody specific to the selected HH gene product and binding of the antibody, if any, is detected. Typically, the antibody is bound to, either directly, or through another moiety (i.e., biotin), a label to facilitate detection of hybridization. Such label can be radioactive, fluorescent, a dye, a stain, or the like.

Thus, antibodies for diagnostic applications, and diagnostic kits including antibodies (and/or other reagents utilized in connection therewith) are provided in accordance with the invention.

EXAMPLE 4

HH Therapy: In Vivo Gene Therapy

The discovery of the HH gene in accordance with the invention also provides a therapeutic for HH disease in the form of gene therapy. In the present example, gene therapy is accomplished in vivo. In in vivo gene therapy, a patient is treated with a gene product in a form that is designed to cause the patient to express the gene.

The coding region of the HH gene, or parts or portions thereof, can be incorporated into a suitable vector for use in the treatment of HH disease. Indeed, the coding region of the HH gene is of a manageable size for incorporation in a viral vector, such as a retroviral or adenoviral vectors. Generally, the vector will be construct to include suitable promoters, enhancers, and the like. Additional information related to the design of HH gene construct for use in gene therapy is provided in Section (III)(B)(1), entitled "Expression Systems."

Viral vector systems have been indicated as highly efficient in transferring genes to mammals containing deficient genes. See, for example, Crystal *Am. J. Med.* 92(6A):44S–52S (1992); Lemarchand et al. *Proc. Nat'l Acad. Sci. USA* 89(14):6482–6486 (1992) the disclosures of which are hereby incorporated by reference.

The viral vector can also be conveniently administered to a patient. For example, administration may be accomplished through, for example, liquid lavage, direct injection, or through ex vivo treatment of cells, followed by reinfusion of such cells into the patient. Particularly preferred tissues for delivery of vectors including the HH gene are the liver and the gut. It will be appreciated that liquid lavage or direct injection can be utilized for delivery of the vector to the gut, while direct injection will presumably be necessary for delivery to the liver.

EXAMPLE 5

HH Therapy: Protein Replacement Therapy

As discussed above, also provided in accordance with the invention is a therapy for HH disease involving replacement of the HH protein product. Where a patient is diagnosed as having HH disease and is not producing, or is underproducing, the normal HH gene product, such patient can be treated by replacing the normal HH gene product to assist the patient's body in combating HH disease.

The HH gene product can be produced through the methods discussed above in connection with the Section entitled "Protein Purification" above.

Delivery of the HH gene product can be accomplished as discussed in connection with Section entitled "Therapeutics" above.

EXAMPLE 6

HH Therapy: Drug Design and Screening

As discussed above in connection with the Section entitled "Pharmacological," the HH gene and parts and portions thereof can be utilized for drug screening. Cell-based and cell-free assays are envisioned in accordance with the invention. As discussed above, a variety of drugs and other therapeutics have been proposed to have activity in HH disease. Compounds such as those described can be assayed in cellular systems containing the HH gene or the mutations therein. Cellular functions such as HH protein folding, iron uptake, transport, metabolism, receptor-like activities, other upstream or downstream processes, such as gene transcription and other signaling events, and the like can be assayed. Each of these functions can be analyzed using conventional techniques that are well known in the art.

It is expected that through use of such assays, compounds can be rapidly screened for potential activity in HH disease and compounds showing high activity can be used for the construction of combinatorial libraries. Candidates from the combinatorial libraries can be re-assayed and those with better activity than the parent compound can be analyzed for clinical development.

EXAMPLE 7

HH Study: Animal Models of HH Disease

As discussed above, through knowledge of the gene-associated mutations responsible for HH disease, it is now possible to prepare transgenic animals as models of the HH disease. Such animals are useful in both understanding the mechanisms of HH disease as well as use in drug discovery efforts. The animals can be used in combination with cell-based or cell-free assays for drug screening programs.

In preparation of transgenic animals in accordance with the invention, genes within embryonic stem cells (ES cells) can be inactivated by homologous recombination. See Capecci supra. (1989). Specifically, an isogenic mouse genomic library (i.e., an Sv-129 library) can be screened with a human HH gene cDNA probe. The resultant clones from the library are then sequenced to ensure sequence identity to the mouse HH gene homologous cDNA. A targeting vector is then constructed from the mouse genomic DNA consisting of two approximately 3 Kb genomic fragments from the mouse HH gene as 5' and 3' homologous arms. These arms would be chosen to flank a region critical to the function of the HH gene product, such as exon 4 (the immunoglobulin-like region which contains the proposed critical β-2-microglobulin interactive domain and essential disulfide linkage). However, other regions could also be targeted.

In place of exon 4, negative and positive selectable markers can be placed, for example, to abolish the activity of the HH gene. As a positive selectable marker a neo gene under control of phosphoglycerate kinase (pgk-1) promoter may be used and as a negative selectable marker the 5' arm of the vector can be flanked by a pgk-1 promoted herpes simplex thymidine kinase (HSV-TK) gene can be used.

The vector is then transfected into R1 ES cells and the transfectants are subjected to positive and negative selection (i.e., G418 and gancyclovir, respectively, where neo and HSV-TK are used). PCR is then used to screen for surviving colonies for the desired homologous recombination events. These are confirmed by Southern blot analysis.

Subsequently, several mutant clones are picked and injected into C57BL/6 blastocytes to produce high-percentage chimeric animals. The animals are then mated to C57BL/6 females. Heterozygous offspring can then be tested for the HH gene mutation by Southern blot analysis. In addition, these animals are tested by RT-PCR to assess whether the targeted homologous recombination results in the ablation of the HH gene mRNA. These results are confirmed by Northern blot analysis and RNase protection assays.

Once established, the HH gene –/– mice can be studied for the development of HH-like disease and can also be utilized to examine which cells and tissue-types are involved in the HH disease process. The animals can also be used to introduce the mutant or normal HH gene or for the introduction of the homologous gene to that species (i.e., mouse) and containing the 24d1, 24d2, or other disease causing mutations. Methods for the above-described transgenic procedures are well known to those versed in the art and are described in detail by Murphy and Carter supra (1993).

The techniques described above can also be used to introduce the 24d1 or 24d2 mutations, or other homologous mutations in the animal, into the homologous animal gene. As will be appreciated, similar techniques to those described above, can be utilized for the creation of many transgenic animal lines, i.e., pig, sheep, goat, ape, orangutan, primate, or the like, and mice are only demonstrative.

EXAMPLE 8

HH Diagnostic: Allele-specific Oligonucleotide-hybridization Assay

As discussed above, an allele-specific oligonucleotide-hybridization assay (Wallace et al., *Nucleic Acids Res.* 6:3543–3556 (1978)) can be used to discriminate between normal and mutated alleles of the hemochromatosis gene.

A sample of DNA or cDNA reverse transcribed from RNA is subjected to PCR so as to amplify the DNA segment that contains the polymorphic site. The PCR product is immobilized on a solid support, denatured and hybridized with 2 separate oligonucleotide probes that anneal to the complementary strand of the immobilized PCR product in an allele-specific fashion. The oligonucleotides are identical in sequence except for the polymorphic site (which is typically near the center of the oligonucleotide sequence). The first oligonucleotide can form a perfect and therefore relatively stable double helix with the PCR product containing allele 1, whereas annealing of oligonucleotide 1 to allele-2-containing PCR product will result in a less stable hybrid due to the interruption of the double helix by the mismatched base-pair. Similarly, oligonucleotide 2 will form a stable hybrid with allele-2 containing PCR product but not with PCR product containing allele 1. Heterozygous DNA samples will give rise to a mixed PCR product that will hybridize to both allele-specific oligonucleotides. The allele-specific oligonucleotide probes are typically between 15 and 20 nucleotides in length with the polymorphic site near the center of the oligonucleotide sequence, as a mismatch near the center is expected to have to have the most destabilizing effect on a heteroduplex.

Prior to performing the allele-specific oligonucleotide-hybridization assay for the A and G alleles at the 24d1 locus, genomic DNA or cDNA reverse-transcribed from RNA is subjected to PCR using the following primers:

```
TGGCAAGGGTAAACAGATCC        (SEQ ID NO:13)

CTCAGGCACTCCTCTCAACC        (SEQ ID NO:14)
```

Prior to performing the allele-specific oligonucleotide-hybridization assay for the two 24d2 alleles, genomic DNA or cDNA reverse-transcribed from RNA is subjected to PCR using the following primers:

```
ACATGGTTAAGGCCTGTTGC        (SEQ ID NO:24)

GCCACATCTGGCTTGAAATT        (SEQ ID NO:25)
```

The PCR is performed in standard PCR-reaction buffer (e.g., 1X PCR reaction buffer with 1.5 mM Mg++ like GENEAMP reaction buffer from Perkin Elmer with 1.5 mM $Mg^{++}$) for 35–30 cycles using an annealing temperature of 60° C.

After PCR, the reaction mixture is boiled for 3 minutes and then chilled on ice. One volume of 20× SSC buffer is added and approximately 2 μl of the mixture spotted onto two duplicate nylon filters (one for each allele) that have been pre-wetted in 10× SSC buffer. Alternatively, a dot-blotting or slot-blotting apparatus may be used. The membranes are soaked in 0.5M NaOH/1.5M NaCl solution, neutralized in 0.5M Tris-HCl, pH 7.5, and subjected to UV crosslinking to form a covalent bond between the denatured PCR product and the filter.

Examples of oligonucleotide sequences specific for the 24d1 and 24d2 alleles are given in the following table. It is possible to design allele-specific oligonucleotides that differ from the ones shown in size and/or position of the polymorphic site. Oligonucleotides of complementary sequence may be used as well.

| Allele | Example of allele-specific oligonucleotides | |
|---|---|---|
| 24d1:G | 5' ATATACGTGCCAGGTGG | (SEQ ID NO:45) |
| 24d1:A | 5' ATATACGTACCAGGTGG | (SEQ ID NO:46) |
| 24d2:C | 5' TCTATGATCATGAGAGT | (SEQ ID NO:47) |
| 24d2:G | 5' TCTATGATGATGAGAGT | (SEQ ID NO:48) |

The oligonucleotides are radiolabeled at the 5' end using gamma $^{32}P$ ATP and T4 polynucleotide kinase using standard procedures (Sambrook, Fritsch, Maniatis, *Molecular Cloning*, 2nd edition, Cold Spring Harbor Laboratory Press, Cold Spring Harbor, N.Y., (1989) 11.31). One membrane containing PCR amplified 24d1 locus is subjected to hybridization with the labeled oligonucleotide probe specific for the 24d1:G allele. The duplicate membrane is hybridized with the oligonucleotide specific for the 24d1:A allele. Similarly, duplicate membranes containing PCR amplified 24d2 locus are subjected to separate hybridizations with the two allele-specific oligonucleotides for 24d2. The stringency of the hybridization conditions (hybridization temperature, salt concentration of the hybridization and post-hybridization wash solutions, temperature and duration of the post-hybridization washes) are empirically determined to optimize sensitivity and specificity of the assay. Guidelines for suitable ranges of hybridization conditions are available in most standard laboratory manuals (e.g., Sambrook, Fritsch, Maniatis, *Molecular Cloning*, 2nd edition, Cold Spring Harbor Laboratory Press, Cold Spring Harbor, N.Y., (1989) 11.45–61).

After the last post-hybridization wash, radiolabeled probe that is bound to the spotted PCR product is detected by autoradiography. DNA samples from patient who are homozygous for the 24d1 G allele give rise to a positive hybridization signal with the 24d1 G-specific oligonucleotide but not with the 24d1A-specific oligonucleotide probe. DNA samples from 24d1:A homozygotes give rise to a positive signal with the 24d1:A-specific, but not with the 24d1:G-specific probe. Heterozygous samples are positive for both probes. 24d2 genotypes are called in an analogous fashion. In order to facilitate the interpretation of hybridization results, suitable control DNA samples of known genotype are processed along with unknown DNA samples.

EXAMPLE 9

HH Diagnostic: Allele-specific PCR Assay

As discussed above, an allele-specific PCR assay (Newton et al, *Nucleic Acids Res*. 17:2503–2516 (1989)) can be used to discriminate between normal and mutated alleles of the hemochromatosis gene.

The allele-specific PCR assay exploits differences in priming efficiency of a perfectly-matched PCR primer and a mismatched PCR primer. Typically, the two allele-specific primers are identical except for the allele-specific nucleotide at the 3' end. The primer specific for allele 1 can form a perfect duplex upon annealing to denatured target DNA containing allele 1, whereas its 3' nucleotide will not be base-paired after annealing to allele-2-containing target DNA. Conversely, the allele-2-specific primer can form a perfect double helix after annealing to allele-2-containing DNA but will have an unpaired 3' nucleotide when annealed to allele-1-containing DNA. Only the cognate primer can be efficiently extended by DNA polymerase. Each allele-specific primer is used in combination with a third, common PCR primer. Depending on the genotype of the DNA sample, either one or the other or both primer-pairs will give rise to a PCR product.

Examples of PCR primer pairs for allele-specific amplification of the 24d1 and 24d2 loci are given in the following table. Suitable alternative allele-specific primers may have more or less nucleotides at their 5' end. It is also possible to design allele-specific primers that can anneal to the other strand of the target DNA. The common PCR primer may be any non-repetitive sequence of 10 or more nucleotides on the complementary strand that is within "PCRable distance" of the allele-specific primer and has a suitable annealing temperature. Suitable primer pairs can be selected using published guidelines (e.g., Kramer, M. F and Coen, D. M. in *Current Protocols in Molecular Biology*, Ausubel, F. M. et al., eds., Wiley, Chapter 15.03) or by using primer-picking programs such as PRIMER (Lincoln, S. E., Daly, M. J., Lander, E. S. 1991. PRIMER: A Computer Program for Automatically Selecting PCR Primers.Version 0.5 Manual. MIT Center for Genome Research and Whitehead Institute for Biomedical Research. Nine Cambridge Center. Cambridge, Massachusetts 02142) or OSP (Hillier, L. and Green, P. (1991): OSP: A computer program for choosing PCR and DNA sequencing primers. PCR Methods and Applications, 1:124–128).

| Allele | Allele-specific PCR primer 5' | SEQ ID NO: | Common PCR primer | SEQ ID NO: | Size (bp) |
|---|---|---|---|---|---|
| 24d1:G | TGGGTGCTCCACCTGGC | 49 | TGGCAAGGGTAAACAGATCC | 13 | 296 |
| 24d1:A | TGGGTGCTCCACCTGGT | 50 | TGGCAAGGGTAAACAGATCC | 13 | 296 |
| 24d2:C | CACACGGCGACTCTCATG | 51 | ACATGGTTAAGGCCTGTTGC | 24 | 159 |
| 24d2:G | CACACGGCGACTCTCATC | 52 | ACATGGTTAAGGCCTGTTGC | 24 | 159 |

The PCR is performed according to standard protocols procedures (e.g., Sambrook, Fritsch, Maniatis, *Molecular Cloning*, 2nd edition, Cold Spring Harbor Laboratory Press, Cold Spring Harbor, N.Y., (1989) 14.18) and the reaction mixture analyzed by electrophoresis on a polyacrylamide or an agarose gel. The PCR product is visualized by EtBr staining. The stringency of the PCR reaction conditions is empirically determined (by changing parameters such as annealing temperature of $MgCl_2$ concentration) to optimize sensitivity and allele-specificity of the assay.

DNA samples from patient who are homozygous for the 24d1:G allele give rise to a positive PCR reaction with the primer pair containing the 24d1:G-specific primer but not with the 24d1:A-specific primer. DNA samples from 24d1:A homozygotes give rise to a positive signal with the 24d1:A-specific, but not the 24d1:G-specific PCR primer. Heterozygous samples are positive in both reactions. 24d2 genotypes are called in an analogous fashion. In order to facilitate the interpretation of PCR results, suitable control DNA samples of known genotype are processed along with unknown DNA samples.

take place, i.e., part of the excitation energy is transferred from the fluorescein molecule to the ROX molecule, which in turn emits a photon. Since the emission spectrum of the acceptor is different than that of the donor, the FRET can be analyzed by measuring the ROX-emission upon excitation of fluorescein. Two separate extension reactions, one with the ROX-labeled ddNTP specific for allele 1 and one with the ROX-labeled ddNTP specific for allele 2, are performed, and each extension reaction is followed by measuring the FRET from fluorescein to ROX. The target region is typically preamplified by PCR.

Examples of oligonucleotide primers and dideoxynucleotide combinations suitable for the discrimination between the 2 respective 24d1 and 24d2 alleles are given in the following table. Two alternative sets are given, one for each strand.

| locus | Primer | SEQ ID NO: | ROX-ddNTP (normal allele) | ROX-ddNTP (mutant allele) |
|---|---|---|---|---|
| 24d1 | (1) F-GGAAGAGCAGAGATATACGT | 53 | ROX-ddG | ROX-ddA |
| 24d1 | (2) F-GGCCTGGGTGCTCCACCTGG | 54 | ROX-ddC | ROX-ddU |
| 24d2 | (3) F-AGCTGTTCGTGTTCTATGAT | 55 | ROX-ddC | ROX-ddG |
| 24d2 | (4) F-CTCCACACGGCGACTCTCAT | 56 | ROX-ddG | ROX-ddC |

EXAMPLE 10
HH Diagnostic: Template-directed Incorporation Assay

As discussed above, the template-directed incorporation assay can be used to discriminate between normal and mutated alleles of the hemochromatosis gene. In this assay, an oligonucleotide primer is designed that anneals to the target DNA such that its 3' end is immediately adjacent to the polymorphic position. DNA polymerase and 4 different dideoxy nucleotides are added. Depending on the allele present, the primer is extended by one of two alternative dideoxy nucleotides.

In one embodiment of this assay (Chen & Kwok, *Nucleic Acids Res.* 25:347–353 (1997)), the primer carries a fluorescent moiety (fluorescein, the "donor") at its 5' end, and the two allele-specific dideoxynucleotides carry another fluorescent dye (ROX, the "acceptor" molecule). After extension of the 5' fluorescein-labeled primer molecule with the ROX-labeled ddNTP dyes, both donor and acceptor are attached to the same molecule and thus in close proximity. Upon excitation of a fluorescein molecule that is in close proximity to a ROX molecule, a physical phenomenon called fluorescence resonance energy transfer (FRET) can After PCR amplification of the 24d1 or 24d2 locus using standard conditions (see above), the PCR product is purified by gel-electrophoresis. Two separate primer-extension reactions (each containing fluorescein-labeled primer, the allele-specific ROX-labeled ddNTP and three unlabeled ddNTPs) are set up and the reaction performed by thermocycling (35 cycles) between 93° C. and 50° C. NaOH is added to the reaction mixtures, and the incorporation of ROX-labeled ddNTP is measured by determining ROX emission (605 nm) upon excitation of fluorescein (488 nm) on a fluorescence spectrophotometer. The data are normalized, processed and plotted as described by Chen & Kwok, *Nucleic Acids Res.* 25:347–353 (1997)).

DNA samples that are homozygous for the normal 24d1 allele will give rise to a positive FRET signal after extension of primer (1) with ROX-ddG whereas the extension-reaction of primer (1) in the presence of ROX-ddA will be negative. In contrast, DNA samples that are homozygous for the mutant 24d1 allele will be positive only in the reaction with ROX-ddA. Heterozygous samples will be positive with both ROX-ddG and ROX-ddA, but the FRET signal will be lower than with homozygous samples. Extension reactions containing Primer (2) and either ROX-ddC or ROX-ddU are analyzed in an analogous fashion, as are the 24d2 genotyping reactions based on allele-specific extension of either primer (3) or primer (4). In order to facilitate the interpretation of the results, DNA samples of known genotype are processed along with unknown DNA samples.

EXAMPLE 11

HH Diagnostic: PNA-mediated PCR-clamping Assay

Many diagnostic methods involve the formation of a hybrid comprising the test DNA and an allele specific probe, usually an DNA oligonucleotide. It is possible to use a peptide nucleic acid oligonucleotide (PNA) probe instead. PNA differ from DNA in that the DNA ribose-phosphate backbone is replaced by a peptide backbone. Due to this chemical difference, PNA-DNA hybrids differ from DNA-DNA hybrids in several respects: PNA-DNA hybrids have a higher thermal stability (because of the lack of electrostatic repulsion between the two backbones); the difference in melting temperature between a perfectly matched and a mismatched hybrid is larger for PNA-DNA than for their DNA-DNA counterparts thus increasing the specificity of the interaction; PNA-DNA hybrids are no substrate for DNA polymerase, i.e., the PNA cannot serve as a PCR primer.

In the following example (based on Orum et al., *Nucleic Acids Res.* 21:5332–5336 (1993) and Thiede et al. *Nucleic Acids Res.* 24, 983–984 (1996)), an allele-specific PNA oligonucleotide competes with the 3' end of a generic DNA-oligonucleotide primer for annealing to the target DNA. If the PNA oligonucleotide matches the sequence of the target strand, it will out-compete the PCR primer resulting in a negative PCR reaction. If the target DNA differs from the PNA probe at one position, the PNA-DNA interaction is much weaker, the PCR primer can anneal and give rise to an amplification product.

The DNA sample to be tested is split into four aliquots. The first aliquot receives a PNA-oligonucleotide that matches the normal 24d1 sequence, the second receives an PNA-oligonucleotide that matches the mutant 24d1 allele, the third and fourth aliquots receive PNA oligos that match normal and mutated 24d2 alleles, respectively. The reactions are complemented with PCR primers to amplify the 24d1 and 24d2 loci, respectively. The various combinations of PNA oligonucleotides and PCR primers are specified below. In this reaction the cognate PNA probe will abolish a reaction. In order to discriminate between specific inhibition and other causes for negative PCR reaction (such as unspecific inhibitors or omission of essential ingredients) PCR primers specific for another, unrelated genomic locus can be included (which should be amplifiable regardless of the which PNA oligonucleotide is present and regardless of the genotype at 24d1 or 24d2 of the DNA sample).

| Allele | PNA | SEQ ID NO: | PCR primer 1 | SEQ ID NO: |
|---|---|---|---|---|
| 24d1:G | GCTCCACCTGGCACG | 57 | CTCAGGCACTCCTCTCAACC | 14 |
| 24d1:A | GCTCCACCTGGTACG | 58 | CTCAGGCACTCCTCTCAACC | 14 |
| 24d2:C | GCGACTCTCATCATC | 59 | GCCACATCTGGCTTGAAATT | 25 |
| 24d2:G | GCGACTCTCATGATC | 60 | GCCACATCTGGCTTGAAATT | 25 |

-continued

| Allele | PCR primer 2 | SEQ ID NO: | Size (bp) |
|---|---|---|---|
| 24d1:G | GGAAGAGCAGAGATATACGT | 53 | 131 |
| 24d1:A | GGAAGAGCAGAGATATACGT | 53 | 131 |
| 24d2:C | AGCTGTTCGTGTTCTATGAT | 55 | 87 |
| 24d2:G | AGCTGTTCGTGTTCTATGAT | 55 | 87 |

The PCR is performed according to standard protocols procedures (e.g., Sambrook, Fritsch, Maniatis, *Molecular Cloning*, 2nd edition, Cold Spring Harbor Laboratory Press, Cold Spring Harbor, N.Y., (1989) 14.18) and the reaction mixture analyzed by electrophoresis on a polyacrylamide or an agarose gel. The PCR product is visualized by EtBr staining. The stringency of the PCR reaction conditions is empirically determined (by changing parameters such as annealing temperature of $MgCl_2$ concentration) to optimize sensitivity and allele-specificity of the assay.

DNA samples from patients who are homozygous for the 24d1:G allele fail to amplify in presence of the 24d1:G-specific PNA but should give rise to a 131-bp PCR product in presence of the 24d1:A-specific PNA oligonucleotide. DNA samples from 24d1:A homozygotes will be negative in the reaction containing the 24d1:A-specific PNA but positive in the reaction with the 24d1:G-specific PNA molecule. Heterozygous samples will be positive in both reactions. 24d2 genotypes are called in an analogous fashion. In order to facilitate the interpretation of PCR results, suitable control DNA samples of known genotype are processed along with unknown DNA samples.

EXAMPLE 12

HH Diagnostic: Ligase-Chain-Reaction Assay

The ligase chain reaction (LCR; Wu & Wallace, *Genomics* 4: 560–569 (1989)) is an amplification method which is based on the template-dependent ligation of two adjacent oligonucleotides. The DNA sample is denatured in the presence of two pairs of oligonucleotides. Upon lowering the reaction temperature, pair 1 will anneal side-by-side on one strand, pair 2 will anneal side-by-side at the identical position on the complementary strand. Two of the oligonucleotides carry a phosphate group at their 5' end thus allowing the enzyme DNA ligase to form a covalent bond between the two oligonucleotides annealed on the same strand. After ligation, the temperature is raised again, and another annealing and ligation cycle is performed. Since non-ligated oligonucleotide pairs can anneal to the ligation products formed in the previous cycle, the amount of ligated oligonucleotides will double with each reaction cycle leading to an exponential amplification of double-stranded DNA consisting of the two ligated complementary oligonucleotide-pairs. Because the ligation does not occur in the presence of a mismatch between the template and one of the two oligonucleotides at any of the positions flanking the ligation junction, an allele-specific LCR amplification assays can be developed (Barany, *Proc. Natl. Acad. Sci. USA* 88: 189–193 (1991)).

Traditionally, the LCR oligonucleotides are radiolabeled and the LCR-amplification product is detected as a radioactive electrophoresis band, which is larger than the input oligonucleotides. Modern high-throughput incarnations of this method use fluorescently-labeled oligonucleotides in combination with ABI-type sequencers or capillaryelectrophoresis systems to resolve input from product oligonucleotides. In the following example, the LCR-product is detected by a solid-phase-capture/detection-tagging strategy similar to that described above for OLA (Nickerson et al., in *Current Protocols in Human Genetics*, Ausubel, F. M. et al., eds., Wiley, Chapter 2.6), i.e., one of the oligonucleotides is biotinylated and its ligation partner is digoxigenin labeled; hence only the ligated product will bind to a streptavidin-coated plate and give rise to a positive reaction with an anti-digoxigenin antibody.

To increase the number of target molecules prior to performing the allele-specific LCR assay for the A and G alleles the 24d1 and 24d2 loci may be preamplified from total genomic DNA or cDNA reverse-transcribed from RNA by PCR using the following primer pairs. This preamplification step is optional. Alternatively one can start with total genomic DNA and perform more LCR cycles to amplify the two loci during the LCR itself.

```
24d1:
TGGCAAGGGTAAACAGATCC      (SEQ ID NO:13)

CTCAGGCACTCCTCTCAACC      (SEQ ID NO:14)

24d2:
ACATGGTTAAGGCCTGTTGC      (SEQ ID NO:24)

GCCACATCTGGCTTGAAATT      (SEQ ID NO:25)
```

The PCR is performed in standard PCR-reaction buffer (e.g., 1X GeneAmp reaction buffer from Perkin Elmer with 1.5 mM Mg++) for 35–30 cycles using an annealing temperature of 60° C.

Two allele-specific LCR-reactions are set up for each locus containing thermostable ligase, and the following combination of oligonucleotides:

| Allele | oligonucleotide-pair 1 | SEQ ID NO: | oligonucleotide-pair 2 | SEQ ID NO: |
|---|---|---|---|---|
| 24d1:G | bio-GCCTGGGTGCTCCACCTGGC | 61 | bio-GAAGAGCAGAGATATACGTG | 63 |
|  | pACGTATATCTCTGCTCTTCC-dig | 62 | pCCAGGTGGAGCACCCAGGCC-dig | 64 |
| 24d1:A | bio-GCCTGGGTGCTCCACCTGGT | 65 | bio-GAAGAGCAGAGATATACGTA | 67 |
|  | pACGTATATCTCTGCTCTTCC-dig | 66 | pCCAGGTGGAGCACCCAGGCC-dig | 68 |
| 24d2:C | bio-TCCACACGGCGACTCTCATG | 69 | bio-GCTGTTCGTGTTCTATGATC | 71 |
|  | pATCATAGAACACGAACAGCT-dig | 70 | pATGAGAGTCGCCGTGTGGAG-dig | 72 |
| 24d2:G | bio-TCCACACGGCGACTCTCATC | 73 | bio-GCTGTTCGTGTTCTATGATG | 75 |
|  | pATCATAGAACACGAACAGCT-dig | 74 | pATGAGAGTCGCCGTGTGGAG-dig | 76 |

The reaction mixes are subjected to 5–10 thermocycles (for PCR amplified targets) or 25–30 thermocycles (for non-amplified samples), with each cycle consisting of a 30 sec denaturation step at 94° C. and a 2 min. ligation step at 60° C.

After the last cycle, the reaction mixtures are transferred to streptavidin-coated microtiter plates to capture biotinylated oligonucleotides. Un-ligated 3'-digoxigenin-labeled oligonucleotides are removed by denaturation and extensive washing. Finally, captured and digoxigenin-containing (i.e., ligated) products are detected with an anti-digoxigenin Fab fragment that is conjugated to alkaline phosphatase, whose presence in turn is assayed by a suitable calorimetric reaction, similar to the detection procedure described above for OLA assays.

EXAMPLE 13

RFLP-Southern Analysis

Genomic DNA from individuals can be digested using restriction endonucleases and size fractionated in agarose gels by electrophoresis (Kan and Dozy, *Lancet* ii:910–912 (1978)). The DNA fragments are then transferred to nylon membranes (or nitrocellulose) and fixed by standard techniques such as chemical or UV crosslinking. A DNA probe such as the cDNA or genomic DNA surrounding the mutation can be labeled by either 32P or other conventional methods and hybridized to the filters, washed and exposed to X-ray film. For detection of the 24d1 mutation, either Rsa I or Sna BI restriction endonucleases can be used. In both cases the 24d1 mutation creates an additional site. For detection of the 24d2 mutation, either Bcl I, Sau 3A, Mbo I, or Dpn II restriction endonucleases can be used. In all cases the 24d2 mutation destroys a site.

EXAMPLE 14

RFLP-PCR Analysis

Genomic DNA from individuals can be amplified using the polymerase chain reaction using oligonucleotide primers that flank the 24d1 and 24d2 mutations. For example the following sets of primers can be used:

```
24d1  5'    TGGCAAGGGTAAACAGATCC 3'    (SEQ ID NO:13)

5'    CTCAGGCACTCCTCTCAACC 3'    (SEQ ID NO:14)
      PCR product = 390 bp
```

-continued
```
24d2  5'    ACATGGTTAAGGCCTGTTGC 3'    (SEQ ID NO:24)

5'    GCCACATCTGGCTTGAAATT 3'    (SEQ ID NO:25)
      PCR product = 208 bp
```

The resulting product sizes are given. These PCR products can be subjected to restriction endonuclease digestion using the same enzymes described in the RFLP—Southern Analysis example. For detection of the 24d1 mutation, either Rsa I or Sna BI restrictions endonucleases can be used. The wild type (unmutated) allele will have a 250 bp and a 140 bp band following Rsa I digestions and size fractionation on agarose gels with ethidium bromide staining. The mutant allele will produce 3 bands of 250 bp, 111 bp, and 29 bp under the same conditions. For detection of the 24d2 mutation, either Bcl I, Sau 3A, Mbo I, or Dpn II restriction endonucleases can be used. In all cases the 24d2 mutation destroys a site. In the example of using Bcl I the wild type allele will result in band sizes of 138 bp and 70 bp. The mutant allele destroys a site resulting in a band size of 208 bp.

INCORPORATION BY REFERENCE

All references (including books, articles, papers, patents, and patent applications) cited herein are hereby expressly incorporated by reference in their entirety for all purposes.

EQUIVALENTS

While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

What is claimed is:

1. An isolated polypeptide comprising the amino acid sequence as shown in SEQ ID NO:2.

2. An isolated polypeptide comprising the amino acid sequence as shown in SEQ ID NO:4.

3. An isolated polypeptide comprising the amino acid sequence as shown in SEQ ID NO:6.

4. An isolated polypeptide comprising the amino acid sequence as shown in SEQ ID NO:8.

5. An isolated polypeptide comprising an alpha1 domain of a MHC Class I protein contained within the amino acid sequence as shown in SEQ ID NO:2.

6. An isolated polypeptide comprising an alpha2 domain of a MHC Class I protein contained within the amino acid sequence as shown in SEQ ID NO:2.

7. An isolated polypeptide comprising an alpha3 domain of a MHC Class I protein contained within the amino acid sequence as shown in SEQ ID NO:2.

8. An isolated polypeptide comprising a transmembrane domain of a MHC Class I protein contained within the amino acid sequence as shown in SEQ ID NO:2.

9. The isolated polypeptide of claim 1, in which amino acid residue #65 is changed from serine to cysteine.

10. The isolated polypeptide of claim 1, which interacts with β-2-microglobulin.

11. The isolated polypeptide of claim 1, which interacts with the transferrin receptor.

12. The isolated polypeptide of claim 1, 2, 3, 4 or 9 which is membrate-associated.

13. The isolated polypeptide of claim 1, 2, 3, 4 or 9 which is fused with a heterologous polypeptide.

14. The isolated polypeptide of claim 1, 2, 3, 4 or 9 which is a naturally occurring polypeptide.

15. The isolated polypeptide of claim 1, 2, 3, 4 or 9 which is produced by a recombinant DNA method.

16. The isolated polypeptide of claim 1, 2, 3, 4 or 9 which is produced by a chemical synthetic method.

17. A pharmaceutical composition comprising the isolated polypeptide of claim 1.

* * * * *

```
                         SEQUENCE LISTING (1) GENERAL INFORMATION:

(iii) NUMBER OF SEQUENCES: 76

(2) INFORMATION FOR SEQ ID NO:1:

(i) SEQUENCE CHARACTERISTICS:
         (A) LENGTH: 10825 base pairs
         (B) TYPE: nucleic acid
         (C) STRANDEDNESS: single
         (D) TOPOLOGY: linear (ii) MOLECULE TYPE: DNA (genomic)

(ix) FEATURE:
         (A) NAME/KEY: CDS
         (B) LOCATION: join(361..436, 3762..4025, 4235..4510,
             5606..5881, 6040..6153, 7107..7147)
         (D) OTHER INFORMATION: /product= "Hereditary Hemochromatosis
             (HH) protein"
             /note= "Normal or wild-type (unaffected)
             Hereditary Hemochromatosis (HH) gene
             allele"

(ix) FEATURE:
         (A) NAME/KEY: -
         (B) LOCATION: 140..7319
         (D) OTHER INFORMATION: /note= "start and stop positions for
             normal or wild-type (unaffected) allele
             cDNA (SEQ ID NO:9)"

(ix) FEATURE:
         (A) NAME/KEY: -
         (B) LOCATION: 3852..3891
         (D) OTHER INFORMATION: /note= "start and stop positions for
             normal or wild-type (unaffected) genomic
             sequence surrounding variant for 24d2(C)
             allele (SEQ ID NO:41)"

(ix) FEATURE:
         (A) NAME/KEY: -
         (B) LOCATION: 5507..6023
         (D) OTHER INFORMATION: /note= "start and stop positions for
             normal or wild-type (unaffected) genomic
             sequence surrounding variant for 24d1(G)
             allele (SEQ ID NO:20)"

(ix) FEATURE:
         (A) NAME/KEY: allele
         (B) LOCATION: replace(3872, "c")
         (D) OTHER INFORMATION: /phenotype= "normal or wild-type
             (unaffected)"
             /label= 24d2

(ix) FEATURE:
         (A) NAME/KEY: allele
         (B) LOCATION: replace(3878, "a")
```

(D) OTHER INFORMATION: /phenotype= "normal or wild-type
                  (unaffected)"
                  /label= 24d7

(ix) FEATURE:
              (A) NAME/KEY: allele
              (B) LOCATION: replace(5834, "g")
              (D) OTHER INFORMATION: /phenotype= "normal or wild-type
                  (unaffected)"
                  /label= 24d1

(xi) SEQUENCE DESCRIPTION: SEQ ID NO:1:

TCTAAGGTTG AGATAAAATT TTTAAATGTA TGATTGAATT TTGAAAATCA TAAATATTTA       60

AATATCTAAA GTTCAGATCA GAACATTGCG AAGCTACTTT CCCCAATCAA CAACACCCCT      120

TCAGGATTTA AAAACCAAGG GGGACACTGG ATCACCTAGT GTTTCACAAG CAGGTACCTT      180

CTGCTGTAGG AGAGAGAGAA CTAAAGTTCT GAAAGACCTG TTGCTTTTCA CCAGGAAGTT      240

TTACTGGGCA TCTCCTGAGC CTAGGCAATA GCTGTAGGGT GACTTCTGGA GCCATCCCCG      300

TTTCCCCGCC CCCCAAAAGA AGCGGAGATT TAACGGGGAC GTGCGGCCAG AGCTGGGGAA      360

ATG GGC CCG CGA GCC AGG CCG GCG CTT CTC CTC CTG ATG CTT TTG CAG       408
Met Gly Pro Arg Ala Arg Pro Ala Leu Leu Leu Leu Met Leu Leu Gln
  1               5                  10                  15

ACC GCG GTC CTG CAG GGG CGC TTG CTG C GTGAGTCCGA GGGCTGCGGG           456
Thr Ala Val Leu Gln Gly Arg Leu Leu
                20                  25

CGAACTAGGG GCGCGGCGGG GGTGGAAAAA TCGAAACTAG CTTTTTCTTT GCGCTTGGGA      516

GTTTGCTAAC TTTGGAGGAC CTGCTCAACC CTATCCGCAA GCCCCTCTCC CTACTTTCTG      576

CGTCCAGACC CCGTGAGGGA GTGCCTACCA CTGAACTGCA GATAGGGGTC CCTCGCCCCA      636

GGACCTGCCC CCTCCCCCGG CTGTCCCGGC TCTGCGGAGT GACTTTTGGA ACCGCCCACT      696

CCCTTCCCCC AACTAGAATG CTTTTAAATA AATCTCGTAG TTCCTCACTT GAGCTGAGCT      756

AAGCCTGGGG CTCCTTGAAC CTGGAACTCG GGTTTATTTC CAATGTCAGC TGTGCAGTTT      816

TTTCCCCAGT CATCTCCAAA CAGGAAGTTC TTCCCTGAGT GCTTGCCGAG AAGGCTGAGC      876

AAACCCACAG CAGGATCCGC ACGGGGTTTC CACCTCAGAA CGAATGCGTT GGGCGGTGGG      936

GGCGCGAAAG AGTGGCGTTG GGGATCTGAA TTCTTCACCA TTCCACCCAC TTTTGGTGAG      996

ACCTGGGGTG GAGGTCTCTA GGGTGGGAGG CTCCTGAGAG AGGCCTACCT CGGGCCTTTC     1056

CCCACTCTTG GCAATTGTTC TTTTGCCTGG AAAATTAAGT ATATGTTAGT TTGAACGTT      1116

TGAACTGAAC AATTCTCTTT TCGGCTAGGC TTTATTGATT TGCAATGTGC TGTGTAATTA     1176

AGAGGCCTCT CTACAAAGTA CTGATAATGA ACATGTAAGC AATGCACTCA CTTCTAAGTT     1236

ACATTCATAT CTGATCTTAT TGATTTTCA CTAGGCATAG GGAGGTAGGA GCTAATAATA      1296

CGTTTATTTT ACTAGAAGTT AACTGGAATT CAGATTATAT AACTCTTTTC AGGTTACAAA     1356

GAACATAAAT AATCTGGTTT TCTGATGTTA TTTCAAGTAC TACAGCTGCT TCTAATCTTA     1416

GTTGACAGTG ATTTTGCCCT GTAGTGTAGC ACAGTGTTCT GTGGGTCACA CGCCGGCCTC     1476

AGCACAGCAC TTTGAGTTTT GGTACTACGT GTATCCACAT TTTACACATG ACAAGAATGA     1536

GGCATGGCAC GGCCTGCTTC CTGGCAAATT TATTCAATGG TACACTGGGC TTTGGTGGCA     1596

GAGCTCATGT CTCCACTTCA TAGCTATGAT TCTTAAACAT CACACTGCAT TAGAGGTTGA     1656

ATAATAAAAT TTCATGTTGA GCAGAAATAT TCATTGTTTA CAAGTGTAAA TGAGTCCCAG     1716

CCATGTGTTG CACTGTTCAA GCCCCAAGGG AGAGAGCAGG GAAACAAGTC TTTACCCTTT     1776

GATATTTTGC ATTCTAGTGG GAGAGATGAC AATAAGCAAA TGAGCAGAAA GATATACAAC     1836

```
-continued

ATCAGGAAAT CATGGGTGTT GTGAGAAGCA GAGAAGTCAG GGCAAGTCAC TCTGGGGCTG      1896

ACACTTGAGC AGAGACATGA AGGAAATAAG AATGATATTG ACTGGGAGCA GTATTTCCCA      1956

GGCAAACTGA GTGGGCCTGG CAAGTTGGAT TAAAAAGCGG GTTTTCTCAG CACTACTCAT      2016

GTGTGTGTGT GTGGGGGGGG GGGGCGGCGT GGGGGTGGGA AGGGGGACTA CCATCTGCAT      2076

GTAGGATGTC TAGCAGTATC CTGTCCTCCC TACTCACTAG GTGCTAGGAG CACTCCCCCA      2136

GTCTTGACAA CCAAAAATGT CTCTAAACTT TGCCACATGT CACCTAGTAG ACAAACTCCT      2196

GGTTAAGAAG CTCGGGTTGA AAAAAATAAA CAAGTAGTGC TGGGGAGTAG AGGCCAAGAA      2256

GTAGGTAATG GGCTCAGAAG AGGAGCCACA AACAAGGTTG TGCAGGCGCC TGTAGGCTGT      2316

GGTGTGAATT CTAGCCAAGG AGTAACAGTG ATCTGTCACA GGCTTTTAAA AGATTGCTCT      2376

GGCTGCTATG TGGAAAGCAG AATGAAGGGA GCAACAGTAA AAGCAGGGAG CCCAGCCAGG      2436

AAGCTGTTAC ACAGTCCAGG CAAGAGGTAG TGGAGTGGGC TGGGTGGGAA CAGAAAAGGG      2496

AGTGACAAAC CATTGTCTCC TGAATATATT CTGAAGGAAG TTGCTGAAGG ATTCTATGTT      2556

GTGTGAGAGA AAGAGAAGAA TTGGCTGGGT GTAGTAGCTC ATGCCAAGGA GGAGGCCAAG      2616

GAGAGCAGAT TCCTGAGCTC AGGAGTTCAA GACCAGCCTG GGCAACACAG CAAAACCCCT      2676

TCTCTACAAA AAATACAAAA ATTAGCTGGG TGTGGTGGCA TGCACCTGTG ATCCTAGCTA      2736

CTCGGGAGGC TGAGGTGGAG GGTATTGCTT GAGCCCAGGA AGTTGAGGCT GCAGTGAGCC      2796

ATGACTGTGC CACTGTACTT CAGCCTAGGT GACAGAGCAA GACCCTGTCT CCCCTGACCC      2856

CCTGAAAAAG AGAAGAGTTA AAGTTGACTT TGTTCTTTAT TTTAATTTTA TTGGCCTGAG      2916

CAGTGGGGTA ATTGGCAATG CCATTTCTGA GATGGTGAAG GCAGAGGAAA GAGCAGTTTG      2976

GGGTAAATCA AGGATCTGCA TTTGGGACAT GTTAAGTTTG AGATTCCAGT CAGGCTTCCA      3036

AGTGGTGAGG CCACATAGGC AGTTCAGTGT AAGAATTCAG GACCAAGGCT GGGCACGGTG      3096

GCTCACTTCT GTAATCCCAG CACTTTGGTG GCTGAGGCAG GTAGATCATT TGAGGTCAGG      3156

AGTTTGAGAC AAGCTTGGCC AACATGGTGA AACCCCATGT CTACTAAAAA TACAAAAATT      3216

AGCCTGGTGT GGTGGCGCAC GCCTATAGTC CCAGGTTTTC AGGAGGCTTA GGTAGGAGAA      3276

TCCCTTGAAC CCAGGAGGTG CAGGTTGCAG TGAGCTGAGA TTGTGCCACT GCACTCCAGC      3336

CTGGGTGATA GAGTGAGACT CTGTCTCAAA AAAAAAAAA AAAAAAAAA AAAAAACTGA       3396

AGGAATTATT CCTCAGGATT TGGGTCTAAT TTGCCCTGAG CACCAACTCC TGAGTTCAAC      3456

TACCATGGCT AGACACACCT TAACATTTTC TAGAATCCAC CAGCTTTAGT GGAGTCTGTC      3516

TAATCATGAG TATTGGAATA GGATCTGGGG GCAGTGAGGG GGTGGCAGCC ACGTGTGGCA      3576

GAGAAAAGCA CACAAGGAAA GAGCACCCAG GACTGTCATA TGGAAGAAAG ACAGGACTGC      3636

AACTCACCCT TCACAAAATG AGGACCAGAC ACAGCTGATG GTATGAGTTG ATGCAGGTGT      3696

GTGGAGCCTC AACATCCTGC TCCCCTCCTA CTACACATGG TTAAGGCCTG TTGCTCTGTC      3756

TCCAG  GT TCA CAC TCT CTG CAC TAC CTC TTC ATG GGT GCC TCA GAG         3802
       Arg Ser His Ser Leu His Tyr Leu Phe Met Gly Ala Ser Glu
               30              35

CAG GAC CTT GGT CTT TCC TTG TTT GAA GCT TTG GGC TAC GTG GAT GAC       3850
Gln Asp Leu Gly Leu Ser Leu Phe Glu Ala Leu Gly Tyr Val Asp Asp
40              45                  50                  55

CAG CTG TTC GTG TTC TAT GAT CAT GAG AGT CGC CGT GTG GAG CCC CGA       3898
Gln Leu Phe Val Phe Tyr Asp His Glu Ser Arg Arg Val Glu Pro Arg
        60                  65                  70

ACT CCA TGG GTT TCC AGT AGA ATT TCA AGC CAG ATG TGG CTG CAG CTG       3946
Thr Pro Trp Val Ser Ser Arg Ile Ser Ser Gln Met Trp Leu Gln Leu
    75                  80                  85
```

-continued

```
AGT CAG AGT CTG AAA GGG TGG GAT CAC ATG TTC ACT GTT GAC TTC TGG      3994
Ser Gln Ser Leu Lys Gly Trp Asp His Met Phe Thr Val Asp Phe Trp
         90                  95                 100

ACT ATT ATG GAA AAT CAC AAC CAC AGC AAG G GTATGTGGAG AGGGGGCCTC      4045
Thr Ile Met Glu Asn His Asn His Ser Lys
       105                 110

ACCTTCCTGA GGTTGTCAGA GCTTTTCATC TTTTCATGCA TCTTGAAGGA AACAGCTGGA    4105

AGTCTGAGGT CTTGTGGGAG CAGGGAAGAG GGAAGGAATT TGCTTCCTGA GATCATTTGG    4165

TCCTTGGGGA TGGTGGAAAT AGGGACCTAT TCCTTTGGTT GCAGTTAACA AGGCTGGGGA    4225

TTTTTCCAG  AG TCC CAC ACC CTG CAG GTC ATC CTG GGC TGT GAA ATG       4272
           Glu Ser His Thr Leu Gln Val Ile Leu Gly Cys Glu Met
               115                 120                 125

CAA GAA GAC AAC AGT ACC GAG GGC TAC TGG AAG TAC GGG TAT GAT GGG      4320
Gln Glu Asp Asn Ser Thr Glu Gly Tyr Trp Lys Tyr Gly Tyr Asp Gly
        130                 135                 140

CAG GAC CAC CTT GAA TTC TGC CCT GAC ACA CTG GAT TGG AGA GCA GCA      4368
Gln Asp His Leu Glu Phe Cys Pro Asp Thr Leu Asp Trp Arg Ala Ala
        145                 150                 155

GAA CCC AGG GCC TGG CCC ACC AAG CTG GAG TGG GAA AGG CAC AAG ATT      4416
Glu Pro Arg Ala Trp Pro Thr Lys Leu Glu Trp Glu Arg His Lys Ile
    160                 165                 170

CGG GCC AGG CAG AAC AGG GCC TAC CTG GAG AGG GAC TGC CCT GCA CAG      4464
Arg Ala Arg Gln Asn Arg Ala Tyr Leu Glu Arg Asp Cys Pro Ala Gln
175             180                 185                 190

CTG CAG CAG TTG CTG GAG CTG GGG AGA GGT GTT TTG GAC CAA CAA G        4510
Leu Gln Gln Leu Leu Glu Leu Gly Arg Gly Val Leu Asp Gln Gln
            195                 200                 205

GTATGGTGGA AACACACTTC TGCCCCTATA CTCTAGTGGC AGAGTGGAGG AGGTTGCAGG    4570

GCACGGAATC CCTGGTTGGA GTTTCAGAGG TGGCTGAGGC TGTGTGCCTC TCCAAATTCT    4630

GGGAAGGGAC TTTCTCAATC CTAGAGTCTC TACCTTATAA TTGAGATGTA TGAGACAGCC    4690

ACAAGTCATG GGTTTAATTT CTTTTCTCCA TGCATATGGC TCAAAGGGAA GTGTCTATGG    4750

CCCTTGCTTT TTATTTAACC AATAATCTTT TGTATATTTA TACCTGTTAA AAATTCAGAA    4810

ATGTCAAGGC CGGGCACGGT GGCTCACCCC TGTAATCCCA GCACTTTGGG AGGCCGAGGC    4870

GGGTGGTCAC AAGGTCAGGA GTTTGAGACC AGCCTGACCA ACATGGTGAA ACCCGTCTCT    4930

AAAAAAATAC AAAAATTAGC TGGTCACAGT CATGCGCACC TGTAGTCCCA GCTAATTGGA    4990

AGGCTGAGGC AGGAGCATCG CTTGAACCTG GGAAGCGGAA GTTGCACTGA GCCAAGATCG    5050

CGCCACTGCA CTCCAGCCTA GGCAGCAGAG TGAGACTCCA TCTTAAAAAA AAAAAAAAAA    5110

AAAAAAGAG AATTCAGAGA TCTCAGCTAT CATATGAATA CCAGGACAAA ATATCAAGTG     5170

AGGCCACTTA TCAGAGTAGA AGAATCCTTT AGGTTAAAAG TTTCTTTCAT AGAACATAGC    5230

AATAATCACT GAAGCTACCT ATCTTACAAG TCCGCTTCTT ATAACAATGC CTCCTAGGTT    5290

GACCCAGGTG AAACTGACCA TCTGTATTCA ATCATTTTCA ATGCACATAA AGGGCAATTT    5350

TATCTATCAG AACAAAGAAC ATGGGTAACA GATATGTATA TTTACATGTG AGGAGAACAA    5410

GCTGATCTGA CTGCTCTCCA AGTGACACTG TGTTAGAGTC CAATCTTAGG ACACAAAATG    5470

GTGTCTCTCC TGTAGCTTGT TTTTTTCTGA AAAGGGTATT TCCTTCCTCC AACCTATAGA    5530

AGGAAGTGAA AGTTCCAGTC TTCCTGGCAA GGGTAAACAG ATCCCCTCTC CTCATCCTTC    5590

CTCTTTCCTG TCAAG  TG CCT CCT TTG GTG AAG GTG ACA CAT CAT GTG ACC    5640
                Val Pro Pro Leu Val Lys Val Thr His His Val Thr
                                210                 215
```

```
TCT TCA GTG ACC ACT CTA CGG TGT CGG GCC TTG AAC TAC TAC CCC CAG         5688
Ser Ser Val Thr Thr Leu Arg Cys Arg Ala Leu Asn Tyr Tyr Pro Gln
        220                 225                 230

AAC ATC ACC ATG AAG TGG CTG AAG GAT AAG CAG CCA ATG GAT GCC AAG         5736
Asn Ile Thr Met Lys Trp Leu Lys Asp Lys Gln Pro Met Asp Ala Lys
    235                 240                 245

GAG TTC GAA CCT AAA GAC GTA TTG CCC AAT GGG GAT GGG ACC TAC CAG         5784
Glu Phe Glu Pro Lys Asp Val Leu Pro Asn Gly Asp Gly Thr Tyr Gln
250                 255                 260                 265

GGC TGG ATA ACC TTG GCT GTA CCC CCT GGG GAA GAG CAG AGA TAT ACG         5832
Gly Trp Ile Thr Leu Ala Val Pro Pro Gly Glu Glu Gln Arg Tyr Thr
                270                 275                 280

TGC CAG GTG GAG CAC CCA GGC CTG GAT CAG CCC CTC ATT GTG ATC TGG G       5881
Cys Gln Val Glu His Pro Gly Leu Asp Gln Pro Leu Ile Val Ile Trp
            285                 290                 295

GTATGTGACT GATGAGAGCC AGGAGCTGAG AAAATCTATT GGGGGTTGAG AGGAGTGCCT       5941

GAGGAGGTAA TTATGGCAGT GAGATGAGGA TCTGCTCTTT GTTAGGGGGT GGGCTGAGGG       6001

TGGCAATCAA AGGCTTTAAC TTGCTTTTTC TGTTTTAG   AG CCC TCA CCG TCT         6053
                                         Glu Pro Ser Pro Ser
                                                         300

GGC ACC CTA GTC ATT GGA GTC ATC AGT GGA ATT GCT GTT TTT GTC GTC         6101
Gly Thr Leu Val Ile Gly Val Ile Ser Gly Ile Ala Val Phe Val Val
            305                 310                 315

ATC TTG TTC ATT GGA ATT TTG TTC ATA ATA TTA AGG AAG AGG CAG GGT         6149
Ile Leu Phe Ile Gly Ile Leu Phe Ile Ile Leu Arg Lys Arg Gln Gly
        320                 325                 330

TCA A GTGAGTAGGA CAAGGGGGA AGTCTCTTAG TACCTCTGCC CCAGGGCACA             6203
Ser
335

GTGGGAAGAG GGGCAGAGGG GATCTGGCAT CCATGGGAAG CATTTTTCTC ATTTATATTC       6263

TTTGGGGACA CCAGCAGCTC CCTGGGAGAC AGAAATAAT GGTTCTCCCC AGAATGAAAG        6323

TCTCTAATTC AACAAACATC TTCAGAGCAC CTACTATTTT GCAAGAGCTG TTTAAGGTAG       6383

TACAGGGGCT TGAGGTTGA GAAGTCACTG TGGCTATTCT CAGAACCCAA ATCTGGTAGG        6443

GAATGAAATT GATAGCAAGT AAATGTAGTT AAAGAAGACC CCATGAGGTC CTAAAGCAGG       6503

CAGGAAGCAA ATGCTTAGGG TGTCAAAGGA AAGAATGATC ACATTCAGCT GGGGATCAAG       6563

ATAGCCTTCT GGATCTTGAA GGAGAAGCTG GATTCCATTA GGTGAGGTTG AAGATGATGG       6623

GAGGTCTACA CAGACGGAGC AACCATGCCA AGTAGGAGAG TATAAGGCAT ACTGGGAGAT       6683

TAGAAATAAT TACTGTACCT TAACCCTGAG TTTGCGTAGC TATCACTCAC CAATTATGCA       6743

TTTCTACCCC CTGAACATCT GTGGTGTAGG GAAAAGAGAA TCAGAAAGAA GCCAGCTCAT       6803

ACAGAGTCCA AGGGTCTTTT GGGATATTGG GTTATGATCA CTGGGGTGTC ATTGAAGGAT       6863

CCTAAGAAAG GAGGACCACG ATCTCCCTTA TATGGTGAAT GTGTTGTTAA GAAGTTAGAT       6923

GAGAGGTGAG GAGACCAGTT AGAAAGCCAA TAAGCATTTC CAGATGAGAG ATAATGGTTC       6983

TTGAAATCCA ATAGTGCCCA GGTCTAAATT GAGATGGGTG AATGAGGAAA ATAAGGAAGA       7043

GAGAAGAGGC AAGATGGTGC CTAGGTTTGT GATGCCTCTT TCCTGGGTCT CTTGTCTCCA       7103

CAG  GA GGA GCC ATG GGG CAC TAC GTC TTA GCT GAA CGT GAG                 7144
     Arg Gly Ala Met Gly His Tyr Val Leu Ala Glu Arg Glu
                  340                 345

TGACACGCAG CCTGCAGACT CACTGTGGGA AGGAGACAAA ACTAGAGACT CAAAGAGGGA       7204

GTGCATTTAT GAGCTCTTCA TGTTTCAGGA GAGAGTTGAA CCTAAACATA GAAATTGCCT       7264

GACGAACTCC TTGATTTTAG CCTTCTCTGT TCATTTCCTC AAAAAGATTT CCCCATTTAG       7324
```

-continued

```
GTTTCTGAGT TCCTGCATGC CGGTGATCCC TAGCTGTGAC CTCTCCCCTG GAACTGTCTC    7384

TCATGAACCT CAAGCTGCAT CTAGAGGCTT CCTTCATTTC CTCCGTCACC TCAGAGACAT    7444

ACACCTATGT CATTTCATTT CCTATTTTTG GAAGAGGACT CCTTAAATTT GGGGGACTTA    7504

CATGATTCAT TTTAACATCT GAGAAAAGCT TTGAACCCTG GGACGTGGCT AGTCATAACC    7564

TTACCAGATT TTTACACATG TATCTATGCA TTTTCTGGAC CCGTTCAACT TTTCCTTTGA    7624

ATCCTCTCTC TGTGTTACCC AGTAACTCAT CTGTCACCAA GCCTTGGGGA TTCTTCCATC    7684

TGATTGTGAT GTGAGTTGCA CAGCTATGAA GGCTGTACAC TGCACGAATG GAAGAGGCAC    7744

CTGTCCCAGA AAAAGCATCA TGGCTATCTG TGGGTAGTAT GATGGGTGTT TTTAGCAGGT    7804

AGGAGGCAAA TATCTTGAAA GGGGTTGTGA AGAGGTGTTT TTTCTAATTG GCATGAAGGT    7864

GTCATACAGA TTTGCAAAGT TAATGGTGC CTTCATTTGG GATGCTACTC TAGTATTCCA     7924

GACCTGAAGA ATCACAATAA TTTTCTACCT GGTCTCTCCT TGTTCTGATA ATGAAAATTA    7984

TGATAAGGAT GATAAAAGCA CTTACTTCGT GTCCGACTCT TCTGAGCACC TACTTACATG    8044

CATTACTGCA TGCACTTCTT ACAATAATTC TATGAGATAG GTACTATTAT CCCCATTTCT    8104

TTTTTAAATG AAGAAAGTGA AGTAGGCCGG GCACGGTGGC TCACGCCTGT AATCCCAGCA    8164

CTTTGGGAGG CCAAAGCGGG TGGATCACGA GGTCAGGAGA TCGAGACCAT CCTGGCTAAC    8224

ATGGTGAAAC CCCATCTCTA ATAAAAATAC AAAAAATTAG CTGGGCGTGG TGGCAGACGC    8284

CTGTAGTCCC AGCTACTCGG AAGGCTGAGG CAGGAGAATG GCATGAACCC AGGAGGCAGA    8344

GCTTGCAGTG AGCCGAGTTT GCGCCACTGC ACTCCAGCCT AGGTGACAGA GTGAGACTCC    8404

ATCTCAAAAA AATAAAAATA AAAATAAAAA AATGAAAAAA AAAGAAAGT GAAGTATAGA     8464

GTATCTCATA GTTTGTCAGT GATAGAAACA GGTTTCAAAC TCAGTCAATC TGACCGTTTG    8524

ATACATCTCA GACACCACTA CATTCAGTAG TTTAGATGCC TAGAATAAAT AGAGAAGGAA    8584

GGAGATGGCT CTTCTCTTGT CTCATTGTGT TTCTTCTGAG TGAGCTTGAA TCACATGAAG    8644

GGGAACAGCA GAAAACAACC AACTGATCCT CAGCTGTCAT GTTTCCTTTA AAAGTCCCTG    8704

AAGGAAGGTC CTGGAATGTG ACTCCCTTGC TCCTCTGTTG CTCTCTTTGG CATTCATTTC    8764

TTTGACCCT ACGCAAGGAC TGTAATTGGT GGGGACAGCT AGTGGCCCTG CTGGGCTTCA     8824

CACACGGTGT CCTCCCTAGG CCAGTGCCTC TGGAGTCAGA ACTCTGGTGG TATTTCCCTC    8884

AATGAAGTGG AGTAAGCTCT CTCATTTTGA GATGGTATAA TGGAAGCCAC CAAGTGGCTT    8944

AGAGGATGCC CAGGTCCTTC CATGGAGCCA CTGGGGTTCC GGTGCACATT AAAAAAAAAA    9004

TCTAACCAGG ACATTCAGGA ATTGCTAGAT TCTGGGAAAT CAGTTCACCA TGTTCAAAAG    9064

AGTCTTTTTT TTTTTTTGA GACTCTATTG CCCAGGCTGG AGTGCAATGG CATGATCTCG     9124

GCTCACTGTA ACCTCTGCCT CCCAGGTTCA AGCGATTCTC CTGTCTCAGC CTCCCAAGTA    9184

GCTGGGATTA CAGGCGTGCA CCACCATGCC CGGCTAATTT TTGTATTTTT AGTAGAGACA    9244

GGGTTTCACC ATGTTGGCCA GGCTGGTCTC GAACTCTCCT GACCTCGTGA TCCGCCTGCC    9304

TCGGCCTCCC AAAGTGCTGA GATTACAGGT GTGAGCCACC CTGCCCAGCC GTCAAAAGAG    9364

TCTTAATATA TATATCCAGA TGGCATGTGT TTACTTTATG TTACTACATG CACTTGGCTG    9424

CATAAATGTG GTACAAGCAT TCTGTCTTGA AGGGCAGGTG CTTCAGGATA CCATATACAG    9484

CTCAGAAGTT TCTTCTTTAG GCATTAAATT TTAGCAAAGA TATCTCATCT CTTCTTTTAA    9544

ACCATTTTCT TTTTTTGTGG TTAGAAAAGT TATGTAGAAA AAAGTAAATG TGATTTACGC    9604

TCATTGTAGA AAAGCTATAA AATGAATACA ATTAAAGCTG TTATTTAATT AGCCAGTGAA    9664
```

-continued

```
AAACTATTAA CAACTTGTCT ATTACCTGTT AGTATTATTG TTGCATTAAA AATGCATATA    9724

CTTTAATAAA TGTATATTGT ATTGTATACT GCATGATTTT ATTGAAGTTC TTGTTCATCT    9784

TGTGTATATA CTTAATCGCT TTGTCATTTT GGAGACATTT ATTTTGCTTC TAATTTCTTT    9844

ACATTTTGTC TTACGGAATA TTTTCATTCA ACTGTGGTAG CCGAATTAAT CGTGTTTCTT    9904

CACTCTAGGG ACATTGTCGT CTAAGTTGTA AGACATTGGT TATTTTACCA GCAAACCATT    9964

CTGAAAGCAT ATGACAAATT ATTTCTCTCT TAATATCTTA CTATACTGAA AGCAGACTGC   10024

TATAAGGCTT CACTTACTCT TCTACCTCAT AAGGAATATG TTACAATTAA TTTATTAGGT   10084

AAGCATTTGT TTTATATTGG TTTTATTTCA CCTGGGCTGA GATTTCAAGA AACACCCCAG   10144

TCTTCACAGT AACACATTTC ACTAACACAT TTACTAAACA TCAGCAACTG TGGCCTGTTA   10204

ATTTTTTTAA TAGAAATTTT AAGTCCTCAT TTTCTTTCGG TGTTTTTTAA GCTTAATTTT   10264

TCTGGCTTTA TTCATAAATT CTTAAGGTCA ACTACATTTG AAAAATCAAA GACCTGCATT   10324

TTAAATTCTT ATTCACCTCT GGCAAAACCA TTCACAAACC ATGGTAGTAA AGAGAAGGGT   10384

GACACCTGGT GGCCATAGGT AAATGTACCA CGGTGGTCCG GTGACCAGAG ATGCAGCGCT   10444

GAGGGTTTTC CTGAAGGTAA AGGAATAAAG AATGGGTGGA GGGGCGTGCA CTGGAAATCA   10504

CTTGTAGAGA AAAGCCCCTG AAAATTTGAG AAAACAAACA AGAAACTACT TACCAGCTAT   10564

TTGAATTGCT GGAATCACAG GCCATTGCTG AGCTGCCTGA ACTGGGAACA CAACAGAAGG   10624

AAAACAAACC ACTCTGATAA TCATTGAGTC AAGTACAGCA GGTGATTGAG GACTGCTGAG   10684

AGGTACAGGC CAAAATTCTT ATGTTGTATT ATAATAATGT CATCTTATAA TACTGTCAGT   10744

ATTTTATAAA ACATTCTTCA CAAACTCACA CACATTTAAA AACAAACAC TGTCTCTAAA    10804

ATCCCCAAAT TTTTCATAAA C                                            10825
```

(2) INFORMATION FOR SEQ ID NO:2:

(i) SEQUENCE CHARACTERISTICS:
        (A) LENGTH: 348 amino acids
        (B) TYPE: amino acid
        (D) TOPOLOGY: linear (ii) MOLECULE TYPE: protein (xi) SEQUENCE DESCRIPTION: SEQ ID NO:2:

```
Met Gly Pro Arg Ala Arg Pro Ala Leu Leu Leu Met Leu Leu Gln
 1               5                  10                  15

Thr Ala Val Leu Gln Gly Arg Leu Leu Arg Ser His Ser Leu His Tyr
             20                  25                  30

Leu Phe Met Gly Ala Ser Glu Gln Asp Leu Gly Leu Ser Leu Phe Glu
         35                  40                      45

Ala Leu Gly Tyr Val Asp Asp Gln Leu Phe Val Phe Tyr Asp His Glu
     50                  55                      60

Ser Arg Arg Val Glu Pro Arg Thr Pro Trp Val Ser Ser Arg Ile Ser
 65                  70                  75                  80

Ser Gln Met Trp Leu Gln Leu Ser Gln Ser Leu Lys Gly Trp Asp His
                 85                  90                  95

Met Phe Thr Val Asp Phe Trp Thr Ile Met Glu Asn His Asn His Ser
                100                 105                 110

Lys Glu Ser His Thr Leu Gln Val Ile Leu Gly Cys Glu Met Gln Glu
            115                 120                 125

Asp Asn Ser Thr Glu Gly Tyr Trp Lys Tyr Gly Tyr Asp Gly Gln Asp
        130                 135                 140
```

```
His Leu Glu Phe Cys Pro Asp Thr Leu Asp Trp Arg Ala Ala Glu Pro
145                 150                 155                 160

Arg Ala Trp Pro Thr Lys Leu Glu Trp Glu Arg His Lys Ile Arg Ala
                165                 170                 175

Arg Gln Asn Arg Ala Tyr Leu Glu Arg Asp Cys Pro Ala Gln Leu Gln
            180                 185                 190

Gln Leu Leu Glu Leu Gly Arg Gly Val Leu Asp Gln Val Pro Pro
        195                 200                 205

Leu Val Lys Val Thr His His Val Thr Ser Ser Val Thr Thr Leu Arg
    210                 215                 220

Cys Arg Ala Leu Asn Tyr Tyr Pro Gln Asn Ile Thr Met Lys Trp Leu
225                 230                 235                 240

Lys Asp Lys Gln Pro Met Asp Ala Lys Glu Phe Glu Pro Lys Asp Val
                245                 250                 255

Leu Pro Asn Gly Asp Gly Thr Tyr Gln Gly Trp Ile Thr Leu Ala Val
            260                 265                 270

Pro Pro Gly Glu Glu Gln Arg Tyr Thr Cys Gln Val Glu His Pro Gly
        275                 280                 285

Leu Asp Gln Pro Leu Ile Val Ile Trp Glu Pro Ser Pro Ser Gly Thr
290                 295                 300

Leu Val Ile Gly Val Ile Ser Gly Ile Ala Val Phe Val Val Ile Leu
305                 310                 315                 320

Phe Ile Gly Ile Leu Phe Ile Ile Leu Arg Lys Arg Gln Gly Ser Arg
                325                 330                 335

Gly Ala Met Gly His Tyr Val Leu Ala Glu Arg Glu
                340                 345

(2) INFORMATION FOR SEQ ID NO:3:

(i) SEQUENCE CHARACTERISTICS:
        (A) LENGTH: 10825 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: join(361..436, 3762..4025, 4235..4510,
            5606..5881, 6040..6153, 7107..7147)
        (D) OTHER INFORMATION: /product= "Hereditary Hemochromatosis
            (HH) protein containing the 24d1
            mutation"
            /note= "Hereditary Hemochromatosis (HH)
            gene 24d1 allele"

(ix) FEATURE:
        (A) NAME/KEY: -
        (B) LOCATION: 140..7319
        (D) OTHER INFORMATION: /note= "start and stop positions for
            24d1 allele cDNA (SEQ ID NO:10)"

(ix) FEATURE:
        (A) NAME/KEY: -
        (B) LOCATION: 3852..3891
        (D) OTHER INFORMATION: /note= "start and stop positions for
            genomic sequence surrounding variant
            for 24d2(C) allele (SEQ ID NO:41)"

(ix) FEATURE:
        (A) NAME/KEY: -
        (B) LOCATION: 5507..6023
        (D) OTHER INFORMATION: /note= "start and stop positions for
            genomic sequence surrounding variant
            for 24d1(A) allele (SEQ ID NO:21)"
```

-continued (ix) FEATURE:
    (A) NAME/KEY: allele
    (B) LOCATION: replace(5834, "a")
    (D) OTHER INFORMATION: /phenotype= "Hereditary Hemochromatosis
        (HH)"
        /label= 24d1

(xi) SEQUENCE DESCRIPTION: SEQ ID NO:3:

```
TCTAAGGTTG AGATAAAATT TTTAAATGTA TGATTGAATT TTGAAAATCA TAAATATTTA      60

AATATCTAAA GTTCAGATCA GAACATTGCG AAGCTACTTT CCCCAATCAA CAACACCCCT     120

TCAGGATTTA AAAACCAAGG GGGACACTGG ATCACCTAGT GTTTCACAAG CAGGTACCTT     180

CTGCTGTAGG AGAGAGAGAA CTAAAGTTCT GAAAGACCTG TTGCTTTTCA CCAGGAAGTT     240

TTACTGGGCA TCTCCTGAGC CTAGGCAATA GCTGTAGGGT GACTTCTGGA GCCATCCCCG     300

TTTCCCCGCC CCCCAAAAGA AGCGGAGATT TAACGGGGAC GTGCGGCCAG AGCTGGGGAA     360

ATG GGC CCG CGA GCC AGG CCG GCG CTT CTC CTC CTG ATG CTT TTG CAG       408
Met Gly Pro Arg Ala Arg Pro Ala Leu Leu Leu Leu Met Leu Leu Gln
 1               5                  10                  15

ACC GCG GTC CTG CAG GGG CGC TTG CTG C GTGAGTCCGA GGGCTGCGGG           456
Thr Ala Val Leu Gln Gly Arg Leu Leu
                20              25

CGAACTAGGG GCGCGGCGGG GGTGGAAAAA TCGAAACTAG CTTTTTCTTT GCGCTTGGGA     516

GTTTGCTAAC TTTGGAGGAC CTGCTCAACC CTATCCGCAA GCCCCTCTCC CTACTTTCTG     576

CGTCCAGACC CCGTGAGGGA GTGCCTACCA CTGAACTGCA GATAGGGGTC CCTCGCCCCA     636

GGACCTGCCC CCTCCCCCGG CTGTCCCGGC TCTGCGGAGT GACTTTTGGA ACCGCCCACT     696

CCCTTCCCCC AACTAGAATG CTTTTAAATA AATCTCGTAG TTCCTCACTT GAGCTGAGCT     756

AAGCCTGGGG CTCCTTGAAC CTGGAACTCG GGTTTATTTC CAATGTCAGC TGTGCAGTTT     816

TTTCCCCAGT CATCTCCAAA CAGGAAGTTC TTCCCTGAGT GCTTGCCGAG AAGGCTGAGC     876

AAACCCACAG CAGGATCCGC ACGGGGTTTC CACCTCAGAA CGAATGCGTT GGGCGGTGGG     936

GGCGCGAAAG AGTGGCGTTG GGGATCTGAA TTCTTCACCA TTCCACCCAC TTTTGGTGAG     996

ACCTGGGGTG GAGGTCTCTA GGGTGGGAGG CTCCTGAGAG AGGCCTACCT CGGGCCTTTC    1056

CCCACTCTTG GCAATTGTTC TTTTGCCTGG AAAATTAAGT ATATGTTAGT TTGAACGTT     1116

TGAACTGAAC AATTCTCTTT TCGGCTAGGC TTTATTGATT TGCAATGTGC TGTGTAATTA    1176

AGAGGCCTCT CTACAAAGTA CTGATAATGA ACATGTAAGC AATGCACTCA CTTCAAGTT     1236

ACATTCATAT CTGATCTTAT TTGATTTTCA CTAGGCATAG GGAGGTAGGA GCTAATAATA    1296

CGTTTATTTT ACTAGAAGTT AACTGGAATT CAGATTATAT AACTCTTTTC AGGTTACAAA    1356

GAACATAAAT AATCTGGTTT TCTGATGTTA TTTCAAGTAC TACAGCTGCT TCTAATCTTA    1416

GTTGACAGTG ATTTTGCCCT GTAGTGTAGC ACAGTGTTCT GTGGGTCACA CGCCGGCCTC    1476

AGCACAGCAC TTTGAGTTTT GGTACTACGT GTATCCACAT TTTACACATG ACAAGAATGA    1536

GGCATGGCAC GGCCTGCTTC CTGGCAAATT TATTCAATGG TACACTGGGC TTTGGTGGCA    1596

GAGCTCATGT CTCCACTTCA TAGCTATGAT TCTTAAACAT CACACTGCAT TAGAGGTTGA    1656

ATAATAAAAT TTCATGTTGA GCAGAAATAT TCATTGTTTA CAAGTGTAAA TGAGTCCCAG    1716

CCATGTGTTG CACTGTTCAA GCCCCAAGGG AGAGAGCAGG GAAACAAGTC TTTACCCTTT    1776

GATATTTTGC ATTCTAGTGG GAGAGATGAC AATAAGCAAA TGAGCAGAAA GATATACAAC    1836

ATCAGGAAAT CATGGGTGTT GTGAGAAGCA GAGAAGTCAG GGCAAGTCAC TCTGGGGCTG    1896

ACACTTGAGC AGAGACATGA AGGAAATAAG AATGATATTG ACTGGGAGCA GTATTTCCCA    1956
```

```
GGCAAACTGA GTGGGCCTGG CAAGTTGGAT TAAAAAGCGG GTTTTCTCAG CACTACTCAT    2016

GTGTGTGTGT GTGGGGGGGG GGGGCGGCGT GGGGGTGGGA AGGGGGACTA CCATCTGCAT    2076

GTAGGATGTC TAGCAGTATC CTGTCCTCCC TACTCACTAG GTGCTAGGAG CACTCCCCCA    2136

GTCTTGACAA CCAAAAATGT CTCTAAACTT TGCCACATGT CACCTAGTAG ACAAACTCCT    2196

GGTTAAGAAG CTCGGGTTGA AAAAAATAAA CAAGTAGTGC TGGGGAGTAG AGGCCAAGAA    2256

GTAGGTAATG GGCTCAGAAG AGGAGCCACA ACAAGGTTG TGCAGGCGCC TGTAGGCTGT     2316

GGTGTGAATT CTAGCCAAGG AGTAACAGTG ATCTGTCACA GGCTTTTAAA AGATTGCTCT    2376

GGCTGCTATG TGGAAAGCAG AATGAAGGGA GCAACAGTAA AGCAGGGAG CCCAGCCAGG     2436

AAGCTGTTAC ACAGTCCAGG CAAGAGGTAG TGGAGTGGGC TGGGTGGGAA CAGAAAAGGG    2496

AGTGACAAAC CATTGTCTCC TGAATATATT CTGAAGGAAG TTGCTGAAGG ATTCTATGTT    2556

GTGTGAGAGA AAGAGAAGAA TTGGCTGGGT GTAGTAGCTC ATGCCAAGGA GGAGGCCAAG    2616

GAGAGCAGAT TCCTGAGCTC AGGAGTTCAA GACCAGCCTG GGCAACACAG CAAAACCCCT    2676

TCTCTACAAA AAATACAAAA ATTAGCTGGG TGTGGTGGCA TGCACCTGTG ATCCTAGCTA    2736

CTCGGGAGGC TGAGGTGGAG GGTATTGCTT GAGCCCAGGA AGTTGAGGCT GCAGTGAGCC    2796

ATGACTGTGC CACTGTACTT CAGCCTAGGT GACAGAGCAA GACCCTGTCT CCCCTGACCC    2856

CCTGAAAAAG AGAAGAGTTA AAGTTGACTT TGTTCTTTAT TTTAATTTTA TTGGCCTGAG    2916

CAGTGGGGTA ATTGGCAATG CCATTTCTGA GATGGTGAAG GCAGAGGAAA GAGCAGTTTG    2976

GGGTAAATCA AGGATCTGCA TTTGGGACAT GTTAAGTTTG AGATTCCAGT CAGGCTTCCA    3036

AGTGGTGAGG CCACATAGGC AGTTCAGTGT AAGAATTCAG GACCAAGGCT GGGCACGGTG    3096

GCTCACTTCT GTAATCCCAG CACTTTGGTG GCTGAGGCAG GTAGATCATT TGAGGTCAGG    3156

AGTTTGAGAC AAGCTTGGCC AACATGGTGA AACCCCATGT CTACTAAAAA TACAAAAATT    3216

AGCCTGGTGT GGTGGCGCAC GCCTATAGTC CCAGGTTTTC AGGAGGCTTA GGTAGGAGAA    3276

TCCCTTGAAC CCAGGAGGTG CAGGTTGCAG TGAGCTGAGA TTGTGCCACT GCACTCCAGC    3336

CTGGGTGATA GAGTGAGACT CTGTCTCAAA AAAAAAAAAA AAAAAAAAA AAAAAACTGA    3396

AGGAATTATT CCTCAGGATT TGGGTCTAAT TTGCCCTGAG CACCAACTCC TGAGTTCAAC    3456

TACCATGGCT AGACACACCT TAACATTTTC TAGAATCCAC CAGCTTTAGT GGAGTCTGTC    3516

TAATCATGAG TATTGGAATA GGATCTGGGG GCAGTGAGGG GGTGGCAGCC ACGTGTGGCA    3576

GAGAAAAGCA CACAAGGAAA GAGCACCCAG GACTGTCATA TGGAAGAAAG ACAGGACTGC    3636

AACTCACCCT TCACAAAATG AGGACCAGAC ACAGCTGATG GTATGAGTTG ATGCAGGTGT    3696

GTGGAGCCTC AACATCCTGC TCCCCTCCTA CTACACATGG TTAAGGCCTG TTGCTCTGTC    3756

TCCAG  GT TCA CAC TCT CTG CAC TAC CTC TTC ATG GGT GCC TCA GAG       3802
       Arg Ser His Ser Leu His Tyr Leu Phe Met Gly Ala Ser Glu
                      30                  35

CAG GAC CTT GGT CTT TCC TTG TTT GAA GCT TTG GGC TAC GTG GAT GAC     3850
Gln Asp Leu Gly Leu Ser Leu Phe Glu Ala Leu Gly Tyr Val Asp Asp
 40              45                  50                  55

CAG CTG TTC GTG TTC TAT GAT CAT GAG AGT CGC CGT GTG GAG CCC CGA     3898
Gln Leu Phe Val Phe Tyr Asp His Glu Ser Arg Arg Val Glu Pro Arg
             60                  65                  70

ACT CCA TGG GTT TCC AGT AGA ATT TCA AGC CAG ATG TGG CTG CAG CTG     3946
Thr Pro Trp Val Ser Ser Arg Ile Ser Ser Gln Met Trp Leu Gln Leu
         75                  80                  85

AGT CAG AGT CTG AAA GGG TGG GAT CAC ATG TTC ACT GTT GAC TTC TGG     3994
Ser Gln Ser Leu Lys Gly Trp Asp His Met Phe Thr Val Asp Phe Trp
```

-continued

```
                  90                  95                 100
ACT ATT ATG GAA AAT CAC AAC CAC AGC AAG G GTATGTGGAG AGGGGGCCTC      4045
Thr Ile Met Glu Asn His Asn His Ser Lys
    105                 110

ACCTTCCTGA GGTTGTCAGA GCTTTTCATC TTTTCATGCA TCTTGAAGGA AACAGCTGGA    4105

AGTCTGAGGT CTTGTGGGAG CAGGGAAGAG GGAAGGAATT TGCTTCCTGA GATCATTTGG    4165

TCCTTGGGGA TGGTGGAAAT AGGGACCTAT TCCTTTGGTT GCAGTTAACA AGGCTGGGGA    4225

TTTTTCCAG  AG TCC CAC ACC CTG CAG GTC ATC CTG GGC TGT GAA ATG       4272
              Glu Ser His Thr Leu Gln Val Ile Leu Gly Cys Glu Met
              115                 120                 125

CAA GAA GAC AAC AGT ACC GAG GGC TAC TGG AAG TAC GGG TAT GAT GGG     4320
Gln Glu Asp Asn Ser Thr Glu Gly Tyr Trp Lys Tyr Gly Tyr Asp Gly
            130                 135                 140

CAG GAC CAC CTT GAA TTC TGC CCT GAC ACA CTG GAT TGG AGA GCA GCA     4368
Gln Asp His Leu Glu Phe Cys Pro Asp Thr Leu Asp Trp Arg Ala Ala
145                 150                 155

GAA CCC AGG GCC TGG CCC ACC AAG CTG GAG TGG GAA AGG CAC AAG ATT     4416
Glu Pro Arg Ala Trp Pro Thr Lys Leu Glu Trp Glu Arg His Lys Ile
160                 165                 170

CGG GCC AGG CAG AAC AGG GCC TAC CTG GAG AGG GAC TGC CCT GCA CAG     4464
Arg Ala Arg Gln Asn Arg Ala Tyr Leu Glu Arg Asp Cys Pro Ala Gln
175                 180                 185                 190

CTG CAG CAG TTG CTG GAG CTG GGG AGA GGT GTT TTG GAC CAA CAA G       4510
Leu Gln Gln Leu Leu Glu Leu Gly Arg Gly Val Leu Asp Gln Gln
                195                 200                 205

GTATGGTGGA AACACACTTC TGCCCCTATA CTCTAGTGGC AGAGTGGAGG AGGTTGCAGG    4570

GCACGGAATC CCTGGTTGGA GTTTCAGAGG TGGCTGAGGC TGTGTGCCTC TCCAAATTCT    4630

GGGAAGGGAC TTTCTCAATC CTAGAGTCTC TACCTTATAA TTGAGATGTA TGAGACAGCC    4690

ACAAGTCATG GGTTTAATTT CTTTTCTCCA TGCATATGGC TCAAAGGGAA GTGTCTATGG    4750

CCCTTGCTTT TTATTTAACC AATAATCTTT TGTATATTTA TACCTGTTAA AAATTCAGAA    4810

ATGTCAAGGC CGGGCACGGT GGCTCACCCC TGTAATCCCA GCACTTTGGG AGGCCGAGGC    4870

GGGTGGTCAC AAGGTCAGGA GTTTGAGACC AGCCTGACCA ACATGGTGAA ACCCGTCTCT    4930

AAAAAAATAC AAAAATTAGC TGGTCACAGT CATGCGCACC TGTAGTCCCA GCTAATTGGA    4990

AGGCTGAGGC AGGAGCATCG CTTGAACCTG GGAAGCGGAA GTTGCACTGA GCCAAGATCG    5050

CGCCACTGCA CTCCAGCCTA GGCAGCAGAG TGAGACTCCA TCTTAAAAAA AAAAAAAAAA    5110

AAAAAAGAG AATTCAGAGA TCTCAGCTAT CATATGAATA CCAGGACAAA ATATCAAGTG     5170

AGGCCACTTA TCAGAGTAGA AGAATCCTTT AGGTTAAAAG TTTCTTTCAT AGAACATAGC    5230

AATAATCACT GAAGCTACCT ATCTTACAAG TCCGCTTCTT ATAACAATGC CTCCTAGGTT    5290

GACCCAGGTG AAACTGACCA TCTGTATTCA ATCATTTTCA ATGCACATAA AGGGCAATTT    5350

TATCTATCAG AACAAAGAAC ATGGGTAACA GATATGTATA TTTACATGTG AGGAGAACAA    5410

GCTGATCTGA CTGCTCTCCA AGTGACACTG TGTTAGAGTC CAATCTTAGG ACACAAAATG    5470

GTGTCTCTCC TGTAGCTTGT TTTTTTCTGA AAAGGGTATT TCCTTCCTCC AACCTATAGA    5530

AGGAAGTGAA AGTTCCAGTC TTCCTGGCAA GGGTAAACAG ATCCCCTCTC CTCATCCTTC    5590

CTCTTTCCTG TCAAG  TG CCT CCT TTG GTG AAG GTG ACA CAT CAT GTG ACC    5640
                 Val Pro Pro Leu Val Lys Val Thr His His Val Thr
                                   210                 215

TCT TCA GTG ACC ACT CTA CGG TGT CGG GCC TTG AAC TAC TAC CCC CAG     5688
Ser Ser Val Thr Thr Leu Arg Cys Arg Ala Leu Asn Tyr Tyr Pro Gln
220                 225                 230
```

```
                                                                -continued

AAC ATC ACC ATG AAG TGG CTG AAG GAT AAG CAG CCA ATG GAT GCC AAG        5736
Asn Ile Thr Met Lys Trp Leu Lys Asp Lys Gln Pro Met Asp Ala Lys
        235                 240                 245

GAG TTC GAA CCT AAA GAC GTA TTG CCC AAT GGG GAT GGG ACC TAC CAG        5784
Glu Phe Glu Pro Lys Asp Val Leu Pro Asn Gly Asp Gly Thr Tyr Gln
250                 255                 260                 265

GGC TGG ATA ACC TTG GCT GTA CCC CCT GGG GAA GAG CAG AGA TAT ACG        5832
Gly Trp Ile Thr Leu Ala Val Pro Pro Gly Glu Glu Gln Arg Tyr Thr
                270                 275                 280

TAC CAG GTG GAG CAC CCA GGC CTG GAT CAG CCC CTC ATT GTG ATC TGG G      5881
Tyr Gln Val Glu His Pro Gly Leu Asp Gln Pro Leu Ile Val Ile Trp
            285                 290                 295

GTATGTGACT GATGAGAGCC AGGAGCTGAG AAAATCTATT GGGGGTTGAG AGGAGTGCCT      5941

GAGGAGGTAA TTATGGCAGT GAGATGAGGA TCTGCTCTTT GTTAGGGGGT GGGCTGAGGG      6001

TGGCAATCAA AGGCTTTAAC TTGCTTTTTC TGTTTTAG  AG CCC TCA CCG TCT         6053
                                              Glu Pro Ser Pro Ser
                                                              300

GGC ACC CTA GTC ATT GGA GTC ATC AGT GGA ATT GCT GTT TTT GTC GTC        6101
Gly Thr Leu Val Ile Gly Val Ile Ser Gly Ile Ala Val Phe Val Val
        305                 310                 315

ATC TTG TTC ATT GGA ATT TTG TTC ATA ATA TTA AGG AAG AGG CAG GGT        6149
Ile Leu Phe Ile Gly Ile Leu Phe Ile Ile Leu Arg Lys Arg Gln Gly
        320                 325                 330

TCA A GTGAGTAGGA ACAAGGGGGA AGTCTCTTAG TACCTCTGCC CCAGGGCACA           6203
Ser
335

GTGGGAAGAG GGGCAGAGGG GATCTGGCAT CCATGGGAAG CATTTTTCTC ATTTATATTC      6263

TTTGGGGACA CCAGCAGCTC CCTGGGAGAC AGAAAATAAT GGTTCTCCCC AGAATGAAAG      6323

TCTCTAATTC AACAAACATC TTCAGAGCAC CTACTATTTT GCAAGAGCTG TTTAAGGTAG      6383

TACAGGGGCT TTGAGGTTGA GAAGTCACTG TGGCTATTCT CAGAACCCAA ATCTGGTAGG      6443

GAATGAAATT GATAGCAAGT AAATGTAGTT AAAGAAGACC CCATGAGGTC CTAAAGCAGG      6503

CAGGAAGCAA ATGCTTAGGG TGTCAAAGGA AGAATGATC ACATTCAGCT GGGGATCAAG       6563

ATAGCCTTCT GGATCTTGAA GGAGAAGCTG GATTCCATTA GGTGAGGTTG AAGATGATGG      6623

GAGGTCTACA CAGACGGAGC AACCATGCCA AGTAGGAGAG TATAAGGCAT ACTGGGAGAT      6683

TAGAAATAAT TACTGTACCT TAACCCTGAG TTTGCGTAGC TATCACTCAC CAATTATGCA      6743

TTTCTACCCC CTGAACATCT GTGGTGTAGG GAAAAGAGAA TCAGAAAGAA GCCAGCTCAT      6803

ACAGAGTCCA AGGGTCTTTT GGGATATTGG GTTATGATCA CTGGGGTGTC ATTGAAGGAT      6863

CCTAAGAAAG GAGGACCACG ATCTCCCTTA TATGGTGAAT GTGTTGTTAA GAAGTTAGAT      6923

GAGAGGTGAG GAGACCAGTT AGAAAGCCAA TAAGCATTTC CAGATGAGAG ATAATGGTTC      6983

TTGAAATCCA ATAGTGCCCA GGTCTAAATT GAGATGGGTG AATGAGGAAA ATAAGGAAGA      7043

GAGAAGAGGC AAGATGGTGC CTAGGTTTGT GATGCCTCTT TCCTGGGTCT CTTGTCTCCA      7103

CAG  GA GGA GCC ATG GGG CAC TAC GTC TTA GCT GAA CGT GAG                7144
     Arg Gly Ala Met Gly His Tyr Val Leu Ala Glu Arg Glu
                     340                 345

TGACACGCAG CCTGCAGACT CACTGTGGGA AGGAGACAAA ACTAGAGACT CAAAGAGGGA      7204

GTGCATTTAT GAGCTCTTCA TGTTTCAGGA GAGAGTTGAA CCTAAACATA GAAATTGCCT      7264

GACGAACTCC TTGATTTTAG CCTTCTCTGT TCATTTCCTC AAAAAGATTT CCCCATTTAG      7324

GTTTCTGAGT TCCTGCATGC CGGTGATCCC TAGCTGTGAC CTCTCCCCTG GAACTGTCTC      7384
```

```
TCATGAACCT CAAGCTGCAT CTAGAGGCTT CCTTCATTTC CTCCGTCACC TCAGAGACAT    7444

ACACCTATGT CATTTCATTT CCTATTTTTG GAAGAGGACT CCTTAAATTT GGGGGACTTA    7504

CATGATTCAT TTTAACATCT GAGAAAAGCT TTGAACCCTG GGACGTGGCT AGTCATAACC    7564

TTACCAGATT TTTACACATG TATCTATGCA TTTTCTGGAC CCGTTCAACT TTTCCTTTGA    7624

ATCCTCTCTC TGTGTTACCC AGTAACTCAT CTGTCACCAA GCCTTGGGGA TTCTTCCATC    7684

TGATTGTGAT GTGAGTTGCA CAGCTATGAA GGCTGTACAC TGCACGAATG GAAGAGGCAC    7744

CTGTCCCAGA AAAAGCATCA TGGCTATCTG TGGGTAGTAT GATGGGTGTT TTTAGCAGGT    7804

AGGAGGCAAA TATCTTGAAA GGGGTTGTGA AGAGGTGTTT TTTCTAATTG GCATGAAGGT    7864

GTCATACAGA TTTGCAAAGT TTAATGGTGC CTTCATTTGG GATGCTACTC TAGTATTCCA    7924

GACCTGAAGA ATCACAATAA TTTTCTACCT GGTCTCTCCT TGTTCTGATA ATGAAAATTA    7984

TGATAAGGAT GATAAAAGCA CTTACTTCGT GTCCGACTCT TCTGAGCACC TACTTACATG    8044

CATTACTGCA TGCACTTCTT ACAATAATTC TATGAGATAG GTACTATTAT CCCCATTTCT    8104

TTTTTAAATG AAGAAAGTGA AGTAGGCCGG GCACGGTGGC TCACGCCTGT AATCCCAGCA    8164

CTTTGGGAGG CCAAAGCGGG TGGATCACGA GGTCAGGAGA TCGAGACCAT CCTGGCTAAC    8224

ATGGTGAAAC CCCATCTCTA ATAAAAATAC AAAAAATTAG CTGGGCGTGG TGGCAGACGC    8284

CTGTAGTCCC AGCTACTCGG AAGGCTGAGG CAGGAGAATG GCATGAACCC AGGAGGCAGA    8344

GCTTGCAGTG AGCCGAGTTT GCGCCACTGC ACTCCAGCCT AGGTGACAGA GTGAGACTCC    8404

ATCTCAAAAA AATAAAAATA AAAATAAAAA AATGAAAAAA AAAGAAAGT GAAGTATAGA    8464

GTATCTCATA GTTTGTCAGT GATAGAAACA GGTTTCAAAC TCAGTCAATC TGACCGTTTG    8524

ATACATCTCA GACACCACTA CATTCAGTAG TTTAGATGCC TAGAATAAAT AGAGAAGGAA    8584

GGAGATGGCT CTTCTCTTGT CTCATTGTGT TTCTTCTGAG TGAGCTTGAA TCACATGAAG    8644

GGGAACAGCA GAAAACAACC AACTGATCCT CAGCTGTCAT GTTTCCTTTA AAAGTCCCTG    8704

AAGGAAGGTC CTGGAATGTG ACTCCCTTGC TCCTCTGTTG CTCTCTTTGG CATTCATTTC    8764

TTTGGACCCT ACGCAAGGAC TGTAATTGGT GGGGACAGCT AGTGGCCCTG CTGGGCTTCA    8824

CACACGGTGT CCTCCCTAGG CCAGTGCCTC TGGAGTCAGA ACTCTGGTGG TATTTCCCTC    8884

AATGAAGTGG AGTAAGCTCT CTCATTTTGA GATGGTATAA TGGAAGCCAC CAAGTGGCTT    8944

AGAGGATGCC CAGGTCCTTC CATGGAGCCA CTGGGGTTCC GGTGCACATT AAAAAAAAAA    9004

TCTAACCAGG ACATTCAGGA ATTGCTAGAT TCTGGGAAAT CAGTTCACCA TGTTCAAAAG    9064

AGTCTTTTTT TTTTTTTTGA GACTCTATTG CCCAGGCTGG AGTGCAATGG CATGATCTCG    9124

GCTCACTGTA ACCTCTGCCT CCCAGGTTCA AGCGATTCTC CTGTCTCAGC CTCCCAAGTA    9184

GCTGGGATTA CAGGCGTGCA CCACCATGCC CGGCTAATTT TTGTATTTTT AGTAGAGACA    9244

GGGTTTCACC ATGTTGGCCA GGCTGGTCTC GAACTCTCCT GACCTCGTGA TCCGCCTGCC    9304

TCGGCCTCCC AAAGTGCTGA GATTACAGGT GTGAGCCACC CTGCCCAGCC GTCAAAAGAG    9364

TCTTAATATA TATATCCAGA TGGCATGTGT TTACTTTATG TTACTACATG CACTTGGCTG    9424

CATAAATGTG GTACAAGCAT TCTGTCTTGA AGGGCAGGTG CTTCAGGATA CCATATACAG    9484

CTCAGAAGTT TCTTCTTTAG GCATTAAATT TTAGCAAAGA TATCTCATCT CTTCTTTTAA    9544

ACCATTTTCT TTTTTTGTGG TTAGAAAAGT TATGTAGAAA AAAGTAAATG TGATTTACGC    9604

TCATTGTAGA AAAGCTATAA AATGAATACA ATTAAAGCTG TTATTTAATT AGCCAGTGAA    9664

AAACTATTAA CAACTTGTCT ATTACCTGTT AGTATTATTG TTGCATTAAA AATGCATATA    9724

CTTTAATAAA TGTATATTGT ATTGTATACT GCATGATTTT ATTGAAGTTC TTGTTCATCT    9784
```

-continued

```
TGTGTATATA CTTAATCGCT TGTCATTTT GGAGACATTT ATTTTGCTTC TAATTTCTTT      9844

ACATTTGTC TTACGGAATA TTTTCATTCA ACTGTGGTAG CCGAATTAAT CGTGTTTCTT      9904

CACTCTAGGG ACATTGTCGT CTAAGTTGTA AGACATTGGT TATTTTACCA GCAAACCATT     9964

CTGAAAGCAT ATGACAAATT ATTTCTCTCT TAATATCTTA CTATACTGAA AGCAGACTGC    10024

TATAAGGCTT CACTTACTCT TCTACCTCAT AAGGAATATG TTACAATTAA TTTATTAGGT   10084

AAGCATTTGT TTTATATTGG TTTTATTTCA CCTGGGCTGA GATTTCAAGA ACACCCCAG    10144

TCTTCACAGT AACACATTTC ACTAACACAT TTACTAAACA TCAGCAACTG TGGCCTGTTA   10204

ATTTTTTTAA TAGAAATTTT AAGTCCTCAT TTTCTTTCGG TGTTTTTTAA GCTTAATTTT   10264

TCTGGCTTTA TTCATAAATT CTTAAGGTCA ACTACATTTG AAAAATCAAA GACCTGCATT   10324

TTAAATTCTT ATTCACCTCT GGCAAAACCA TTCACAAACC ATGGTAGTAA AGAGAAGGGT   10384

GACACCTGGT GGCCATAGGT AAATGTACCA CGGTGGTCCG GTGACCAGAG ATGCAGCGCT   10444

GAGGGTTTTC CTGAAGGTAA AGGAATAAAG AATGGGTGGA GGGGCGTGCA CTGGAAATCA   10504

CTTGTAGAGA AAAGCCCCTG AAAATTTGAG AAAACAAACA AGAAACTACT TACCAGCTAT   10564

TTGAATTGCT GGAATCACAG GCCATTGCTG AGCTGCCTGA ACTGGGAACA CAACAGAAGG   10624

AAAACAAACC ACTCTGATAA TCATTGAGTC AAGTACAGCA GGTGATTGAG GACTGCTGAG   10684

AGGTACAGGC CAAAATTCTT ATGTTGTATT ATAATAATGT CATCTTATAA TACTGTCAGT   10744

ATTTTATAAA ACATTCTTCA CAAACTCACA CACATTTAAA AACAAAACAC TGTCTCTAAA   10804

ATCCCCAAAT TTTTCATAAA C                                             10825
```

(2) INFORMATION FOR SEQ ID NO:4:

(i) SEQUENCE CHARACTERISTICS:
        (A) LENGTH: 348 amino acids
        (B) TYPE: amino acid
        (D) TOPOLOGY: linear (ii) MOLECULE TYPE: protein (xi) SEQUENCE DESCRIPTION: SEQ ID NO:4:

```
Met Gly Pro Arg Ala Arg Pro Ala Leu Leu Leu Met Leu Leu Gln
 1               5                  10                  15

Thr Ala Val Leu Gln Gly Arg Leu Leu Arg Ser His Ser Leu His Tyr
                20                  25                  30

Leu Phe Met Gly Ala Ser Glu Gln Asp Leu Gly Leu Ser Leu Phe Glu
            35                  40                  45

Ala Leu Gly Tyr Val Asp Asp Gln Leu Phe Val Phe Tyr Asp His Glu
        50                  55                  60

Ser Arg Arg Val Glu Pro Arg Thr Pro Trp Val Ser Ser Arg Ile Ser
65                  70                  75                  80

Ser Gln Met Trp Leu Gln Leu Ser Gln Ser Leu Lys Gly Trp Asp His
                85                  90                  95

Met Phe Thr Val Asp Phe Trp Thr Ile Met Glu Asn His Asn His Ser
            100                 105                 110

Lys Glu Ser His Thr Leu Gln Val Ile Leu Gly Cys Glu Met Gln Glu
        115                 120                 125

Asp Asn Ser Thr Glu Gly Tyr Trp Lys Tyr Gly Tyr Asp Gly Gln Asp
    130                 135                 140

His Leu Glu Phe Cys Pro Asp Thr Leu Asp Trp Arg Ala Ala Glu Pro
145                 150                 155                 160
```

```
Arg Ala Trp Pro Thr Lys Leu Glu Trp Glu Arg His Lys Ile Arg Ala
                165                 170                 175

Arg Gln Asn Arg Ala Tyr Leu Glu Arg Asp Cys Pro Ala Gln Leu Gln
            180                 185                 190

Gln Leu Leu Glu Leu Gly Arg Gly Val Leu Asp Gln Val Pro Pro
        195                 200                 205

Leu Val Lys Val Thr His His Val Thr Ser Ser Val Thr Thr Leu Arg
    210                 215                 220

Cys Arg Ala Leu Asn Tyr Tyr Pro Gln Asn Ile Thr Met Lys Trp Leu
225                 230                 235                 240

Lys Asp Lys Gln Pro Met Asp Ala Lys Glu Phe Glu Pro Lys Asp Val
                245                 250                 255

Leu Pro Asn Gly Asp Gly Thr Tyr Gln Gly Trp Ile Thr Leu Ala Val
            260                 265                 270

Pro Pro Gly Glu Glu Gln Arg Tyr Thr Tyr Gln Val Glu His Pro Gly
        275                 280                 285

Leu Asp Gln Pro Leu Ile Val Ile Trp Glu Pro Ser Pro Ser Gly Thr
    290                 295                 300

Leu Val Ile Gly Val Ile Ser Gly Ile Ala Val Phe Val Val Ile Leu
305                 310                 315                 320

Phe Ile Gly Ile Leu Phe Ile Ile Leu Arg Lys Arg Gln Gly Ser Arg
                325                 330                 335

Gly Ala Met Gly His Tyr Val Leu Ala Glu Arg Glu
            340                 345

(2) INFORMATION FOR SEQ ID NO:5:

(i) SEQUENCE CHARACTERISTICS:
        (A) LENGTH: 10825 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: join(361..436, 3762..4025, 4235..4510,
            5606..5881, 6040..6153, 7107..7147)
        (D) OTHER INFORMATION: /product= "Hereditary Hemochromatosis
            (HH) protein containing the 24d2
            mutation"
            /note= "Hereditary Hemochromatosis (HH)
            gene 24d2 allele"

(ix) FEATURE:
        (A) NAME/KEY: -
        (B) LOCATION: 140..7319
        (D) OTHER INFORMATION: /note= "start and stop positions for
            24d2 allele cDNA (SEQ ID NO:11)"

(ix) FEATURE:
        (A) NAME/KEY: -
        (B) LOCATION: 3852..3891
        (D) OTHER INFORMATION: /note= "start and stop positions for
            genomic sequence surrounding variant
            for 24d2(G) allele (SEQ ID NO:42)"

(ix) FEATURE:
        (A) NAME/KEY: -
        (B) LOCATION: 5507..6023
        (D) OTHER INFORMATION: /note= "start and stop positions for
            genomic sequence surrounding variant
            for 24d1(G) allele (SEQ ID NO:20)"

(ix) FEATURE:
        (A) NAME/KEY: allele
```

(B) LOCATION: replace(3872, "g")
(D) OTHER INFORMATION: /phenotype= "Hereditary Hemochromatosis (HH)"
    /label= 24d2

(xi) SEQUENCE DESCRIPTION: SEQ ID NO:5:

| | | |
|---|---|---|
| TCTAAGGTTG AGATAAAATT TTTAAATGTA TGATTGAATT TTGAAAATCA TAAATATTTA | 60 |
| AATATCTAAA GTTCAGATCA GAACATTGCG AAGCTACTTT CCCCAATCAA CAACACCCCT | 120 |
| TCAGGATTTA AAAACCAAGG GGGACACTGG ATCACCTAGT GTTTCACAAG CAGGTACCTT | 180 |
| CTGCTGTAGG AGAGAGAGAA CTAAAGTTCT GAAAGACCTG TTGCTTTTCA CCAGGAAGTT | 240 |
| TTACTGGGCA TCTCCTGAGC CTAGGCAATA GCTGTAGGGT GACTTCTGGA GCCATCCCCG | 300 |
| TTTCCCCGCC CCCCAAAAGA AGCGGAGATT TAACGGGGAC GTGCGGCCAG AGCTGGGGAA | 360 |

```
ATG GGC CCG CGA GCC AGG CCG GCG CTT CTC CTC CTG ATG CTT TTG CAG        408
Met Gly Pro Arg Ala Arg Pro Ala Leu Leu Leu Leu Met Leu Leu Gln
 1               5                  10                  15

ACC GCG GTC CTG CAG GGG CGC TTG CTG C GTGAGTCCGA GGGCTGCGGG            456
Thr Ala Val Leu Gln Gly Arg Leu Leu
                20                  25
```

| | |
|---|---|
| CGAACTAGGG GCGCGGCGGG GGTGGAAAAA TCGAAACTAG CTTTTTCTTT GCGCTTGGGA | 516 |
| GTTTGCTAAC TTTGGAGGAC CTGCTCAACC CTATCCGCAA GCCCCTCTCC CTACTTTCTG | 576 |
| CGTCCAGACC CCGTGAGGGA GTGCCTACCA CTGAACTGCA GATAGGGGTC CCTCGCCCCA | 636 |
| GGACCTGCCC CCTCCCCCGG CTGTCCCGGC TCTGCGGAGT GACTTTTGGA ACCGCCCACT | 696 |
| CCCTTCCCCC AACTAGAATG CTTTTAAATA AATCTCGTAG TTCCTCACTT GAGCTGAGCT | 756 |
| AAGCCTGGGG CTCCTTGAAC CTGGAACTCG GGTTTATTTC CAATGTCAGC TGTGCAGTTT | 816 |
| TTTCCCCAGT CATCTCCAAA CAGGAAGTTC TTCCCTGAGT GCTTGCCGAG AAGGCTGAGC | 876 |
| AAACCCACAG CAGGATCCGC ACGGGGTTTC CACCTCAGAA CGAATGCGTT GGGCGGTGGG | 936 |
| GGCGCGAAAG AGTGGCGTTG GGGATCTGAA TTCTTCACCA TTCCACCCAC TTTTGGTGAG | 996 |
| ACCTGGGGTG GAGGTCTCTA GGGTGGGAGG CTCCTGAGAG AGGCCTACCT CGGGCCTTTC | 1056 |
| CCCACTCTTG GCAATTGTTC TTTTGCCTGG AAAATTAAGT ATATGTTAGT TTTGAACGTT | 1116 |
| TGAACTGAAC AATTCTCTTT TCGGCTAGGC TTTATTGATT TGCAATGTGC TGTGTAATTA | 1176 |
| AGAGGCCTCT CTACAAAGTA CTGATAATGA ACATGTAAGC AATGCACTCA CTTCTAAGTT | 1236 |
| ACATTCATAT CTGATCTTAT TTGATTTTCA CTAGGCATAG GGAGGTAGGA GCTAATAATA | 1296 |
| CGTTTATTTT ACTAGAAGTT AACTGGAATT CAGATTATAT AACTCTTTTC AGGTTACAAA | 1356 |
| GAACATAAAT AATCTGGTTT TCTGATGTTA TTTCAAGTAC TACAGCTGCT TCTAATCTTA | 1416 |
| GTTGACAGTG ATTTTGCCCT GTAGTGTAGC ACAGTGTTCT GTGGGTCACA CGCCGGCCTC | 1476 |
| AGCACAGCAC TTTGAGTTTT GGTACTACGT GTATCCACAT TTTACACATG ACAAGAATGA | 1536 |
| GGCATGGCAC GGCCTGCTTC CTGGCAAATT TATTCAATGG TACACTGGGC TTTGGTGGCA | 1596 |
| GAGCTCATGT CTCCACTTCA TAGCTATGAT TCTTAAACAT CACACTGCAT TAGAGGTTGA | 1656 |
| ATAATAAAAT TTCATGTTGA GCAGAAATAT TCATTGTTTA CAAGTGTAAA TGAGTCCCAG | 1716 |
| CCATGTGTTG CACTGTTCAA GCCCCAAGGG AGAGAGCAGG GAAACAAGTC TTTACCCTTT | 1776 |
| GATATTTTGC ATTCTAGTGG GAGAGATGAC AATAAGCAAA TGAGCAGAAA GATATACAAC | 1836 |
| ATCAGGAAAT CATGGGTGTT GTGAGAAGCA GAGAAGTCAG GGCAAGTCAC TCTGGGGCTG | 1896 |
| ACACTTGAGC AGAGACATGA AGGAAATAAG AATGATATTG ACTGGGAGCA GTATTTCCCA | 1956 |
| GGCAAACTGA GTGGGCCTGG CAAGTTGGAT TAAAAAGCGG GTTTTCTCAG CACTACTCAT | 2016 |

```
GTGTGTGTGT GTGGGGGGGG GGGGCGGCGT GGGGGTGGGA AGGGGGACTA CCATCTGCAT       2076

GTAGGATGTC TAGCAGTATC CTGTCCTCCC TACTCACTAG GTGCTAGGAG CACTCCCCCA       2136

GTCTTGACAA CCAAAAATGT CTCTAAACTT TGCCACATGT CACCTAGTAG ACAAACTCCT       2196

GGTTAAGAAG CTCGGGTTGA AAAAAATAAA CAAGTAGTGC TGGGGAGTAG AGGCCAAGAA       2256

GTAGGTAATG GGCTCAGAAG AGGAGCCACA ACAAGGTTG TGCAGGCGCC TGTAGGCTGT        2316

GGTGTGAATT CTAGCCAAGG AGTAACAGTG ATCTGTCACA GGCTTTTAAA AGATTGCTCT      2376

GGCTGCTATG TGGAAAGCAG AATGAAGGGA GCAACAGTAA AAGCAGGGAG CCCAGCCAGG      2436

AAGCTGTTAC ACAGTCCAGG CAAGAGGTAG TGGAGTGGGC TGGGTGGGAA CAGAAAAGGG      2496

AGTGACAAAC CATTGTCTCC TGAATATATT CTGAAGGAAG TTGCTGAAGG ATTCTATGTT      2556

GTGTGAGAGA AAGAGAAGAA TTGGCTGGGT GTAGTAGCTC ATGCCAAGGA GGAGGCCAAG      2616

GAGAGCAGAT TCCTGAGCTC AGGAGTTCAA GACCAGCCTG GCAACACAG CAAAACCCCT       2676

TCTCTACAAA AAATACAAAA ATTAGCTGGG TGTGGTGGCA TGCACCTGTG ATCCTAGCTA      2736

CTCGGGAGGC TGAGGTGGAG GGTATTGCTT GAGCCCAGGA AGTTGAGGCT GCAGTGAGCC      2796

ATGACTGTGC CACTGTACTT CAGCCTAGGT GACAGAGCAA GACCCTGTCT CCCCTGACCC      2856

CCTGAAAAAG AGAAGAGTTA AAGTTGACTT TGTTCTTTAT TTTAATTTTA TTGGCCTGAG      2916

CAGTGGGGTA ATTGGCAATG CCATTTCTGA GATGGTGAAG GCAGAGGAAA GAGCAGTTTG      2976

GGGTAAATCA AGGATCTGCA TTTGGGACAT GTTAAGTTTG AGATTCCAGT CAGGCTTCCA      3036

AGTGGTGAGG CCACATAGGC AGTTCAGTGT AAGAATTCAG GACCAAGGCT GGGCACGGTG      3096

GCTCACTTCT GTAATCCCAG CACTTTGGTG GCTGAGGCAG GTAGATCATT TGAGGTCAGG      3156

AGTTTGAGAC AAGCTTGGCC AACATGGTGA AACCCCATGT CTACTAAAAA TACAAAAATT      3216

AGCCTGGTGT GGTGGCGCAC GCCTATAGTC CCAGGTTTTC AGGAGGCTTA GGTAGGAGAA      3276

TCCCTTGAAC CCAGGAGGTG CAGGTTGCAG TGAGCTGAGA TTGTGCCACT GCACTCCAGC      3336

CTGGGTGATA GAGTGAGACT CTGTCTCAAA AAAAAAAAA AAAAAAAAA AAAAAACTGA        3396

AGGAATTATT CCTCAGGATT TGGGTCTAAT TTGCCCTGAG CACCAACTCC TGAGTTCAAC      3456

TACCATGGCT AGACACACCT TAACATTTTC TAGAATCCAC CAGCTTTAGT GGAGTCTGTC      3516

TAATCATGAG TATTGGAATA GGATCTGGGG GCAGTGAGGG GGTGGCAGCC ACGTGTGGCA      3576

GAGAAAAGCA CACAAGGAAA GAGCACCCAG GACTGTCATA TGGAAGAAAG ACAGGACTGC      3636

AACTCACCCT TCACAAAATG AGGACCAGAC ACAGCTGATG GTATGAGTTG ATGCAGGTGT      3696

GTGGAGCCTC AACATCCTGC TCCCCTCCTA CTACACATGG TTAAGGCCTG TTGCTCTGTC      3756

TCCAG  GT TCA CAC TCT CTG CAC TAC CTC TTC ATG GGT GCC TCA GAG          3802
       Arg Ser His Ser Leu His Tyr Leu Phe Met Gly Ala Ser Glu
                      30                  35

CAG GAC CTT GGT CTT TCC TTG TTT GAA GCT TTG GGC TAC GTG GAT GAC        3850
Gln Asp Leu Gly Leu Ser Leu Phe Glu Ala Leu Gly Tyr Val Asp Asp
 40              45                  50                  55

CAG CTG TTC GTG TTC TAT GAT GAT GAG AGT CGC CGT GTG GAG CCC CGA        3898
Gln Leu Phe Val Phe Tyr Asp Asp Glu Ser Arg Arg Val Glu Pro Arg
             60                  65                  70

ACT CCA TGG GTT TCC AGT AGA ATT TCA AGC CAG ATG TGG CTG CAG CTG        3946
Thr Pro Trp Val Ser Ser Arg Ile Ser Ser Gln Met Trp Leu Gln Leu
         75                  80                  85

AGT CAG AGT CTG AAA GGG TGG GAT CAC ATG TTC ACT GTT GAC TTC TGG        3994
Ser Gln Ser Leu Lys Gly Trp Asp His Met Phe Thr Val Asp Phe Trp
     90                  95                  100

ACT ATT ATG GAA AAT CAC AAC CAC AGC AAG G GTATGTGGAG AGGGGGCCTC        4045
```

```
Thr Ile Met Glu Asn His Asn His Ser Lys
    105                 110

ACCTTCCTGA GGTTGTCAGA GCTTTTCATC TTTTCATGCA TCTTGAAGGA AACAGCTGGA    4105

AGTCTGAGGT CTTGTGGGAG CAGGGAAGAG GGAAGGAATT TGCTTCCTGA GATCATTTGG    4165

TCCTTGGGGA TGGTGGAAAT AGGGACCTAT TCCTTTGGTT GCAGTTAACA AGGCTGGGGA    4225

TTTTTCCAG AG TCC CAC ACC CTG CAG GTC ATC CTG GGC TGT GAA ATG         4272
           Glu Ser His Thr Leu Gln Val Ile Leu Gly Cys Glu Met
               115                 120                 125

CAA GAA GAC AAC AGT ACC GAG GGC TAC TGG AAG TAC GGG TAT GAT GGG      4320
Gln Glu Asp Asn Ser Thr Glu Gly Tyr Trp Lys Tyr Gly Tyr Asp Gly
            130                 135                 140

CAG GAC CAC CTT GAA TTC TGC CCT GAC ACA CTG GAT TGG AGA GCA GCA      4368
Gln Asp His Leu Glu Phe Cys Pro Asp Thr Leu Asp Trp Arg Ala Ala
            145                 150                 155

GAA CCC AGG GCC TGG CCC ACC AAG CTG GAG TGG GAA AGG CAC AAG ATT      4416
Glu Pro Arg Ala Trp Pro Thr Lys Leu Glu Trp Glu Arg His Lys Ile
        160                 165                 170

CGG GCC AGG CAG AAC AGG GCC TAC CTG GAG AGG GAC TGC CCT GCA CAG      4464
Arg Ala Arg Gln Asn Arg Ala Tyr Leu Glu Arg Asp Cys Pro Ala Gln
175                 180                 185                 190

CTG CAG CAG TTG CTG GAG CTG GGG AGA GGT GTT TTG GAC CAA CAA G        4510
Leu Gln Gln Leu Leu Glu Leu Gly Arg Gly Val Leu Asp Gln Gln
                195                 200                 205

GTATGGTGGA AACACACTTC TGCCCCTATA CTCTAGTGGC AGAGTGGAGG AGGTTGCAGG    4570

GCACGGAATC CCTGGTTGGA GTTTCAGAGG TGGCTGAGGC TGTGTGCCTC TCCAAATTCT    4630

GGGAAGGGAC TTTCTCAATC CTAGAGTCTC TACCTTATAA TTGAGATGTA TGAGACAGCC    4690

ACAAGTCATG GGTTTAATTT CTTTTCTCCA TGCATATGGC TCAAAGGGAA GTGTCTATGG    4750

CCCTTGCTTT TTATTTAACC AATAATCTTT TGTATATTTA TACCTGTTAA AAATTCAGAA    4810

ATGTCAAGGC CGGGCACGGT GGCTCACCCC TGTAATCCCA GCACTTTGGG AGGCCGAGGC    4870

GGGTGGTCAC AAGGTCAGGA GTTTGAGACC AGCCTGACCA ACATGGTGAA ACCCGTCTCT    4930

AAAAAAATAC AAAAATTAGC TGGTCACAGT CATGCGCACC TGTAGTCCCA GCTAATTGGA    4990

AGGCTGAGGC AGGAGCATCG CTTGAACCTG GGAAGCGGAA GTTGCACTGA GCCAAGATCG    5050

CGCCACTGCA CTCCAGCCTA GGCAGCAGAG TGAGACTCCA TCTTAAAAAA AAAAAAAAAA    5110

AAAAAAGAG AATTCAGAGA TCTCAGCTAT CATATGAATA CCAGGACAAA ATATCAAGTG     5170

AGGCCACTTA TCAGAGTAGA AGAATCCTTT AGGTTAAAAG TTTCTTTCAT AGAACATAGC    5230

AATAATCACT GAAGCTACCT ATCTTACAAG TCCGCTTCTT ATAACAATGC CTCCTAGGTT    5290

GACCCAGGTG AAACTGACCA TCTGTATTCA ATCATTTTCA ATGCACATAA AGGGCAATTT    5350

TATCTATCAG AACAAAGAAC ATGGGTAACA GATATGTATA TTTACATGTG AGGAGAACAA    5410

GCTGATCTGA CTGCTCTCCA AGTGACACTG TGTTAGAGTC CAATCTTAGG ACACAAAATG    5470

GTGTCTCTCC TGTAGCTTGT TTTTTTCTGA AAAGGGTATT TCCTTCCTCC AACCTATAGA    5530

AGGAAGTGAA AGTTCCAGTC TTCCTGGCAA GGGTAAACAG ATCCCCTCTC CTCATCCTTC    5590

CTCTTTCCTG TCAAG TG CCT CCT TTG GTG AAG GTG ACA CAT CAT GTG ACC      5640
                Val Pro Pro Leu Val Lys Val Thr His His Val Thr
                                    210                 215

TCT TCA GTG ACC ACT CTA CGG TGT CGG GCC TTG AAC TAC TAC CCC CAG      5688
Ser Ser Val Thr Thr Leu Arg Cys Arg Ala Leu Asn Tyr Tyr Pro Gln
        220                 225                 230

AAC ATC ACC ATG AAG TGG CTG AAG GAT AAG CAG CCA ATG GAT GCC AAG      5736
Asn Ile Thr Met Lys Trp Leu Lys Asp Lys Gln Pro Met Asp Ala Lys
```

```
           235                 240                 245
GAG TTC GAA CCT AAA GAC GTA TTG CCC AAT GGG GAT GGG ACC TAC CAG          5784
Glu Phe Glu Pro Lys Asp Val Leu Pro Asn Gly Asp Gly Thr Tyr Gln
250                 255                 260                 265

GGC TGG ATA ACC TTG GCT GTA CCC CCT GGG GAA GAG CAG AGA TAT ACG          5832
Gly Trp Ile Thr Leu Ala Val Pro Pro Gly Glu Glu Gln Arg Tyr Thr
                270                 275                 280

TGC CAG GTG GAG CAC CCA GGC CTG GAT CAG CCC CTC ATT GTG ATC TGG G        5881
Cys Gln Val Glu His Pro Gly Leu Asp Gln Pro Leu Ile Val Ile Trp
                285                 290                 295

GTATGTGACT GATGAGAGCC AGGAGCTGAG AAAATCTATT GGGGGTTGAG AGGAGTGCCT        5941

GAGGAGGTAA TTATGGCAGT GAGATGAGGA TCTGCTCTTT GTTAGGGGGT GGGCTGAGGG        6001

TGGCAATCAA AGGCTTTAAC TTGCTTTTTC TGTTTTAG  AG CCC TCA CCG TCT           6053
                                           Glu Pro Ser Pro Ser
                                                          300

GGC ACC CTA GTC ATT GGA GTC ATC AGT GGA ATT GCT GTT TTT GTC GTC          6101
Gly Thr Leu Val Ile Gly Val Ile Ser Gly Ile Ala Val Phe Val Val
                305                 310                 315

ATC TTG TTC ATT GGA ATT TTG TTC ATA ATA TTA AGG AAG AGG CAG GGT          6149
Ile Leu Phe Ile Gly Ile Leu Phe Ile Ile Leu Arg Lys Arg Gln Gly
                320                 325                 330

TCA A GTGAGTAGGA ACAAGGGGGA AGTCTCTTAG TACCTCTGCC CCAGGGCACA             6203
Ser
335

GTGGGAAGAG GGGCAGAGGG GATCTGGCAT CCATGGGAAG CATTTTTCTC ATTTATATTC        6263

TTTGGGGACA CCAGCAGCTC CCTGGGAGAC AGAAAATAAT GGTTCTCCCC AGAATGAAAG        6323

TCTCTAATTC AACAAACATC TTCAGAGCAC CTACTATTTT GCAAGAGCTG TTTAAGGTAG        6383

TACAGGGGCT TTGAGGTTGA GAAGTCACTG TGGCTATTCT CAGAACCCAA ATCTGGTAGG        6443

GAATGAAATT GATAGCAAGT AAATGTAGTT AAAGAAGACC CCATGAGGTC CTAAAGCAGG        6503

CAGGAAGCAA ATGCTTAGGG TGTCAAAGGA AGAATGATC ACATTCAGCT GGGGATCAAG         6563

ATAGCCTTCT GGATCTTGAA GGAGAAGCTG GATTCCATTA GGTGAGGTTG AAGATGATGG        6623

GAGGTCTACA CAGACGGAGC AACCATGCCA AGTAGGAGAG TATAAGGCAT ACTGGGAGAT        6683

TAGAAATAAT TACTGTACCT TAACCCTGAG TTTGCGTAGC TATCACTCAC CAATTATGCA        6743

TTTCTACCCC CTGAACATCT GTGGTGTAGG GAAAAGAGAA TCAGAAAGAA GCCAGCTCAT        6803

ACAGAGTCCA AGGGTCTTTT GGGATATTGG GTTATGATCA CTGGGGTGTC ATTGAAGGAT       6863

CCTAAGAAAG GAGGACCACG ATCTCCCTTA TATGGTGAAT GTGTTGTTAA GAAGTTAGAT        6923

GAGAGGTGAG GAGACCAGTT AGAAAGCCAA TAAGCATTTC CAGATGAGAG ATAATGGTTC        6983

TTGAAATCCA ATAGTGCCCA GGTCTAAATT GAGATGGGTG AATGAGGAAA ATAAGGAAGA        7043

GAGAAGAGGC AAGATGGTGC CTAGGTTTGT GATGCCTCTT TCCTGGGTCT CTTGTCTCCA        7103

CAG  GA GGA GCC ATG GGG CAC TAC GTC TTA GCT GAA CGT GAG                  7144
     Arg Gly Ala Met Gly His Tyr Val Leu Ala Glu Arg Glu
                    340                 345

TGACACGCAG CCTGCAGACT CACTGTGGGA AGGAGACAAA ACTAGAGACT CAAAGAGGGA        7204

GTGCATTTAT GAGCTCTTCA TGTTTCAGGA GAGAGTTGAA CCTAAACATA GAAATTGCCT        7264

GACGAACTCC TTGATTTTAG CCTTCTCTGT TCATTTCCTC AAAAAGATTT CCCCATTTAG        7324

GTTTCTGAGT TCCTGCATGC CGGTGATCCC TAGCTGTGAC CTCTCCCCTG GAACTGTCTC        7384

TCATGAACCT CAAGCTGCAT CTAGAGGCTT CCTTCATTTC CTCCGTCACC TCAGAGACAT        7444

ACACCTATGT CATTTCATTT CCTATTTTTG GAAGAGGACT CCTTAAATTT GGGGACTTA        7504
```

```
CATGATTCAT TTTAACATCT GAGAAAAGCT TTGAACCCTG GGACGTGGCT AGTCATAACC    7564
TTACCAGATT TTTACACATG TATCTATGCA TTTTCTGGAC CCGTTCAACT TTTCCTTTGA    7624
ATCCTCTCTC TGTGTTACCC AGTAACTCAT CTGTCACCAA GCCTTGGGGA TTCTTCCATC    7684
TGATTGTGAT GTGAGTTGCA CAGCTATGAA GGCTGTACAC TGCACGAATG GAAGAGGCAC    7744
CTGTCCCAGA AAAAGCATCA TGGCTATCTG TGGGTAGTAT GATGGGTGTT TTTAGCAGGT    7804
AGGAGGCAAA TATCTTGAAA GGGGTTGTGA AGAGGTGTTT TTTCTAATTG GCATGAAGGT    7864
GTCATACAGA TTTGCAAAGT TTAATGGTGC CTTCATTTGG GATGCTACTC TAGTATTCCA    7924
GACCTGAAGA ATCACAATAA TTTTCTACCT GGTCTCTCCT TGTTCTGATA ATGAAAATTA    7984
TGATAAGGAT GATAAAAGCA CTTACTTCGT GTCCGACTCT TCTGAGCACC TACTTACATG    8044
CATTACTGCA TGCACTTCTT ACAATAATTC TATGAGATAG GTACTATTAT CCCCATTTCT    8104
TTTTTAAATG AAGAAAGTGA AGTAGGCCGG GCACGGTGGC TCACGCCTGT AATCCCAGCA    8164
CTTTGGGAGG CCAAAGCGGG TGGATCACGA GGTCAGGAGA TCGAGACCAT CCTGGCTAAC    8224
ATGGTGAAAC CCCATCTCTA ATAAAAATAC AAAAAATTAG CTGGGCGTGG TGGCAGACGC    8284
CTGTAGTCCC AGCTACTCGG AAGGCTGAGG CAGGAGAATG GCATGAACCC AGGAGGCAGA    8344
GCTTGCAGTG AGCCGAGTTT GCGCCACTGC ACTCCAGCCT AGGTGACAGA GTGAGACTCC    8404
ATCTCAAAAA AATAAAAATA AAAATAAAAA AATGAAAAAA AAAAGAAAGT GAAGTATAGA    8464
GTATCTCATA GTTTGTCAGT GATAGAAACA GGTTTCAAAC TCAGTCAATC TGACCGTTTG    8524
ATACATCTCA GACACCACTA CATTCAGTAG TTTAGATGCC TAGAATAAAT AGAGAAGGAA    8584
GGAGATGGCT CTTCTCTTGT CTCATTGTGT TTCTTCTGAG TGAGCTTGAA TCACATGAAG    8644
GGGAACAGCA GAAAACAACC AACTGATCCT CAGCTGTCAT GTTTCCTTTA AAAGTCCCTG    8704
AAGGAAGGTC CTGGAATGTG ACTCCCTTGC TCCTCTGTTG CTCTCTTTGG CATTCATTTC    8764
TTTGGACCCT ACGCAAGGAC TGTAATTGGT GGGACAGCT AGTGGCCCTG CTGGGCTTCA     8824
CACACGGTGT CCTCCCTAGG CCAGTGCCTC TGGAGTCAGA ACTCTGGTGG TATTTCCCTC    8884
AATGAAGTGG AGTAAGCTCT CTCATTTTGA GATGGTATAA TGGAAGCCAC CAAGTGGCTT    8944
AGAGGATGCC CAGGTCCTTC CATGGAGCCA CTGGGGTTCC GGTGCACATT AAAAAAAAAA    9004
TCTAACCAGG ACATTCAGGA ATTGCTAGAT TCTGGGAAAT CAGTTCACCA TGTTCAAAAG    9064
AGTCTTTTTT TTTTTTTGA GACTCTATTG CCCAGGCTGG AGTGCAATGG CATGATCTCG     9124
GCTCACTGTA ACCTCTGCCT CCCAGGTTCA AGCGATTCTC CTGTCTCAGC CTCCCAAGTA    9184
GCTGGGATTA CAGGCGTGCA CCACCATGCC CGGCTAATTT TTGTATTTTT AGTAGAGACA    9244
GGGTTTCACC ATGTTGGCCA GGCTGGTCTC GAACTCTCCT GACCTCGTGA TCCGCCTGCC    9304
TCGGCCTCCC AAAGTGCTGA GATTACAGGT GTGAGCCACC CTGCCCAGCC GTCAAAAGAG    9364
TCTTAATATA TATATCCAGA TGGCATGTGT TTACTTTATG TTACTACATG CACTTGGCTG    9424
CATAAATGTG GTACAAGCAT TCTGTCTTGA AGGGCAGGTG CTTCAGGATA CCATATACAG    9484
CTCAGAAGTT TCTTCTTTAG GCATTAAATT TTAGCAAAGA TATCTCATCT CTTCTTTTAA    9544
ACCATTTTCT TTTTTTGTGG TTAGAAAAGT TATGTAGAAA AAAGTAAATG TGATTTACGC    9604
TCATTGTAGA AAAGCTATAA AATGAATACA ATTAAAGCTG TTATTTAATT AGCCAGTGAA    9664
AAACTATTAA CAACTTGTCT ATTACCTGTT AGTATTATTG TTGCATTAAA AATGCATATA    9724
CTTTAATAAA TGTATATTGT ATTGTATACT GCATGATTTT ATTGAAGTTC TTGTTCATCT    9784
TGTGTATATA CTTAATCGCT TTGTCATTTT GGAGACATTT ATTTTGCTTC TAATTTCTTT    9844
```

-continued

```
ACATTTTGTC TTACGGAATA TTTTCATTCA ACTGTGGTAG CCGAATTAAT CGTGTTTCTT      9904

CACTCTAGGG ACATTGTCGT CTAAGTTGTA AGACATTGGT TATTTTACCA GCAAACCATT      9964

CTGAAAGCAT ATGACAAATT ATTTCTCTCT TAATATCTTA CTATACTGAA AGCAGACTGC     10024

TATAAGGCTT CACTTACTCT TCTACCTCAT AAGGAATATG TTACAATTAA TTTATTAGGT     10084

AAGCATTTGT TTTATATTGG TTTTATTTCA CCTGGGCTGA GATTTCAAGA AACACCCCAG     10144

TCTTCACAGT AACACATTTC ACTAACACAT TTACTAAACA TCAGCAACTG TGGCCTGTTA     10204

ATTTTTTTAA TAGAAATTTT AAGTCCTCAT TTTCTTTCGG TGTTTTTTAA GCTTAATTTT     10264

TCTGGCTTTA TTCATAAATT CTTAAGGTCA ACTACATTTG AAAAATCAAA GACCTGCATT     10324

TTAAATTCTT ATTCACCTCT GGCAAAACCA TTCACAAACC ATGGTAGTAA AGAGAAGGGT     10384

GACACCTGGT GGCCATAGGT AAATGTACCA CGGTGGTCCG GTGACCAGAG ATGCAGCGCT     10444

GAGGGTTTTC CTGAAGGTAA AGGAATAAAG AATGGGTGGA GGGGCGTGCA CTGGAAATCA     10504

CTTGTAGAGA AAAGCCCCTG AAAATTTGAG AAAACAAACA AGAAACTACT TACCAGCTAT     10564

TTGAATTGCT GGAATCACAG GCCATTGCTG AGCTGCCTGA ACTGGGAACA CAACAGAAGG     10624

AAAACAAACC ACTCTGATAA TCATTGAGTC AAGTACAGCA GGTGATTGAG GACTGCTGAG     10684

AGGTACAGGC CAAAATTCTT ATGTTGTATT ATAATAATGT CATCTTATAA TACTGTCAGT     10744

ATTTTATAAA ACATTCTTCA CAAACTCACA CACATTTAAA AACAAACAC TGTCTCTAAA      10804

ATCCCCAAAT TTTTCATAAA C                                               10825
```

(2) INFORMATION FOR SEQ ID NO:6:

(i) SEQUENCE CHARACTERISTICS:
        (A) LENGTH: 348 amino acids
        (B) TYPE: amino acid
        (D) TOPOLOGY: linear (ii) MOLECULE TYPE: protein (xi) SEQUENCE DESCRIPTION: SEQ ID NO:6:

```
Met Gly Pro Arg Ala Arg Pro Ala Leu Leu Leu Met Leu Leu Gln
 1               5                  10                  15

Thr Ala Val Leu Gln Gly Arg Leu Leu Arg Ser His Ser Leu His Tyr
                20                  25                  30

Leu Phe Met Gly Ala Ser Glu Gln Asp Leu Gly Leu Ser Leu Phe Glu
            35                  40                  45

Ala Leu Gly Tyr Val Asp Asp Gln Leu Phe Val Phe Tyr Asp Asp Glu
        50                  55                  60

Ser Arg Arg Val Glu Pro Arg Thr Pro Trp Val Ser Ser Arg Ile Ser
65                  70                  75                  80

Ser Gln Met Trp Leu Gln Leu Ser Gln Ser Leu Lys Gly Trp Asp His
                85                  90                  95

Met Phe Thr Val Asp Phe Trp Thr Ile Met Glu Asn His Asn His Ser
            100                 105                 110

Lys Glu Ser His Thr Leu Gln Val Ile Leu Gly Cys Glu Met Gln Glu
        115                 120                 125

Asp Asn Ser Thr Glu Gly Tyr Trp Lys Tyr Gly Tyr Asp Gly Gln Asp
    130                 135                 140

His Leu Glu Phe Cys Pro Asp Thr Leu Asp Trp Arg Ala Ala Glu Pro
145                 150                 155                 160

Arg Ala Trp Pro Thr Lys Leu Glu Trp Glu Arg His Lys Ile Arg Ala
                165                 170                 175
```

```
Arg Gln Asn Arg Ala Tyr Leu Glu Arg Asp Cys Pro Ala Gln Leu Gln
            180                 185                 190

Gln Leu Leu Glu Leu Gly Arg Gly Val Leu Asp Gln Gln Val Pro Pro
        195                 200                 205

Leu Val Lys Val Thr His His Val Thr Ser Ser Val Thr Thr Leu Arg
        210                 215                 220

Cys Arg Ala Leu Asn Tyr Tyr Pro Gln Asn Ile Thr Met Lys Trp Leu
225                 230                 235                 240

Lys Asp Lys Gln Pro Met Asp Ala Lys Glu Phe Glu Pro Lys Asp Val
                245                 250                 255

Leu Pro Asn Gly Asp Gly Thr Tyr Gln Gly Trp Ile Thr Leu Ala Val
            260                 265                 270

Pro Pro Gly Glu Glu Gln Arg Tyr Thr Cys Gln Val Glu His Pro Gly
        275                 280                 285

Leu Asp Gln Pro Leu Ile Val Ile Trp Glu Pro Ser Pro Ser Gly Thr
290                 295                 300

Leu Val Ile Gly Val Ile Ser Gly Ile Ala Val Phe Val Val Ile Leu
305                 310                 315                 320

Phe Ile Gly Ile Leu Phe Ile Ile Leu Arg Lys Arg Gln Gly Ser Arg
                325                 330                 335

Gly Ala Met Gly His Tyr Val Leu Ala Glu Arg Glu
                340                 345

(2) INFORMATION FOR SEQ ID NO:7:

(i) SEQUENCE CHARACTERISTICS:
        (A) LENGTH: 10825 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: join(361..436, 3762..4025, 4235..4510,
            5606..5881, 6040..6153, 7107..7147)
        (D) OTHER INFORMATION: /product= "Hereditary Hemochromatosis
            (HH) protein containing both the 24d1
            and 24d2 mutations"
            /note= "Hereditary Hemochromatosis (HH)
            gene containing a combination of both
            24d1 and 24d2 alleles"

(ix) FEATURE:
        (A) NAME/KEY: -
        (B) LOCATION: 140..7319
        (D) OTHER INFORMATION: /note= "start and stop positions for
            cDNA containing a combination of both
            24d1 and 24d2 alleles
            (SEQ ID NO:12)"

(ix) FEATURE:
        (A) NAME/KEY: -
        (B) LOCATION: 3852..3891
        (D) OTHER INFORMATION: /note= "start and stop positions for
            genomic sequence surrounding variant
            for 24d2(G) allele (SEQ ID NO:42)"

(ix) FEATURE:
        (A) NAME/KEY: -
        (B) LOCATION: 5507..6023
        (D) OTHER INFORMATION: /note= "start and stop positions for
            genomic sequence surrounding variant
            for 24d1(A) allele (SEQ ID NO:21)"

(ix) FEATURE:
        (A) NAME/KEY: allele
```

```
              (B) LOCATION: replace(3872, "g")
              (D) OTHER INFORMATION: /phenotype= "Hereditary Hemochromatosis
                   (HH)"
                   /label= 24d2

(ix) FEATURE:
              (A) NAME/KEY: allele
              (B) LOCATION: replace(5834, "a")
              (D) OTHER INFORMATION: /phenotype= "Hereditary Hemochromatosis
                   (HH)"
                   /label= 24d1

(xi) SEQUENCE DESCRIPTION: SEQ ID NO:7:

TCTAAGGTTG AGATAAAATT TTTAAATGTA TGATTGAATT TTGAAAATCA TAAATATTTA      60

AATATCTAAA GTTCAGATCA GAACATTGCG AAGCTACTTT CCCCAATCAA CAACACCCCT    120

TCAGGATTTA AAAACCAAGG GGGACACTGG ATCACCTAGT GTTTCACAAG CAGGTACCTT    180

CTGCTGTAGG AGAGAGAGAA CTAAAGTTCT GAAAGACCTG TTGCTTTTCA CCAGGAAGTT    240

TTACTGGGCA TCTCCTGAGC CTAGGCAATA GCTGTAGGGT GACTTCTGGA GCCATCCCCG    300

TTTCCCCGCC CCCCAAAAGA AGCGGAGATT TAACGGGGAC GTGCGGCCAG AGCTGGGGAA    360

ATG GGC CCG CGA GCC AGG CCG GCG CTT CTC CTC CTG ATG CTT TTG CAG       408
Met Gly Pro Arg Ala Arg Pro Ala Leu Leu Leu Leu Met Leu Leu Gln
 1               5                  10                  15

ACC GCG GTC CTG CAG GGG CGC TTG CTG C GTGAGTCCGA GGGCTGCGGG           456
Thr Ala Val Leu Gln Gly Arg Leu Leu
             20                  25

CGAACTAGGG GCGCGGCGGG GGTGGAAAAA TCGAAACTAG CTTTTTCTTT GCGCTTGGGA    516

GTTTGCTAAC TTTGGAGGAC CTGCTCAACC CTATCCGCAA GCCCCTCTCC CTACTTTCTG    576

CGTCCAGACC CCGTGAGGGA GTGCCTACCA CTGAACTGCA GATAGGGGTC CCTCGCCCCA    636

GGACCTGCCC CCTCCCCCGG CTGTCCCGGC TCTGCGGAGT GACTTTTGGA ACCGCCCACT    696

CCCTTCCCCC AACTAGAATG CTTTTAAATA AATCTCGTAG TTCCTCACTT GAGCTGAGCT    756

AAGCCTGGGG CTCCTTGAAC CTGGAACTCG GGTTTATTTC CAATGTCAGC TGTGCAGTTT    816

TTTCCCCAGT CATCTCCAAA CAGGAAGTTC TTCCCTGAGT GCTTGCCGAG AAGGCTGAGC    876

AAACCCACAG CAGGATCCGC ACGGGGTTTC CACCTCAGAA CGAATGCGTT GGGCGGTGGG    936

GGCGCGAAAG AGTGGCGTTG GGGATCTGAA TTCTTCACCA TTCCACCCAC TTTTGGTGAG    996

ACCTGGGGTG GAGGTCTCTA GGGTGGGAGG CTCCTGAGAG AGGCCTACCT CGGGCCTTTC   1056

CCCACTCTTG GCAATTGTTC TTTTGCCTGG AAAATTAAGT ATATGTTAGT TTTGAACGTT   1116

TGAACTGAAC AATTCTCTTT TCGGCTAGGC TTTATTGATT TGCAATGTGC TGTGTAATTA   1176

AGAGGCCTCT CTACAAAGTA CTGATAATGA ACATGTAAGC AATGCACTCA CTTCTAAGTT   1236

ACATTCATAT CTGATCTTAT TTGATTTTCA CTAGGCATAG GGAGGTAGGA GCTAATAATA   1296

CGTTTATTTT ACTAGAAGTT AACTGGAATT CAGATTATAT AACTCTTTTC AGGTTACAAA   1356

GAACATAAAT AATCTGGTTT TCTGATGTTA TTTCAAGTAC TACAGCTGCT TCTAATCTTA   1416

GTTGACAGTG ATTTTGCCCT GTAGTGTAGC ACAGTGTTCT GTGGGTCACA CGCCGGCCTC   1476

AGCACAGCAC TTTGAGTTTT GGTACTACGT GTATCCACAT TTACACATG  ACAAGAATGA   1536

GGCATGGCAC GGCCTGCTTC CTGGCAAATT TATTCAATGG TACACTGGGC TTTGGTGGCA   1596

GAGCTCATGT CTCCACTTCA TAGCTATGAT TCTTAAACAT CACACTGCAT TAGAGGTTGA   1656

ATAATAAAAT TTCATGTTGA GCAGAAATAT TCATTGTTTA CAAGTGTAAA TGAGTCCCAG   1716

CCATGTGTTG CACTGTTCAA GCCCCAAGGG AGAGAGCAGG GAAACAAGTC TTTACCCTTT   1776

GATATTTTGC ATTCTAGTGG GAGAGATGAC AATAAGCAAA TGAGCAGAAA GATATACAAC   1836
```

| | |
|---|---|
| ATCAGGAAAT CATGGGTGTT GTGAGAAGCA GAGAAGTCAG GGCAAGTCAC TCTGGGGCTG | 1896 |
| ACACTTGAGC AGAGACATGA AGGAAATAAG AATGATATTG ACTGGGAGCA GTATTTCCCA | 1956 |
| GGCAAACTGA GTGGGCCTGG CAAGTTGGAT TAAAAAGCGG GTTTTCTCAG CACTACTCAT | 2016 |
| GTGTGTGTGT GTGGGGGGGG GGGGCGGCGT GGGGGTGGGA AGGGGGACTA CCATCTGCAT | 2076 |
| GTAGGATGTC TAGCAGTATC CTGTCCTCCC TACTCACTAG GTGCTAGGAG CACTCCCCCA | 2136 |
| GTCTTGACAA CCAAAAATGT CTCTAAACTT TGCCACATGT CACCTAGTAG ACAAACTCCT | 2196 |
| GGTTAAGAAG CTCGGGTTGA AAAAAATAAA CAAGTAGTGC TGGGGAGTAG AGGCCAAGAA | 2256 |
| GTAGGTAATG GGCTCAGAAG AGGAGCCACA AACAAGGTTG TGCAGGCGCC TGTAGGCTGT | 2316 |
| GGTGTGAATT CTAGCCAAGG AGTAACAGTG ATCTGTCACA GGCTTTTAAA AGATTGCTCT | 2376 |
| GGCTGCTATG TGGAAAGCAG AATGAAGGGA GCAACAGTAA AAGCAGGGAG CCCAGCCAGG | 2436 |
| AAGCTGTTAC ACAGTCCAGG CAAGAGGTAG TGGAGTGGGC TGGGTGGGAA CAGAAAAGGG | 2496 |
| AGTGACAAAC CATTGTCTCC TGAATATATT CTGAAGGAAG TTGCTGAAGG ATTCTATGTT | 2556 |
| GTGTGAGAGA AAGAGAAGAA TTGGCTGGGT GTAGTAGCTC ATGCCAAGGA GGAGGCCAAG | 2616 |
| GAGAGCAGAT TCCTGAGCTC AGGAGTTCAA GACCAGCCTG GGCAACACAG CAAAACCCCT | 2676 |
| TCTCTACAAA AAATACAAAA ATTAGCTGGG TGTGGTGGCA TGCACCTGTG ATCCTAGCTA | 2736 |
| CTCGGGAGGC TGAGGTGGAG GGTATTGCTT GAGCCCAGGA AGTTGAGGCT GCAGTGAGCC | 2796 |
| ATGACTGTGC CACTGTACTT CAGCCTAGGT GACAGAGCAA GACCCTGTCT CCCCTGACCC | 2856 |
| CCTGAAAAAG AGAAGAGTTA AAGTTGACTT TGTTCTTTAT TTTAATTTTA TTGGCCTGAG | 2916 |
| CAGTGGGGTA ATTGGCAATG CCATTTCTGA GATGGTGAAG GCAGAGGAAA GAGCAGTTTG | 2976 |
| GGGTAAATCA AGGATCTGCA TTTGGGACAT GTTAAGTTTG AGATTCCAGT CAGGCTTCCA | 3036 |
| AGTGGTGAGG CCACATAGGC AGTTCAGTGT AAGAATTCAG GACCAAGGCT GGGCACGGTG | 3096 |
| GCTCACTTCT GTAATCCCAG CACTTTGGTG GCTGAGGCAG GTAGATCATT TGAGGTCAGG | 3156 |
| AGTTTGAGAC AAGCTTGGCC AACATGGTGA AACCCCATGT CTACTAAAAA TACAAAAATT | 3216 |
| AGCCTGGTGT GGTGGCGCAC GCCTATAGTC CCAGGTTTTC AGGAGGCTTA GGTAGGAGAA | 3276 |
| TCCCTTGAAC CCAGGAGGTG CAGGTTGCAG TGAGCTGAGA TTGTGCCACT GCACTCCAGC | 3336 |
| CTGGGTGATA GAGTGAGACT CTGTCTCAAA AAAAAAAAA AAAAAAAAA AAAAAACTGA | 3396 |
| AGGAATTATT CCTCAGGATT TGGGTCTAAT TTGCCCTGAG CACCAACTCC TGAGTTCAAC | 3456 |
| TACCATGGCT AGACACACCT TAACATTTTC TAGAATCCAC CAGCTTTAGT GGAGTCTGTC | 3516 |
| TAATCATGAG TATTGGAATA GGATCTGGGG GCAGTGAGGG GGTGGCAGCC ACGTGTGGCA | 3576 |
| GAGAAAAGCA CACAAGGAAA GAGCACCCAG GACTGTCATA TGGAAGAAAG ACAGGACTGC | 3636 |
| AACTCACCCT TCACAAAATG AGGACCAGAC ACAGCTGATG GTATGAGTTG ATGCAGGTGT | 3696 |
| GTGGAGCCTC AACATCCTGC TCCCCTCCTA CTACACATGG TTAAGGCCTG TTGCTCTGTC | 3756 |

| | | |
|---|---|---|
| TCCAG GT TCA CAC TCT CTG CAC TAC CTC TTC ATG GGT GCC TCA GAG<br>    Arg Ser His Ser Leu His Tyr Leu Phe Met Gly Ala Ser Glu<br>                30                      35 | | 3802 |
| CAG GAC CTT GGT CTT TCC TTG TTT GAA GCT TTG GGC TAC GTG GAT GAC<br>Gln Asp Leu Gly Leu Ser Leu Phe Glu Ala Leu Gly Tyr Val Asp Asp<br> 40              45                  50                  55 | | 3850 |
| CAG CTG TTC GTG TTC TAT GAT GAT GAG AGT CGC CGT GTG GAG CCC CGA<br>Gln Leu Phe Val Phe Tyr Asp Asp Glu Ser Arg Arg Val Glu Pro Arg<br>             60                  65                  70 | | 3898 |
| ACT CCA TGG GTT TCC AGT AGA ATT TCA AGC CAG ATG TGG CTG CAG CTG<br>Thr Pro Trp Val Ser Ser Arg Ile Ser Ser Gln Met Trp Leu Gln Leu | | 3946 |

```
                75                  80                  85
AGT CAG AGT CTG AAA GGG TGG GAT CAC ATG TTC ACT GTT GAC TTC TGG        3994
Ser Gln Ser Leu Lys Gly Trp Asp His Met Phe Thr Val Asp Phe Trp
         90                  95                 100

ACT ATT ATG GAA AAT CAC AAC CAC AGC AAG G GTATGTGGAG AGGGGGCCTC        4045
Thr Ile Met Glu Asn His Asn His Ser Lys
    105                 110

ACCTTCCTGA GGTTGTCAGA GCTTTTCATC TTTTCATGCA TCTTGAAGGA AACAGCTGGA      4105

AGTCTGAGGT CTTGTGGGAG CAGGGAAGAG GGAAGGAATT TGCTTCCTGA GATCATTTGG      4165

TCCTTGGGGA TGGTGGAAAT AGGGACCTAT TCCTTTGGTT GCAGTTAACA AGGCTGGGGA      4225

TTTTTCCAG  AG TCC CAC ACC CTG CAG GTC ATC CTG GGC TGT GAA ATG         4272
              Glu Ser His Thr Leu Gln Val Ile Leu Gly Cys Glu Met
                  115                 120                 125

CAA GAA GAC AAC AGT ACC GAG GGC TAC TGG AAG TAC GGG TAT GAT GGG       4320
Gln Glu Asp Asn Ser Thr Glu Gly Tyr Trp Lys Tyr Gly Tyr Asp Gly
             130                 135                 140

CAG GAC CAC CTT GAA TTC TGC CCT GAC ACA CTG GAT TGG AGA GCA GCA       4368
Gln Asp His Leu Glu Phe Cys Pro Asp Thr Leu Asp Trp Arg Ala Ala
         145                 150                 155

GAA CCC AGG GCC TGG CCC ACC AAG CTG GAG TGG GAA AGG CAC AAG ATT       4416
Glu Pro Arg Ala Trp Pro Thr Lys Leu Glu Trp Glu Arg His Lys Ile
    160                 165                 170

CGG GCC AGG CAG AAC AGG GCC TAC CTG GAG AGG GAC TGC CCT GCA CAG       4464
Arg Ala Arg Gln Asn Arg Ala Tyr Leu Glu Arg Asp Cys Pro Ala Gln
175                 180                 185                 190

CTG CAG CAG TTG CTG GAG CTG GGG AGA GGT GTT TTG GAC CAA CAA G         4510
Leu Gln Gln Leu Leu Glu Leu Gly Arg Gly Val Leu Asp Gln Gln
                 195                 200                 205

GTATGGTGGA AACACACTTC TGCCCCTATA CTCTAGTGGC AGAGTGGAGG AGGTTGCAGG      4570

GCACGGAATC CCTGGTTGGA GTTTCAGAGG TGGCTGAGGC TGTGTGCCTC TCCAAATTCT      4630

GGGAAGGGAC TTTCTCAATC CTAGAGTCTC TACCTTATAA TTGAGATGTA TGAGACAGCC      4690

ACAAGTCATG GGTTTAATTT CTTTTCTCCA TGCATATGGC TCAAAGGGAA GTGTCTATGG      4750

CCCTTGCTTT TTATTTAACC AATAATCTTT TGTATATTTA TACCTGTTAA AAATTCAGAA      4810

ATGTCAAGGC CGGGCACGGT GGCTCACCCC TGTAATCCCA GCACTTTGGG AGGCCGAGGC      4870

GGGTGGTCAC AAGGTCAGGA GTTTGAGACC AGCCTGACCA ACATGGTGAA ACCCGTCTCT      4930

AAAAAAATAC AAAAATTAGC TGGTCACAGT CATGCGCACC TGTAGTCCCA GCTAATTGGA      4990

AGGCTGAGGC AGGAGCATCG CTTGAACCTG GGAAGCGGAA GTTGCACTGA GCCAAGATCG      5050

CGCCACTGCA CTCCAGCCTA GGCAGCAGAG TGAGACTCCA TCTTAAAAAA AAAAAAAAAA      5110

AAAAAAAGAG AATTCAGAGA TCTCAGCTAT CATATGAATA CCAGGACAAA ATATCAAGTG      5170

AGGCCACTTA TCAGAGTAGA AGAATCCTTT AGGTTAAAAG TTTCTTTCAT AGAACATAGC      5230

AATAATCACT GAAGCTACCT ATCTTACAAG TCCGCTTCTT ATAACAATGC TCCTAGGTT       5290

GACCCAGGTG AAACTGACCA TCTGTATTCA ATCATTTTCA ATGCACATAA AGGGCAATTT      5350

TATCTATCAG AACAAAGAAC ATGGGTAACA GATATGTATA TTTACATGTG AGGAGAACAA      5410

GCTGATCTGA CTGCTCTCCA AGTGCACACTG TGTTAGAGTC CAATCTTAGG ACACAAAATG     5470

GTGTCTCTCC TGTAGCTTGT TTTTTTCTGA AAAGGGTATT TCCTTCCTCC AACCTATAGA      5530

AGGAAGTGAA AGTTCCAGTC TTCCTGGCAA GGGTAAACAG ATCCCCTCTC CTCATCCTTC      5590

CTCTTTCCTG TCAAG  TG CCT CCT TTG GTG AAG GTG ACA CAT CAT GTG ACC      5640
                 Val Pro Pro Leu Val Lys Val Thr His His Val Thr
                                  210                 215
```

| | | |
|---|---|---|
| TCT TCA GTG ACC ACT CTA CGG TGT CGG GCC TTG AAC TAC TAC CCC CAG<br>Ser Ser Val Thr Thr Leu Arg Cys Arg Ala Leu Asn Tyr Tyr Pro Gln<br>          220                  225                230 | 5688 |
| AAC ATC ACC ATG AAG TGG CTG AAG GAT AAG CAG CCA ATG GAT GCC AAG<br>Asn Ile Thr Met Lys Trp Leu Lys Asp Lys Gln Pro Met Asp Ala Lys<br>     235                  240                  245 | 5736 |
| GAG TTC GAA CCT AAA GAC GTA TTG CCC AAT GGG GAT GGG ACC TAC CAG<br>Glu Phe Glu Pro Lys Asp Val Leu Pro Asn Gly Asp Gly Thr Tyr Gln<br>250                255                  260              265 | 5784 |
| GGC TGG ATA ACC TTG GCT GTA CCC CCT GGG GAA GAG CAG AGA TAT ACG<br>Gly Trp Ile Thr Leu Ala Val Pro Pro Gly Glu Glu Gln Arg Tyr Thr<br>              270                  275                  280 | 5832 |
| TAC CAG GTG GAG CAC CCA GGC CTG GAT CAG CCC CTC ATT GTG ATC TGG G<br>Tyr Gln Val Glu His Pro Gly Leu Asp Gln Pro Leu Ile Val Ile Trp<br>         285                  290                  295 | 5881 |
| GTATGTGACT GATGAGAGCC AGGAGCTGAG AAAATCTATT GGGGGTTGAG AGGAGTGCCT | 5941 |
| GAGGAGGTAA TTATGGCAGT GAGATGAGGA TCTGCTCTTT GTTAGGGGGT GGGCTGAGGG | 6001 |
| TGGCAATCAA AGGCTTTAAC TTGCTTTTTC TGTTTTAG  AG CCC TCA CCG TCT<br>                                                                  Glu Pro Ser Pro Ser<br>                                                                                 300 | 6053 |
| GGC ACC CTA GTC ATT GGA GTC ATC AGT GGA ATT GCT GTT TTT GTC GTC<br>Gly Thr Leu Val Ile Gly Val Ile Ser Gly Ile Ala Val Phe Val Val<br>             305                  310                  315 | 6101 |
| ATC TTG TTC ATT GGA ATT TTG TTC ATA ATA TTA AGG AAG AGG CAG GGT<br>Ile Leu Phe Ile Gly Ile Leu Phe Ile Ile Leu Arg Lys Arg Gln Gly<br>     320                  325                  330 | 6149 |
| TCA A GTGAGTAGGA ACAAGGGGGA AGTCTCTTAG TACCTCTGCC CCAGGGCACA<br>Ser<br>335 | 6203 |
| GTGGGAAGAG GGGCAGAGGG GATCTGGCAT CCATGGGAAG CATTTTTCTC ATTTATATTC | 6263 |
| TTTGGGGACA CCAGCAGCTC CCTGGGAGAC AGAAAATAAT GGTTCTCCCC AGAATGAAAG | 6323 |
| TCTCTAATTC AACAAACATC TTCAGAGCAC CTACTATTTT GCAAGAGCTG TTTAAGGTAG | 6383 |
| TACAGGGGCT TTGAGGTTGA GAAGTCACTG TGGCTATTCT CAGAACCCAA ATCTGGTAGG | 6443 |
| GAATGAAATT GATAGCAAGT AAATGTAGTT AAAGAAGACC CCATGAGGTC CTAAAGCAGG | 6503 |
| CAGGAAGCAA ATGCTTAGGG TGTCAAAGGA AAGAATGATC ACATTCAGCT GGGGATCAAG | 6563 |
| ATAGCCTTCT GGATCTTGAA GGAGAAGCTG GATTCCATTA GGTGAGGTTG AAGATGATGG | 6623 |
| GAGGTCTACA CAGACGGAGC AACCATGCCA AGTAGGAGAG TATAAGGCAT ACTGGGAGAT | 6683 |
| TAGAAATAAT TACTGTACCT TAACCCTGAG TTTGCGTAGC TATCACTCAC CAATTATGCA | 6743 |
| TTTCTACCCC CTGAACATCT GTGGTGTAGG GAAAAGAGAA TCAGAAAGAA GCCAGCTCAT | 6803 |
| ACAGAGTCCA AGGGTCTTTT GGATATTGG GTTATGATCA CTGGGGTGTC ATTGAAGGAT | 6863 |
| CCTAAGAAAG GAGGACCACG ATCTCCCTTA TATGGTGAAT GTGTTGTTAA GAAGTTAGAT | 6923 |
| GAGAGGTGAG GAGACCAGTT AGAAAGCCAA TAAGCATTTC CAGATGAGAG ATAATGGTTC | 6983 |
| TTGAAATCCA ATAGTGCCCA GGTCTAAATT GAGATGGGTG AATGAGGAAA ATAAGGAAGA | 7043 |
| GAGAAGAGGC AAGATGGTGC CTAGGTTTGT GATGCCTCTT TCCTGGGTCT CTTGTCTCCA | 7103 |
| CAG  GA GGA GCC ATG GGG CAC TAC GTC TTA GCT GAA CGT GAG<br>        Arg Gly Ala Met Gly His Tyr Val Leu Ala Glu Arg Glu<br>                                  340                          345 | 7144 |
| TGACACGCAG CCTGCAGACT CACTGTGGGA AGGAGACAAA ACTAGAGACT CAAAGAGGGA | 7204 |
| GTGCATTTAT GAGCTCTTCA TGTTTCAGGA GAGAGTTGAA CCTAAACATA GAAATTGCCT | 7264 |

```
GACGAACTCC TTGATTTTAG CCTTCTCTGT TCATTTCCTC AAAAAGATTT CCCCATTTAG    7324

GTTTCTGAGT TCCTGCATGC CGGTGATCCC TAGCTGTGAC CTCTCCCCTG GAACTGTCTC    7384

TCATGAACCT CAAGCTGCAT CTAGAGGCTT CCTTCATTTC CTCCGTCACC TCAGAGACAT    7444

ACACCTATGT CATTTCATTT CCTATTTTTG GAAGAGGACT CCTTAAATTT GGGGGACTTA    7504

CATGATTCAT TTTAACATCT GAGAAAAGCT TTGAACCCTG GACGTGGCT AGTCATAACC     7564

TTACCAGATT TTTACACATG TATCTATGCA TTTTCTGGAC CCGTTCAACT TTTCCTTTGA    7624

ATCCTCTCTC TGTGTTACCC AGTAACTCAT CTGTCACCAA GCCTTGGGGA TTCTTCCATC    7684

TGATTGTGAT GTGAGTTGCA CAGCTATGAA GGCTGTACAC TGCACGAATG GAAGAGGCAC    7744

CTGTCCCAGA AAAAGCATCA TGGCTATCTG TGGGTAGTAT GATGGGTGTT TTTAGCAGGT    7804

AGGAGGCAAA TATCTTGAAA GGGGTTGTGA AGAGGTGTTT TTTCTAATTG GCATGAAGGT    7864

GTCATACAGA TTTGCAAAGT TTAATGGTGC CTTCATTTGG GATGCTACTC TAGTATTCCA    7924

GACCTGAAGA ATCACAATAA TTTTCTACCT GGTCTCTCCT TGTTCTGATA ATGAAAATTA    7984

TGATAAGGAT GATAAAAGCA CTTACTTCGT GTCCGACTCT TCTGAGCACC TACTTACATG    8044

CATTACTGCA TGCACTTCTT ACAATAATTC TATGAGATAG GTACTATTAT CCCCATTTCT    8104

TTTTTAAATG AAGAAAGTGA AGTAGGCCGG GCACGGTGGC TCACGCCTGT AATCCCAGCA    8164

CTTTGGGAGG CCAAAGCGGG TGGATCACGA GGTCAGGAGA TCGAGACCAT CCTGGCTAAC    8224

ATGGTGAAAC CCCATCTCTA ATAAAAATAC AAAAAATTAG CTGGGCGTGG TGGCAGACGC    8284

CTGTAGTCCC AGCTACTCGG AAGGCTGAGG CAGGAGAATG GCATGAACCC AGGAGGCAGA    8344

GCTTGCAGTG AGCCGAGTTT GCGCCACTGC ACTCCAGCCT AGGTGACAGA GTGAGACTCC    8404

ATCTCAAAAA AATAAAAATA AAAATAAAAA AATGAAAAAA AAAAGAAAGT GAAGTATAGA    8464

GTATCTCATA GTTTGTCAGT GATAGAAACA GGTTTCAAAC TCAGTCAATC TGACCGTTTG    8524

ATACATCTCA GACACCACTA CATTCAGTAG TTTAGATGCC TAGAATAAAT AGAGAAGGAA    8584

GGAGATGGCT CTTCTCTTGT CTCATTGTGT TTCTTCTGAG TGAGCTTGAA TCACATGAAG    8644

GGGAACAGCA GAAAACAACC AACTGATCCT CAGCTGTCAT GTTTCCTTTA AAAGTCCCTG    8704

AAGGAAGGTC CTGGAATGTG ACTCCCTTGC TCCTCTGTTG CTCTCTTTGG CATTCATTTC    8764

TTTGGACCCT ACGCAAGGAC TGTAATTGGT GGGGACAGCT AGTGGCCCTG CTGGGCTTCA    8824

CACACGGTGT CCTCCCTAGG CCAGTGCCTC TGGAGTCAGA ACTCTGGTGG TATTTCCCTC    8884

AATGAAGTGG AGTAAGCTCT CTCATTTTGA GATGGTATAA TGGAAGCCAC CAAGTGGCTT    8944

AGAGGATGCC CAGGTCCTTC CATGGAGCCA CTGGGGTTCC GGTGCACATT AAAAAAAAAA    9004

TCTAACCAGG ACATTCAGGA ATTGCTAGAT TCTGGGAAAT CAGTTCACCA TGTTCAAAAG    9064

AGTCTTTTTT TTTTTTTTGA GACTCTATTG CCCAGGCTGG AGTGCAATGG CATGATCTCG    9124

GCTCACTGTA ACCTCTGCCT CCCAGGTTCA AGCGATTCTC CTGTCTCAGC CTCCCAAGTA    9184

GCTGGGATTA CAGGCGTGCA CCACCATGCC CGGCTAATTT TTGTATTTTT AGTAGAGACA    9244

GGGTTTCACC ATGTTGGCCA GGCTGGTCTC GAACTCTCCT GACCTCGTGA TCCGCCTGCC    9304

TCGGCCTCCC AAAGTGCTGA GATTACAGGT GTGAGCCACC CTGCCCAGCC GTCAAAAGAG    9364

TCTTAATATA TATATCCAGA TGGCATGTGT TTACTTTATG TTACTACATG CACTTGGCTG    9424

CATAAATGTG GTACAAGCAT TCTGTCTTGA AGGGCAGGTG CTTCAGGATA CCATATACAG    9484

CTCAGAAGTT TCTTCTTTAG GCATTAAATT TTAGCAAAGA TATCTCATCT CTTCTTTTAA    9544

ACCATTTTCT TTTTTTGTGG TTAGAAAAGT TATGTAGAAA AAAGTAAATG TGATTTACGC    9604

TCATTGTAGA AAAGCTATAA AATGAATACA ATTAAAGCTG TTATTTAATT AGCCAGTGAA    9664
```

```
AAACTATTAA CAACTTGTCT ATTACCTGTT AGTATTATTG TTGCATTAAA AATGCATATA      9724

CTTTAATAAA TGTATATTGT ATTGTATACT GCATGATTTT ATTGAAGTTC TTGTTCATCT      9784

TGTGTATATA CTTAATCGCT TTGTCATTTT GGAGACATTT ATTTTGCTTC TAATTTCTTT      9844

ACATTTTGTC TTACGGAATA TTTTCATTCA ACTGTGGTAG CCGAATTAAT CGTGTTTCTT      9904

CACTCTAGGG ACATTGTCGT CTAAGTTGTA AGACATTGGT TATTTTACCA GCAAACCATT      9964

CTGAAAGCAT ATGACAAATT ATTTCTCTCT TAATATCTTA CTATACTGAA AGCAGACTGC     10024

TATAAGGCTT CACTTACTCT TCTACCTCAT AAGGAATATG TTACAATTAA TTTATTAGGT     10084

AAGCATTTGT TTTATATTGG TTTTATTTCA CCTGGGCTGA GATTTCAAGA ACACCCCAG      10144

TCTTCACAGT AACACATTTC ACTAACACAT TTACTAAACA TCAGCAACTG TGGCCTGTTA     10204

ATTTTTTTAA TAGAAATTTT AAGTCCTCAT TTTCTTTCGG TGTTTTTTAA GCTTAATTTT     10264

TCTGGCTTTA TTCATAAATT CTTAAGGTCA ACTACATTTG AAAAATCAAA GACCTGCATT     10324

TTAAATTCTT ATTCACCTCT GGCAAAACCA TTCACAAACC ATGGTAGTAA AGAGAAGGGT     10384

GACACCTGGT GGCCATAGGT AAATGTACCA CGGTGGTCCG GTGACCAGAG ATGCAGCGCT     10444

GAGGGTTTTC CTGAAGGTAA AGGAATAAAG AATGGGTGGA GGGGCGTGCA CTGGAAATCA     10504

CTTGTAGAGA AAAGCCCCTG AAAATTTGAG AAAACAAACA AGAAACTACT TACCAGCTAT     10564

TTGAATTGCT GGAATCACAG GCCATTGCTG AGCTGCCTGA ACTGGGAACA CAACAGAAGG     10624

AAAACAAACC ACTCTGATAA TCATTGAGTC AAGTACAGCA GGTGATTGAG GACTGCTGAG     10684

AGGTACAGGC CAAAATTCTT ATGTTGTATT ATAATAATGT CATCTTATAA TACTGTCAGT     10744

ATTTTATAAA ACATTCTTCA CAAACTCACA CACATTTAAA AACAAAACAC TGTCTCTAAA     10804

ATCCCCAAAT TTTTCATAAA C                                              10825
```

(2) INFORMATION FOR SEQ ID NO:8:

(i) SEQUENCE CHARACTERISTICS:
        (A) LENGTH: 348 amino acids
        (B) TYPE: amino acid
        (D) TOPOLOGY: linear (ii) MOLECULE TYPE: protein (xi) SEQUENCE DESCRIPTION: SEQ ID NO:8:

```
Met Gly Pro Arg Ala Arg Pro Ala Leu Leu Leu Met Leu Leu Gln
 1               5                  10                  15

Thr Ala Val Leu Gln Gly Arg Leu Leu Arg Ser His Ser Leu His Tyr
                20                  25                  30

Leu Phe Met Gly Ala Ser Glu Gln Asp Leu Gly Leu Ser Leu Phe Glu
        35                  40                  45

Ala Leu Gly Tyr Val Asp Asp Gln Leu Phe Val Phe Tyr Asp Asp Glu
    50                  55                  60

Ser Arg Arg Val Glu Pro Arg Thr Pro Trp Val Ser Ser Arg Ile Ser
65                  70                  75                  80

Ser Gln Met Trp Leu Gln Leu Ser Gln Ser Leu Lys Gly Trp Asp His
                85                  90                  95

Met Phe Thr Val Asp Phe Trp Thr Ile Met Glu Asn His Asn His Ser
            100                 105                 110

Lys Glu Ser His Thr Leu Gln Val Ile Leu Gly Cys Glu Met Gln Glu
        115                 120                 125

Asp Asn Ser Thr Glu Gly Tyr Trp Lys Tyr Gly Tyr Asp Gly Gln Asp
    130                 135                 140
```

```
His Leu Glu Phe Cys Pro Asp Thr Leu Asp Trp Arg Ala Ala Glu Pro
145                 150                 155                 160

Arg Ala Trp Pro Thr Lys Leu Glu Trp Glu Arg His Lys Ile Arg Ala
            165                 170                 175

Arg Gln Asn Arg Ala Tyr Leu Glu Arg Asp Cys Pro Ala Gln Leu Gln
        180                 185                 190

Gln Leu Leu Glu Leu Gly Arg Gly Val Leu Asp Gln Gln Val Pro Pro
        195                 200                 205

Leu Val Lys Val Thr His His Val Thr Ser Ser Val Thr Thr Leu Arg
    210                 215                 220

Cys Arg Ala Leu Asn Tyr Tyr Pro Gln Asn Ile Thr Met Lys Trp Leu
225                 230                 235                 240

Lys Asp Lys Gln Pro Met Asp Ala Lys Glu Phe Glu Pro Lys Asp Val
                245                 250                 255

Leu Pro Asn Gly Asp Gly Thr Tyr Gln Gly Trp Ile Thr Leu Ala Val
                260                 265                 270

Pro Pro Gly Glu Glu Gln Arg Tyr Thr Tyr Gln Val Glu His Pro Gly
            275                 280                 285

Leu Asp Gln Pro Leu Ile Val Ile Trp Glu Pro Ser Pro Ser Gly Thr
290                 295                 300

Leu Val Ile Gly Val Ile Ser Gly Ile Ala Val Phe Val Val Ile Leu
305                 310                 315                 320

Phe Ile Gly Ile Leu Phe Ile Ile Leu Arg Lys Arg Gln Gly Ser Arg
                325                 330                 335

Gly Ala Met Gly His Tyr Val Leu Ala Glu Arg Glu
            340                 345

(2) INFORMATION FOR SEQ ID NO:9:

(i) SEQUENCE CHARACTERISTICS:
        (A) LENGTH: 1440 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 222..1268

(ix) FEATURE:
        (A) NAME/KEY: allele
        (B) LOCATION: replace(408, "c")
        (D) OTHER INFORMATION: /phenotype= "normal or wild-type
            (unaffected)"
            /label= 24d2

(ix) FEATURE:
        (A) NAME/KEY: allele
        (B) LOCATION: replace(414, "a")
        (D) OTHER INFORMATION: /phenotype= "normal or wild-type
            (unaffected)"
            /label= 24d7

(ix) FEATURE:
        (A) NAME/KEY: allele
        (B) LOCATION: replace(1066, "g")
        (D) OTHER INFORMATION: /phenotype= "normal or wild-type
            (unaffected)"
            /label= 24d1

(xi) SEQUENCE DESCRIPTION: SEQ ID NO:9:

GGGGACACTG GATCACCTAG TGTTTCACAA GCAGGTACCT TCTGCTGTAG GAGAGAGAGA      60
```

-continued

```
ACTAAAGTTC TGAAAGACCT GTTGCTTTTC ACCAGGAAGT TTTACTGGGC ATCTCCTGAG     120

CCTAGGCAAT AGCTGTAGGG TGACTTCTGG AGCCATCCCC GTTTCCCCGC CCCCCAAAAG     180

AAGCGGAGAT TTAACGGGGA CGTGCGGCCA GAGCTGGGGA A ATG GGC CCG CGA         233
                                              Met Gly Pro Arg
                                               1

GCC AGG CCG GCG CTT CTC CTC CTG ATG CTT TTG CAG ACC GCG GTC CTG       281
Ala Arg Pro Ala Leu Leu Leu Leu Met Leu Leu Gln Thr Ala Val Leu
 5              10                  15                  20

CAG GGG CGC TTG CTG CGT TCA CAC TCT CTG CAC TAC CTC TTC ATG GGT       329
Gln Gly Arg Leu Leu Arg Ser His Ser Leu His Tyr Leu Phe Met Gly
             25                  30                  35

GCC TCA GAG CAG GAC CTT GGT CTT TCC TTG TTT GAA GCT TTG GGC TAC       377
Ala Ser Glu Gln Asp Leu Gly Leu Ser Leu Phe Glu Ala Leu Gly Tyr
         40                  45                  50

GTG GAT GAC CAG CTG TTC GTG TTC TAT GAT CAT GAG AGT CGC CGT GTG       425
Val Asp Asp Gln Leu Phe Val Phe Tyr Asp His Glu Ser Arg Arg Val
             55                  60                  65

GAG CCC CGA ACT CCA TGG GTT TCC AGT AGA ATT TCA AGC CAG ATG TGG       473
Glu Pro Arg Thr Pro Trp Val Ser Ser Arg Ile Ser Ser Gln Met Trp
 70                  75                  80

CTG CAG CTG AGT CAG AGT CTG AAA GGG TGG GAT CAC ATG TTC ACT GTT       521
Leu Gln Leu Ser Gln Ser Leu Lys Gly Trp Asp His Met Phe Thr Val
 85                  90                  95                 100

GAC TTC TGG ACT ATT ATG GAA AAT CAC AAC CAC AGC AAG GAG TCC CAC       569
Asp Phe Trp Thr Ile Met Glu Asn His Asn His Ser Lys Glu Ser His
                 105                 110                 115

ACC CTG CAG GTC ATC CTG GGC TGT GAA ATG CAA GAA GAC AAC AGT ACC       617
Thr Leu Gln Val Ile Leu Gly Cys Glu Met Gln Glu Asp Asn Ser Thr
             120                 125                 130

GAG GGC TAC TGG AAG TAC GGG TAT GAT GGG CAG GAC CAC CTT GAA TTC       665
Glu Gly Tyr Trp Lys Tyr Gly Tyr Asp Gly Gln Asp His Leu Glu Phe
         135                 140                 145

TGC CCT GAC ACA CTG GAT TGG AGA GCA GCA GAA CCC AGG GCC TGG CCC       713
Cys Pro Asp Thr Leu Asp Trp Arg Ala Ala Glu Pro Arg Ala Trp Pro
     150                 155                 160

ACC AAG CTG GAG TGG GAA AGG CAC AAG ATT CGG GCC AGG CAG AAC AGG       761
Thr Lys Leu Glu Trp Glu Arg His Lys Ile Arg Ala Arg Gln Asn Arg
165                 170                 175                 180

GCC TAC CTG GAG AGG GAC TGC CCT GCA CAG CTG CAG CAG TTG CTG GAG       809
Ala Tyr Leu Glu Arg Asp Cys Pro Ala Gln Leu Gln Gln Leu Leu Glu
                 185                 190                 195

CTG GGG AGA GGT GTT TTG GAC CAA CAA GTG CCT CCT TTG GTG AAG GTG       857
Leu Gly Arg Gly Val Leu Asp Gln Gln Val Pro Pro Leu Val Lys Val
             200                 205                 210

ACA CAT CAT GTG ACC TCT TCA GTG ACC ACT CTA CGG TGT CGG GCC TTG       905
Thr His His Val Thr Ser Ser Val Thr Thr Leu Arg Cys Arg Ala Leu
         215                 220                 225

AAC TAC TAC CCC CAG AAC ATC ACC ATG AAG TGG CTG AAG GAT AAG CAG       953
Asn Tyr Tyr Pro Gln Asn Ile Thr Met Lys Trp Leu Lys Asp Lys Gln
     230                 235                 240

CCA ATG GAT GCC AAG GAG TTC GAA CCT AAA GAC GTA TTG CCC AAT GGG      1001
Pro Met Asp Ala Lys Glu Phe Glu Pro Lys Asp Val Leu Pro Asn Gly
245                 250                 255                 260

GAT GGG ACC TAC CAG GGC TGG ATA ACC TTG GCT GTA CCC CCT GGG GAA      1049
Asp Gly Thr Tyr Gln Gly Trp Ile Thr Leu Ala Val Pro Pro Gly Glu
                 265                 270                 275

GAG CAG AGA TAT ACG TGC CAG GTG GAG CAC CCA GGC CTG GAT CAG CCC      1097
Glu Gln Arg Tyr Thr Cys Gln Val Glu His Pro Gly Leu Asp Gln Pro
```

```
                   280                 285                 290
CTC ATT GTG ATC TGG GAG CCC TCA CCG TCT GGC ACC CTA GTC ATT GGA       1145
Leu Ile Val Ile Trp Glu Pro Ser Pro Ser Gly Thr Leu Val Ile Gly
        295                 300                 305

GTC ATC AGT GGA ATT GCT GTT TTT GTC GTC ATC TTG TTC ATT GGA ATT       1193
Val Ile Ser Gly Ile Ala Val Phe Val Val Ile Leu Phe Ile Gly Ile
        310                 315                 320

TTG TTC ATA ATA TTA AGG AAG AGG CAG GGT TCA AGA GGA GCC ATG GGG       1241
Leu Phe Ile Ile Leu Arg Lys Arg Gln Gly Ser Arg Gly Ala Met Gly
325                 330                 335                 340

CAC TAC GTC TTA GCT GAA CGT GAG TGACACGCAG CCTGCAGACT CACTGTGGGA      1295
His Tyr Val Leu Ala Glu Arg Glu
                345

AGGAGACAAA ACTAGAGACT CAAAGAGGGA GTGCATTTAT GAGCTCTTCA TGTTTCAGGA     1355

GAGAGTTGAA CCTAAACATA GAAATTGCCT GACGAACTCC TTGATTTTAG CCTTCTCTGT     1415

TCATTTCCTC AAAAAGATTT CCCCA                                           1440

(2) INFORMATION FOR SEQ ID NO:10:

(i) SEQUENCE CHARACTERISTICS:
        (A) LENGTH: 1440 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 222..1268

(ix) FEATURE:
        (A) NAME/KEY: allele
        (B) LOCATION: replace(1066, "a")
        (D) OTHER INFORMATION: /phenotype= "Hereditary Hemochromatosis
            (HH)"
            /label= 24d1

(xi) SEQUENCE DESCRIPTION: SEQ ID NO:10:

GGGGACACTG GATCACCTAG TGTTTCACAA GCAGGTACCT TCTGCTGTAG GAGAGAGAGA     60

ACTAAAGTTC TGAAAGACCT GTTGCTTTTC ACCAGGAAGT TTTACTGGGC ATCTCCTGAG     120

CCTAGGCAAT AGCTGTAGGG TGACTTCTGG AGCCATCCCC GTTTCCCCGC CCCCCAAAAG     180

AAGCGGAGAT TTAACGGGGA CGTGCGGCCA GAGCTGGGGA A ATG GGC CCG CGA         233
                                               Met Gly Pro Arg
                                                 1

GCC AGG CCG GCG CTT CTC CTC CTG ATG CTT TTG CAG ACC GCG GTC CTG       281
Ala Arg Pro Ala Leu Leu Leu Leu Met Leu Leu Gln Thr Ala Val Leu
 5                  10                  15                  20

CAG GGG CGC TTG CTG CGT TCA CAC TCT CTG CAC TAC CTC TTC ATG GGT       329
Gln Gly Arg Leu Leu Arg Ser His Ser Leu His Tyr Leu Phe Met Gly
            25                  30                  35

GCC TCA GAG CAG GAC CTT GGT CTT TCC TTG TTT GAA GCT TTG GGC TAC       377
Ala Ser Glu Gln Asp Leu Gly Leu Ser Leu Phe Glu Ala Leu Gly Tyr
                40                  45                  50

GTG GAT GAC CAG CTG TTC GTG TTC TAT GAT CAT GAG AGT CGC CGT GTG       425
Val Asp Asp Gln Leu Phe Val Phe Tyr Asp His Glu Ser Arg Arg Val
        55                  60                  65

GAG CCC CGA ACT CCA TGG GTT TCC AGT AGA ATT TCA AGC CAG ATG TGG       473
Glu Pro Arg Thr Pro Trp Val Ser Ser Arg Ile Ser Ser Gln Met Trp
    70                  75                  80

CTG CAG CTG AGT CAG AGT CTG AAA GGG TGG GAT CAC ATG TTC ACT GTT       521
```

```
Leu Gln Leu Ser Gln Ser Leu Lys Gly Trp Asp His Met Phe Thr Val
 85                  90                  95                 100

GAC TTC TGG ACT ATT ATG GAA AAT CAC AAC CAC AGC AAG GAG TCC CAC      569
Asp Phe Trp Thr Ile Met Glu Asn His Asn His Ser Lys Glu Ser His
                105                 110                 115

ACC CTG CAG GTC ATC CTG GGC TGT GAA ATG CAA GAA GAC AAC AGT ACC      617
Thr Leu Gln Val Ile Leu Gly Cys Glu Met Gln Glu Asp Asn Ser Thr
            120                 125                 130

GAG GGC TAC TGG AAG TAC GGG TAT GAT GGG CAG GAC CAC CTT GAA TTC      665
Glu Gly Tyr Trp Lys Tyr Gly Tyr Asp Gly Gln Asp His Leu Glu Phe
                135                 140                 145

TGC CCT GAC ACA CTG GAT TGG AGA GCA GCA GAA CCC AGG GCC TGG CCC      713
Cys Pro Asp Thr Leu Asp Trp Arg Ala Ala Glu Pro Arg Ala Trp Pro
150                 155                 160

ACC AAG CTG GAG TGG GAA AGG CAC AAG ATT CGG GCC AGG CAG AAC AGG      761
Thr Lys Leu Glu Trp Glu Arg His Lys Ile Arg Ala Arg Gln Asn Arg
165                 170                 175                 180

GCC TAC CTG GAG AGG GAC TGC CCT GCA CAG CTG CAG CAG TTG CTG GAG      809
Ala Tyr Leu Glu Arg Asp Cys Pro Ala Gln Leu Gln Gln Leu Leu Glu
                185                 190                 195

CTG GGG AGA GGT GTT TTG GAC CAA CAA GTG CCT CCT TTG GTG AAG GTG      857
Leu Gly Arg Gly Val Leu Asp Gln Gln Val Pro Pro Leu Val Lys Val
                200                 205                 210

ACA CAT CAT GTG ACC TCT TCA GTG ACC ACT CTA CGG TGT CGG GCC TTG      905
Thr His His Val Thr Ser Ser Val Thr Thr Leu Arg Cys Arg Ala Leu
                215                 220                 225

AAC TAC TAC CCC CAG AAC ATC ACC ATG AAG TGG CTG AAG GAT AAG CAG      953
Asn Tyr Tyr Pro Gln Asn Ile Thr Met Lys Trp Leu Lys Asp Lys Gln
                230                 235                 240

CCA ATG GAT GCC AAG GAG TTC GAA CCT AAA GAC GTA TTG CCC AAT GGG     1001
Pro Met Asp Ala Lys Glu Phe Glu Pro Lys Asp Val Leu Pro Asn Gly
245                 250                 255                 260

GAT GGG ACC TAC CAG GGC TGG ATA ACC TTG GCT GTA CCC CCT GGG GAA     1049
Asp Gly Thr Tyr Gln Gly Trp Ile Thr Leu Ala Val Pro Pro Gly Glu
                265                 270                 275

GAG CAG AGA TAT ACG TAC CAG GTG GAG CAC CCA GGC CTG GAT CAG CCC     1097
Glu Gln Arg Tyr Thr Tyr Gln Val Glu His Pro Gly Leu Asp Gln Pro
                280                 285                 290

CTC ATT GTG ATC TGG GAG CCC TCA CCG TCT GGC ACC CTA GTC ATT GGA     1145
Leu Ile Val Ile Trp Glu Pro Ser Pro Ser Gly Thr Leu Val Ile Gly
                295                 300                 305

GTC ATC AGT GGA ATT GCT GTT TTT GTC GTC ATC TTG TTC ATT GGA ATT     1193
Val Ile Ser Gly Ile Ala Val Phe Val Val Ile Leu Phe Ile Gly Ile
            310                 315                 320

TTG TTC ATA ATA TTA AGG AAG AGG CAG GGT TCA AGA GGA GCC ATG GGG     1241
Leu Phe Ile Ile Leu Arg Lys Arg Gln Gly Ser Arg Gly Ala Met Gly
325                 330                 335                 340

CAC TAC GTC TTA GCT GAA CGT GAG TGACACGCAG CCTGCAGACT CACTGTGGGA    1295
His Tyr Val Leu Ala Glu Arg Glu
                345

AGGAGACAAA ACTAGAGACT CAAAGAGGGA GTGCATTTAT GAGCTCTTCA TGTTTCAGGA   1355

GAGAGTTGAA CCTAAACATA GAAATTGCCT GACGAACTCC TTGATTTTAG CCTTCTCTGT   1415

TCATTTCCTC AAAAAGATTT CCCCA                                        1440

(2) INFORMATION FOR SEQ ID NO:11:

(i) SEQUENCE CHARACTERISTICS:
        (A) LENGTH: 1440 base pairs
        (B) TYPE: nucleic acid
```

-continued

```
      (C) STRANDEDNESS: single
      (D) TOPOLOGY: linear (ii) MOLECULE TYPE: cDNA (ix) FEATURE:
      (A) NAME/KEY: CDS
      (B) LOCATION: 222..1268

(ix) FEATURE:
      (A) NAME/KEY: allele
      (B) LOCATION: replace(408, "g")
      (D) OTHER INFORMATION: /phenotype= "Hereditary Hemochromatosis
          (HH)"
          /label= 24d2

(xi) SEQUENCE DESCRIPTION: SEQ ID NO:11:

GGGGACACTG GATCACCTAG TGTTTCACAA GCAGGTACCT TCTGCTGTAG GAGAGAGAGA      60

ACTAAAGTTC TGAAAGACCT GTTGCTTTTC ACCAGGAAGT TTTACTGGGC ATCTCCTGAG     120

CCTAGGCAAT AGCTGTAGGG TGACTTCTGG AGCCATCCCC GTTTCCCCGC CCCCCAAAAG    180

AAGCGGAGAT TTAACGGGGA CGTGCGGCCA GAGCTGGGGA A ATG GGC CCG CGA        233
                                              Met Gly Pro Arg
                                                1

GCC AGG CCG GCG CTT CTC CTC CTG ATG CTT TTG CAG ACC GCG GTC CTG      281
Ala Arg Pro Ala Leu Leu Leu Leu Met Leu Leu Gln Thr Ala Val Leu
  5              10                  15                  20

CAG GGG CGC TTG CTG CGT TCA CAC TCT CTG CAC TAC CTC TTC ATG GGT      329
Gln Gly Arg Leu Leu Arg Ser His Ser Leu His Tyr Leu Phe Met Gly
             25                  30                  35

GCC TCA GAG CAG GAC CTT GGT CTT TCC TTG TTT GAA GCT TTG GGC TAC      377
Ala Ser Glu Gln Asp Leu Gly Leu Ser Leu Phe Glu Ala Leu Gly Tyr
         40                  45                  50

GTG GAT GAC CAG CTG TTC GTG TTC TAT GAT GAT GAG AGT CGC CGT GTG      425
Val Asp Asp Gln Leu Phe Val Phe Tyr Asp Asp Glu Ser Arg Arg Val
     55                  60                  65

GAG CCC CGA ACT CCA TGG GTT TCC AGT AGA ATT TCA AGC CAG ATG TGG      473
Glu Pro Arg Thr Pro Trp Val Ser Ser Arg Ile Ser Ser Gln Met Trp
 70                  75                  80

CTG CAG CTG AGT CAG AGT CTG AAA GGG TGG GAT CAC ATG TTC ACT GTT      521
Leu Gln Leu Ser Gln Ser Leu Lys Gly Trp Asp His Met Phe Thr Val
 85                  90                  95                 100

GAC TTC TGG ACT ATT ATG GAA AAT CAC AAC CAC AGC AAG GAG TCC CAC      569
Asp Phe Trp Thr Ile Met Glu Asn His Asn His Ser Lys Glu Ser His
                105                 110                 115

ACC CTG CAG GTC ATC CTG GGC TGT GAA ATG CAA GAA GAC AAC AGT ACC      617
Thr Leu Gln Val Ile Leu Gly Cys Glu Met Gln Glu Asp Asn Ser Thr
            120                 125                 130

GAG GGC TAC TGG AAG TAC GGG TAT GAT GGG CAG GAC CAC CTT GAA TTC      665
Glu Gly Tyr Trp Lys Tyr Gly Tyr Asp Gly Gln Asp His Leu Glu Phe
        135                 140                 145

TGC CCT GAC ACA CTG GAT TGG AGA GCA GCA GAA CCC AGG GCC TGG CCC      713
Cys Pro Asp Thr Leu Asp Trp Arg Ala Ala Glu Pro Arg Ala Trp Pro
    150                 155                 160

ACC AAG CTG GAG TGG GAA AGG CAC AAG ATT CGG GCC AGG CAG AAC AGG      761
Thr Lys Leu Glu Trp Glu Arg His Lys Ile Arg Ala Arg Gln Asn Arg
165                 170                 175                 180

GCC TAC CTG GAG AGG GAC TGC CCT GCA CAG CTG CAG CAG TTG CTG GAG      809
Ala Tyr Leu Glu Arg Asp Cys Pro Ala Gln Leu Gln Gln Leu Leu Glu
                185                 190                 195

CTG GGG AGA GGT GTT TTG GAC CAA CAA GTG CCT CCT TTG GTG AAG GTG      857
Leu Gly Arg Gly Val Leu Asp Gln Gln Val Pro Pro Leu Val Lys Val
            200                 205                 210
```

-continued

```
ACA CAT CAT GTG ACC TCT TCA GTG ACC ACT CTA CGG TGT CGG GCC TTG        905
Thr His His Val Thr Ser Ser Val Thr Thr Leu Arg Cys Arg Ala Leu
        215                 220                 225

AAC TAC TAC CCC CAG AAC ATC ACC ATG AAG TGG CTG AAG GAT AAG CAG        953
Asn Tyr Tyr Pro Gln Asn Ile Thr Met Lys Trp Leu Lys Asp Lys Gln
        230                 235                 240

CCA ATG GAT GCC AAG GAG TTC GAA CCT AAA GAC GTA TTG CCC AAT GGG       1001
Pro Met Asp Ala Lys Glu Phe Glu Pro Lys Asp Val Leu Pro Asn Gly
245                 250                 255                 260

GAT GGG ACC TAC CAG GGC TGG ATA ACC TTG GCT GTA CCC CCT GGG GAA       1049
Asp Gly Thr Tyr Gln Gly Trp Ile Thr Leu Ala Val Pro Pro Gly Glu
                265                 270                 275

GAG CAG AGA TAT ACG TGC CAG GTG GAG CAC CCA GGC CTG GAT CAG CCC       1097
Glu Gln Arg Tyr Thr Cys Gln Val Glu His Pro Gly Leu Asp Gln Pro
                280                 285                 290

CTC ATT GTG ATC TGG GAG CCC TCA CCG TCT GGC ACC CTA GTC ATT GGA       1145
Leu Ile Val Ile Trp Glu Pro Ser Pro Ser Gly Thr Leu Val Ile Gly
                295                 300                 305

GTC ATC AGT GGA ATT GCT GTT TTT GTC GTC ATC TTG TTC ATT GGA ATT       1193
Val Ile Ser Gly Ile Ala Val Phe Val Val Ile Leu Phe Ile Gly Ile
        310                 315                 320

TTG TTC ATA ATA TTA AGG AAG AGG CAG GGT TCA AGA GGA GCC ATG GGG       1241
Leu Phe Ile Ile Leu Arg Lys Arg Gln Gly Ser Arg Gly Ala Met Gly
325                 330                 335                 340

CAC TAC GTC TTA GCT GAA CGT GAG TGACACGCAG CCTGCAGACT CACTGTGGGA      1295
His Tyr Val Leu Ala Glu Arg Glu
                345

AGGAGACAAA ACTAGAGACT CAAAGAGGGA GTGCATTTAT GAGCTCTTCA TGTTTCAGGA     1355

GAGAGTTGAA CCTAAACATA GAAATTGCCT GACGAACTCC TTGATTTTAG CCTTCTCTGT     1415

TCATTTCCTC AAAAAGATTT CCCCA                                           1440

(2) INFORMATION FOR SEQ ID NO:12:

(i) SEQUENCE CHARACTERISTICS:
        (A) LENGTH: 1440 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 222..1268

(ix) FEATURE:
        (A) NAME/KEY: allele
        (B) LOCATION: replace(408, "g")
        (D) OTHER INFORMATION: /phenotype= "Hereditary Hemochromatosis
            (HH)"
            /label= 24d2

(ix) FEATURE:
        (A) NAME/KEY: allele
        (B) LOCATION: replace(1066, "a")
        (D) OTHER INFORMATION: /phenotype= "Hereditary Hemochromatosis
            (HH)"
            /label= 24d1

(xi) SEQUENCE DESCRIPTION: SEQ ID NO:12:

GGGGACACTG GATCACCTAG TGTTTCACAA GCAGGTACCT TCTGCTGTAG GAGAGAGAGA       60

ACTAAAGTTC TGAAAGACCT GTTGCTTTTC ACCAGGAAGT TTTACTGGGC ATCTCCTGAG      120

CCTAGGCAAT AGCTGTAGGG TGACTTCTGG AGCCATCCCC GTTTCCCCGC CCCCCAAAAG      180
```

```
AAGCGGAGAT TTAACGGGGA CGTGCGGCCA GAGCTGGGGA A ATG GGC CCG CGA          233
                                              Met Gly Pro Arg
                                                1

GCC AGG CCG GCG CTT CTC CTC CTG ATG CTT TTG CAG ACC GCG GTC CTG        281
Ala Arg Pro Ala Leu Leu Leu Leu Met Leu Leu Gln Thr Ala Val Leu
 5              10                  15                  20

CAG GGG CGC TTG CTG CGT TCA CAC TCT CTG CAC TAC CTC TTC ATG GGT        329
Gln Gly Arg Leu Leu Arg Ser His Ser Leu His Tyr Leu Phe Met Gly
                25                  30                  35

GCC TCA GAG CAG GAC CTT GGT CTT TCC TTG TTT GAA GCT TTG GGC TAC        377
Ala Ser Glu Gln Asp Leu Gly Leu Ser Leu Phe Glu Ala Leu Gly Tyr
            40                  45                  50

GTG GAT GAC CAG CTG TTC GTG TTC TAT GAT GAT GAG AGT CGC CGT GTG        425
Val Asp Asp Gln Leu Phe Val Phe Tyr Asp Asp Glu Ser Arg Arg Val
        55                  60                  65

GAG CCC CGA ACT CCA TGG GTT TCC AGT AGA ATT TCA AGC CAG ATG TGG        473
Glu Pro Arg Thr Pro Trp Val Ser Ser Arg Ile Ser Ser Gln Met Trp
    70                  75                  80

CTG CAG CTG AGT CAG AGT CTG AAA GGG TGG GAT CAC ATG TTC ACT GTT        521
Leu Gln Leu Ser Gln Ser Leu Lys Gly Trp Asp His Met Phe Thr Val
 85                  90                  95                 100

GAC TTC TGG ACT ATT ATG GAA AAT CAC AAC CAC AGC AAG GAG TCC CAC        569
Asp Phe Trp Thr Ile Met Glu Asn His Asn His Ser Lys Glu Ser His
                105                 110                 115

ACC CTG CAG GTC ATC CTG GGC TGT GAA ATG CAA GAA GAC AAC AGT ACC        617
Thr Leu Gln Val Ile Leu Gly Cys Glu Met Gln Glu Asp Asn Ser Thr
            120                 125                 130

GAG GGC TAC TGG AAG TAC GGG TAT GAT GGG CAG GAC CAC CTT GAA TTC        665
Glu Gly Tyr Trp Lys Tyr Gly Tyr Asp Gly Gln Asp His Leu Glu Phe
        135                 140                 145

TGC CCT GAC ACA CTG GAT TGG AGA GCA GCA GAA CCC AGG GCC TGG CCC        713
Cys Pro Asp Thr Leu Asp Trp Arg Ala Ala Glu Pro Arg Ala Trp Pro
    150                 155                 160

ACC AAG CTG GAG TGG GAA AGG CAC AAG ATT CGG GCC AGG CAG AAC AGG        761
Thr Lys Leu Glu Trp Glu Arg His Lys Ile Arg Ala Arg Gln Asn Arg
165                 170                 175                 180

GCC TAC CTG GAG AGG GAC TGC CCT GCA CAG CTG CAG CAG TTG CTG GAG        809
Ala Tyr Leu Glu Arg Asp Cys Pro Ala Gln Leu Gln Gln Leu Leu Glu
                185                 190                 195

CTG GGG AGA GGT GTT TTG GAC CAA CAA GTG CCT CCT TTG GTG AAG GTG        857
Leu Gly Arg Gly Val Leu Asp Gln Gln Val Pro Pro Leu Val Lys Val
            200                 205                 210

ACA CAT CAT GTG ACC TCT TCA GTG ACC ACT CTA CGG TGT CGG GCC TTG        905
Thr His His Val Thr Ser Ser Val Thr Thr Leu Arg Cys Arg Ala Leu
        215                 220                 225

AAC TAC TAC CCC CAG AAC ATC ACC ATG AAG TGG CTG AAG GAT AAG CAG        953
Asn Tyr Tyr Pro Gln Asn Ile Thr Met Lys Trp Leu Lys Asp Lys Gln
    230                 235                 240

CCA ATG GAT GCC AAG GAG TTC GAA CCT AAA GAC GTA TTG CCC AAT GGG       1001
Pro Met Asp Ala Lys Glu Phe Glu Pro Lys Asp Val Leu Pro Asn Gly
245                 250                 255                 260

GAT GGG ACC TAC CAG GGC TGG ATA ACC TTG GCT GTA CCC CCT GGG GAA       1049
Asp Gly Thr Tyr Gln Gly Trp Ile Thr Leu Ala Val Pro Pro Gly Glu
                265                 270                 275

GAG CAG AGA TAT ACG TAC CAG GTG GAG CAC CCA GGC CTG GAT CAG CCC       1097
Glu Gln Arg Tyr Thr Tyr Gln Val Glu His Pro Gly Leu Asp Gln Pro
            280                 285                 290

CTC ATT GTG ATC TGG GAG CCC TCA CCG TCT GGC ACC CTA GTC ATT GGA       1145
Leu Ile Val Ile Trp Glu Pro Ser Pro Ser Gly Thr Leu Val Ile Gly
```

```
                     295                 300                 305
GTC ATC AGT GGA ATT GCT GTT TTT GTC GTC ATC TTG TTC ATT GGA ATT        1193
Val Ile Ser Gly Ile Ala Val Phe Val Val Ile Leu Phe Ile Gly Ile
    310                 315                 320

TTG TTC ATA ATA TTA AGG AAG AGG CAG GGT TCA AGA GGA GCC ATG GGG        1241
Leu Phe Ile Ile Leu Arg Lys Arg Gln Gly Ser Arg Gly Ala Met Gly
325                 330                 335                 340

CAC TAC GTC TTA GCT GAA CGT GAG TGACACGCAG CCTGCAGACT CACTGTGGGA       1295
His Tyr Val Leu Ala Glu Arg Glu
                345

AGGAGACAAA ACTAGAGACT CAAAGAGGGA GTGCATTTAT GAGCTCTTCA TGTTTCAGGA      1355

GAGAGTTGAA CCTAAACATA GAAATTGCCT GACGAACTCC TTGATTTTAG CCTTCTCTGT      1415

TCATTTCCTC AAAAAGATTT CCCCA                                            1440

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:13:

TGGCAAGGGT AAACAGATCC                                                  20

(2) INFORMATION FOR SEQ ID NO:14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:14:

CTCAGGCACT CCTCTCAACC                                                  20

(2) INFORMATION FOR SEQ ID NO:15:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 1
        (D) OTHER INFORMATION: /mod_base= OTHER
            /note= "N = 5'-biotinylated guanine
            (bio-G)"

(xi) SEQUENCE DESCRIPTION: SEQ ID NO:15:

NGAAGAGCAG AGATATACGT G                                                21

(2) INFORMATION FOR SEQ ID NO:16:

(i) SEQUENCE CHARACTERISTICS:
        (A) LENGTH: 21 base pairs
        (B) TYPE: nucleic acid
        (C) STRANDEDNESS: single
```

```
            (D) TOPOLOGY: linear (ii) MOLECULE TYPE: DNA (ix) FEATURE:
            (A) NAME/KEY: modified_base
            (B) LOCATION: 1
            (D) OTHER INFORMATION: /mod_base= OTHER
                  /note= "N = 5'-biotinylated guanine
                  (bio-G)"

(xi) SEQUENCE DESCRIPTION: SEQ ID NO:16:

NGAAGAGCAG AGATATACGT A                                        21

(2) INFORMATION FOR SEQ ID NO:17:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: modified_base
            (B) LOCATION: 1
            (D) OTHER INFORMATION: /mod_base= OTHER
                  /note= "N = 5'-phosphorylated cytosine
                  (p-C)"

(ix) FEATURE:
            (A) NAME/KEY: modified_base
            (B) LOCATION: 18
            (D) OTHER INFORMATION: /mod_base= OTHER
                  /note= "N = 3'-digoxigenin-conjugated
                  guanine (G-dig)"

(xi) SEQUENCE DESCRIPTION: SEQ ID NO:17:

NCAGGTGGAG CACCCAGN                                            18

(2) INFORMATION FOR SEQ ID NO:18:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:18:

CTGAAAGGGT GGGATCACAT                                          20

(2) INFORMATION FOR SEQ ID NO:19:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:19:

CAAGGAGTTC GTCAGGCAAT                                          20

(2) INFORMATION FOR SEQ ID NO:20:

(i) SEQUENCE CHARACTERISTICS:
            (A) LENGTH: 517 base pairs
```

```
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: -
            (B) LOCATION: 1..517
            (D) OTHER INFORMATION: /note= "normal or wild-type
                (unaffected) genomic sequence surrounding variant for
                24d1(G) allele corresponding to positions
                5507-6023 of genomic sequence containing
                the HH gene (SEQ ID NO:1)"

(ix) FEATURE:
            (A) NAME/KEY: allele
            (B) LOCATION: replace(328, "g")
            (D) OTHER INFORMATION: /phenotype= "normal or wild-type
                (unaffected)"
                /label= 24d1

(xi) SEQUENCE DESCRIPTION: SEQ ID NO:20:

TATTTCCTTC CTCCAACCTA TAGAAGGAAG TGAAAGTTCC AGTCTTCCTG GCAAGGGTAA      60

ACAGATCCCC TCTCCTCATC CTTCCTCTTT CCTGTCAAGT GCCTCCTTTG GTGAAGGTGA     120

CACATCATGT GACCTCTTCA GTGACCACTC TACGGTGTCG GGCCTTGAAC TACTACCCCC     180

AGAACATCAC CATGAAGTGG CTGAAGGATA AGCAGCCAAT GGATGCCAAG GAGTTCGAAC     240

CTAAAGACGT ATTGCCCAAT GGGGATGGGA CCTACCAGGG CTGGATAACC TTGGCTGTAC     300

CCCCTGGGGA AGAGCAGAGA TATACGTGCC AGGTGGAGCA CCCAGGCCTG GATCAGCCCC     360

TCATTGTGAT CTGGGGTATG TGACTGATGA GAGCCAGGAG CTGAGAAAAT CTATTGGGGG     420

TTGAGAGGAG TGCCTGAGGA GGTAATTATG GCAGTGAGAT GAGGATCTGC TCTTTGTTAG     480

GGGGTGGGCT GAGGGTGGCA ATCAAAGGCT TTAACTT                              517

(2) INFORMATION FOR SEQ ID NO:21:

(i) SEQUENCE CHARACTERISTICS:
            (A) LENGTH: 517 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: -
            (B) LOCATION: 1..517
            (D) OTHER INFORMATION: /note= "genomic sequence surrounding
                variant for 24d1(A) allele corresponding
                to positions 5507-6023 of genomic
                sequence containing the HH gene
                (SEQ ID NO:3)"

(ix) FEATURE:
            (A) NAME/KEY: allele
            (B) LOCATION: replace(328, "a")
            (D) OTHER INFORMATION: /phenotype= "Hereditary Hemochromatosis
                (HH)"
                /label= 24d1

(xi) SEQUENCE DESCRIPTION: SEQ ID NO:21:

TATTTCCTTC CTCCAACCTA TAGAAGGAAG TGAAAGTTCC AGTCTTCCTG GCAAGGGTAA      60

ACAGATCCCC TCTCCTCATC CTTCCTCTTT CCTGTCAAGT GCCTCCTTTG GTGAAGGTGA     120

CACATCATGT GACCTCTTCA GTGACCACTC TACGGTGTCG GGCCTTGAAC TACTACCCCC     180

AGAACATCAC CATGAAGTGG CTGAAGGATA AGCAGCCAAT GGATGCCAAG GAGTTCGAAC     240
```

```
CTAAAGACGT ATTGCCCAAT GGGGATGGGA CCTACCAGGG CTGGATAACC TTGGCTGTAC        300

CCCCTGGGGA AGAGCAGAGA TATACGTACC AGGTGGAGCA CCCAGGCCTG GATCAGCCCC        360

TCATTGTGAT CTGGGGTATG TGACTGATGA GAGCCAGGAG CTGAGAAAAT CTATTGGGGG        420

TTGAGAGGAG TGCCTGAGGA GGTAATTATG GCAGTGAGAT GAGGATCTGC TCTTTGTTAG        480

GGGGTGGGCT GAGGGTGGCA ATCAAAGGCT TTAACTT                                517
```

(2) INFORMATION FOR SEQ ID NO:22:

(i) SEQUENCE CHARACTERISTICS:
        (A) LENGTH: 361 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: Protein
        (B) LOCATION: 1..361
        (D) OTHER INFORMATION: /note= "Rabbit leukocyte antigen (RLA)"

(xi) SEQUENCE DESCRIPTION: SEQ ID NO:22:

```
Met Gly Ser Ile Pro Pro Arg Thr Leu Leu Leu Leu Ala Gly Ala
1               5                  10                  15

Leu Thr Leu Lys Asp Thr Gln Ala Gly Ser His Ser Met Arg Tyr Phe
                20                  25                  30

Tyr Thr Ser Val Ser Arg Pro Gly Leu Gly Glu Pro Arg Phe Ile Ile
                35                  40                  45

Val Gly Tyr Val Asp Asp Thr Gln Phe Val Arg Phe Asp Ser Asp Ala
    50                  55                  60

Ala Ser Pro Arg Met Glu Gln Arg Ala Pro Trp Met Gly Gln Val Glu
65                  70                  75                  80

Pro Glu Tyr Trp Asp Gln Gln Thr Gln Ile Ala Lys Asp Thr Ala Gln
                85                  90                  95

Thr Phe Arg Val Asn Leu Asn Thr Ala Leu Arg Tyr Tyr Asn Gln Ser
                100                 105                 110

Ala Ala Gly Ser His Thr Phe Gln Thr Met Phe Gly Cys Glu Val Trp
            115                 120                 125

Ala Asp Gly Arg Phe Phe His Gly Tyr Arg Gln Tyr Ala Tyr Asp Gly
    130                 135                 140

Ala Asp Tyr Ile Ala Leu Asn Glu Asp Leu Arg Ser Trp Thr Ala Ala
145                 150                 155                 160

Asp Thr Ala Ala Gln Asn Thr Gln Arg Lys Trp Glu Ala Ala Gly Glu
                165                 170                 175

Ala Glu Arg His Arg Ala Tyr Leu Glu Arg Glu Cys Val Glu Trp Leu
            180                 185                 190

Arg Arg Tyr Leu Glu Met Gly Lys Glu Thr Leu Gln Arg Ala Asp Pro
        195                 200                 205

Pro Lys Ala His Val Thr His His Pro Ala Ser Asp Arg Glu Ala Thr
    210                 215                 220

Leu Arg Cys Trp Ala Leu Gly Phe Tyr Pro Ala Glu Ile Ser Leu Thr
225                 230                 235                 240

Trp Gln Arg Asp Gly Glu Asp Gln Thr Gln Asp Thr Glu Leu Val Glu
                245                 250                 255

Thr Arg Pro Gly Gly Asp Gly Thr Phe Gln Lys Trp Ala Ala Val Val
            260                 265                 270
```

```
Val Pro Ser Gly Glu Glu Gln Arg Tyr Thr Cys Arg Val Gln His Glu
            275                 280                 285

Gly Leu Pro Glu Pro Leu Thr Leu Thr Trp Glu Pro Pro Ala Gln Pro
            290                 295                 300

Thr Ala Leu Ile Val Gly Ile Val Ala Gly Val Leu Gly Val Leu Leu
305                 310                 315                 320

Ile Leu Gly Ala Val Val Ala Val Val Arg Arg Lys Lys His Ser Ser
                325                 330                 335

Asp Gly Lys Gly Gly Arg Tyr Thr Pro Ala Ala Gly Gly His Arg Asp
            340                 345                 350

Gln Gly Ser Asp Asp Ser Leu Met Pro
            355                 360

(2) INFORMATION FOR SEQ ID NO:23:

(i) SEQUENCE CHARACTERISTICS:
        (A) LENGTH: 365 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: Protein
        (B) LOCATION: 1..365
        (D) OTHER INFORMATION: /note= "Human Major Histocompatability
            Class I (MHC) protein"

(xi) SEQUENCE DESCRIPTION: SEQ ID NO:23:

Met Ala Val Met Ala Pro Arg Thr Leu Val Leu Leu Leu Ser Gly Ala
1               5                   10                  15

Leu Ala Leu Thr Gln Thr Trp Ala Gly Ser His Ser Met Arg Tyr Phe
                20                  25                  30

Phe Thr Ser Val Ser Arg Pro Gly Arg Gly Glu Pro Arg Phe Ile Ala
            35                  40                  45

Val Gly Tyr Val Asp Asp Thr Gln Phe Val Arg Phe Asp Ser Asp Ala
    50                  55                  60

Ala Ser Gln Arg Met Glu Pro Arg Ala Pro Trp Ile Glu Gln Glu Gly
65              70                  75                  80

Pro Glu Tyr Trp Asp Gly Glu Thr Arg Lys Val Lys Ala His Ser Gln
                85                  90                  95

Thr His Arg Val Asp Leu Gly Thr Leu Arg Gly Tyr Tyr Asn Gln Ser
            100                 105                 110

Glu Ala Gly Ser His Thr Leu Gln Met Met Phe Gly Cys Asp Val Gly
            115                 120                 125

Ser Asp Trp Arg Phe Leu Arg Gly Tyr His Gln Tyr Ala Tyr Asp Gly
    130                 135                 140

Lys Asp Tyr Ile Ala Leu Lys Glu Asp Leu Arg Ser Trp Thr Ala Ala
145                 150                 155                 160

Asp Met Ala Ala Gln Thr Thr Lys His Lys Trp Glu Ala Ala His Val
                165                 170                 175

Ala Glu Gln Leu Arg Ala Tyr Leu Glu Gly Thr Cys Val Glu Trp Leu
            180                 185                 190

Arg Arg Tyr Leu Glu Asn Gly Lys Glu Thr Leu Gln Arg Thr Asp Ala
            195                 200                 205

Pro Lys Thr His Met Thr His His Ala Val Ser Asp His Glu Ala Thr
210                 215                 220
```

```
Leu Arg Cys Trp Ala Leu Ser Phe Tyr Pro Ala Glu Ile Thr Leu Thr
225                 230                 235                 240

Trp Gln Arg Asp Gly Glu Asp Gln Thr Gln Asp Thr Glu Leu Val Glu
            245                 250                 255

Thr Arg Pro Ala Gly Asp Gly Thr Phe Gln Lys Trp Ala Ala Val Val
            260                 265                 270

Val Pro Ser Gly Gln Glu Gln Arg Tyr Thr Cys His Val Gln His Glu
            275                 280                 285

Gly Leu Pro Lys Pro Leu Thr Leu Arg Trp Glu Pro Ser Ser Gln Pro
290                 295                 300

Thr Ile Pro Ile Val Gly Ile Ile Ala Gly Leu Val Leu Phe Gly Ala
305                 310                 315                 320

Val Ile Thr Gly Ala Val Val Ala Ala Val Met Trp Arg Arg Lys Ser
            325                 330                 335

Ser Asp Arg Lys Gly Gly Ser Tyr Ser Gln Ala Ala Ser Ser Asp Ser
            340                 345                 350

Ala Gln Gly Ser Asp Val Ser Leu Thr Ala Cys Lys Val
            355                 360                 365

(2) INFORMATION FOR SEQ ID NO:24:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:24:

ACATGGTTAA GGCCTGTTGC                                                        20

(2) INFORMATION FOR SEQ ID NO:25:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:25:

GCCACATCTG GCTTGAAATT                                                        20

(2) INFORMATION FOR SEQ ID NO:26:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 1
        (D) OTHER INFORMATION: /mod_base= OTHER
            /note= "N = 5'-biotinylated adenine
            (bio-A)"

(xi) SEQUENCE DESCRIPTION: SEQ ID NO:26:

NGCTGTTCGT GTTCTATGAT C                                                      21
```

(2) INFORMATION FOR SEQ ID NO:27:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 1
        (D) OTHER INFORMATION: /mod_base= OTHER
            /note= "N = 5'-biotinylated adenine
            (bio-A)"

(xi) SEQUENCE DESCRIPTION: SEQ ID NO:27:

NGCTGTTCGT GTTCTATGAT G                                        21

(2) INFORMATION FOR SEQ ID NO:28:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: modified_base
        (B) LOCATION: 1
        (D) OTHER INFORMATION: /mod_base= OTHER
            /note= "N = 5'-phosphorylated adenine
            (p-A)"

(ix) FEATURE:
        (A) NAME/KEY: modified_base
        (B) LOCATION: 19
        (D) OTHER INFORMATION: /mod_base= OTHER
            /note= "N = 3'-digoxigenin-conjugated
            adenine (A-dig)"

(xi) SEQUENCE DESCRIPTION: SEQ ID NO:28:

NTGAGAGTCG CCGTGTGGN                                           19

(2) INFORMATION FOR SEQ ID NO:29:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:29:

GGAAGAGCAG AGATATACGT GCCAGGTGGA GCACCCAGG                     39

(2) INFORMATION FOR SEQ ID NO:30:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:30:

GGAAGAGCAG AGATATACGT ACCAGGTGGA GCACCCAGG                              39

(2) INFORMATION FOR SEQ ID NO:31:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:31:

CAAAAGAAGC GGAGATTTAA CG                                               22

(2) INFORMATION FOR SEQ ID NO:32:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:32:

AGATTTAACG GGGACGTGC                                                   19

(2) INFORMATION FOR SEQ ID NO:33:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:33:

AGAGGTCACA TGATGTGTCA CC                                               22

(2) INFORMATION FOR SEQ ID NO:34:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:34:

AGGAGGCACT TGTTGGTCC                                                   19

(2) INFORMATION FOR SEQ ID NO:35:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:35:

AAAATCACAA CCACAGCAAA G                                                21

(2) INFORMATION FOR SEQ ID NO:36:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:36:

TTCCCACAGT GAGTCTGCAG                                                    20

(2) INFORMATION FOR SEQ ID NO:37:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:37:

CAATGGGGAT GGGACCTAC                                                     19

(2) INFORMATION FOR SEQ ID NO:38:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:38:

ATATACGTGC CAGGTGGAGC                                                    20

(2) INFORMATION FOR SEQ ID NO:39:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:39:

CCTCTTCACA ACCCCTTTCA                                                    20

(2) INFORMATION FOR SEQ ID NO:40:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:40:

CATAGCTGTG CAACTCACAT CA                                                 22

(2) INFORMATION FOR SEQ ID NO:41:

(i) SEQUENCE CHARACTERISTICS:
        (A) LENGTH: 40 base pairs
        (B) TYPE: nucleic acid (C) STRANDEDNESS: single
            (D) TOPOLOGY: linear (ii) MOLECULE TYPE: DNA (genomic)

(xi) SEQUENCE DESCRIPTION: SEQ ID NO:41:

AGCTGTTCGT GTTCTATGAT CATGAGAGTC GCCGTGTGGA            40

(2) INFORMATION FOR SEQ ID NO:42:

(i) SEQUENCE CHARACTERISTICS:
            (A) LENGTH: 40 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:42:

AGCTGTTCGT GTTCTATGAT GATGAGAGTC GCCGTGTGGA            40

(2) INFORMATION FOR SEQ ID NO:43:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:43:

TGTTCTATGA TCATGAGAGT CGCCGTGTGG AG                    32

(2) INFORMATION FOR SEQ ID NO:44:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:44:

TGTTCTATGA TCATGAGTGT CGCCGTGTGG AG                    32

(2) INFORMATION FOR SEQ ID NO:45:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:45:

ATATACGTGC CAGGTGG                                     17

(2) INFORMATION FOR SEQ ID NO:46:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:46:

ATATACGTAC CAGGTGG                                                    17

(2) INFORMATION FOR SEQ ID NO:47:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:47:

TCTATGATCA TGAGAGT                                                    17

(2) INFORMATION FOR SEQ ID NO:48:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:48:

TCTATGATGA TGAGAGT                                                    17

(2) INFORMATION FOR SEQ ID NO:49:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:49:

TGGGTGCTCC ACCTGGC                                                    17

(2) INFORMATION FOR SEQ ID NO:50:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:50:

TGGGTGCTCC ACCTGGT                                                    17

(2) INFORMATION FOR SEQ ID NO:51:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:51:

CACACGGCGA CTCTCATG                                                   18

(2) INFORMATION FOR SEQ ID NO:52:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:52:

CACACGGCGA CTCTCATC                                      18

(2) INFORMATION FOR SEQ ID NO:53:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: modified_base
        (B) LOCATION: 1
        (D) OTHER INFORMATION: /mod_base= OTHER
            /note= "N = fluorescein-labeled guanine"

(xi) SEQUENCE DESCRIPTION: SEQ ID NO:53:

NGAAGAGCAG AGATATACGT                                  20

(2) INFORMATION FOR SEQ ID NO:54:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: modified_base
        (B) LOCATION: 1
        (D) OTHER INFORMATION: /mod_base= OTHER
            /note= "N = fluorescein-labeled guanine"

(xi) SEQUENCE DESCRIPTION: SEQ ID NO:54:

NGCCTGGGTG CTCCACCTGG                                  20

(2) INFORMATION FOR SEQ ID NO:55:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: modified_base
        (B) LOCATION: 1
        (D) OTHER INFORMATION: /mod_base= OTHER
            /note= "N = fluorescein-labeled arginine"

(xi) SEQUENCE DESCRIPTION: SEQ ID NO:55:

NGCTGTTCGT GTTCTATGAT                                  20

(2) INFORMATION FOR SEQ ID NO:56:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: modified_base
        (B) LOCATION: 1
        (D) OTHER INFORMATION: /mod_base= OTHER
            /note= "N = fluorescein-labeled cytosine"

(xi) SEQUENCE DESCRIPTION: SEQ ID NO:56:

NTCCACACGG CGACTCTCAT                                                20

(2) INFORMATION FOR SEQ ID NO:57:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:57:

GCTCCACCTG GCACG                                                     15

(2) INFORMATION FOR SEQ ID NO:58:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:58:

GCTCCACCTG GTACG                                                     15

(2) INFORMATION FOR SEQ ID NO:59:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:59:

GCGACTCTCA TCATC                                                     15

(2) INFORMATION FOR SEQ ID NO:60:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:60:

```
GCGACTCTCA TGATC                                                      15

(2) INFORMATION FOR SEQ ID NO:61:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: modified_base
        (B) LOCATION: 1
        (D) OTHER INFORMATION: /mod_base= OTHER
            /note= "N = 5'-biotinylated guanine
            (bio-G)"

(xi) SEQUENCE DESCRIPTION: SEQ ID NO:61:

NCCTGGGTGC TCCACCTGGC                                                 20

(2) INFORMATION FOR SEQ ID NO:62:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: modified_base
        (B) LOCATION: 1
        (D) OTHER INFORMATION: /mod_base= OTHER
            /note= "N = 5'-phosphorylated adenine
            (p-A)"

(ix) FEATURE:
        (A) NAME/KEY: modified_base
        (B) LOCATION: 20
        (D) OTHER INFORMATION: /mod_base= OTHER
            /note= "N = 3'-digoxigenin-conjugated
            cytosine (C-dig)"

(xi) SEQUENCE DESCRIPTION: SEQ ID NO:62:

NCGTATATCT CTGCTCTTCN                                                 20

(2) INFORMATION FOR SEQ ID NO:63:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: modified_base
        (B) LOCATION: 1
        (D) OTHER INFORMATION: /mod_base= OTHER
            /note= "N = 5'-biotinylated guanine
            (bio-G)"

(xi) SEQUENCE DESCRIPTION: SEQ ID NO:63:

NAAGAGCAGA GATATACGTG                                                 20

(2) INFORMATION FOR SEQ ID NO:64:

(i) SEQUENCE CHARACTERISTICS:
```

```
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: modified_base
            (B) LOCATION: 1
            (D) OTHER INFORMATION: /mod_base= OTHER
                /note= "N = 5'-phosphorylated cytosine
                (p-C)"

(ix) FEATURE:
            (A) NAME/KEY: modified_base
            (B) LOCATION: 20
            (D) OTHER INFORMATION: /mod_base= OTHER
                /note= "N = 3'-digoxigenin-conjugated
                cytosine (C-dig)"

(xi) SEQUENCE DESCRIPTION: SEQ ID NO:64:

NCAGGTGGAG CACCCAGGCN                                                       20

(2) INFORMATION FOR SEQ ID NO:65:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: modified_base
            (B) LOCATION: 1
            (D) OTHER INFORMATION: /mod_base= OTHER
                /note= "N = 5'-biotinylated guanine
                (bio-G)"

(xi) SEQUENCE DESCRIPTION: SEQ ID NO:65:

NCCTGGGTGC TCCACCTGGT                                                       20

(2) INFORMATION FOR SEQ ID NO:66:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: modified_base
            (B) LOCATION: 1
            (D) OTHER INFORMATION: /mod_base= OTHER
                /note= "N = 5'-phosphorylated adenine
                (p-A)"

(ix) FEATURE:
            (A) NAME/KEY: modified_base
            (B) LOCATION: 20
            (D) OTHER INFORMATION: /mod_base= OTHER
                /note= "N = 3'-digoxigenin-conjugated
                cytosine (C-dig)"

(xi) SEQUENCE DESCRIPTION: SEQ ID NO:66:

NCGTATATCT CTGCTCTTCN                                                       20

(2) INFORMATION FOR SEQ ID NO:67:
```

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: modified_base
        (B) LOCATION: 1
        (D) OTHER INFORMATION: /mod_base= OTHER
            /note= "N = 5'-biotinylated guanine
            (bio-G)"

(xi) SEQUENCE DESCRIPTION: SEQ ID NO:67:

NAAGAGCAGA GATATACGTA                                            20

(2) INFORMATION FOR SEQ ID NO:68:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: modified_base
        (B) LOCATION: 1
        (D) OTHER INFORMATION: /mod_base= OTHER
            /note= "N = 5'-phosphorylated cytosine
            (p-C)"

(ix) FEATURE:
        (A) NAME/KEY: modified_base
        (B) LOCATION: 20
        (D) OTHER INFORMATION: /mod_base= OTHER
            /note= "N = 3'-digoxigenin-conjugated
            cytosine (C-dig)"

(xi) SEQUENCE DESCRIPTION: SEQ ID NO:68:

NCAGGTGGAG CACCCAGGCN                                            20

(2) INFORMATION FOR SEQ ID NO:69:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: modified_base
        (B) LOCATION: 1
        (D) OTHER INFORMATION: /mod_base= OTHER
            /note= "N = 5'-biotinylated thymine
            (bio-T)"

(xi) SEQUENCE DESCRIPTION: SEQ ID NO:69:

NCCACACGGC GACTCTCATG                                            20

(2) INFORMATION FOR SEQ ID NO:70:

(i) SEQUENCE CHARACTERISTICS:
        (A) LENGTH: 20 base pairs
        (B) TYPE: nucleic acid
        (C) STRANDEDNESS: single
        (D) TOPOLOGY: linear

```
        (ii) MOLECULE TYPE: DNA (genomic)

(ix) FEATURE:
              (A) NAME/KEY: modified_base
              (B) LOCATION: 1
              (D) OTHER INFORMATION: /mod_base= OTHER
                    /note= "N = 5'-phosphorylated adenine
                    (p-A)"

(ix) FEATURE:
              (A) NAME/KEY: modified_base
              (B) LOCATION: 20
              (D) OTHER INFORMATION: /mod_base= OTHER
                    /note= "N = 3'-digoxigenin-conjugated
                    thymine (T-dig)"

(xi) SEQUENCE DESCRIPTION: SEQ ID NO:70:

NTCATAGAAC ACGAACAGCN                                                  20

(2) INFORMATION FOR SEQ ID NO:71:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: DNA (genomic)

(ix) FEATURE:
              (A) NAME/KEY: modified_base
              (B) LOCATION: 1
              (D) OTHER INFORMATION: /mod_base= OTHER
                    /note= "N = 5'-biotinylated guanine
                    (bio-G)"

(xi) SEQUENCE DESCRIPTION: SEQ ID NO:71:

NCTGTTCGTG TTCTATGATC                                                  20

(2) INFORMATION FOR SEQ ID NO:72:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: DNA (genomic)

(ix) FEATURE:
              (A) NAME/KEY: modified_base
              (B) LOCATION: 1
              (D) OTHER INFORMATION: /mod_base= OTHER
                    /note= "N = 5'-phosphorylated adenine
                    (p-A)"

(ix) FEATURE:
              (A) NAME/KEY: modified_base
              (B) LOCATION: 20
              (D) OTHER INFORMATION: /mod_base= OTHER
                    /note= "N = 3'-digoxigenin-conjugated
                    guanine (G-dig)"

(xi) SEQUENCE DESCRIPTION: SEQ ID NO:72:

NTGAGAGTCG CCGTGTGGAN                                                  20

(2) INFORMATION FOR SEQ ID NO:73:

(i) SEQUENCE CHARACTERISTICS:
              (A) LENGTH: 20 base pairs
              (B) TYPE: nucleic acid
              (C) STRANDEDNESS: single
              (D) TOPOLOGY: linear
```

```
     (ii) MOLECULE TYPE: DNA (genomic)

(ix) FEATURE:
          (A) NAME/KEY: modified_base
          (B) LOCATION: 1
          (D) OTHER INFORMATION: /mod_base= OTHER
              /note= "N = 5'-biotinylated thymine
              (bio-T)"

(xi) SEQUENCE DESCRIPTION: SEQ ID NO:73:

NCCACACGGC GACTCTCATC                                                   20

(2) INFORMATION FOR SEQ ID NO:74:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: DNA (genomic)

(ix) FEATURE:
          (A) NAME/KEY: modified_base
          (B) LOCATION: 1
          (D) OTHER INFORMATION: /mod_base= OTHER
              /note= "N = 5'-phosphorylated adenine
              (p-A)"

(ix) FEATURE:
          (A) NAME/KEY: modified_base
          (B) LOCATION: 20
          (D) OTHER INFORMATION: /mod_base= OTHER
              /note= "N = 3'-digoxigenin-conjugated
              thymine (T-dig)"

(xi) SEQUENCE DESCRIPTION: SEQ ID NO:74:

NTCATAGAAC ACGAACAGCN                                                   20

(2) INFORMATION FOR SEQ ID NO:75:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: DNA (genomic)

(ix) FEATURE:
          (A) NAME/KEY: modified_base
          (B) LOCATION: 1
          (D) OTHER INFORMATION: /mod_base= OTHER
              /note= "N = 5'-biotinylated guanine
              (bio-G)"

(xi) SEQUENCE DESCRIPTION: SEQ ID NO:75:

NCTGTTCGTG TTCTATGATG                                                   20

(2) INFORMATION FOR SEQ ID NO:76:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: DNA (genomic)

(ix) FEATURE:
          (A) NAME/KEY: modified_base
          (B) LOCATION: 1
```

-continued

```
        (D) OTHER INFORMATION: /mod_base= OTHER
            /note= "N = 5'-phosphorylated adenine
            (p-A)"

(ix) FEATURE:
        (A) NAME/KEY: modified_base
        (B) LOCATION: 20
        (D) OTHER INFORMATION: /mod_base= OTHER
            /note= "N = 3'-digoxigenin-conjugated
            guanine (G-dig)"

(xi) SEQUENCE DESCRIPTION: SEQ ID NO:76:

NTGAGAGTCG CCGTGTGGAN                                                   20
```